US011993663B2

(12) United States Patent
Huh et al.

(10) Patent No.: US 11,993,663 B2
(45) Date of Patent: May 28, 2024

(54) LOW-VISCOSITY ANTIGEN BINDING PROTEINS AND METHODS OF MAKING THEM

(71) Applicant: AMGEN INC., Thousand Oaks, CA (US)

(72) Inventors: Joon Hoi Huh, Culver City, CA (US); Riki Stevenson, Ventura, CA (US); Pavel Bondarenko, Thousand Oaks, CA (US); Andrew Nichols, Calabasas, CA (US); Da Ren, Thousand Oaks, CA (US); Neeraj Jagdish Agrawal, Natick, MA (US); Richard Smith, Belmont, CA (US)

(73) Assignee: AMGEN INC., Thousand Oaks, CA (US)

( * ) Notice: Subject to any disclaimer, the term of this patent is extended or adjusted under 35 U.S.C. 154(b) by 243 days.

(21) Appl. No.: 17/346,156

(22) Filed: Jun. 11, 2021

(65) Prior Publication Data

US 2021/0371544 A1 Dec. 2, 2021

Related U.S. Application Data

(62) Division of application No. 16/338,292, filed as application No. PCT/US2017/053967 on Sep. 28, 2017, now Pat. No. 11,059,908.

(60) Provisional application No. 62/546,469, filed on Aug. 16, 2017, provisional application No. 62/430,773, filed on Dec. 6, 2016, provisional application No. 62/401,770, filed on Sep. 29, 2016.

(51) Int. Cl.

*C07K 16/40* (2006.01)
*C07K 16/28* (2006.01)
*G01N 11/14* (2006.01)

(52) U.S. Cl.

CPC .......... *C07K 16/40* (2013.01); *C07K 16/2869* (2013.01); *C07K 2317/21* (2013.01); *C07K 2317/24* (2013.01); *C07K 2317/52* (2013.01); *C07K 2317/55* (2013.01); *C07K 2317/90* (2013.01); *C07K 2317/92* (2013.01); *C07K 2317/94* (2013.01); *G01N 11/14* (2013.01)

(58) Field of Classification Search

CPC ................ C07K 16/40; C07K 16/2869; C07K 2317/94; C07K 2317/52; C07K 2317/90; C07K 2317/21; C07K 2317/24; C07K 2317/55; C07K 2317/92; G01N 11/14

See application file for complete search history.

(56) References Cited

U.S. PATENT DOCUMENTS

| | | | |
|---|---|---|---|
| 4,816,397 | A | 3/1989 | Boss et al. |
| 4,816,567 | A | 3/1989 | Cabilly et al. |
| 5,939,598 | A | 8/1999 | Kucherlapati et al. |
| 8,545,849 | B2 | 10/2013 | Borras et al. |
| 9,695,233 | B2 | 7/2017 | Duerr et al. |
| 10,294,303 | B2 | 5/2019 | Yie et al. |
| 10,570,198 | B2 | 2/2020 | Borras et al. |
| 2013/0064825 | A1 | 3/2013 | Chan et al. |
| 2014/0017244 | A1 | 1/2014 | Duerr et al. |
| 2017/0275370 | A1 | 9/2017 | Yie et al. |
| 2019/0276546 | A1 | 12/2019 | Yie et al. |
| 2020/0095310 | A1 | 3/2020 | Regula et al. |

FOREIGN PATENT DOCUMENTS

| | | | | |
|---|---|---|---|---|
| EP | 0 173 494 | A2 | 3/1986 | |
| EP | 0 171 496 | B1 | 5/1993 | |
| EP | 3026061 | A1 | 6/2016 | |
| GB | 2 177 096 | B | 5/1989 | |
| JP | 2015527064 | A | 9/2015 | |
| WO | 2012154999 | A1 | 11/2012 | |
| WO | 2014009465 | A1 | 1/2014 | |
| WO | WO-2014009465 | A1 * | 1/2014 | ............. A61P 27/02 |
| WO | 2017112824 | A2 | 6/2017 | |

OTHER PUBLICATIONS

Yadav, S., Establishing a Link Between Amino Acid Sequences and Self-Associating and Viscoelastic Behavior of Two Closely Related Monoclonal Antibodies, 2011, Pharm Res 28(1750-1764) (Year: 2011).*

JP Application 2019-516945 Office Action (dated Nov. 4, 2022) 5 pages.

Yamauchi, Shape and size of proteins in hydrodynamics, Kagaku To Seibutsu, 1982, vol. 20, No. 5, pp. 296-304.

U.S. Appl. No. 62/387,486, Yie, J. et al.

Carraway, K. L. and Koshland, Jr., D. E., "Carbodiimide modification of proteins," Methods Enzymol 25:616-623 (1972).

Chaudhri, A. et al., "The role of amino acid sequence in the self-association of therapeutic monoclonal antibodies: insights from coarse-grained modeling," The Journal of Physical Chemistry B, 1 17(5):1269-1279 (2013).

Cheng, W. et al., "Linking the solution viscosity of an IgG2 monoclonal antibody to its structure as a function of pH and temperature," J. Pharm Sci., 102(12):4291-4304 (2013).

Chothia, C. et al., "Structural repertoire of the human VH segments," J. Mol. Biol., 227(3):799-817 (1992).

Chothia, C. et al., "Canonical structures for the hypervariable regions of immunoglobulins," J. Mol. Biol., 196:901-917 (1987).

(Continued)

*Primary Examiner* — Daniel E Kolker
*Assistant Examiner* — Maureen Varina Driscoll
(74) *Attorney, Agent, or Firm* — Melissa E. Karabinis

(57) ABSTRACT

The present invention concerns a method for preparing antigen binding proteins specific for PCSK9 with reduced viscosity. The method proceeds by replacing residues in high viscosity variable domain subfamilies with residues in correlating low viscosity subfamilies. The method further comprises substituting residues in the Fc domain with residues associated with low viscosity and adding charged residues to the C-terminus of the Fc domain. The present invention further concerns antigen binding proteins produced by this method.

12 Claims, 28 Drawing Sheets

Specification includes a Sequence Listing.

(56) References Cited

OTHER PUBLICATIONS

Chilean Application No. 201900835, Office Action (dated Feb. 15, 2021).
Chilean Application No. 201900835, Office Action (dated Aug. 23, 2021).
Connolly, B. D. et al., "Weak interactions govern the viscosity of concentrated antibody solutions: high-throughput analysis using the diffusion interaction parameter," Biophys. J., 103(1):69-78 (2012).
Diebolder, C. A. et al., "Complement is Activated by IgG Hexamers Assembled at the Cell Suliace," Science, 343(6176):1260-1263 (2014).
Edelman, G. Nl. et al., "The covalent structure of an entire gamma immunoglobulin molecule," Proc. Natl. Acad. Sci. USA, 63(1):78-85 (1969).
Eurasian Application No. 201990837, Office Action (dated Mar. 26, 2021).
European Application No. 17794111.9, Office Action (dated Aug. 27, 2021).
Ewert, S. et al., "Stability improvement of antibodies for extracellular and intracellular applications: CDR grafting to stable frameworks and structure-based framework engineering," Methods, 34(2): 184-199 (2004).
Ewert, S. et al., "Structure-based improvement of the biophysical properties of immunoglobulin VH domains with a generalizable approach," Biochemistry, 42: 1517-1528 (2003).
Ewert, S. et al., "Biophysical properties of human antibody variable domains," J. Mal. Biol., 325:531-553 (2003).
Ford, C. F. et al., "Fusion tails for the recovery and purification of recombinant proteins," Protein Expression and Purification, 2(2-3):95-107 (1991).
Grussenmeyer, T. et al., "Complexes of polyoma virus medium T antigen and cellular proteins," Proc. Natl. Acad. Sci. USA, 82:7952 (1985).
Guo, Z. et al., "Structure-activity relationship for hydrophobic salts as viscosity-lowering excipients for concentrated solutions of monoclonal antibodies," Pharm Res., 29:3102-3109 (2012).
Honegger, A. et al., "Yet another numbering scheme for immunoglobulin variable domains: an automatic modeling and analysis tool," J. Mol. Biol., 309:657-670 (2001).
Hopp, T. P. et al., A Short Polypeptide Marker Sequence Useful for Recombinant Protein Identification and Purification, Nature Biotechnology, 6: 1204-1210 (1988).
Horton, J. D., Cohen, J.C. & Hobbs, H. H., "1\rfolecular Biology of PCSK9: Its Role in LDL Metabolism," Trends Biochem. Sci., 32(2):71-77. doi: 10.1016/j.tibs.2006.12.008, Seidah & Prat (2007).
Jackson, S. et al., "The Crystal Structure of PCSK9: a Regulator of Plasma LDL-Cholesterol," Structure, 15:545-552 (2007).
Japanese Application No. 2019-516945, Office Action (dated Sep. 21, 2021).
Jefferis, R. and Lefranc, M-P., Human immunoglobulin allotypes: possible implications for immunogenicity, mAbs, 1 :332-338 (2009).
Kabat, E. A. et al., Sequences of Proteins of Immunological Interest, Fifth Edition, Public Health Service, National Institutes of Health, Bethesda, MD, Publication No. 91-3242 (1991) (Table of Contents Only).
Kanai, S. et al., "Reversible self-association of a concentrated monoclonal antibody solution mediated by Fab-Fab interaction that impacts solution viscosity," *Journal of Pharmaceutical Sciences*, 97(10):4219-4227 (2008).
Ketchem, R. R. et al., "Mitigation of monoclonal antibody viscosity by modification of protein surface charge," Abstracts of Papers; ACS National Meeting & Exposition, American Chemical Society, US, 243rd , p. 1, (2012) URL:http://abstracts/acs/org/chem/243nm//program/view.php?obj_id=122153&terms=abstract.
Lemaigre, F. P. et al., "Transcriptional control of genes that regulate glycolysis and gluconeogenesis in adult liver," Biochem. J., 303: 1-14 (1994).
Li, L. et al., "Concentration dependent viscosity of monoclonal antibody solutions: explaining experimental behavior in terms of molecular properties," Phann. Res., 31 :3161-3178 (2014).
Lo Eken, M. R., "Effects of mutation of the CREB binding site of the somatostatin promoter on cyclic AMP responsiveness in CV-I cells," *Gene Expr*., 3(3):253-264(12) (1993).
McGehee, R. E. et al., "Differentiation-specific element: a cis-acting developmental switch required for the sustained transcriptional expression of the angiotensinogen gene during hormonal-induced differentiation of 3T3-L1 fibroblasts to adipocytes, " *Mal. Endocrinol*., 7(4):551-560 (1993).
Morrison, S. L. et al., "Chimeric human antibody molecules: mouse antigen-binding domains with human constant region domains," *Proc. Natl. Acad Sci. US.A*., 81(21):6851-6855 (1984).
Neergaard, M. S. et al., "Viscosity of high concentration protein formulations of monoclonal antibodies of IgG1 and IgG4 subclass—prediction of viscosity through protein-protein interaction measurements," *Eur J. Phann. Sci*., 49:400-410 (2013).
Nilsson, B. et al., "Expression and purification of recombinant insulin-like growth factors from *Escherichia coli, " Methods Enzymol*., 198:3-16 (1991).
Nilsson, B. et al., "Immobilization and purification of enzymes with staphylococcal protein A gene fusion vectors," *EMBO J*., 4(4):1075-1080 (1985).
O'Reilly, M.A. et al., "Identification of an activating transcription factor (ATF) binding site in the human transforming growth factor-β2 promoter," *J. Biol. Chem*., 267(28):19938-19943 (1992).
Paul, W., ed., Fundamental Immunology, Chapter 7, 2nd Edition, Raven Press, NY (1989).
Ropartz, C., Schanfield, M. S., Steinberg, A.G., "Review of the notation for the allotypic and related markers of human immunoglobulins," WHO meeting on human immunoglobulin allotypic markers, Held Jul. 16-19, 1974, Rouen, France, Report Amended Jun. 1976, J. Immunogenet, 3:357-362 (1976).
Rothlisberger, D. et al., "Domain interactions in the Fab fragment: a comparative evaluation of the single-chain Fv and Fab format engineered with variable domains of different stability," *J. Mal. Biol*., 347:773-789 (2005).
Seidah, N. G. & Prat, A., "The proprotein convertases are potential targets in the treatment of dyslipidemia," J. Mol. Med. (Berl), 85(7):685-696 (2007).
Singaporean Application No. 11201902880Q, Written Opinion (dated Jul. 7, 2020).
Shukla, A. A. et al., "Downstream processing of monoclonal antibodie—Application of platform approaches," *J Chrom. B*, 848:28-39 (2007).
Singh, S. N. et al., "Dipole-Dipole Interaction in Antibody Solutions: Correlation with Viscosity Behavior at High Concentrations," *Pharm.Res*., 31(9):2549-2558 (2014).
Smith, D. B. et al., "Single-step purification of polypeptides expressed in *Escherichia coli* as fusions with glutathione S-transferase," *Gene*, 67(1 ):31-40 (1988).
Takeda, S. et al., "Construction of chimaeric processed immunoglobulin genes containing mouse variable and human constant region sequences," *Nature*, 314:452-454 (1985).
Tomlinson, I. M. et al., "The structural repertoire of the human V kappa domain," *EMBO J*., 14:4628-4638 (1995).
Treisman, R. "The SRE: a growth factor response transcriptional regulator," *Seminars in Cancer Biol*., 1 (1):47-58 (1990).
Tseng, C. C. et al., "Postprandial stimulation of insulin release by glucose-dependent insulinotropic polypeptide (GIP). Effect of a specific glucose-dependent insulinotropic polypeptide receptor antagonist in the rat" *J. Clin. Invest*., 98(11):2440-2445 (1996).
Van Den Bremer, E. T. J. et al., "Human IgG is produced in a pro-form that requires clipping of C-terminal lysines for maximal complement activation," *mAbs*, 7( 4):672-680 (2015).
Vidarsson, G. et al., "IgG subclasses and allotypes: from structure to effector functions," *Front. Immunol*., 5: 1-17 (2014).
Yadav, S. et al., "The influence of charge distribution on self-association and viscosity behavior of monoclonal antibody solutions," *Mol. Pharm*., 9(4):791-802 (2012).
Yadav, S. et al., "Viscosity behavior of high-concentration monoclonal antibody solutions: correlation with interaction parameter and electroviscous effects," *J. Pharm. Sci*., 101(3):998-1011 (2012).

(56) References Cited

OTHER PUBLICATIONS

Yadav, S. et al., "Establishing a Link Between Amino Acid Sequences and Self-Associating Viscoelastic Behavior of Two Closely Related Monoclonal Antibodies," Pharm. Res., 28(7):1750-1764 (2011).
Ye, J. et al., "Characterization of a Silencer Regulatory Element in the Human Interferon-y Promoter," *J Biol Chem*., 269(41):25728-25734 (1994).
JP Application 2019516945 Office Action (dated Jun. 7, 2022).
Chaudhri, et al., Antibodies: Insights from Coarse-Grained Modeling, The Journal of Physical Chemistry B, vol. 117, No. 5, 7 (Feb. 2013).
IN Application 201917016348, Office Action, dated Mar. 27, 2023.
JP Application 2022-043944, Office Action (dated Jul. 24, 2023).
BR Application 112019006486-9 Office Action, 6 pages, (dated Oct. 5, 2022).
Chaudhri et al., "The Role of Amino Acid Sequence in the Self-Association of Therapeutic Monoclonal Antibodies: Insights from Coarse-Grained Modeling," J. Phys. Chem. B, vol. 117 (5), pp. 1269-1279 (2013).
CN Application No. 201780073880.7, Office Action (dated Jul. 22, 2022).
Yadav et al., "Establishing a Link Between Amino Acid Sequences and Self-Associating and Viscoelastic Behavior of Two Closely Related Monoclonal Antibodies", Pharm Res., vol. 28 (7), pp. 1750-1764 (2011).
Yadav et al., "The Influence of Charge Distribution on Self-Association and Viscosity Behavior of Monoclonal Antibody Solutions", Mol. Pharmaceutics, vol. 9, pp. 791-802 (2012).
Dudgeon, et al. General strategy for the generation of human antibody variable domains with increased aggregation resistance; Proceedings of the National Academy of Sciences of the United States of America, Early Edition (Jul. 27, 2012).
Office Action BR 202103596 (dated Aug. 24, 2023).

* cited by examiner

FIG. 1A

| Target (informal name) | mAb | Conc. mg/ml | Visc. cP | HC Type (including allotypes) | LC Type | VL Germline | VH Germline | pI | HC SEQ ID NO | LC SEQ ID NO |
|---|---|---|---|---|---|---|---|---|---|---|
| anti-amyloid | A | 142.2 | 5.0 | IgG1 (f) (R;EM) | Kappa | VK2\|A23 | VH2\|2-26 | 9.0 | 168 | 166 |
| GMCSF (247) | B | 139.7 | 5.6 | IgG2 | Kappa | VK3\|A27 | VH1\|1-02 | 8.7 | 4 | 2 |
| CGRPR | C | 136.6 | 6.3 | IgG2 | Lambda | VL1\|1g | VH3\|3-15 | 8.6 | 180 | 178 |
| RANKL | D | 152.7 | 6.6 | IgG2 | Kappa | VK3\|A27 | VH3\|3-23 | 8.6 | 172 | 170 |
| Sclerostin (27H6) | E | 145.0 | 6.7 | IgG2 | Kappa | VK2\|O1 | VH3\|3-48 | 6.6 | 8 | 6 |
| IL-1R1 | F | 153.9 | 6.7 | IgG2 | Kappa | VK6\|A10 | VH5\|5-51 | 7.4 | 12 | 10 |
| Myostatin | G | 141.0 | 6.8 | IgG1 (z) (K;EM) | Kappa | VK1\|O18 | VH3\|3-07 | 8.7 | 16 | 14 |
| B7RP1 | H | 137.5 | 7.7 | IgG2 | Kappa | VK1\|L15 | VH3\|3-07 | 7.7 | 20 | 18 |
| Amyloid | I | 140.6 | 8.2 | IgG1 (za) (K;DL) | Kappa | VK2\|A17 | VH2\|2-70 | 8.7 | 24 | 22 |
| GMCSF (3.112) | J | 156.0 | 8.2 | IgG2 | Kappa | VK3\|A27 | VH1\|1-02 | 8.8 | 28 | 26 |
| CGRP (32H7) | K | 159.5 | 8.3 | IgG2 | Kappa | VK3\|A27 | VH3\|3-33 | 8.7 | 32 | 30 |
| CGRP (3B6.2) | L | 161.1 | 8.4 | IgG2 | Lambda | VL3\|3I | VH1\|1-02 | 8.6 | 36 | 34 |
| PCSK9 (8A3.1) | M | 150.0 | 9.1 | IgG2 | Kappa | VK2\|A19 | VH3\|3-07 | 6.7 | 40 | 38 |
| PCSK9 (492) | N | 150.0 | 9.2 | IgG2 | Kappa | VK2\|A19 | VH3\|3-07 | 6.9 | 44 | 42 |
| CGRP | O | 155.2 | 9.6 | IgG2 | Lambda | VL1\|1b | VH3\|3-33 | 8.8 | 48 | 46 |
| Hepcidin | P | 147.1 | 9.9 | IgG2 | Lambda | VL3\|3r | VH3\|3-33 | 7.3 | 52 | 50 |
| TNFR p55 ) | Q | 157.0 | 10.0 | IgG2 | Kappa | VK3\|A27 | VH3\|3-23 | 8.2 | 56 | 54 |
| OX40L | R | 144.5 | 10.0 | IgG2 | Kappa | VK2\|A23 | VH3\|3-33 | 8.7 | 60 | 58 |
| HGF | S | 155.8 | 10.6 | IgG2 | Kappa | VK3\|L16 | VH4\|4-59 | 8.1 | 64 | 62 |
| GMCSF | T | 162.5 | 11.0 | IgG2 | Kappa | VK4\|B3 | VH1\|1-02 | 8.1 | 68 | 66 |
| Glucagon R | V | 146.0 | 12.1 | IgG2 | Kappa | VK1\|A30 | VH3\|3-33 | 8.4 | 72 | 70 |
| GMCSF (4.381) | U | 144.5 | 12.1 | IgG2 | Kappa | VK3\|A27 | VH1\|1-02 | 8.4 | 76 | 74 |

FIG. 1B

| Target (informal name) | mAb | Conc. mg/ml | Visc. cP | HC Type (including allotypes) | LC Type | VL Germline | VH Germline | pI | HC SEQ ID NO | LC SEQ ID NO |
|---|---|---|---|---|---|---|---|---|---|---|
| Sclerostin (13F3) | W | 155.0 | 12.1 | IgG2 | Kappa | VK1|L19 | VH1|1-46 | 7.8 | 80 | 78 |
| CD-22 | X | 143.7 | 12.2 | IgG1 (f) (R;EM) | Kappa | VK1|O18 | VH1|1-69 | 8.3 | 84 | 82 |
| INFgR | Y | 154.2 | 12.2 | IgG1 (za) (K;DL) | Kappa | VK3|A27 | VH5|5-51 | 8.8 | 88 | 86 |
| Ang2 | Z | 151.5 | 12.4 | IgG2 | Kappa | VK2|A19 | VH3|3-48 | 7.4 | 92 | 90 |
| TRAILR2 | AA | 158.3 | 12.5 | IgG1 (f) (R;EM) | Kappa | VK3|A27 | VH4|4-30 | 8.7 | 96 | 94 |
| EGFR | AB | 141.7 | 14.0 | IgG2 | Kappa | VK1|O18 | VH4|4-61 | 6.8 | 100 | 98 |
| IL-4R | AC | 145.8 | 15.2 | IgG2 | Kappa | VK3|A27 | VH3|3-48 | 8.6 | 104 | 102 |
| IL-15 | AD | 149.0 | 16.3 | IgG1 (f) (R;EM) | Kappa | VK3|A27 | VH5|5-51 | 8.8 | 108 | 106 |
| IGF1R | AE | 159.2 | 17.3 | IgG1 (za) (K;DL) | Kappa | VK2|A19 | VH4|4-04 | 8.6 | 112 | 110 |
| IL-17R | AF | 150.9 | 19.1 | IgG2 | Kappa | VK3|L16 | VH1|1-18 | 8.6 | 116 | 114 |
| Dkk1 (6.37.5) | AG | 159.4 | 19.6 | IgG2 | Kappa | VK2|A2 | VH3|3-33 | 8.2 | 120 | 118 |
| Sclerostin | AH | 134.8 | 20.9 | IgG2 | Kappa | VK1|O2 | VH1|1-e | 7.4 | 124 | 122 |
| TSLP | AI | 134.2 | 21.4 | IgG2 | Lambda | VL3|3h | VH3|3-33 | 7.2 | 128 | 126 |
| Dkk1 (11H10) | AJ | 145.3 | 22.5 | IgG2 | Kappa | VK3|L6 | VH3|3-48 | 8.2 | 132 | 130 |
| PCSK9 | AK | 145.2 | 22.8 | IgG2 | Lambda | VL2|2a2 | VH1|1-18 | 8.1 | 136 | 134 |
| GIPR (2G10.006) | AQ | 150.0 | 19.1 | IgG1 (z) (K;EM) | Kappa | VK3|L16 | VH3|3-33 | 8.1 | 160 | 158 |
| Activin | AL | 133.9 | 29.4 | IgG2 | Lambda | VL3|3r | VH1|1-18 | 7.0 | 140 | 138 |
| Sclerostin (2B8) | AM | 150.0 | 30.0 | IgG2 | Lambda | VL6|6a | VH3|3-33 | 6.7 | 144 | 142 |
| Sclerostin | AN | 141.4 | 30.4 | IgG2 | Kappa | VK1|O2 | VH1|1-18 | 6.8 | 148 | 146 |
| c-fms | AO | 146.9 | 32.1 | IgG2 | Kappa | VK4|B3 | VH1|1-18 | 6.5 | 152 | 150 |
| α4β7 | AP | 154.9 | 32.7 | IgG2 | Kappa | VK1|L19 | VH1|1-24 | 6.5 | 156 | 154 |

FIG. 1C

| Target (informal name) | mAb | SEQ ID NOS | | | | | | | |
|---|---|---|---|---|---|---|---|---|---|
| | | HC FR1 | HC FR2 | HC FR3 | HC FR4 | LC FR1 | LC FR2 | LC FR3 | LC FR4 |
| anti-amyloid | A | 280 | 281 | 282 | 283 | 189 | 190 | 191 | 192 |
| GMCSF (247) | B | 300 | 285 | 301 | 276 | 197 | 194 | 198 | 196 |
| CGRPR | C | 316 | 317 | 318 | 287 | 257 | 258 | 259 | 250 |
| RANKL | D | 291 | 292 | 293 | 276 | 193 | 194 | 195 | 196 |
| Sclerostin (27H6) | E | 304 | 292 | 349 | 276 | 246 | 225 | 226 | 188 |
| IL-1R1 | F | 277 | 278 | 279 | 276 | 185 | 186 | 187 | 188 |
| Myostatin | G | 304 | 289 | 346 | 287 | 205 | 206 | 219 | 231 |
| B7RP1 | H | 304 | 289 | 305 | 276 | 205 | 229 | 207 | 196 |
| Amyloid | I | 333 | 281 | 334 | 276 | 235 | 236 | 226 | 237 |
| GMCSF (3.112) | J | 344 | 285 | 345 | 283 | 193 | 194 | 201 | 196 |
| CGRP (32H7) | K | 302 | 289 | 338 | 287 | 193 | 194 | 198 | 231 |
| CGRP (3B6.2) | L | 299 | 285 | 339 | 287 | 266 | 267 | 268 | 269 |
| PCSK9 (8A3.1) | M | 304 | 289 | 315 | 287 | 227 | 225 | 226 | 188 |
| PCSK9 (492) | N | 304 | 289 | 314 | 287 | 227 | 225 | 228 | 188 |
| CGRP | O | 302 | 289 | 306 | 287 | 254 | 255 | 256 | 250 |
| Hepcidin | P | 302 | 289 | 303 | 283 | 263 | 264 | 265 | 250 |
| TNFR p55 ) | Q | 291 | 292 | 293 | 276 | 193 | 199 | 198 | 196 |
| OX40L | R | 302 | 289 | 303 | 276 | 189 | 190 | 213 | 214 |
| HGF | S | 273 | 274 | 275 | 276 | 181 | 182 | 183 | 184 |
| GMCSF | T | 299 | 285 | 301 | 276 | 215 | 211 | 216 | 217 |
| Glucagon R | V | 302 | 289 | 310 | 287 | 205 | 222 | 223 | 188 |
| GMCSF (4.381) | U | 299 | 285 | 301 | 276 | 193 | 202 | 203 | 204 |

FIG. 1D

| Target (Informal name) | mAb | SEQ ID NOS | | | | | | | |
|---|---|---|---|---|---|---|---|---|---|
| | | HC FR1 | HC FR2 | HC FR3 | HC FR4 | LC FR1 | LC FR2 | LC FR3 | LC FR4 |
| Sclerostin (13F3) | W | 347 | 285 | 348 | 276 | 203 | 245 | 207 | 214 |
| CD-22 | X | 307 | 308 | 309 | 287 | 218 | 206 | 219 | 220 |
| INFγR | Y | 329 | 330 | 331 | 332 | 193 | 194 | 198 | 214 |
| Ang2 | Z | 326 | 292 | 305 | 276 | 227 | 225 | 226 | 231 |
| TRAILR2 | AA | 319 | 320 | 321 | 287 | 193 | 200 | 198 | 196 |
| EGFR | AB | 335 | 336 | 337 | 283 | 205 | 206 | 221 | 188 |
| IL-4R | AC | 304 | 292 | 305 | 276 | 193 | 194 | 198 | 196 |
| IL-15 | AD | 322 | 323 | 324 | 276 | 193 | 194 | 198 | 230 |
| IGF1R | AE | 311 | 312 | 313 | 283 | 224 | 225 | 226 | 196 |
| IL-17R | AF | 299 | 285 | 328 | 276 | 181 | 232 | 233 | 188 |
| Dkk1 (6.37.5) | AG | 302 | 289 | 341 | 276 | 240 | 241 | 242 | 243 |
| Sclerostin | AH | 294 | 285 | 295 | 276 | 205 | 206 | 207 | 196 |
| TSLP | AI | 288 | 289 | 290 | 283 | 251 | 252 | 253 | 250 |
| Dkk1 (11H10) | AJ | 340 | 292 | 305 | 287 | 238 | 194 | 239 | 231 |
| PCSK9 | AK | 284 | 285 | 286 | 287 | 247 | 248 | 249 | 250 |
| GIPR (2G10.006) | AQ | 302 | 342 | 303 | 276 | 181 | 194 | 234 | 188 |
| Activin | AL | 299 | 285 | 325 | 283 | 260 | 261 | 262 | 250 |
| Sclerostin (2B8) | AM | 302 | 289 | 303 | 287 | 270 | 271 | 272 | 250 |
| Sclerostin | AN | 327 | 285 | 328 | 287 | 205 | 206 | 207 | 188 |
| c-fms | AO | 299 | 285 | 328 | 276 | 210 | 211 | 212 | 214 |
| α4β7 | AP | 296 | 297 | 298 | 276 | 208 | 206 | 209 | 196 |
| c-kit | BA | 299 | 285 | 295 | 276 | 210 | 211 | 212 | 188 |

FIG. 2

| Chain | High viscosity subfamily | Low viscosity subfamily | p-value | Residues in high viscosity subfamily, positions in Aho numbering, residues in low viscosity subfamily | | | | |
|---|---|---|---|---|---|---|---|---|
| | | | | FR1 | CDR1 | FR2 | CDR2 | FR3 |
| Heavy | VH1|1-18 | VH1|3-02 | 0.0002 | | S38G, G40Y, S42H | | S59N, Y61N, N65S, N67G, | T82R, T86I, R94S, S95R |
| Heavy | VH3|3-33 | VH3|3-07 | 0.076 | Q1E, P17G | G40W, M41_, H42S | | V57S/Q, W/S59K/R, Y60Q, N67E | S86A |
| Light | VK3|L16 | VK3|A27 | 0.031 | M4L, V13L | _33S | | D58G | A76D, S95P, Q97E, S98P |

FIG. 9A

| VH1\|1-18 and VH1\|1-02 Global sequence parameters | | | | | CDR1 | | | CDR2 | | | | | FR3 | | | | | | | | |
|---|---|---|---|---|---|---|---|---|---|---|---|---|---|---|---|---|---|---|---|---|---|
| | | | | | 32 | 33 | 35 | 52 | 53 | 54 | 55 | 57 | 67 | 68 | 69 | 70 | 71 | 72 | 73 | 74 | 75 |
| | | | | | 31 | 33 | 35 | 52 | a | 53 | 54 | 56 | 66 | 67 | 68 | 69 | 70 | 71 | 72 | 73 | 74 |
| | | | | | 31 | 33 | 35 | 52 | a | 53 | 54 | 56 | 66 | 67 | 68 | 69 | 70 | 71 | 72 | 73 | 74 |
| mAbs | Visc, cP | pI | VL | VH1 | 33 | 40 | 42 | 59 | 60 | 61 | 65 | 67 | 77 | 78 | 79 | 80 | 81 | 82 | 83 | 84 | 85 |
| VBase | | | | VH1\|1-02 | G | Y | H | N | P | N | S | G | R | V | T | M | T | R | D | T | S |
| B | 5.6 | 8.7 | VK3\|A27 | VH1\|1-02 | G | Y | H | N | P | N | S | G | R | V | T | M | T | R | D | T | S |
| J | 8.2 | 8.8 | VK3\|A27 | VH1\|1-02 | G | Y | H | N | P | N | S | G | R | V | T | M | T | R | D | T | S |
| L | 8.4 | 8.8 | VL3\|3l | VH1\|1-02 | G | Y | H | N | P | N | S | G | R | V | T | M | T | R | D | T | S |
| T | 11.0 | 8.1 | VK4\|B3 | VH1\|1-02 | G | Y | H | N | P | N | S | G | R | V | T | M | T | R | D | T | S |
| U | 12.1 | 8.4 | VK3\|A27 | VH1\|1-02 | G | Y | H | N | P | N | S | G | R | V | T | M | T | R | D | T | S |
| AF | 19.1 | 8.6 | VK3\|L16 | VH1\|1-18 | R | G | S | S | T | Y | S | N | R | V | T | M | T | T | D | T | S |
| AK | 22.8 | 8.1 | VL2\|2a2 | VH1\|1-18 | S | G | S | S | F | Y | N | N | R | G | T | M | T | T | D | P | S |
| AL | 29.4 | 7.0 | VL3\|3r | VH1\|1-18 | S | G | S | I | P | Y | N | N | R | V | T | M | T | T | D | T | S |
| AN | 30.4 | 6.8 | VK1\|O2 | VH1\|1-18 | D | N | H | N | P | N | S | G | R | V | T | M | T | T | D | T | S |
| AO | 32.1 | 6.6 | VK4\|B3 | VH1\|1-18 | S | G | S | S | A | Y | N | N | R | V | T | M | T | T | D | T | S |
| Vbase | | | | VH1\|1-18 | S | G | S | S | A | Y | N | N | R | V | T | M | T | T | D | T | S |
| p-value | 0.0002 | 0.03 | | | | | | | | | | | | | | | | | | | |

FIG. 9B

| FR3 | | | | | | | | | | | | | | | | | | | | | | | VH | VL | Schem |
|---|---|---|---|---|---|---|---|---|---|---|---|---|---|---|---|---|---|---|---|---|---|---|---|---|---|
| 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 52 | 12 | EU |
| 75 | 76 | 77 | 78 | 79 | 80 | 81 | 82 | a | b | c | 83 | 84 | 85 | 86 | 87 | 88 | 89 | 90 | 91 | 92 | 93 | 94 | 50 | 13 | Kabat |
| 75 | 76 | 77 | 78 | 79 | 80 | 81 | 82 | a | b | c | 83 | 84 | 85 | 86 | 87 | 88 | 89 | 90 | 91 | 92 | 93 | 94 | 52 | 13 | Chothia |
| 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | 59 | 13 | Aho |
| I | S | T | A | Y | M | E | L | S | P | L | R | S | D | D | T | A | V | Y | Y | C | A | R | | | |
| I | S | T | A | Y | M | E | L | S | R | L | R | S | D | D | T | A | V | Y | Y | C | A | R | N | L | |
| I | S | T | A | S | M | E | L | S | R | L | R | S | D | D | T | A | V | Y | F | C | A | R | N | L | |
| I | S | T | A | Y | M | E | L | S | R | L | R | S | D | D | T | A | V | Y | F | C | A | R | N | V | |
| I | S | T | A | Y | M | E | L | S | R | L | R | S | D | D | T | A | V | Y | Y | C | A | R | N | V | |
| I | S | T | A | Y | M | E | L | S | R | L | R | S | D | D | T | A | V | Y | Y | C | A | R | N | L | |
| T | S | T | A | Y | M | E | L | R | S | L | R | S | D | D | T | A | V | Y | Y | C | A | R | S | V | |
| T | S | T | A | Y | M | E | L | R | S | L | R | S | D | D | T | A | V | Y | Y | C | A | R | S | G | |
| T | S | T | A | Y | M | E | L | R | S | L | R | S | D | D | T | A | V | Y | F | C | A | R | I | V | |
| T | S | T | A | Y | M | E | L | R | S | L | R | S | D | D | T | A | V | Y | Y | C | A | R | N | A | |
| T | S | T | A | Y | M | E | L | R | S | L | R | S | D | D | T | A | V | Y | Y | C | A | R | S | V | |
| T | S | T | A | Y | M | E | L | R | S | L | R | S | D | D | T | A | V | Y | Y | C | A | R | | | |

FIG. 10

| mAb mutant symbols | Heavy chain mutations | Light chain mutations |
|---|---|---|
| AK | AK_HC | AK_LC |
| AK (82 94 95) | AK_HC: [T82R, R94S, S95R] | AK_LC |
| AK (59 82 94 95) | AK_HC: [S59K, T82R, R94S, S95R] | AK_LC |
| AK (82 94 95 13) | AK_HC: [T82R, R94S, S95R] | AK_LC: [G13L] |
| AK (59 82 94 95 13) | AK_HC: [S59K, T82R, R94S, S95R] | AK_LC: [G13L] |
| AO | AO_HC | AO_LC |
| AO (82 94 95) | AO_HC: [T82R, R94S, S95R] | AO_LC |
| AO (59 82 94 95) | AO_HC: [S59K, T82R, R94S, S95R] | AO_LC |
| AO (82 94 95 13) | AO_HC: [T82R, R94S, S95R] | AO_LC: [V13L] |
| AO (59 82 94 95 13) | AO_HC: [S59K, T82R, R94S, S95R] | AO_LC: [V13L] |

FIG. 11

| VH3\|3-07 and VH3\|3-33 Global Sequence Parameters | | | | | FR1 | | CDR1 | | | CDR2 | | | | FR3 | Scheme |
|---|---|---|---|---|---|---|---|---|---|---|---|---|---|---|---|
| | | | | | 1 | 16 | 33 | 34 | 35 | 50 | 52 | 53 | 57 | 78 | EU |
| | | | | | 1 | 16 | 33 | 34 | 35 | 50 | 52 | 52a | 56 | 74 | Kabat |
| | | | | | 1 | 16 | 33 | 34 | 35 | 50 | 52 | 52a | 56 | 74 | Chothia |
| mAb | Visc, cP | pI | VL | VH3 | 1 | 17 | 40 | 41 | 42 | 57 | 59 | 60 | 67 | 85 | Aho |
| VBase | | | | VH3\|3-07 | E | G | W | M | S | N | K | Q | E | A | |
| G | 6.8 | 8.7 | VK1\|O18 | VH3\|3-07 | E | G | W | | N | Q | R | L | A | A | |
| H | 7.7 | 7.7 | VK1\|L15 | VH3\|3-07 | E | G | W | | S | Y | K | Q | E | A | |
| K | 8.3 | 8.7 | VK3\|A27 | VH3\|3-33 | Q | R | G | M | H | V | W | Y | N | S | |
| M | 9.1 | 6.7 | VK2\|A19 | VH3\|3-07 | E | G | W | | S | S | K | Q | E | A | |
| N | 9.2 | 6.9 | VK2\|A19 | VH3\|3-07 | E | G | W | | S | S | K | Q | E | A | |
| O | 9.6 | 8.8 | VL1\|1b | VH3\|3-33 | Q | R | G | M | H | V | S | F | I | S | |
| P | 9.9 | 7.3 | VL3\|3r | VH3\|3-33 | Q | R | G | M | H | V | W | Y | N | S | |
| R | 10.0 | 8.7 | VK2\|A23 | VH3\|3-33 | Q | R | G | M | H | V | W | Y | N | S | |
| V | 12.1 | 8.4 | VK1\|A30 | VH3\|3-33 | Q | R | G | M | H | V | W | Y | N | S | |
| AG | 19.6 | 8.2 | VK2\|A2 | VH3\|3-33 | Q | R | G | M | H | V | S | Y | D | A | |
| AI | 21.4 | 7.2 | VL3\|3h | VH3\|3-33 | Q | R | G | M | H | V | W | Y | N | S | |
| AQ | 19.1 | 8.1 | VK3\|L16 | VH3\|3-33 | Q | R | G | M | H | A | W | F | D | S | |
| AM | 30.0 | 6.7 | VL6\|6a | VH3\|3-33 | Q | R | A | M | H | V | W | Y | N | S | |
| VBase | | | | VH3\|3-33 | Q | R | G | M | H | V | W | Y | N | S | |
| p-value | 0.076 | 0.300 | | | | | | | | | | | | | |

FIG. 12

<table>
<tr><td colspan="5" rowspan="4">VK3|A27 and VK3|L Global Sequence Parameters</td><td colspan="2">FR1</td><td colspan="2">CDR1</td><td>CDR2</td><td colspan="4">FR3</td><td>Scheme</td></tr>
<tr><td>4</td><td>12</td><td>31</td><td>33</td><td>51</td><td>66</td><td>85</td><td>87</td><td>88</td><td>EU</td></tr>
<tr><td>4</td><td>12</td><td>31</td><td>33</td><td>51</td><td>65</td><td>82b</td><td>83</td><td>84</td><td>Kabat</td></tr>
<tr><td>4</td><td>12</td><td>31</td><td>33</td><td>51</td><td>65</td><td>82b</td><td>83</td><td>84</td><td>Chothia</td></tr>
<tr><td>mAb</td><td>Visc, cP</td><td>pI</td><td>VH</td><td>VK3</td><td>4</td><td>13</td><td>33</td><td>40</td><td>58</td><td>76</td><td>95</td><td>97</td><td>98</td><td>Aho</td></tr>
<tr><td>VBase</td><td></td><td></td><td></td><td>VK3|A27</td><td>L</td><td>L</td><td>S</td><td>Y</td><td>G</td><td>D</td><td>R</td><td>E</td><td>P</td><td></td></tr>
<tr><td>B</td><td>5.6</td><td>8.7</td><td>VH1|1-02</td><td>VK3|A27</td><td>L</td><td>L</td><td>S</td><td>Y</td><td>G</td><td>D</td><td>R</td><td>E</td><td>P</td><td></td></tr>
<tr><td>D</td><td>6.6</td><td>8.6</td><td>VH3|3-23</td><td>VK3|A27</td><td>L</td><td>L</td><td>G</td><td>Y</td><td>G</td><td>D</td><td>R</td><td>E</td><td>P</td><td></td></tr>
<tr><td>J</td><td>8.2</td><td>8.8</td><td>VH1|1-02</td><td>VK3|A27</td><td>L</td><td>L</td><td>S</td><td>Y</td><td>G</td><td>D</td><td>R</td><td>E</td><td>P</td><td></td></tr>
<tr><td>K</td><td>8.3</td><td>8.7</td><td>VH3|3-33</td><td>VK3|A27</td><td>L</td><td>L</td><td>S</td><td>Y</td><td>G</td><td>D</td><td>R</td><td>E</td><td>P</td><td></td></tr>
<tr><td>Q</td><td>10.0</td><td>8.2</td><td>VH3|3-23</td><td>VK3|A27</td><td>L</td><td>L</td><td>S</td><td>Y</td><td>G</td><td>D</td><td>R</td><td>E</td><td>P</td><td></td></tr>
<tr><td>S</td><td>10.6</td><td>8.1</td><td>VH4|4-59</td><td>VK3|L16</td><td>M</td><td>V</td><td>-</td><td>N</td><td>G</td><td>A</td><td>S</td><td>Q</td><td>S</td><td></td></tr>
<tr><td>U</td><td>12.1</td><td>8.4</td><td>VH1|1-02</td><td>VK3|A27</td><td>L</td><td>L</td><td>N</td><td>Y</td><td>G</td><td>D</td><td>R</td><td>E</td><td>P</td><td></td></tr>
<tr><td>Y</td><td>12.2</td><td>8.8</td><td>VH5|5-51</td><td>VK3|A27</td><td>L</td><td>L</td><td>S</td><td>Y</td><td>G</td><td>D</td><td>R</td><td>E</td><td>P</td><td></td></tr>
<tr><td>AA</td><td>12.5</td><td>8.7</td><td>VH4|4-30</td><td>VK3|A27</td><td>L</td><td>L</td><td>R</td><td>Y</td><td>G</td><td>D</td><td>R</td><td>E</td><td>P</td><td></td></tr>
<tr><td>AC</td><td>15.2</td><td>8.6</td><td>VH3|3-48</td><td>VK3|A27</td><td>L</td><td>L</td><td>N</td><td>Y</td><td>G</td><td>D</td><td>R</td><td>E</td><td>P</td><td></td></tr>
<tr><td>AD</td><td>16.3</td><td>8.8</td><td>VH5|5-51</td><td>VK3|A27</td><td>L</td><td>L</td><td>S</td><td>Y</td><td>G</td><td>D</td><td>R</td><td>E</td><td>P</td><td></td></tr>
<tr><td>AF</td><td>19.1</td><td>8.6</td><td>VH1|1-18</td><td>VK3|L16</td><td>M</td><td>V</td><td>-</td><td>N</td><td>D</td><td>A</td><td>S</td><td>Q</td><td>S</td><td></td></tr>
<tr><td>AJ</td><td>22.5</td><td>8.2</td><td>VH3|3-48</td><td>VK3|L6</td><td>L</td><td>L</td><td>-</td><td>Y</td><td>D</td><td>A</td><td>S</td><td>E</td><td>P</td><td></td></tr>
<tr><td>AQ</td><td>19.1</td><td>8.1</td><td>VH3|3-33</td><td>VK3|L16</td><td>M</td><td>V</td><td>-</td><td>N</td><td>G</td><td>A</td><td>S</td><td>Q</td><td>S</td><td></td></tr>
<tr><td>Vbase</td><td></td><td></td><td></td><td>VK3|L16</td><td>M</td><td>V</td><td>-</td><td>N</td><td>G</td><td>A</td><td>S</td><td>Q</td><td>S</td><td></td></tr>
<tr><td>p-value</td><td>0.007</td><td>0.011</td><td colspan="12"></td></tr>
</table>

FIG. 15

| Sample | Viscosity (cP) @ 1000s-1 @ 25C | Relative viscosity |
|---|---|---|
| Antibody AK | 43.7 | 100% |
| Fab Mutant | 25.6 | 59% |
| Fc Mutant | 34.8 | 80% |
| Double Mutant | 22.6 | 52% |

Carboxylic Acid EDC o-Acylisourea Active Ester Crosslinked Proteins Isourea By-product

FIG. 17

| Protein | Target | Monomer | Dimer | Other | Viscosity at 150 mg/mL at 25°C |
|---|---|---|---|---|---|
| ASA1 | | Yes | Yes | No | ~ 2-4 cP in A5 |
| ASA2 | | Yes | Yes | No | ~ 2-4 cP in A5 |
| Ab BA | C-kit | Yes | Yes | Yes | ~50 cP in A52Su |
| Ab AH | sclerostin | Yes | Yes | Yes | ~22 cP in A52Su |
| Ab AN | sclerostin | Yes | Yes | Yes | ~30 cP in A52Su |

| AQ mutant symbols | AQ HC mutations in Aho (Linear) numbering | AQ LC mutations in Aho (Linear) numbering | Conc, mg/mL | Visc, cP | STDEV, cP | Visc Rel to AQ |
|---|---|---|---|---|---|---|
| AQ | AQ_HC | AQ_LC | 151.1 | 19.1 | 0.6 | 1 |
| AQ (HC 1, 17, 85) | AQ_HC: Q1(1)E, R17(16)G, S85(75)A | AQ_LC | 151.7 | 15.8 | 0.8 | 0.87 |
| AQ (LC 4 13 76 95 97 98) | AQ_HC: | AQ_LC: M4(4)L, V13(13)L, A76(60)D, S95(77)R, Q97(79)E, S98(80)P | 149.1 | 12.7 | 0.4 | 0.67 |
| AQ (HC 1, 17, 85) (LC 4 13 76 95 97 98) | AQ_HC: Q1(1)E, R17(16)G, S85(75)A | AQ_LC: M4(4)L, V13(13)L, A76(60)D, S95(77)R, Q97(79)E, S98(80)P | 152.6 | 24.2 | 1 | 1.26 |

FIG. 21

| Group # | Test Material | Dose Level (mg/kg) | Dose Volume (mL/kg) | Dose Concentration (mg/mL) | # Animals |
|---|---|---|---|---|---|
| 1 | Antibody AK (control) | 10 | 0.071 | 140 | 4 |
| | Diluent (procedural control) | 0 | 0.071 | 0 | |
| 2 | Antibody AK (Fab mutation) | 10 | 0.048 | 210 | 4 |
| | Diluent (procedural control) | 0 | 0.048 | 0 | |
| 3 | Antibody AK (Fc mutation) | 10 | 0.048 | 210 | 4 |
| 4 | Antibody AK (Fab and Fc double mutation) | 10 | 0.048 | 210 | 4 |

FIG. 22

| Dose Group and Level | $T_{max}$ (Day) | $C_{max}$ (µg/mL) | $AUC_{last}$ (day*µg/mL) | $AUC_{last/D}$ (day*kg*µg/mL*mg) |
|---|---|---|---|---|
| Antibody AK 10 mg/kg | 2.5 | 87.8 | 923 | 92.3 |
| Antibody AK (Fab mutation) 10 mg/kg | 2.5 | 91.1 | 807 | 80.7 |
| Antibody AK (Fc mutation) 10 mg/kg | 0.81 | 125 | 1020 | 102 |
| Antibody AK (Fab + Fc mutation) 10 mg/kg | 1 | 112 | 740 | 74.0 |

FIG. 23

| LDL-C % pretest * | | | | | | | | | | | | | | | |
|---|---|---|---|---|---|---|---|---|---|---|---|---|---|---|---|
| | Days post dose | | | | | | | | | | | | | | |
| Animal # | pretest (Day 1 CLAB) | 1.02 | 2 | 3 | 4 | 6 | 8 | 11 | 15 | 18 | 22 | 25 | 29 | 36 | 43 |
| 1001 | 100.00% | 101.75% | 66.67% | 40.35% | 36.84% | 29.82% | 33.33% | 29.82% | 15.79% | 24.56% | 21.05% | 22.81% | 31.58% | 57.89% | 59.65% |
| 1002 | 100.00% | 95.00% | 52.50% | 45.00% | 37.50% | 37.50% | 47.50% | 20.00% | 7.50% | 50.00% | 32.50% | 30.00% | 42.50% | 60.00% | 70.00% |
| 1003 | 100.00% | 111.11% | 58.33% | 27.78% | 27.78% | 22.22% | 22.22% | 36.11% | 8.33% | 25.00% | 22.22% | 19.44% | 61.11% | 97.22% | 97.22% |
| 1004 | 100.00% | 106.97% | 52.24% | 35.82% | 32.84% | 29.85% | 19.40% | 14.93% | 4.48% | 4.48% | 19.40% | 19.40% | 83.58% | 98.51% | 100.00% |
| mean | 100.00% | 103.50% | 57.50% | 37.50% | 34.00% | 30.00% | 29.50% | 24.00% | 9.00% | 23.00% | 23.00% | 22.50% | 56.50% | 79.00% | 82.00% |
| 2001 | 100.00% | 106.52% | 58.70% | 34.78% | 26.09% | 28.26% | 30.43% | 26.09% | 21.74% | 52.17% | 32.61% | 39.13% | 39.13% | 54.35% | 69.57% |
| 2002 | 100.00% | 100.00% | 48.57% | 34.29% | 31.43% | 28.57% | 25.71% | 8.57% | 8.57% | 25.71% | 28.57% | 42.86% | 65.71% | 120.00% | 102.86% |
| 2003 | 100.00% | 110.34% | 63.79% | 32.76% | 32.76% | 24.14% | 13.79% | 18.97% | 5.17% | 15.52% | 18.97% | 24.14% | 41.38% | 60.34% | 67.24% |
| 2004 | 100.00% | 114.29% | 62.86% | 37.14% | 31.43% | 25.71% | 22.86% | 28.57% | 20.00% | 22.86% | 31.43% | 31.43% | 48.57% | 65.71% | 77.14% |
| mean | 100.00% | 108.05% | 59.20% | 34.48% | 30.46% | 26.44% | 22.41% | 21.26% | 13.22% | 28.74% | 27.01% | 33.33% | 47.13% | 71.84% | 77.01% |
| 3001 | 102.63% | 63.16% | 42.11% | 31.58% | 28.95% | 23.68% | 18.42% | 7.89% | 23.68% | 28.95% | 76.32% | 113.16% | 126.32% | 97.37% | 94.87% |
| 3002 | 104.17% | 50.00% | 29.17% | 27.08% | 29.17% | 18.75% | 14.58% | 6.25% | 16.67% | 25.00% | 52.08% | 81.25% | 89.58% | 79.17% | 76.00% |
| 3003 | 100.00% | 37.21% | 18.60% | 18.60% | 6.98% | 6.98% | 6.98% | 6.98% | 6.98% | 39.53% | 67.44% | 116.28% | 95.35% | 102.33% | 102.33% |
| 3004 | 100.00% | 55.00% | 40.00% | 32.50% | 27.50% | 25.00% | 27.50% | 20.00% | 22.50% | 25.00% | 22.50% | 32.50% | 37.50% | 60.00% | 60.00% |
| mean | 100.00% | 101.78% | 50.88% | 31.95% | 27.22% | 23.08% | 18.34% | 16.57% | 10.06% | 17.16% | 29.59% | 54.44% | 85.80% | 85.98% | 82.25% |
| 4001 | 100.00% | 105.88% | 76.47% | 56.86% | 47.06% | 45.10% | 35.29% | 39.22% | 25.49% | 31.37% | 31.37% | 37.25% | 64.71% | 92.16% | 96.08% |
| 4002 | 100.00% | 102.17% | 54.35% | 39.13% | 32.61% | 30.43% | 21.74% | 26.09% | 15.22% | 26.09% | 28.26% | 34.78% | 34.78% | 67.39% | 82.61% |
| 4003 | 100.00% | 94.92% | 54.24% | 35.59% | 30.51% | 20.34% | 22.03% | 27.12% | 15.25% | 23.73% | 57.63% | 45.76% | 67.80% | 74.58% | 81.36% |
| 4104 | 100.00% | 102.99% | 56.72% | 32.84% | 34.33% | 35.82% | 28.36% | 29.85% | 31.34% | 25.37% | 28.36% | 26.87% | 44.78% | 55.22% | 59.70% |
| mean | 100.00% | 101.35% | 60.08% | 40.33% | 35.37% | 32.74% | 26.91% | 30.94% | 22.42% | 25.91% | 35.77% | 35.87% | 53.35% | 71.30% | 78.48% |

LOW-VISCOSITY ANTIGEN BINDING PROTEINS AND METHODS OF MAKING THEM

CROSS REFERENCES TO RELATED APPLICATIONS

This application is divisional of U.S. Ser. No. 16/338,292, filed Mar. 29, 2019, which is a national stage application under 35 U.S.C. § 371 of International Application No. PCT/US17/53967, having an international filing date of Sep. 28, 2017, which claims the priority of U.S. Provisional Application No. 62/546,469, filed on Aug. 16, 2017; U.S. Provisional Application No. 62/430,773, filed on Dec. 6, 2016; and U.S. Provisional Application No. 62/401,770, filed Sep. 29, 2016, each of which is hereby incorporated by reference in its entirety for all purposes.

FIELD OF THE INVENTION

This invention relates to biopharmaceuticals, particularly to therapeutic antigen binding proteins, methods of use thereof, pharmaceutical compositions thereof, and processes of making them. In particular, this invention relates to antigen binding proteins, particularly antibodies, mutated to reduce viscosity.

BRIEF DESCRIPTION OF THE SEQUENCE LISTING

Incorporated herein by reference in its entirety is a Sequence Listing entitled, "A-2063-US-PSP3_SeqList_ST25.txt", comprising SEQ ID NO:1 through SEQ ID NO:379, which includes nucleic acid and/or amino acid sequences disclosed herein. The Sequence Listing has been submitted herein in ASCII text format via EFS, and thus constitutes both the paper and computer readable form thereof. The Sequence Listing was first created using PatentIn on Aug. 16, 2017, and is 4.32 MB in size.

BACKGROUND OF THE INVENTION

Currently, monoclonal antibodies (mAbs) are the most popular modality of modern therapeutic proteins on the market and under development. The differences between antibodies are predominantly in the antigen binding domains or complementary determining regions (CDRs). These differences in the CDRs are thought to result in differences in transient protein-protein interaction propensity that manifest themselves as bulk solution viscosity. Several groups have described the presence of reversible clusters of antibodies in viscous antibody solutions (predominantly dimers). Several theoretical descriptions of polymer viscosity have been proposed to explain the interactions of these clusters as a mechanism for bulk solution viscosity behavior.

Antibodies usually work as antagonists and, therefore, large amounts, often exceeding 100 mg per dose, are required to block undesirable interactions. For patient comfort, a single subcutaneous injection of a 1 mL volume is the most preferred mode of administration. The need to administer large amounts of mAbs in a relatively small volume has required high concentration formulations at or exceeding 100 mg/ml. Antibodies are large biopolymers with molecular weights of about 150 kDa, and their high concentrations result in high sheer stress and high viscosity due to protein-protein and protein-wall interactions during filtration and passage through the injection needles and in subcutaneous space. High viscosity presents challenges in the manufacture of therapeutic antigen binding proteins as well as in their administration to patients, including prohibitively high back pressure during injections leading to malfunction of injections devices, difficulty of manual administration, decreased bio-availability and patient discomfort.

The development and use of high concentration therapeutic monoclonal antibody solutions has accelerated as the cost of biopharmaceutical production has decreased. In some cases, these antibody solutions possess viscous solution attributes that can make manufacturing and administration of the intended dose challenging. The differences in the CDRs that appear to determine if an antibody is "viscous" or "not viscous" are likely related to the propensity of the CDRs to drive protein-protein interaction.

Significant efforts are underway in the industry to understand the nature of interactions leading to high viscosity and to reduce the viscosity of high viscosity antibody formulations. The most important parameters affecting viscosity of the antibody formulations include:

- intermolecular interactions defined by the pI of the protein and the pH of the solution. Cheng et al. (2013), "Linking the solution viscosity of an IgG2 monoclonal antibody to its structure as a function of pH and temperature," *J. Pharm Sci.* 102: 4291-4304.
- Charge interactions. Yadav et al. (2012), "Viscosity behavior of high-concentration monoclonal antibody solutions: correlation with interaction parameter and electroviscous effects," *J. Pharm Sci.* 101: 998-1011; Yadav et al. (2012), "The influence of charge distribution on self-association and viscosity behavior of monoclonal antibody solutions." *Mol Pharm* 9(4): 791-802; Singh et al. (2014), "Dipole-Dipole Interaction in Antibody Solutions: Correlation with Viscosity Behavior at High Concentration," *Pharm Res.* 31(9): 2549-2558; Chaudhri et al. (2013), "The role of amino acid sequence in the self-association of therapeutic monoclonal antibodies: insights from coarse-grained modeling," *J. Phys. Chem. B* 117: 1269-1279.
- Hydrophobic interactions. Guo et al. (2012), "Structure-activity relationship for hydrophobic salts as viscosity-lowering excipients for concentrated solutions of monoclonal antibodies," *Pharm Res* 29: 3102-3109.

The highest solution viscosity was observed under conditions with the most negative diffusion interaction parameter kD, the highest apparent radius and the lowest net charge. Neergaard et al. (2013), "Viscosity of high concentration protein formulations of monoclonal antibodies of the IgG1 and IgG4 subclass—prediction of viscosity through protein-protein interaction measurements," *Eur. J. Pharm Sci.* 49: 400-410. The diffusion interaction parameter (kD), a component of the osmotic second virial coefficient (B(2)) correlated well (R>0.9) with the viscosity of concentrated mAb solutions, while the mAb net charge correlated weakly (R<0.6), indicating that weak intermolecular interactions are important in governing the viscoelastic behavior of concentrated mAb solutions. Connolly, et al. (2012), "Weak interactions govern the viscosity of concentrated antibody solutions: high-throughput analysis using the diffusion interaction parameter," *Biophys. J.* 103: 69-78. In a study reported in this specification, primary sequences linked to 3D structure were utilized. See Honegger et al. (2001), "Yet another numbering scheme for immunoglobulin variable domains: an automatic modeling and analysis tool," *J. Mol. Biol.* 309: 657-670. Viscosity values of several mAb molecules were measured to develop a model for viscosity prediction of mAbs via machine learning algorithms. Structural position, charge and hydrophobicity were the main parameters of amino acids utilized for the model.

Viscosity of monoclonal antibodies was assessed using molecular information in the following articles: Li, L. et al. (2014), "Concentration dependent viscosity of monoclonal antibody solutions: explaining experimental behavior in terms of molecular properties," *Pharm. Res.* 31: 3161-3178; and Sharma et al. (2014), "In silico selection of therapeutic antibodies for development: viscosity, clearance, and chemical stability," *Proc. Natl. Acad. Sci. U.S.A* 111: 18601-6.

The net result of the interactions between antibodies is either an extended transient network of interactions (a percolating network) that result in a viscous solution or the formation of larger oligomers that then somehow influence the solution rheology as larger structures. In studies reported in this specification, a small number of viscous antibodies was used as the subject for biochemical and biophysical analysis in an attempt to deduce specific protein-protein interactions that might lead to a viscous antibody solution.

The Aho numbering approach was utilized in the past to improve stability and other biophysical properties. Ewert et al. (2003), "Structure-based improvement of the biophysical properties of immunoglobulin VH domains with a generalizable approach," *Biochemistry* 42: 1517-1528; Ewert et al. (2003), "Biophysical properties of human antibody variable domains," *J. Mol. Biol.* 325: 531-553; Ewert et al. (2004), "Stability improvement of antibodies for extracellular and intracellular applications: CDR grafting to stable frameworks and structure-based framework engineering," *Methods* 34: 184-199; and Rothlisberger et al. (2005), "Domain interactions in the Fab fragment: a comparative evaluation of the single-chain Fv and Fab format engineered with variable domains of different stability," *J Mol. Biol.* 347: 773-789. The Aho numbering system was also utilized in the past to reduce propensity for aggregaton. Borras et al. (2013), U.S. Pat. No. 8,545,849.

SUMMARY OF THE INVENTION

This invention relates to methods for reducing viscosity of antigen binding proteins by modifying sequences in framework regions and/or the Fc domain that are shown to be associated with high viscosity.

In the process details which follow, all variable region amino acids are identified by Aho numbering, all amino acids from conserved regions are identified by EU numbering. Aho numbering is aligned and correlated with the other main numbering schemes including EU (Edelman et al. (1969), "The covalent structure of an entire gamma immunoglobulin molecule," *Proc. Natl. Acad. Sci. U.S.A* 63, 78-85), Kabat (Kabat et al. (1991), *Sequences of proteins of immunological interest*, Fifth Edition. NIH Publication No. 91-3242), Chothia (Chothia et al., (1992), "Structural repertoire of the human VH segments," *J. Mol. Biol.* 227: 799-817); (Tomlinson et al., (1995), "The structural repertoire of the human V kappa domain," *EMBO J* 14: 4628-4638). Any of the four numbering systems can be interchangeably used to identify the preferred amino acid substitutions described in this specification.

If the antigen binding protein comprises the VH1|1-18 germline subfamily, the method comprises modifying the VH1 sequence to comprise one or more substitutions selected from $82X^1$, $94X^2$, and $95X^3$, wherein is a basic residues (R, K or H), $X^2$ is a polar, uncharged residue (S, T, N or Q) and $X^3$ is a basic residue (R, K, or H). All residues are identified by the Aho numbering system. Preferred mutations for the VH1|1-18 germline subfamily are 82R, 94S, and 95R. The method as applied to the VH1|1-18 germline subfamily may further comprise substitution $59X^{20}$ wherein $X^{20}$ is a basic residue (R, K or H), with the mutation 59K preferred.

If the antigen binding protein comprises the VH3|3-33 germline subfamily, the method comprises modifying the VH3 sequence to comprise one or more substitutions selected from $1X^4$, $17X^5$, and $85X^6$, wherein $X^4$ is a charged negative residue (D or E), $X^5$ is a small hydrophobic residue (G, A, V, I, L, or M), and $X^6$ is a small hydrophobic residue (G.A, V, I, L, or M). All residues are identified by the Aho numbering system. Preferred mutations for the VH3|3-33 germline subfamily are 1E, 17G, and 85A.

If the antigen binding protein comprises the VK3|L16 germline subfamily, the method comprises modifying the VK3 sequence to comprise one or more substitutions selected from $4X^{10}$, $13X^{11}$, $76X^{12}$, 78F, $95X^{13}$, $97X^{14}$, and 98P, wherein $X^{10}$ is selected from G, A, V, I, L, and M, $X^{11}$ is selected from G, A, V, I, L, and M, $X^{12}$ is selected from D and E, $X^{13}$ is selected from R, K and H, and $X^{14}$ is selected from D and E. All residues are identified by the Aho numbering system. Preferred mutations for the VK3|L16 germline subfamily are 4L, 13L, 76D, 95R, 97E, and 98P.

If the antigen binding protein comprises the VK3|L6 germline subfamily, the method comprises modifying the VK3 sequence to comprise one or more substitutions selected from $76X^{12}$ and $95X^{13}$. Preferred mutations for the VK3|L6 germline subfamily are 76D and 95R.

The methods of this invention further comprise modifying the Fc domain to comprise one or more substitutions selected from $253X^{15}$, $440X^{16}$, and $439X^{17}$, wherein $X^{15}$ is a small hydrophobic residue (G, A, V, I, L, or M), $X^{16}$ is a basic residue (R, K, or H), and $X^{17}$ is a charged negative residue (D or E), wherein the Fc domain sequence comprises only one of $440X^{16}$ and $439X^{17}$. All residues are identified by the EU numbering system. Preferred mutations of the Fc domain are 253A, 440K, and 439E.

The methods of this invention further comprise modifying the C-terminus of the Fc domain sequence to comprise $X^{18}X^{19}$ wherein $X^{18}$ is one to four amino acids selected from D and E or from H, K, and R, and $X^{19}$ is selected from P, M, G, A, V, I, L, S, T, N, Q, F, Y and W and is absent when $X^{18}$ comprises D or E, is present when $X^{18}$ comprises K or R at its C-terminal end, and is present or absent when $X^{18}$ comprises H at its C-terminal end. Preferred Fc C-terminal modifications comprise KP, KKP, KKKP, E or EE at the C-terminus.

The foregoing methods are preferably applied to the high viscosity antibodies shown in FIGS. 1A and 1B hereinafter. The part of the method involving the VH1|1-18 sequence is preferably applied to antibodies AF, AK, AL, AN, and AO from FIG. 1B. The part of the method involving the VH3|3-33 sequence is preferably applied to antibodies AQ, AM, AI, and AG from FIG. 1B. The part of the method involving the VK3|L16 sequence is preferably applied to antibodies AF and AQ from FIG. 1B. The part of the method involving the VK3|L6 sequence is preferably applied to antibody AJ.

The methods of this invention further comprise a method of preparing an antigen binding protein that reaches maximum serum concentration faster than does a parental antibody when the antigen binding protein and the parental antibody are administered at the same concentration, which comprises introducing sequence modification $440X^{16}$ in the parental antibody wherein $X^{16}$ is selected from R, K, and H. In a preferred method, the sequence-modified antigen binding protein reaches maximum serum concentration after subcutaneous injection at least twice as fast as the parental antibody. Also within this invention is a method of preparing an antigen binding protein that reaches a maximum serum concentration after subcutaneous injection that is higher than that of a parental antibody when the antigen binding protein and the parental antibody are administered at the same concentration, which comprises introducing sequence modification $440X^{16}$ in the parental antibody wherein $X^{16}$ is selected from R, K, and H. In a preferred method, the sequence-modified antigen binding protein reaches a maximum serum concentration that is at least about 25% higher than that of the parental antibody. In each of these methods, the preferred $X^{16}$ is K and the preferred parental antibody is a PCSK9 polypeptide (antibody AK most preferred).

The invention further relates to a mutant antigen binding protein, which comprises one or more sequences selected from:

a. a VH1|1-18 germline subfamily sequence comprising one or more substitutions selected from $82X^1$, $94X^2$, and $95X^3$, wherein $X^1$ is selected from R, K and H, $X^2$ is selected from S, T, N and Q and $X^3$ is selected from R, K, and H;

b. a VH3|3-33 germline subfamily sequence comprising one or more substitutions selected from $1X^4$, $17X^5$, and $85X^6$, wherein $X^4$ is selected from D and E, $X^5$ is selected from G, A, V, I, L, and M, and $X^6$ is selected from G.A, V, I, L, and M;

c. a VK3|L16 germline subfamily, comprising one or more substitutions selected from $4X^{10}$, $13X^{11}$, $76X^{12}$, 78F, $95X^{13}$, $97X^{14}$, and 98P, wherein $X^{10}$ is selected from G, A, V, I, L, and M, $X^{11}$ is selected from G, A, V, I, L, and M, $X^{12}$ is selected from D and E, $X^{13}$ is selected from R, K and H, and $X^{14}$ is selected from D and E, wherein the mutant antigen binding protein does not comprise only substitution 78F;

d. a VK3|IL6 germline subfamily, comprising one or more substitutions selected from $76X^{12}$ and $95X^{13}$;

e. an Fc domain sequence comprising one or more substitutions selected from $253X^{10}$, $440X^{11}$, and $439X^{12}$, wherein $X^{10}$ is selected from G, A, V, I, L, and M, $X^{11}$ is selected from R, K, and H, and $X^{12}$ is selected from D and E, wherein the antigen binding protein comprises at least one of $253X^{15}$ or modifications selected from subparagraphs a, b, c, d and f when $X^{16}$ is K and $X^{17}$ is E and the antigen binding protein specifically binds CD20; and f. an Fc domain sequence comprising at the C-terminus $X^{18}X^{19}$ wherein $X^{18}$ is one to four amino acids selected from D and E or from H, K, and R, and $X^{19}$ is selected from P, M, G, A, V, I, L, S, T, N, Q, F, Y and W and is absent when $X^{18}$ comprises D or E, is present when $X^{18}$ comprises K or R at its C-terminal end, and is present or absent when $X^{18}$ comprises H at its C-terminal end, and wherein the antigen binding protein comprises at least one of $253X^{15}$ or substitutions selected from subparagraphs a through e when PGKP, PGKKP, PGKKKP, or PGE appears at the C-terminus and the antigen binding protein specifically binds CD20 or CD38. Preferred Fc C-terminal modifications comprise KP, KKP, KKKP, E or EE at the C-terminus;

wherein the variable region amino acids are numbered according to the Aho numbering system and all amino acids from conserved regions including Fc are according to EU numbering.

Preferred antigen binding proteins in accordance with this invention are those wherein the foregoing modifications are applied to antibodies of FIGS. 1A and 1B hereinafter. Also preferred are antigen binding proteins wherein:

the VH1|1-18 germline subfamily sequence comprises one or more substitutions selected from 82R, 94S, and 95R, with antigen binding proteins having all such substitutions most preferred;

the VH3|3-33 germline subfamily sequence comprises one or more of substitutions 1E, 17G, and 85A, with antigen binding proteins having all such substitutions most preferred;

the VK3|L16 germline subfamily sequence comprises one or more substitutions selected from 4L, 13L, 76D, 95R, 97E, and 98P, with antigen binding proteins having all such substitutions most preferred;

the VK3|L6 germline subfamily sequence comprises one or more substitutions selected from 76D and 95R, with antigen binding proteins having both such substitutions most preferred;

the Fc domain sequence comprises one or more substitutions selected from 253A, 440K, and 439E, with antigen binding proteins having all such substitutions most preferred; and the Fc domain C-terminus comprises a sequence selected from KP, KKP, KKKP, and E.

All of the foregoing preferred amino acid substitutions in variable regions are identified by the Aho numbering system. All residues in conserved regions including Fc are identified by the EU numbering system.

Preferred antigen binding proteins in accordance with this invention include: antibodies AF, AK, AL, AN and AO from FIG. 1B having one or more, most preferably all, of the foregoing VH1|1-18 germline subfamily substitutions; antibodies AQ, AM, AI, and AG from FIG. 1B having one or more, most preferably all, of the VH3|3-33 germline subfamily substitutions; antibodies AF and AQ having one or more, most preferably all, of the VK3|L16 germline subfamily substitutions; antibody AJ from FIG. 1B having one or more, most preferably all, of the VK3|L6 germline subfamily substitutions; and antibodies BA, AH, and AN from FIG. 1B having one or more, preferably all, of the Fc substitutions noted above.

Due to the foregoing sequence modifications, the invention further relates to antigen binding proteins that specifically bind to PCSK9 comprising a heavy chain sequence selected from SEQ ID NOS: 352, 353, 354, 366, and 368, preferably also comprising a light chain sequence of SEQ ID NO: 351.

Due to the foregoing sequence modifications, the invention also relates to antigen binding proteins that specifically bind c-fms comprising a heavy chain sequence selected from SEQ ID NOS: 356, 357, and 358, preferably further comprising a light chain sequence of SEQ ID NO: 355.

Due to the foregoing sequence modifications, the invention also relates to antigen binding proteins that specifically bind GIPR comprising a heavy chain sequence selected from SEQ ID NOS: 359, 361, 362, 364, and 368, preferably further comprising a light chain sequence selected from SEQ ID NOS: 360, 363, 365, and 367.

All modified antigen binding proteins are useful for the same indications as described previously for the unmodified antibodies.

Each of the antigen binding proteins from FIGS. 1A and 1B having mutated heavy chains is preferred to further comprise a light chain sequence as noted in the unmodified parent antibody of FIGS. 1A and 1B. Each of the foregoing antigen binding proteins having a mutated light chain is preferred to further comprise a heavy chain sequence as noted above or as appearing in the unmodified parent antibody of FIGS. 1A and 1B.

The invention further comprises antigen binding proteins as described above that have improved pharmacokinetic properties. The invention comprises an antigen binding protein optionally having any of the aforementioned sequence modifications wherein:

a. the antigen binding protein comprises the sequence modification $440X^{16}$ relative to a parental antibody lacking the $440X^{16}$ sequence modification,
b. the antigen binding protein reaches maximum serum concentration after subcutaneous injection faster than does the parental antibody when the antigen binding protein and the parental antibody are administered at the same concentration, and
c. the antigen binding protein reaches a maximum serum concentration after subcutaneous injection that is higher than that of the parental antibody when the antigen binding protein and the parental antibody are administered at the same concentration.

The preferred parental antibody for such an antigen binding protein is a PCSK9 binding polypeptide, with antibody AK most preferred. The preferred substituent $X^{16}$ in such an antigen binding protein is K. Further within this invention is a method of treating hypercholesterolemia with such an antigen binding protein.

The invention also relates to isolated nucleic acids encoding the antigen binding proteins of the invention, as well as vectors comprising the nucleic acids, host cells comprising the vectors, and methods of making and using the antigen binding proteins.

In other embodiments, the present invention provides compositions comprising the antigen binding proteins and kits comprising the antigen binding proteins, as well as articles of manufacture comprising the antigen binding proteins.

BRIEF DESCRIPTION OF THE FIGURES

FIGS. 1A and 1B show a table of viscosity values measured for IgG1 and IgG2 monoclonal antibodies formulated at 150 mg/mL in a formulation buffer including 20 mM acetate and 9% sucrose at pH 5.2 (without polysorbate). FIGS. 1A and 1B show the targets of the antibodies studied as well as their light and heavy chain types, germline subfamilies, concentration, pI, and viscosity. Each antibody in FIGS. 1A and 1B has the amino acid sequences as noted in the figures and the Sequence Listing. The heavy and light chain amino acid sequences are encoded by nucleic acids having the SEQ ID NOS immediately preceding them in the Sequence Listing.

FIGS. 1C and 1D show the sequence identification numbers (SEQ ID NOS) for the framework regions and Fc regions of the antibodies of FIGS. 1A and 1B. FIG. 1D also shows antibody BA, which is discussed in FIG. 17.

FIG. 2 shows high viscosity and low viscosity subtype pairs identified in this specification.

FIG. 9 is a table showing global sequence parameters of mAbs high viscosity VH1|1-18 and low viscosity VH1|1-02 subtypes (germlines). The mAbs in FIG. 9 are sorted by viscosity. The table includes their mAb symbols, measured viscosity values, calculated pI values, and VL and VH germlines. For VH germlines, higher viscosity VH1|1-18 are shown in bold and underlined. Heavy chain framework 3 sequences are shown. Residues correlating with high viscosity are in bold and underlined. VBase sequences are added for VH1|1-18 and VH1|1-02 germline subfamilies for comparison to illustrate that the different residues are typical residues for the subfamilies.

FIG. 10 is a table showing produced and characterized mutants of the AK and AO antibodies.

FIG. 11 is a table showing global sequence parameters of thirteen mAbs with VH3 heavy chains. FIG. 11 includes the mAb symbols, measured viscosity values, calculated pI values, HC and LC types, and VL and VH subtypes (germlines). Higher viscosity VH3|3-33 subfamily is shown in bold and underlined. Residues correlating with high viscosity are bold and underlined. VBase sequences are added for VH3|3-33 and VH3|3-07 germline subfamilies for comparison to illustrate that the different residues are typical for those subfamilies.

FIG. 12 is a table showing global sequence parameters of fourteen mAbs with VK3 light chains. The mAbs in FIG. 12 are sorted by viscosity, including their mAb symbols, measured viscosity values, calculated pI values, HC and LC types, and VL and VH subtypes (germlines). Higher viscosity VK3|L16 and VK3|L6 subfamilies are in bold and underlined. Light chain residues that are consistently different between VK3|L16 and VK3|L6 subfamilies as compared to the VK3|A27 subfamily are shown on the right side. Residues correlating with high viscosity in the VK3|L16 and VK3|L6 subfamilies are bold and underlined. VBase sequences are added for VK3|L16 and VK3|A27 germline subfamilies for comparison to illustrate that the different residues are typical residues for the subfamilies.

FIG. 15 is a table showing the absolute and relative viscosity values of parent antibody AK and various mutants. The parent antibody AK and the mutants are used in a nonhuman primate study of the pharmacokinetics and pharmacodynamics of antibody AK and low viscosity mutants.

FIG. 17 is a table showing the viscosity of proteins selected for Fc mutations to lower viscosity variants.

FIG. 21 shows a summary of the experimental design for a single-dose subcutaneous bolus pharmacokinetic study in male cynomolgus monkeys as described in further detail in a working example hereinafter.

FIG. 22 shows mean pharmacokinetic parameter estimates of antibody AK or low viscosity mutant homologues after subcutaneous administration of 10 mg/kg to male cynomolgus monkeys (N=4 males). Introduction of a mutation in the Fc region that reduces viscosity reduces Tmax and increases Cmax.

FIG. 23 shows the percentage of LDL-C compared to pretest (Day CLAB). * Percent change is expressed as the individual animal post-dose value divided by the Day 1 pretest value. All four antibodies (parent antibody AK, AK Fc mutant, AK Fab mutant and AK double Fc/Fab mutant) all induce reductions in LDL-C.

DETAILED DESCRIPTION OF THE INVENTION

Definition of Terms

Figures 3A, 3B, 3C:
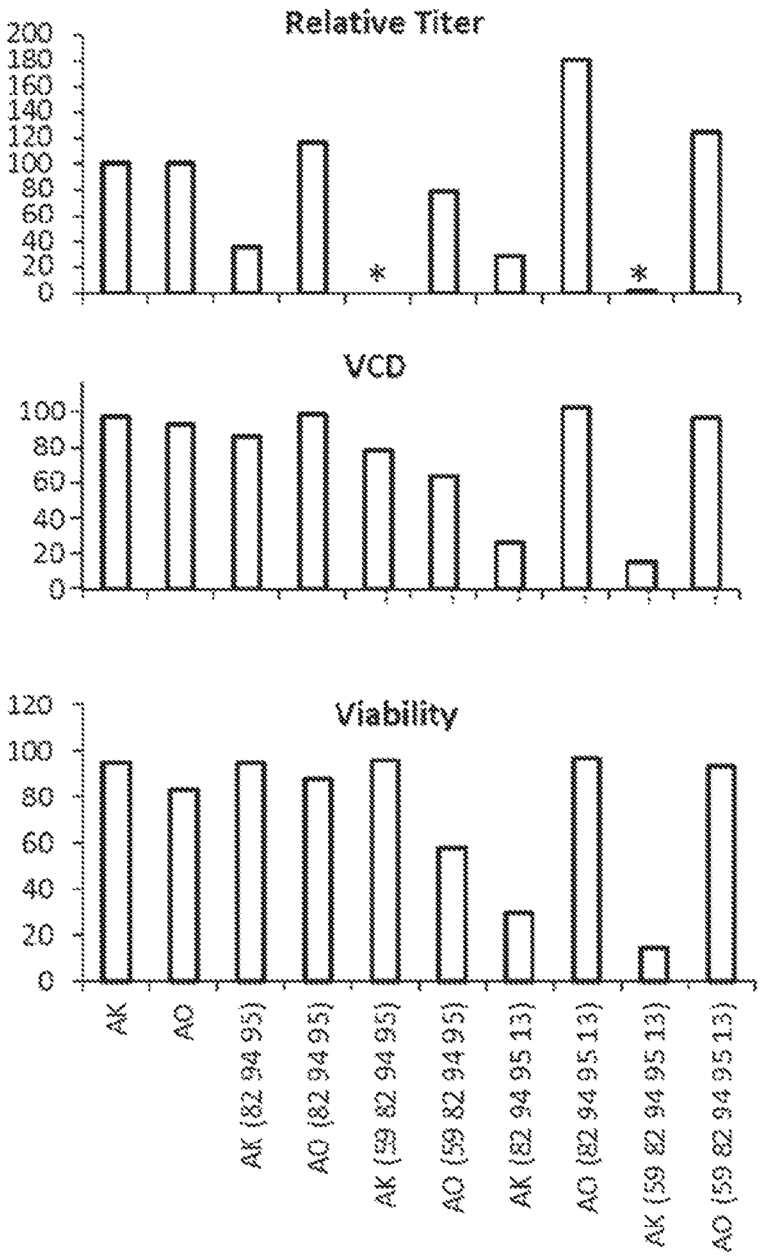
FIG. 3 shows expression results for AK and AO antibody molecules and their mutants, including relative values for titer, final viable cell density (VCD) and viability at harvest after 7 days of cell culture. AK values are at 100%.

In the description that follows, a number of terms are used extensively. The following definitions are provided to facilitate understanding of the invention.

Unless otherwise specified, "a", "an", "the", and "at least one" are used interchangeably and mean one or more than one.

"Antigen binding protein" refers to a protein or polypeptide that comprises an antigen-binding region or antigen-binding portion that has a strong affinity for another molecule to which it binds (antigen). Antigen-binding proteins encompass antibodies, peptibodies, antibody fragments (e.g., Fab, Fab', $F(ab')_2$, Fv, single domain antibody), antibody derivatives, antibody analogs, fusion proteins, and antigen receptors including chimeric antigen receptors (CARs).

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules that lack antigen specificity. Polypeptides of the latter kind are, for example, produced at low levels by the lymph system and at increased levels by myelomas. Thus, as used herein, the term "antibody" or "antibody peptide(s)" refers to an intact antibody, an antibody that competes for specific binding with an antibody disclosed in this specification, or an antigen-binding fragment (e.g., Fab, Fab', $F(ab')_2$, Fv, single domain antibody) thereof that competes with the intact antibody for specific binding and includes chimeric, humanized, fully human, and bispecific antibodies. In certain embodiments, antigen-binding fragments are produced, for example, by recombinant DNA techniques. In additional embodiments, antigen-binding fragments are produced by enzymatic or chemical cleavage of intact antibodies. Antigen-binding fragments include, but are not limited to, Fab, Fab', $F(ab)^2$, $F(ab')^2$, Fv, and single-chain antibodies. Examples of antibodies suitable for use in the invention include, without limitation, the antibodies listed in FIGS. 1A and 1B as well as Abagovomab, Abciximab, Actoxumab, Adalimumab, Afelimomab, Afutuzumab, Alacizumab, Alacizumab pegol, ALD518, Alemtuzumab, Alirocumab, Alemtuzumab, Altumomab, Amatuximab, Anatumomab mafenatox, Anrukinzumab, Apolizumab, Arcitumomab, Aselizumab, Altinumab, Atlizumab, Atorolimiumab, tocilizumab, Bapineuzumab, Basiliximab, Bavituximab, Bectumomab, Belimumab, Benralizumab, Bertilimumab, Besilesomab, Bevacizumab, Bezlotoxumab, Biciromab, Bivatuzumab, Bivatuzumab mertansine, Blinatumomab, Blosozumab, Brentuximab vedotin, Briakinumab, Brodalumab, Canakinumab, Cantuzumab mertansine, Cantuzumab mertansine, Caplacizumab, Capromab pendetide, Carlumab, Catumaxomab, CC49, Cedelizumab, Certolizumab pegol, Cetuximab, Citatuzumab bogatox, Cixutumumab, Clazakizumab, Clenoliximab, Clivatuzumab tetraxetan, Conatumumab, Crenezumab, CR6261, Dacetuzumab, Daclizumab, Dalotuzumab, Daratumumab, Demcizumab, Denosumab, Detumomab, Dorlimomab aritox, Drozitumab, Duligotumab, Dupilumab, Ecromeximab, Eculizumab, Edobacomab, Edrecolomab, Efalizumab, Efungumab, Elotuzumab, Elsilimomab, Enavatuzumab, Enlimomab pegol, Enokizumab, Enokizumab, Enoticumab, Enoticumab, Ensituximab, Epitumomab cituxetan, Epratuzumab, Erenumab, Erlizumab, Ertumaxomab, Etaracizumab, Etrolizumab, Evolocumab, Exbivirumab, Exbivirumab, Fanolesomab, Faralimomab, Farletuzumab, Fasinumab, FBTA05, Felvizumab, Fezakinumab, Ficlatuzumab, Figitumumab, Flanvotumab, Fontolizumab, Foralumab, Foravirumab, Fresolimumab, Fulranumab, Futuximab, Galiximab, Ganitumab, Gantenerumab, Gavilimomab, Gemtuzumab ozogamicin, Gevokizumab, Girentuximab, Glembatumumab vedotin, Golimumab, Gomiliximab, GS6624, Ibalizumab, Ibritumomab tiuxetan, Icrucumab, Igovomab, Imciromab, Imgatuzumab, Inclacumab, Indatuximab ravtansine, Infliximab, Intetumumab, Inolimomab, Inotuzumab ozogamicin, Ipilimumab, Iratumumab, Itolizumab, Ixekizumab, Keliximab, Labetuzumab, Lebrikizumab, Lemalesomab, Lerdelimumab, Lexatumumab, Libivirumab, Ligelizumab, Lintuzumab, Lirilumab, Lorvotuzumab mertansine, Lucatumumab, Lumiliximab, Mapatumumab, Maslimomab, Mavrilimumab, Matuzumab, Mepolizumab, Metelimumab, Milatuzumab, Minretumomab, Mitumomab, Mogamulizumab, Morolimumab, Motavizumab, Moxetumomab pasudotox, Muromonab-CD3, Nacolomab tafenatox, Namilumab, Naptumomab estafenatox, Narnatumab, Natalizumab, Nebacumab, Necitumumab, Nerelimomab, Nesvacumab, Nimotuzumab, Nivolumab, Nofetumomab merpentan, Ocaratuzumab, Ocrelizumab, Odulimomab, Ofatumumab, Olaratumab, Olokizumab, Omalizumab, Onartuzumab, Oportuzumab monatox, Oregovomab, Orticumab, Otelixizumab, Oxelumab, Ozanezumab, Ozoralizumab, Pagibaximab, Palivizumab, Panitumumab, Panobacumab, Parsatuzumab, Pascolizumab, Pateclizumab, Patritumab, Pemtumomab, Perakizumab, Pertuzumab, Pexelizumab, Pidilizumab, Pintumomab, Placulumab, Ponezumab, Prezalumab, Priliximab, Pritumumab, PRO 140, Quilizumab, Racotumomab, Radretumab, Rafivirumab, Ramucirumab, Ranibizumab, Raxibacumab, Regavirumab, Reslizumab, Rilotumumab, Rituximab, Robatumumab, Roledumab, Romosozumab, Rontalizumab, Rovelizumab, Ruplizumab, Samalizumab, Sarilumab, Satumomab pendetide, Secukinumab, Sevirumab, Sibrotuzumab, Sifalimumab, Siltuximab, Simtuzumab, Siplizumab, Sirukumab, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tanezumab, Taplitumomab paptox, Tefibazumab, Telimomab aritox, Tenatumomab, Tefibazumab, Telimomab aritox, Tenatumomab, Teneliximab, Teplizumab, Teprotumumab, Tezepelumab, TGN1412, Tremelimumab, Ticilimumab, Tildrakizumab, Tigatuzumab, TNX-650, Tocilizumab, Toralizumab, Tositumomab, Tralokinumab, Trastuzumab, TRBS07, Tregalizumab, Tremelimumab, Tucotuzumab celmoleukin, Tuvirumab, Ublituximab, Urelumab, Urtoxazumab, Ustekinumab, Vapaliximab, Vatelizumab, Vedolizumab, Veltuzumab, Vepalimomab, Vesencumab, Visilizumab, Volociximab, Vorsetuzumab mafodotin, Votumumab, Zalutumumab, Zanolimumab, Zatuximab, Ziralimumab and Zolimomab aritox.

The term "isolated antibody" as used herein refers to an antibody that has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The term "bind(ing)" of an antigen or other polypeptide includes, but is not limited to, the binding of a ligand polypeptide of the present invention to a receptor; the binding of a receptor polypeptide of the present invention to a ligand; the binding of an antibody of the present invention to an antigen or epitope; the binding of an antigen or epitope of the present invention to an antibody; the binding of an antibody of the present invention to an anti-idiotypic antibody; the binding of an anti-idiotypic antibody of the present invention to a ligand; the binding of an anti-idiotypic antibody of the present invention to a receptor; the binding of an anti-anti-idiotypic antibody of the present invention to a ligand, receptor or antibody, etc.

The term "immunoglobulin" refers to a protein consisting of one or more polypeptides substantially encoded by immunoglobulin genes. One form of immunoglobulin constitutes the basic structural unit of an antibody. This form is a tetramer and consists of two identical pairs of immunoglobulin chains, each pair having one light and one heavy chain. In each pair, the light and heavy chain variable regions are together responsible for binding to an antigen, and the constant regions are responsible for the antibody effector functions.

Full-length immunoglobulin "light chains" (about 25 Kd or about 214 amino acids) are encoded by a variable region gene at the $NH_2$-terminus (about 110 amino acids) and a kappa or lambda constant region gene at the COOH-terminus. Full-length immunoglobulin "heavy chains" (about 50 Kd or about 446 amino acids), are similarly encoded by a variable region gene (about 116 amino acids) and one of the other aforementioned constant region genes (about 330 amino acids). Heavy chains are classified as gamma, mu, alpha, delta, or epsilon, and define the antibody's isotype as IgG (such as IgG1, IgG2, IgG3 and IgG4), IgM, IgA, IgD and IgE, respectively. Within light and heavy chains, the variable and constant regions are joined by a "J" region of about 12 or more amino acids, with the heavy chain also including a "D" region of about 10 more amino acids. (See generally, *Fundamental Immunology* (Paul, W., ed., 2nd Edition, Raven Press, NY (1989)), Chapter 7 (incorporated by reference in its entirety for all purposes).

An immunoglobulin light or heavy chain variable domain or region comprises "framework regions" (FRs) interrupted by "complementarity determining regions" (CDRs). Kabat et al. (1991), *Sequences of Proteins of Immunological Interest,* 5th Edition, Public Health Service, National Institutes of Health, Bethesda, Md. (1991); Chothia et al. (1987), *J. Mol. Biol.* 196: 901-917 (both of which are incorporated herein by reference). FR residues are those variable domain residues other than CDR region residues as herein defined. The sequences of the framework regions of different light or heavy chains are relatively conserved within a species. Thus, a "human framework region" is a framework region that is substantially identical (about 85% or more, usually 90-95% or more) to the framework region of a naturally occurring human immunoglobulin. The framework region of an antibody, that is the combined framework regions of the constituent light and heavy chains, serves to position and align the CDR's. The CDR's are primarily responsible for binding to an epitope of an antigen. Accordingly, the term "humanized" immunoglobulin refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor". Constant regions need not be present, but if they are, they must be substantially identical to human immunoglobulin constant regions—i.e., at least about 85-90%, preferably about 95% or more identical. Hence, all parts of a humanized immunoglobulin, except possibly the CDR's, are substantially identical to corresponding parts of natural human immunoglobulin sequences. Further, one or more residues in the human framework region may be back mutated to the parental sequence to retain optimal antigen-binding affinity and specificity. In this way, certain framework residues from the non-human parent antibody are retained in the humanized antibody in order to retain the binding properties of the parent antibody while minimizing its immunogenicity. The term "human framework region" as used herein includes regions with such back mutations. A "humanized antibody" is an antibody comprising a humanized light chain and a humanized heavy chain immunoglobulin. For example, a humanized antibody would not encompass a typical chimeric antibody as defined below, e.g., because the entire variable region of a chimeric antibody is non-human.

The monoclonal antibodies and antibody constructs of the present invention specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is/are identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al. (1984), *Proc. Natl. Acad. Sci. USA,* 81: 6851-6855). Chimeric antibodies of interest herein include "primitized" antibodies comprising variable domain antigen-binding sequences derived from a non-human primate (e.g., Old World Monkey, Ape, etc.) and human constant region sequences. A variety of approaches for making chimeric antibodies have been described. See e.g., Morrison et al. (1985), *Proc. Natl. Acad. Sci. U.S.A.* 81:6851; Takeda et al. (1985), *Nature* 314:452, Cabilly et al., U.S. Pat. No. 4,816,567; Boss et al., U.S. Pat. No. 4,816,397; Tanaguchi et al., EP 0171496; EP 0173494; and GB 2177096.

The terms "human antibody" and "fully human antibody" each refer to an antibody that has an amino acid sequence of a human immunoglobulin, including antibodies isolated from human immunoglobulin libraries or from animals transgenic for one or more human immunoglobulins and that do not express endogenous immunoglobulins; for example, Xenomouse® antibodies and antibodies as described by Kucherlapati et al. in U.S. Pat. No. 5,939,598.

The term "genetically altered antibodies" means antibodies wherein the amino acid sequence has been varied from that of a native antibody. Because of the relevance of recombinant DNA techniques in the generation of antibodies, one need not be confined to the sequences of amino acids found in natural antibodies; antibodies can be redesigned to obtain desired characteristics. The possible variations are many and range from changes to just one or a few amino acids to complete redesign of, for example, the variable and/or constant region. Changes in the constant region will, in general, be made in order to improve or alter characteristics, such as complement fixation, interaction with membranes and other effector functions, as well as manufacturability and viscosity. Changes in the variable region will be made in order to improve the antigen binding characteristics.

A "Fab fragment" is comprised of one light chain and the $C_{H1}$ and variable regions of one heavy chain. The heavy chain of a Fab molecule cannot form a disulfide bond with another heavy chain molecule.

A "Fab' fragment" contains one light chain and one heavy chain that contains more of the constant region, between the $C_{H1}$ and $C_{H2}$ domains, such that an interchain disulfide bond can be formed between two heavy chains to form a $F(ab')_2$ molecule.

A "$F(ab')_2$ fragment" contains two light chains and two heavy chains containing a portion of the constant region between the $C_{H1}$ and $C_{H2}$ domains, such that an interchain disulfide bond is formed between two heavy chains.

The terms "Fv fragment" and "single chain antibody" refer to polypeptides containing antibody variable regions from both heavy and light chains but lacking constant regions. Like a whole antibody, it is able to bind selectively to a specific antigen. With a molecular weight of only about 25 kDa, Fv fragments are much smaller than common antibodies (150-160 kD) which are composed of two heavy protein chains and two light chains, and even smaller than Fab fragments (about 50 kDa, one light chain and half a heavy chain).

A "single domain antibody" is an antibody fragment consisting of a single domain Fv unit, e.g., $V_H$ or $V_L$. Like a whole antibody, it is able to bind selectively to a specific antigen. With a molecular weight of only 12-15 kDa, single-domain antibodies are much smaller than common antibodies (150-160 kDa) which are composed of two heavy protein chains and two light chains, and even smaller than Fab fragments (.about.50 kDa, one light chain and half a heavy chain) and single-chain variable fragments (.about.25 kDa, two variable domains, one from a light and one from a heavy chain). The first single-domain antibodies were engineered from heavy-chain antibodies found in camelids. Although most research into single-domain antibodies is currently based on heavy chain variable domains, light chain variable domains and nanobodies derived from light chains have also been shown to bind specifically to target epitopes.

The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

In some embodiments, an antigen binding protein of the present invention selectively inhibits the human antigen of the antibody from which it is derived. For example, the antigen binding protein having the sequence of antibody AF as substituted as described herein will selectively inhibit the antigen in FIG. 1B of antibody AF. An antibody or functional fragment thereof "selectively inhibits" a specific receptor or ligand relative to other receptors or ligands when the IC50 of the antibody in an inhibition assay of the specific receptor is at least 50-fold lower than the IC50 in an inhibition assay of another "reference" ligand or receptor. An "IC50" is the dose/concentration required to achieve 50% inhibition of a biological or biochemical function. With radioactive ligands, IC50 is the concentration of a competing ligand that displaces 50% of the specific binding of the radioactive ligand. The IC50 of any particular substance or antagonist can be determined by constructing a dose-response curve and examining the effect of different concentrations of the drug or antagonist on reversing agonist activity in a particular functional assay. IC50 values can be calculated for a given antagonist or drug by determining the concentration needed to inhibit half of the maximum biological response of the agonist. Thus, the IC50 value for any anti-PCSK9 antibody or functional fragment thereof, for example, can be calculated by determining the concentration of the antibody or fragment needed to inhibit half of the maximum biological response of PCSK9 in activating the human PCSK9 receptor in any functional assay. An antibody or functional fragment thereof that selectively inhibits a specific ligand or receptor is understood to be a neutralizing antibody or neutralizing fragment with respect to that ligand or receptor. Thus, in some embodiments, the anti-PCSK9 antibody or functional fragment is a neutralizing antibody or fragment of human PCSK9.

The substituted antigen binding proteins of the present invention can cross-block the unsubstituted antibodies from which they are derived. The terms "cross-block," "cross-blocked," and "cross-blocking" are used interchangeably herein to mean the ability of an antigen binding protein to interfere with the binding of other antigen binding proteins (e.g., antibodies or binding fragments) to a target (e.g., human PCSK9). The extent to which an antibody or binding fragment is able to interfere with the binding of another to a target and therefore whether it can be said to cross-block, can be determined using competition binding assays. In some embodiments, a cross-blocking antigen binding protein of this invention reduces binding of a reference antibody to the target antigen between about 40% and 100%, such as about 60% and about 100%, specifically preferably between about 70% and 100%, and more specifically preferably between about 80% and 100%. A particularly suitable quantitative assay for detecting cross-blocking uses a Biacore machine which measures the extent of interactions using surface plasmon resonance technology. Another suitable quantitative cross-blocking assay uses a FACS-based approach to measure competition between antibodies in terms of their binding to the target antigen.

The term "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., .alpha.-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids", which comprise naturally-occurring or modified nucleic acid bases attached to a polyamide backbone. Nucleic acids can be either single stranded or double stranded.

The term "complement of a nucleic acid molecule" refers to a nucleic acid molecule having a complementary nucleotide sequence and reverse orientation as compared to a reference nucleotide sequence.

The term "degenerate nucleotide sequence" denotes a sequence of nucleotides that includes one or more degenerate codons as compared to a reference nucleic acid molecule that encodes a polypeptide. Degenerate codons contain different triplets of nucleotides, but encode the same amino acid residue (i.e., GAU and GAC triplets each encode Asp).

An "isolated nucleic acid molecule" is a nucleic acid molecule that is not integrated in the genomic DNA of an organism. For example, a DNA molecule that encodes a heavy chain of an antibody that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

A "nucleic acid molecule construct" is a nucleic acid molecule, either single- or double-stranded, that has been modified through human intervention to contain segments of nucleic acid combined and juxtaposed in an arrangement not existing in nature.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand. The term "cDNA" also refers to a clone of a cDNA molecule synthesized from an RNA template.

A "promoter" is a nucleotide sequence that directs the transcription of a structural gene. Typically, a promoter is located in the 5' non-coding region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee et al. (1993), *Mol. Endocrinol.,* 7:551), cyclic AMP response elements (CREs), serum response elements (SREs; Treisman (1990), *Seminars in Cancer Biol.,* 1:47), glucocorticoid response elements (GREs), and binding sites for other transcription factors, such as CRE/ATF (O'Reilly et al. (1992), *J. Biol. Chem.,* 267:19938), AP2 (Ye et al. (1994), *J. Biol. Chem.,* 269:25728), SP1, cAMP response element binding protein (CREB; Loeken (1993), *Gene Expr.,* 3:253) and octamer factors (see, in general, Watson et al. (1987), eds., *Molecular Biology of the Gene,* 4th Edition, The Benjamin/Cummings Publishing Company, Inc., and Lemaigre et al. (1994), *Biochem. J.,* 303:1). If a promoter is an inducible promoter, then the rate of transcription increases in response to an inducing agent. In contrast, the rate of transcription is not regulated by an inducing agent if the promoter is a constitutive promoter. Repressible promoters are also known.

A "regulatory element" is a nucleotide sequence that modulates the activity of a core promoter. For example, a regulatory element may contain a nucleotide sequence that binds with cellular factors enabling transcription exclusively or preferentially in particular cells, tissues, or organelles. These types of regulatory elements are normally associated with genes that are expressed in a "cell-specific", "tissue-specific", or "organelle-specific" manner.

An "enhancer" is a type of regulatory element that can increase the efficiency of transcription, regardless of the distance or orientation of the enhancer relative to the start site of transcription.

"Heterologous DNA" refers to a DNA molecule, or a population of DNA molecules, that does not exist naturally within a given host cell. DNA molecules heterologous to a particular host cell may contain DNA derived from the host cell species (i.e., endogenous DNA) so long as that host DNA is combined with non-host DNA (i.e., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

A "recombinant host" is a cell that contains a heterologous nucleic acid molecule, such as a cloning vector or expression vector. In the present context, an example of a recombinant host is a cell that produces an antagonist of the present invention from an expression vector. In contrast, such an antagonist can be produced by a cell that is a "natural source" of said antagonist, and that lacks an expression vector.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

A "fusion protein" is a hybrid protein expressed by a nucleic acid molecule comprising nucleotide sequences of at least two genes. For example, a fusion protein can comprise at least part of an antibody heavy chain fused with a polypeptide that binds an affinity matrix or another target of interest.

The term "receptor" denotes a cell-associated protein that binds to a bioactive molecule termed a "ligand." This interaction mediates the effect of the ligand on the cell. Receptors can be membrane-bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). Membrane-bound receptors are characterized by a multi-domain structure comprising an extracellular ligand-binding domain and an intracellular effector domain that is typically involved in signal transduction. In certain membrane-bound receptors, the extracellular ligand-binding domain and the intracellular effector domain are located in separate polypeptides that comprise the complete functional receptor. In general, the binding of ligand to receptor results in a conformational change in the receptor that causes an interaction between the effector domain and other molecule(s) in the cell, which in turn leads to an alteration in the metabolism of the cell. Metabolic events that are often linked to receptor-ligand interactions include gene transcription, phosphorylation, dephosphorylation, increased cyclic AMP production, mobilization of cellular calcium, mobilization of membrane lipids, cell adhesion, hydrolysis of inositol lipids and hydrolysis of phospholipids.

The term "expression" refers to the biosynthesis of a gene product. For example, in the case of a structural gene, expression involves transcription of the structural gene into mRNA and the translation of mRNA into one or more polypeptides.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of less than $10^9 M^{-1}$.

A "detectable label" is a molecule or atom which can be conjugated to an antibody moiety to produce a molecule useful for diagnosis. Examples of detectable labels include chelators, photoactive agents, radioisotopes, fluorescent agents, paramagnetic ions, or other marker moieties.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a polyhistidine tract, protein A (Nilsson et al. (1985), *EMBO J.* 4:1075; Nilsson et al. (1991), *Methods Enzymol.,* 198:3), glutathione S transferase (Smith et al. (1988), *Gene,* 67:31), Glu-Glu affinity tag (Grussenmeyer et al (1985), *Proc. Natl. Acad. Sci. USA* 82:7952), substance P, FLAG® peptide (Hopp et al. (1988), *Biotechnology* 6:1204), streptavidin binding peptide, or other antigenic epitope or binding domain. See, in general, Ford et al. (1991), *Protein Expression and Purification,* 2:95. DNA molecules encoding affinity tags are available from commercial suppliers (e.g., Pharmacia Biotech, Piscataway, N.J.).

The terms "acidic residue" and "charged negative residue" refer to amino acid residues having sidechains comprising acidic groups. Exemplary acidic or charged negative residues include D and E.

The term "amide residue" refers to amino acids having sidechains comprising amide derivatives of acidic groups. Exemplary amide residues include N and Q.

The term "aromatic residue" refers to amino acid residues having sidechains comprising aromatic groups. Exemplary aromatic residues include F, Y, and W.

The terms "basic residue" and "charged positive residue" refer to amino acid residues having sidechains comprising basic groups. Exemplary basic or charged positive residues include H, K, and R.

The terms "hydrophilic residue" and "polar uncharged residue" refer to amino acid residues having sidechains comprising polar groups. Exemplary hydrophilic or polar uncharged residues include C, S, T, N, and Q.

The terms "non-functional residue" and "small hydrophobic residue" refer to amino acid residues having sidechains that lack acidic, basic, or aromatic groups. Exemplary non-functional, small hydrophobic residues include M, G, A, V, I, L and norleucine (Nle).

One aspect of this invention concerns PCSK9 binding polypeptides. "PCSK9-binding polypeptide" means a polypeptide that binds proprotein convertase subtilisin/kexin type 9 (PCSK9) protein. In some cases, the PCSK9-binding polypeptide blocks binding of PCSK9 to low-density lipid receptors (LDLRs). Such blocking PCSK9-binding polypeptides can be monoclonal antibodies (mAbs) and can be one of the following:

- a. a mAb comprising a heavy chain polypeptide having an amino acid sequence of SEQ ID NO: 136 and a light chain polypeptide having an amino acid sequence of SEQ ID NO: 134 (antibody AK, evolocumab), or an antigen-binding fragment thereof;
- b. a mAb that competes with evolocumab for binding to PCSK9;
- c. a mAb comprising:
  - i. a heavy chain polypeptide comprising the following complementarity determining regions (CDRs): a heavy chain CDR1 that is a CDR1 in SEQ ID NOs: 376 or 378; a heavy chain CDR2 that is a CDR2 in SEQ ID Nos: 376 or 378; a heavy chain CDR3 that is a CDR3 in SEQ ID NOs: 376 or 378, and
  - ii. a light chain polypeptide comprising the following CDRs: a light chain CDR1 that is a CDR1 in SEQ ID NOs: 377 or 379; a light chain CDR2 that a CDR2 in SEQ ID NOs: 377 or 379; and a light chain CDR3 that is a CDR3 in SEQ ID NOs: 377 or 379;
- d. a mAb that binds to at least one of the following residues of PCSK9, the PCSK9 comprising an amino acid sequence of SEQ ID NO: 369: S153, D188, I189, Q190, S191, D192, R194, E197, G198, R199, V200, D224, R237, and D238, K243, S373, D374, S376, T377, F379, I154, T1897, H193, E195, I196, M201, V202, C223, T228, S235, G236, A239, G244, M247, I369, S372, C375, C378, R237, and D238;
- e. a mAb that binds to PCSK9 at an epitope on PCSK9 that overlaps with an epitope that is bound by an antibody that comprises:
  - i. a heavy chain variable region of the amino acid sequence in SEQ ID NO: 136; and
  - ii. a light chain variable region of the amino acid sequence in SEQ ID NO: 134, and
  - iii. wherein the epitope of the mAb further overlaps with a site to which binds an epidermal growth factor-like repeat A (EGF-A) domain of the low density lipoprotein receptor (LDLR) protein (Horton, Cohen, & Hobbs (2007), *Trends Biochem Sci,* 32(2), 71-77. doi: 10.1016/j.tibs.2006.12.008; Seidah & Prat (2007), *J Mol Med* (*Berl*), 85(7), 685-696;
- f. a mAb that comprises a heavy chain polypeptide comprising the following complementarity determining regions (CDRs):
  - i. heavy chain CDR1, CDR2, and CDR3 having an amino acid sequence of SEQ ID NOs: 373, 374, and 375, respectively; and
  - ii. light chain CDR1, CDR2, and CDR3 having an amino acid sequence of SEQ ID NOs: 369, 370, and 371, respectively; or
- g. a mAb that comprises the heavy chain variant region sequence of SEQ ID NO:

378 and the light chain variant region sequence of SEQ ID NO: 379.

PREFERRED EMBODIMENTS

Correlation of Global Sequence Features to Viscosity

The main goal of the study reported in Example 1 of this specification was to identify a link between viscosity and amino acid sequence, or global sequence features of IgG monoclonal antibodies with the purpose of reducing viscosity of high-concentration monoclonal antibody formulations. For that, viscosity values of 43 different monoclonal antibodies were measured at 150 mg/ml to provide a wide range of values from 5 to 33 cP (FIGS. 1A and 1B). Main global sequence features of the monoclonal antibodies, such as light and heavy chain types, their subtypes (germlines), and pI were calculated and correlated to viscosity, but did not immediately reveal significant correlations (FIGS. 1A and 1B). Polymorphisms (known as allotypes) within the IgG isotypes were described using serological reagents derived from humans (Ropartz, C., Schanfield, M. S., and Steinberg, A. G. (1976), "Review of the notation for the allotypic and related markers of human immunoglobulins," WHO meeting on human immunoglobulin allotypic markers, held 16-19 Jul. 1974, Rouen, France; report amended June 1976*, J Immunogenet.* 3, 357-362) and correlated to certain amino acid residues in several specific positions in conserved regions of heavy and light chains (Jefferis and Lefranc (2009) Human immunoglobulin allotypes: possible implications for immunogenicity, mAbs 1, 332-338.) (Vidarsson, G., Dekkers, G., and Rispens, T. (2014) IgG subclasses and allotypes: from structure to effector functions, Front Immunol. 5, 1-17). The allotypes introduce a few different residues (described below) in otherwise conserved regions of light and heavy chains. All kappa light chains used in this study were the same (3) allotype (featuring residues A153, V191 in EU numbering). All IgG2 heavy light chains were the same (n−) allotype (featuring P189). Four IgG1 heavy chain allotypes were described (including the following related residues in EU numbering): f (R214); z (K214); a (D356, L358) and x (G431) (Jefferis & Lefranc, 2009) (Vidarsson et al., 2014). IgG1 heavy chains with alternative residues in the positions E356, M358 and A431 do not constitute allotypes because these amino acid residues are present in other IgG subclasses. IgG1 allotype (x) was not present in the study; all IgG1 heavy chains had A431. IgG1 heavy chain allotypes (f), (z), (a) and related residues are shown in FIGS. 1A and 1B.

The antibodies in FIGS. 1A and 1B are sorted by viscosity. The table in FIGS. 1A and 1B includes the monoclonal antibody name, measured concentrations, measured viscosity values and global sequence parameters including type, subtype and calculated pI. IgG1 type, lambda light chains and VH1 heavy chain subtype are in boldface type.

IgG1 and IgG2 heavy chains and kappa and lambda light chains were rather evenly distributed across the viscosity range. A sequence assessment of subtypes revealed several high viscosity and low viscosity subtype pairs: VH1|1-18 and VH1|1-02; VH3|3-33 and VH3|3-07; VK3|L16 and VK3|A27 with the probability of random correlation at 0.0002; 0.076 and 0.031, respectively, correlating to viscosity residues (FIG. 2). The study looked for viscosity correlations to D and J region sequences but found no significant correlation.

FIG. 2 shows p-values, which indicate probability of random correlation to viscosity. FIG. 2 also shows residues in high viscosity subtype, positions in Aho numbering, and residues in low viscosity subtypes.

Among the fourteen IgG molecules of VH1 subtype, high viscosity was strongly associated with VH1 1-18 subtype and low viscosity with VH1 1-01 subtype with the very low probability of this being a random coincidence (FIG. 9).

In order to assess the correlation between the two subtypes and viscosity, probability of the same population mean by Student's t-test was calculated for VH1|1-02 versus VH1|1-18, VH3|3-33 versus VH3|3-07 and VK3|L16 versus VK3|A27 using t-test two-sample equal variants with a two-tailed distribution.

An association (t-test, p=0.031) of light chain VK3|L16 with high viscosity and VK3|A27 with low viscosity was detected (FIG. 2, FIG. 12, left side). VK3|L16 versus VK3|A27 and VH3|3-33 versus VH3|3-07 are discussed further in this specification. Due to the strong correlation to viscosity, VH1|1-18 and VH1|1-02 were further evaluated as follows. As the next step, 43 antibody chain sequences were aligned and assessed as follows.

Sequence Alignment and Numbering System

Several IgG numbering systems exist, including:

EU—Edelman et al. (1969), "The covalent structure of an entire gamma immunoglobulin molecule," *Proc. Natl. Acad. Sci. U.S.A* 63, 78-85;

Kabat—Kabat et al. (1991), *Sequences of proteins of immunological interest*, Fifth Edition. NIH Publication No. 91-3242;

Chothia—Chothia et al. (1992), "Structural repertoire of the human VH segments," *J. Mol. Biol.* 227: 799-817; Tomlinson et al., (1995), "The structural repertoire of the human V kappa domain. EMBO J. 14: 4628-4638;

Aho—Hoenegger et al. (2001), "Yet another numbering scheme for immunoglobulin variable domains: an automatic modeling and analysis tool," *J. Mol. Biol.* 309, 657-670;

and others. All four numbering systems mentioned above are illustrated in FIG. 9, right side for frame region 3 of the heavy chain of VH1 subtype. The Aho scheme was built by utilizing spatial positions of amino acid residues derived from more than 400 crystal structures of variable domains of different antibodies. The Aho numbering system defined by A. Honegger (citation above) was used in this work because it is a 3D structure-based numbering system. This creates an advantage specifically for residues in CDRs: Residues with the same numbers are located in similar spatial areas and are comparable across different IgG sequences. Since residue positions in the Aho numbering scheme are related to tertiary structure, they should be more associated with biophysical and biochemical properties and, possibly, viscosity. Aho numbering is aligned and correlated with the other main numbering schemes as it is shown in several tables of this specification. Any of the four numbering systems can be interchangeably used to identify the preferred amino acid substitutions. The heavy chain variable region ends at the following residues for different numbering systems: 149 Aho, 117 EU, 113 Kabat, 113 Chothia. The light chain variable region ends at 149 Aho, 107 EU, 107 Kabat, 107 Chothia. Aho numbering allocates more numbers for CDR regions instead of using letters for CDR residues as in Kabat and Chothia (for example 82b for Kabat and Chothia). As a result, Aho numbers for the same residues are often larger. Each variable region includes three complementarity determining regions (CDRs) and four framework regions (FRs) in the following sequence: FR1-CDR1-FR2-CDR2-FR3-CDR3-FR4. While CDRs provide great sequence diversity with the purpose of binding to antigens (CDR3 regions bind most often), FR sequences are more conserved and contain only a few differences, some of which are subtype specific.

Correlation of Sequences to Viscosity

In addition to assessing the global sequence features, the variable regions' sequences were aligned to identify the residues responsible for the viscosity differences. In addition to visual observations, a software machine learning algorithm was developed and applied to identify the residues impacting viscosity the most and to predict antibodies' viscosity values from their sequences. The predictive model was constructed using charge and hydrophobicity of residues in Aho-aligned positions.

Heavy chain VH1 sequence alignment and assessment of the five sequences of high-viscosity VH1 1-18 subtype and five sequences of low-viscosity VH1 1-02 subtype molecules revealed that only 4 residues were different between the two subtypes in frames, all four located in framework 3 (FIG. 9, right side). A larger number of sequence differences were observed in CDRs, but they were left beyond the scope of the study, since CDRs are often involved in binding to the antigens, and engineering (mutating residues in) CDRs with a goal of reducing viscosity would carry a significant risk of losing potency. The subtype-related differences in viscosity and residues in FR3 indicated that the following amino acid substitutions could potentially reduce viscosity in Aho numbering: T82R, T86I, R94S and S95R. The software algorithm supported the four substitutions and also suggested that the following two substitutions correlated with reduction of viscosity: light chain G13V/L in FR1 and heavy chain S59R/K from the edge of CDR2, the latter correlation observed in VH3 subtype (FIG. 9, right side).

In Silico Assessment of Suggested Amino Acid Substitutions

VHT82R. R82 occurs with high frequency in VH1-02. IgG structure modeling indicated that heavy chain Aho position 82 is a part of the upper core of the globulin fold and does not typically contact the antigen, but it can directly contact CDR backbones according to Ewert et al. (2003), "Biophysical properties of human antibody variable domains," *J. Mol. Biol.* 325: 531-553. HC82 has very conserved main chain-side chain H-bond interactions with CDR 1 and CDR2 backbone amides (Honegger et al., supra). R82 may also coordinate the backbone oxygen atoms of the CDR2 loop.

VH R94S and S95R. S94 and R95 occur with high frequency in VH1-02. These positions are located on the surface, away from the antigen binding domain and are considered a part of the lower core.

T86I. 186 occurs with high frequency in VH1-02. The data suggest substituting a hydrophobic residue (I) for hydrophilic one (T) on the surface, which can potentially lead to aggregation.

VH S59R/K—Within VH1 and VH3, a hydrophilic position 59 associates with lower viscosity. VH S59R/K position has high structural and sequence variability, is fairly solvent exposed, and is directly in between residues 58 and 60, which are part of the upper core and may affect binding. The structure will likely depend directly on the differences in residues 58 and 60 (especially 58 if it is buried). R/K59 has low frequency of occurrence (below 2%), and was not observed in VH1 according to the amino acid residue frequency analysis. All R/K59s are accommodated within the VH3 dataset except one (VH4).

VL G13V/L—This position is structurally buried and is a part of the lower core of the variable domain according to Ewert et al., supra. From this point of view, a G13V mutation to a more hydrophobic residue should make the core stronger.

To summarize, in silico sequence analysis indicated that the proposed mutations do not introduce any additional glycosylation sites or sites susceptible to rapid degradation under physiological or mildly acidic formulation conditions (NG, NS, NT, DG, DH). VH T82R, T86I, R94S and S95R mutations would provide a switch from subtype VH1-18 to VH1-02 in frame region 3, so they should not introduce any unusual or rare motifs. The addition of VH S59R and VL G13V mutations was suggested by the software from the VH3 subtype, outside of VH1. None of the mutation sites is positioned close to the binding regions, except for S59R, which is at the edge of HC CDR2 and, therefore, represents a mild risk of interfering with potency/binding. Arginine is a very low frequency residue in position 59 (R59), so prediction of its impact is difficult. T86I was identified as a high risk for aggregation and removed from the list of mutations.

Produced Mutants and their Expression, Potency, Chemical Modifications, Glycosylation and Viscosity.

Taking into account the above considerations, several mutants were produced for two IgG2 antibodies AK and AO of the high-viscosity VH1-18 subtype with the goal of reducing viscosity while maintaining potency (FIG. 9B). FIG. 9B includes monoclonal antibody mutant symbols and related mutations on the heavy and light chain.

A very low expression level was observed for both AK mutants containing the S59R substitution (marked with * on FIG. 3). Viability and viable cell density was also low for one of them, AK (59 82 94 95 13). On the other hand, antibody AO mutants containing the S59R substitution produced a titer comparable to that of the AO parent molecule. Although the statistics were not sufficient to make a general conclusion about heavy chain position 59, the case suggested that a single amino acid substitution may dramatically alter expression. Chemical modifications, including oxidation, deamidation, isomerization and the glycosylation pattern, were similar among the two parents and their mutants as measured by peptide mapping LC-MS analysis.

Figure 4:
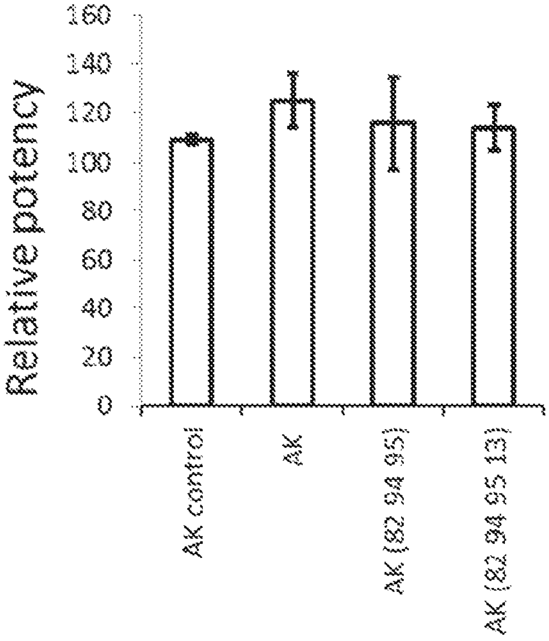
FIG. 4 shows potency of AK parent antibodies (AK control, AK) and their mutants.
Figure 5:
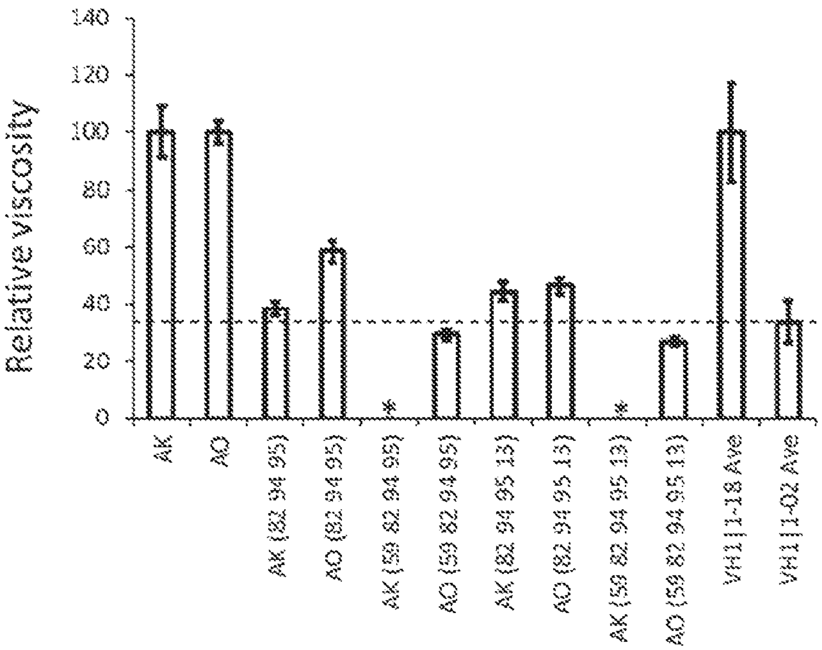
FIG. 5 shows viscosity of mutants relative to the parent AK and AO antibodies. Average viscosity values of high viscosity VH1|1-18 and low viscosity VH1|1-02 from the set of 43 antibodies are also shown for comparison.

Potency values of the parent AK antibody and the two well-expressed mutants, measured through binding to PCSK9, were similar (FIG. 4). Finally, measured viscosity values of the AK and AO mutants were significantly lower than the parents, as predicted (FIG. 5). For example, the AK (82 94 95) mutant was at only 39% of the parent's viscosity. Viscosity of both AO mutants containing the S59R substitution was even lower, at approximately 28% of the parent's viscosity (FIG. 5). The S59R mutants did not express well for the AK antibody and the viscosity could not be measured. Average viscosity values for VH1|1-18 and VH1|1-02 germline subfamilies were added for comparison. A total of 12 consistent sequence differences were identified between VH1|1-18 and VH1|1-02 subfamilies, including 8 in CDRs and 4 in frame regions (FIG. 9). Three sites, all in frame region 3, were selected for amino acid substitutions from high viscosity VH1|1-18 to low viscosity VH1|1-02. The three point mutations in frames were introduced in two mAbs of VH1|1-18 subfamily (AK and AO) to convert only these residues to the residues present in VH1|1-02. Although chances to achieve the possible 2-fold decrease in viscosity were theoretically low (3/12), these substitutions rather unexpectedly produced desirable outcome: with only three substitutions the viscosity decreased approximately two-fold in both antibody molecules.

Viscosity Versus pI

Figure 6:
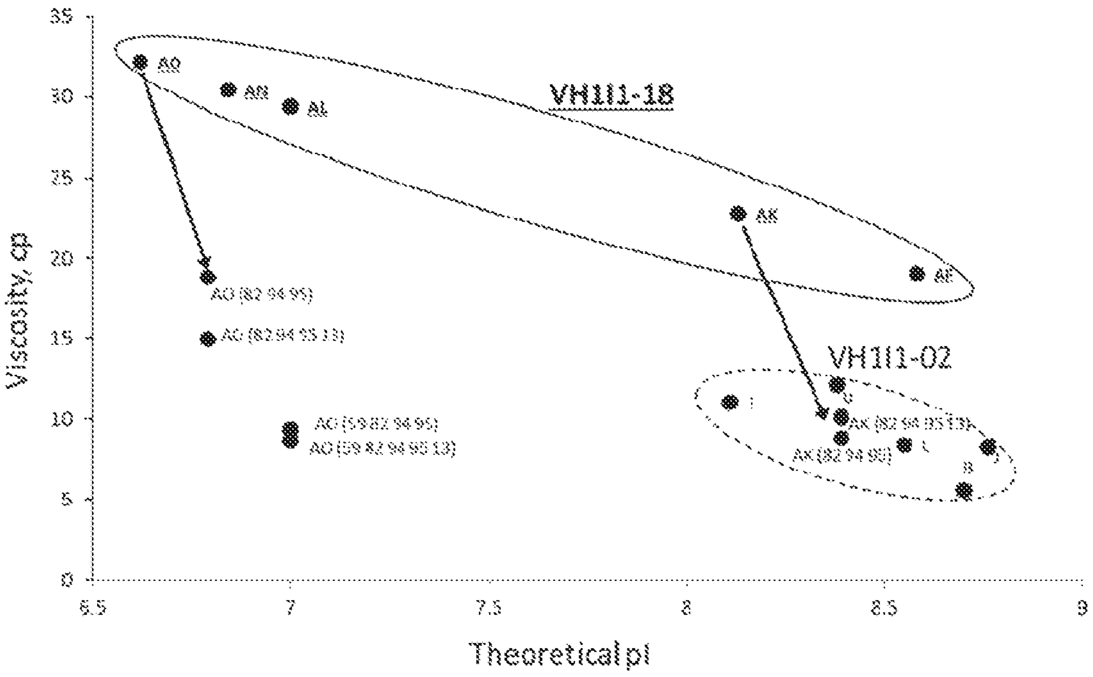
FIG. 6 shows measured viscosity values of mAbs of the high viscosity VH1|1-18 and the low viscosity VH1|1-02 subtypes versus calculated whole molecule pI values. The low-viscosity mutants of AK and AO antibodies are also shown.

Although the dependence of viscosity from pI was not clear from the whole set of the 43 mAbs, the VH1 subset clearly showed that viscosity steadily increased when pI values of the mAbs decrease from pI 8.5 to pI 6.5 in the pH 5.2 formulation (FIG. 6). The shift between the high-viscosity VH1|1-18 mAbs and low-viscosity VH1|1-02 mAbs can be also seen. As predicted, T82R, R94S and S95R mutants of AK and AO antibodies moved approximately two fold down along the viscosity scale from the VH1|1-18 to the VH1|1-02 area on the plot (FIG. 6). Mutants AO (59 82 94 95) and AO (59 82 94 95 13) moved to even lower viscosity and to slightly higher pI, indicating that the S59R substitution, adopted from outside of the VH1 group, was effective in further reducing viscosity. Unfortunately, AK mutants containing R59 were not expressed well, suggesting that appearance of the low-frequency arginine residue in position 59 may affect expression.

An increase in pI for antibodies in formulations with pH<pI (for example, the mildly acidic formulation used in this study) typically leads to a decrease in viscosity. This result can be explained by the columbic repulsion of the positively charged antibody molecules. It is known that proteins, including antibodies, show poor solubility and high precipitation, which affect viscosity, at high concentrations. It is interesting that the VH1|1-18 to VH1|1-02 substitutions in frame region 3 resulted in a two-fold decrease in viscosity and only a minor increase in antibody pI values, suggesting that not the charge increase, but rather some structural changes may be responsible for the dramatic decrease in viscosity.

After superimposing crystallography structures of hundreds of Fab domains, hydrogen bond interactions for every VH and VL position were identified (Honegger et al. (2001), "Yet another numbering scheme for immunoglobulin variable domains: an automatic modeling and analysis tool," *J. Mol. Biol.* 309: 657-670). The data indicate that the identified positions may be bound to other residues through main-chain and side-chain hydrogen bond interactions (for Type III AK and AO antibody molecules). For example, 94 was bound to 77 in some VH Type III immunoglobulin structures; 95 to 18; 59 to 67, 66, 65, 61, 60 and VL13 to 146, 148. Hence, residue substitutions at these positions may change the interactions and the immunoglobulin fold. The crystal structure of AK antibody (Jackson et al., 2007), "The Crystal Structure of PCSK9: a Regulator of Plasma LDL-Cholesterol," *Structure* 15: 545-52) suggests that all three positions 82, 94 and 95 are on the very periphery of the Fab regions and exposed to solvent and other antibody molecules. Changes in FR3 positions in VH3 (FIG. 11) and VK3 (FIG. 12) also correlate to viscosity. One explanation of their role in viscosity is that these positions in FR3 are on the periphery of the molecule and are actively engaged in the intermolecular interactions during shear stress associated with motion through the injection needles and viscosity measurements.

Figure 8:
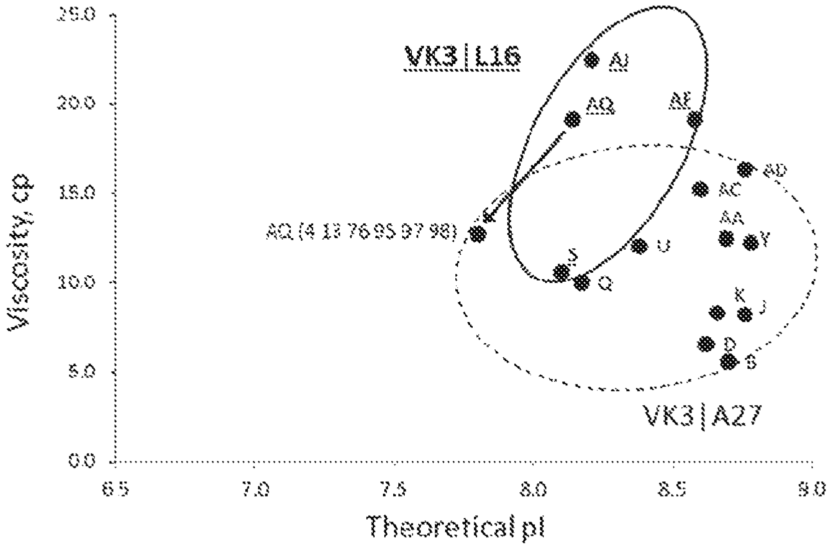
FIG. 8 shows measured viscosity values of mAbs with high viscosity VK3|L16 and VK3|L6 subfamilies and the low viscosity VK3|A27 subfamily versus calculated whole molecule pI values. The low-viscosity mutant AQ (4 13 76 95 97 98) is also shown.

Lower viscosity VK3|A27 and higher viscosity VK3|L16 antibodies showed inverse correlation between viscosity and pI (FIG. 8, FIG. 12).

Figure 7:
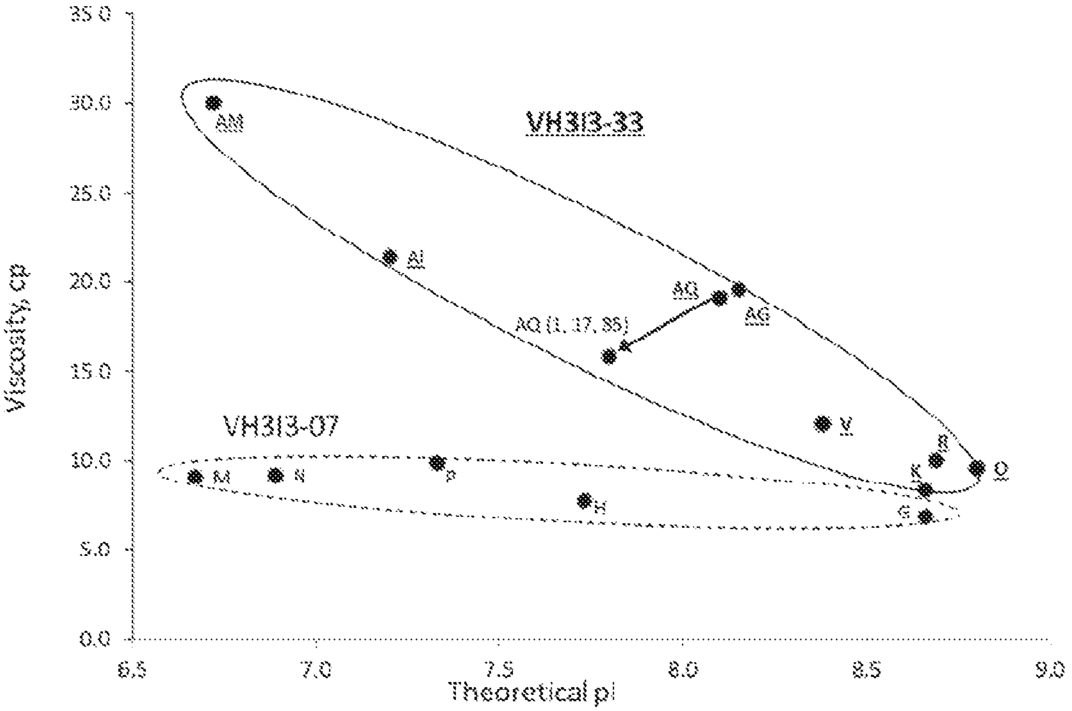
FIG. 7 shows measured viscosity values of mAbs of the high viscosity VH3|3-33 and the low viscosity VH3|3-07 subtypes versus calculated whole molecule pI. The low-viscosity mutant AQ (1, 17, 85) is also shown.

It needs to be mentioned that pI was a not very strong but in some cases useful predictor of viscosity. In general, viscosity decreased with increasing pI, and pI should be taken into account. For example, viscosity values of VH3|3-33 become lower and similar to VH3|3-07 for higher pI antibody molecules (FIG. 7). Hence, pI should be taken into account when predicting viscosity of VH3|3-33.

Proposed Viscosity Reduction for VH3 and VK3 Germline Families

High-viscosity VH3|3-33 and low-viscosity VH3|3-07 antibodies on average have a large difference in viscosity, while occupying a similar pI range (FIG. 7). Unexpectedly, on average, VH3|3-07 had lower viscosity and also lower pI, which contradicts typical behavior reported in the literature. Viscosity values of the following VH3|3-33 molecules can be reduced by the mutations: AQ, AM, AI, AG.

Monoclonal antibodies with high-viscosity VK3|L16 and low-viscosity VK3|A27 light chains also showed a large viscosity difference while showing relatively small difference in pI values, again suggesting a structural difference between subfamilies (FIG. 8). Viscosity values of the following VK3|L16 molecule can be reduced by the mutations described in FIG. 11: antibodies AQ and AF.

Figure 13A:
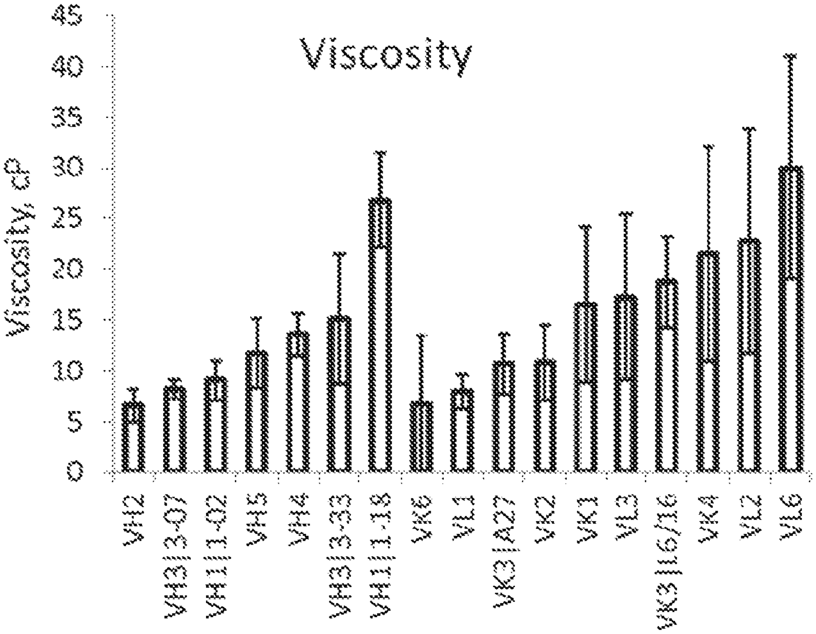
FIGS. 13A and 13B show average values for measured viscosity and calculated pI values for intact antibody molecules containing the specified heavy chain and light chain germline families and germline subfamilies of VH1, VH3 and VK3. The X-axis contains families and the number of members in each family and subfamily.
Figure 13B:
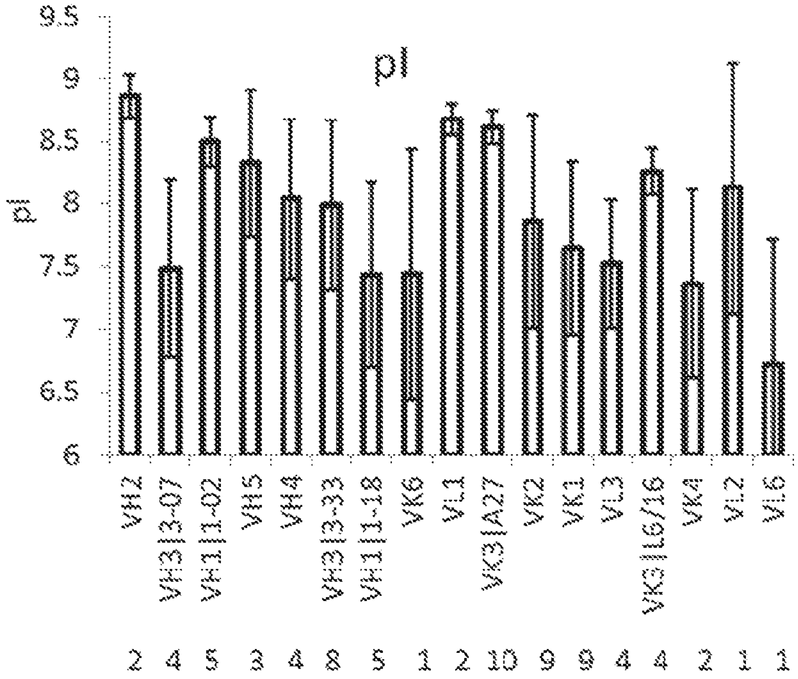
Figure 14A:
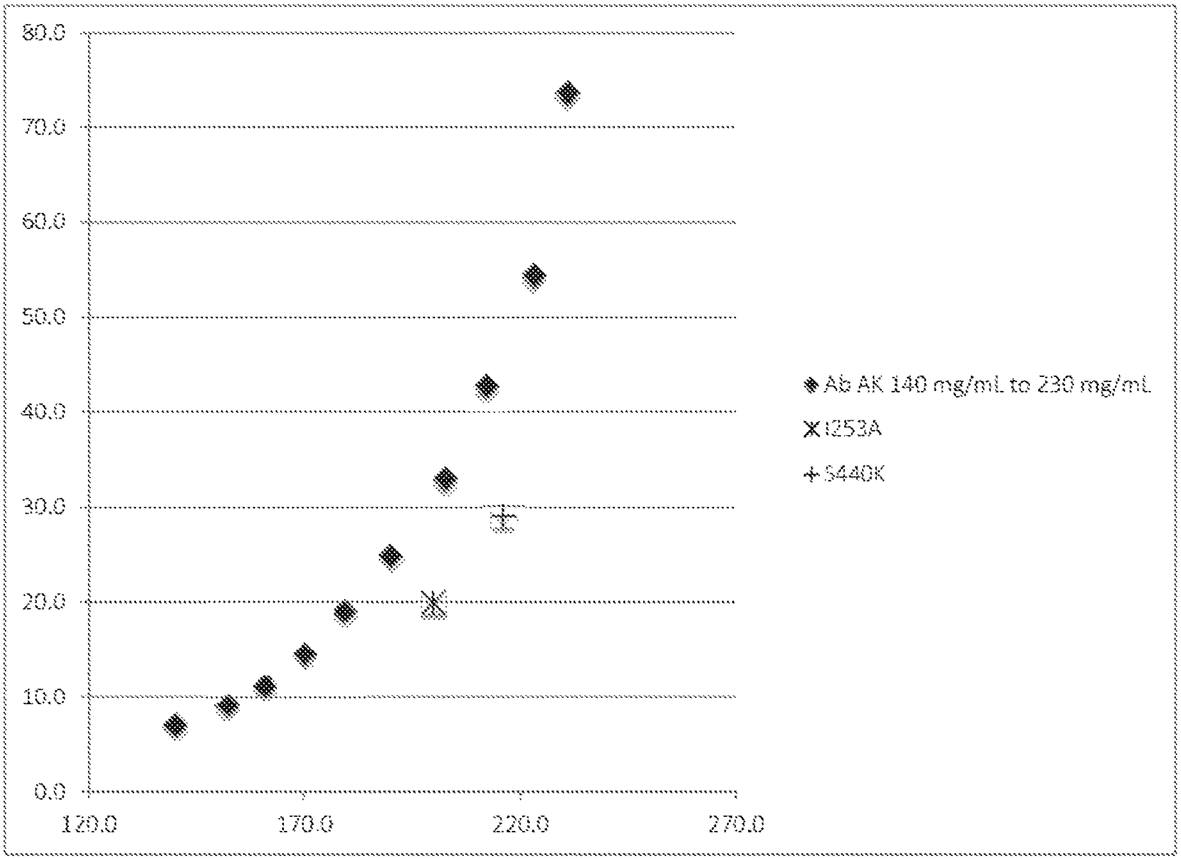
FIG. 14A shows that mutations in the Fc-Fc interaction surface can decrease solution viscosity. The viscosity of concentrations of antibody AK and antibody AK mutants I253A and S440K are shown.
Figure 14B:
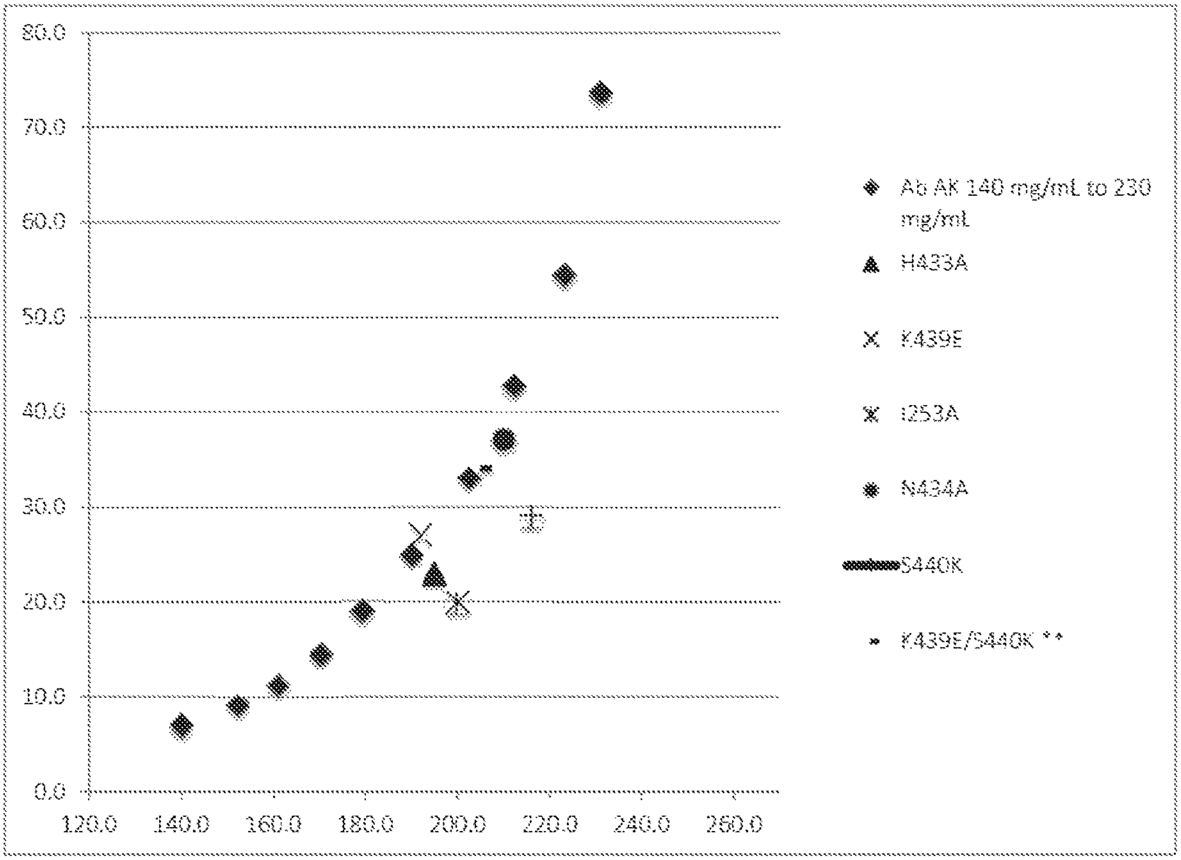
FIG. 14B shows that a double mutant that restores wild type complement activity also restores wild type viscosity. The figure shows the viscosity of concentrations of antibody AK, antibody AK mutant I253A, antibody AK mutant S440K, and antibody AK double mutant K439E/S440K. The figure also shows the viscosity of antibody AK mutant K439E, antibody AK mutant H433A, and antibody AK mutant N434A which do not decrease viscosity relative to the antibody AK parent.

The analysis of global sequence features revealed the following high/low viscosity pairs: VH1|1-18/VH1|1-02; VK3|L16/VK3|A27; and VH3|3-33/VH3|3-07 with p-values of the correlation at 0.0002, 0.031 and 0.076, respectively (FIG. 2). Sequence positions and residues correlating to the viscosity differences were identified, and can be considered as candidates for viscosity lowering point mutations (FIG. 2). The performed above correlation of VH and VL families to viscosity indicates that theoretically antibodies with the following VH and VL combinations should have the lowest viscosity (FIGS. 13A and B): VH2, VH3|3-07, VH1|1-02 for VH and VK3, VL1, VK3|A27 for VL. Three antibodies of VH1|1-02 and VK3|A27 configuration practically occurred in our set and they indeed exhibited low viscosity values: B (5.6 cP), J (8.2 cP), Y (12.1 cP).

Chemical Cross-Linking Studies

A broad survey of the potential protein-protein interactions in viscous antibody solutions was attempted using chemical cross-linking at high protein concentrations. Chemical cross-linking is a classic biochemical technique used to demonstrate that specific portions of proteins interact with each other. In this paper we describe the use of a zero length chemical cross-linking reagent to identify potential protein-protein interactions in high concentration viscous antibody solutions. The chemical cross-linking results of viscous and non-viscous antibodies are used to construct a model of potential protein-protein interactions in solution.

Chemical cross-linking with EDC reveals the presence of a common chemically cross-linkable oligomeric distribution. The chemical cross-link that results in the oligomeric pattern is surprisingly not inter-molecular but rather an intra-molecular cross-link. The intra-molecular cross-link between the top of the Fc and the bottom of a Fab results in an antibody conformation that may favor the formation of Fc-Fc mediated antibody oligomers. The 1HZH antibody crystal structure contains an antibody hexamer in the asymmetric unit that has one Fab arm pinned against the Fc domain to facilitate the Fc-Fc interaction critical to form the IgG1 hexamer. The appearance of this conformation may or may not be critical to the formation of the hexamer in the protein crystal. The increased propensity to form the hexamer in solution when the Fab-Fc intra-molecular chemical cross-link is present suggests that the Fab arm pinned to the Fc may have increased propensity to form Fc-Fc based antibody oligomers.

Decreasing Fc-Fc Interactions can Decrease Solution Viscosity

The scientific literature includes research on hexamer formation of antibodies related to interaction with Clq1 and CDC activity. Diebolder et al. found that anti-CD20 antibodies with certain Fc point mutations, including K439E and S440K, abrogated CDC activity but that the associated K439E/S440K double mutant restored CDC activity. Also I253A mutation decreased CDC activity. Diebolder et al. (2014), "Complement is Activated by IgG Hexamers Assembled at the Cell Surface," *Science* 343: 1260-3. Diebolder et al. did not associate the mutants they disclose with an effect on antibody viscosity. Similarly, van den Bremer et al (2015) found that charged residues at the C-terminus of an antibody could decrease Clq1 interaction due to a decreased ability to form IgG hexamer structures. The authors did not associate the presence of charged residues at the C-terminus of IgGs to an effect on antibody solution viscosity.

The observation of a hexamer of antibodies in viscous antibody solutions suggested that the Fc-Fc interactions that are present in the antibody hexamer crystal structure as well as the structure thought to form prior to the recruitment of Clq1 (complement) are likely present in viscous antibody solutions in the absence of the chemical cross-linker EDC. In order to test whether the Fc-Fc interaction might contribute to solution viscosity, Fc mutants based on the work done by Diebolder et al. were generated at Amgen. The materials were then evaluated in anti-PCSK9 formulation buffer by cone and plate rheology. The comparison of parent anti-PCSK9 antibody AK and Fc mutant anti-PCSK9 antibodies demonstrated that decreasing the affinity of Fc for Fc does decrease the solution viscosity of the antibody. The point mutants retained FcRn binding capacity and there were no changes to bioactivity. The ability of a double mutant which restored wild-type complement activity to return to wild type viscosity demonstrates that the decrease in viscosity can be reversed if the ability of Fc-Fc interactions is restored to wild-type levels. Taken together with the observation of Fc-Fc mediated oligomeric species increasing solution viscosity, there is a common Fc-mediated protein-protein interaction that contributes to antibody solution viscosity. It needs to be noted that out of five mutations, S440K, I253A, K439E, H433A, N434A identified by Diebolder et al. as reducing CDC activity and tested for viscosity in this work, only the first two showed reduced viscosity in high concentration anti-PCSK9 formulation, while K439E, H433A and N343A did not reduce viscosity in high concentration anti-PCSK9 formulation, indicating that direct correlation does not exist and that people skilled in the art could not correctly anticipate lower viscosity from the information provided by Diebolder et al. The K439E mutant was also evaluated in a high protein concentration sucrose formulation and found to be less viscous than the parent anti-PCSK9 mutant at the same concentration. The presence of Arginine in the anti-PCSK9 formulation may have contributed to charge screening that may have decreased the effectiveness of the negative charge introduced in the K439E mutant to decrease Fc-Fc interactions. The H433A and the N434A mutants have no obvious charge screening sensitivity like the K439E mutant.

The Fc-Fc interaction may influence solution viscosity by increasing the number of potential interactions possible in two potential ways. It could increase the number of interactions per antibody from two CDR mediated interactions to two CDR mediated interactions plus 2 Fc mediated interactions per antibody or it could change the number of free CDR ends available in oligomers present in solution. Given the fact that the Fc domain of IgG1, IgG2, IgG3 and IgG4 antibodies are highly similar, it is likely that the Fc-Fc mediated interactions are present in all antibodies. The analysis of non-viscous antibodies shows that the intramolecular cross-link which indicates the presence of an Fc-Fc interaction is absent in contrast to a viscous antibody at the same concentration. This suggests that the Fc-Fc interaction, although theoretically possible, is absent in non-viscous antibodies. The CDR next nearest neighbor interaction may influence the relative distance between Fc's as well as the relative orientation to enhance Fc-Fc interaction. This may explain why viscous antibodies have an Fc-Fc interaction while non-viscous antibodies do not at room temperature.

The presence of an Fc-Fc interaction also increases the likelihood that an oligomer of antibodies (dimer, trimer, tetramer, etc.) contains the maximum number of free CDR ends. The larger number of free CDR ends increases the number of CDR next nearest neighbor interactions. This in turn may increase network formation propensity and increase solution viscosity as a result of more efficient "percolation."

C-Terminal Modifications to Reduce Viscosity

Certain modifications at the antibody C-terminus interfere with C1q binding and complement-dependent cytotoxicity (CDC). Van den Bremer et al. (2015), "Human IgG is produced in a pro-form that requires clipping of C-terminal lysines for maximal complement activation," *mAbs* 7(4): 672-80. The authors found that C-terminal lysine and C-terminal glutamic acid likely decreases the propensity of the Fc-Fc interactions that lead to a hexamer of antibodies that can most efficiently interact with Clq1. The authors constructed mutants of a CD20 antibody and a CD38 antibody having PGKP, PGKKP, PGKKKP, and PGE at the C-terminus. They found that these mutants showed significantly reduced or completely lost CDC activity. Thus, one may conclude that the mutations blocked the hexamerization previously correlated by the authors with CDC activity. Given the present correlation of hexamerization with viscosity, such mutations should also reduce viscosity of antigen binding proteins. It is thus reasonable to conclude that placement of positively charged or negatively charged amino acids at the C-terminus, whether placed there by addition or substitution of existing C-terminal amino acids, will reduce the viscosity of an antigen binding protein.

Sequence Modification to Improve Pharmacokinetic Parameters

This invention also includes the discovery of improved pharmacokinetic properties in antigen binding proteins having mutations that may also reduce viscosity. In particular, S440K mutations have been found to improve both Tmax (the time after dosing at which the maximum concentration was observed) and Cmax (the maximum observed concentration measured after dosing). Mutants of antibody AK having S440K, optionally with other mutations, have been found to have Tmax reduced by more than half that of the parental antibody AK after subcutaneous injection of the mutants and the parental antibody at the same concentration. Such mutants have also been found to have Cmax that is 28% or 42% higher after subcutaneous injection of the mutants and the parental antibody. See FIG. 22.

Nucleic Acids, Vectors, Host Cells

The invention also includes isolated nucleic acids encoding the bispecific antibodies of the invention, which includes, for instance, the light chain, light chain variable region, light chain constant region, heavy chain, heavy chain variable region, heavy chain constant region, linkers, and any and all components and combinations thereof of the bispecific antibodies disclosed herein. Nucleic acids of the invention include nucleic acids having at least 80%, more preferably at least about 90%, more preferably at least about 95%, and most preferably at least about 98% homology to nucleic acids of the invention. The terms "percent similarity", "percent identity" and "percent homology" when referring to a particular sequence are used as set forth in the University of Wisconsin GCG® software program. Nucleic acids of the invention also include complementary nucleic acids. In some instances, the sequences will be fully complementary (no mismatches) when aligned. In other instances, there may be up to about a 20% mismatch in the sequences. In some embodiments of the invention are provided nucleic acids encoding both a heavy chain and a light chain of an antibody of the invention.

Nucleic acids of the invention can be cloned into a vector, such as a plasmid, cosmid, bacmid, phage, artificial chromosome (BAC, YAC) or virus, into which another genetic sequence or element (either DNA or RNA) may be inserted so as to bring about the replication of the attached sequence or element. In some embodiments, the expression vector contains a constitutively active promoter segment (such as but not limited to CMV, SV40, Elongation Factor or LTR sequences) or an inducible promoter sequence such as the steroid inducible pIND vector (Invitrogen), where the expression of the nucleic acid can be regulated. Expression vectors of the invention may further comprise regulatory sequences, for example, an internal ribosomal entry site. The expression vector can be introduced into a cell by transfection, for example.

In another embodiment, the present invention provides an expression vector comprising the following operably linked elements; a transcription promoter; a first nucleic acid molecule encoding the heavy chain of a bispecific antigen binding protein, antibody or antigen-binding fragment of the invention; a second nucleic acid molecule encoding the light chain of a bispecific antigen binding protein, antibody or antigen-binding fragment of the invention; and a transcription terminator. In another embodiment, the present invention provides an expression vector comprising the following operably linked elements; a first transcription promoter; a first nucleic acid molecule encoding the heavy chain of a bispecific antigen binding protein, antibody or antigen-binding fragment of the invention; a first transcription terminator; a second transcription promoter a second nucleic acid molecule encoding the light chain of a bispecific antigen binding protein, antibody or antigen-binding fragment of the invention; and a second transcription terminator.

A secretory signal peptide sequence can also, optionally, be encoded by the expression vector, operably linked to the coding sequence of interest, so that the expressed polypeptide can be secreted by the recombinant host cell, for more facile isolation of the polypeptide of interest from the cell, if desired.

Recombinant host cells comprising such vectors and expressing the heavy and light chains are also provided.

Purification

Methods of antibody purification are known in the art and can be employed with production of the antibodies and bispecific antibodies of the present invention. In some embodiments of the invention, methods for antibody purification include filtration, affinity column chromatography, cation exchange chromatography, anion exchange chromatography, and concentration. The filtration step preferably comprises ultrafiltration, and more preferably ultrafiltration and diafiltration. Filtration is preferably performed at least about 5-50 times, more preferably 10 to 30 times, and most preferably 14 to 27 times. Affinity column chromatography, may be performed using, for example, PROSEP® Affinity Chromatography (Millipore, Billerica, Mass.). In a preferred embodiment, the affinity chromatography step comprises PROSEP®-vA column chromatography. Eluate may be washed in a solvent detergent. Cation exchange chromatography may include, for example, SP-Sepharose Cation Exchange Chromatography. Anion exchange chromatography may include, for example but not limited to, Q-Sepharose Fast Flow Anion Exchange. The anion exchange step is preferably non-binding, thereby allowing removal of contaminants including DNA and BSA. The antibody product is preferably nanofiltered, for example, using a Pall DV 20 Nanofilter. The antibody product may be concentrated, for example, using ultrafiltration and diafiltration. The method may further comprise a step of size exclusion chromatography to remove aggregates. Further parameters of purification appear in the working examples hereinafter.

The bispecific antibodies, antibodies or antigen-binding fragments may also be produced by other methods known in the art, for example by chemical coupling of antibodies and antibody fragments.

Each manuscript, research paper, review article, abstract, patent application, patent or other publication cited in this specification is hereby incorporated by reference in its entirety.

WORKING EXAMPLES

The invention is further illuminated by the following working examples, which exemplify but do not limit the scope of the invention Example 1

Fab Mutations

Materials

A set of 43 human and humanized recombinant monoclonal antibody molecules with different targets and different sequences were produced and purified according to a standard procedure (FIGS. 1A and 1B). The set with equivalent purity of >98% by size exclusion chromatography (SEC) was collected. Samples were concentrated in a 3 mL maximum volume using Amicon Ultrafiltration Stirred Cell Model 8003 (Millipore, Billerica, MA) at 2-8° C. at a maximum pressure of 30±10 psi. They were concentrated up to 150 mg/mL according to approximate volume depletion in a formulation buffer containing 20 mM acetate, 9% sucrose at pH 5.2 (without polysorbate), and final concentrations were determined (±10%) using the protein's absorbance at 280 nm (after dilution to end up within 0.1-1 absorbance units (AU)) and a protein-specific extinction coefficient.

Several low viscosity mutants of two mAbs were produced, purified and formulated according to a similar standard procedure. They included an antibody against proprotein convertase subtilisin/kexin type 9 (PCSK9, antibody AK) and against macrophage colony-stimulating factor (M-CSF, AO).

Viscosity Measurements

Viscosity analysis was performed on a Brookfield LV-DVIII cone and plate instrument (Brookfield Engineering, Middleboro, MA., USA) using a CP-40 spindle and sample cup. All measurements were performed at 25° C., controlled by a water bath attached to the sample cup. Multiple viscosity measurements were collected, manually within a defined torque range (10-90%) by increasing the RPM of the spindle. Measurements were averaged in order to report one viscosity value per sample to simplify the resulting comparison chart Sequence Alignment A structure-based sequence alignment was performed by an Ab Initio software tool developed using Excel Macros downloaded from the Department of Biochemistry of Zurich University.

Example 2

Fc Mutations

Expression and Purification of Mutants

Materials and Methods

Figure 16:
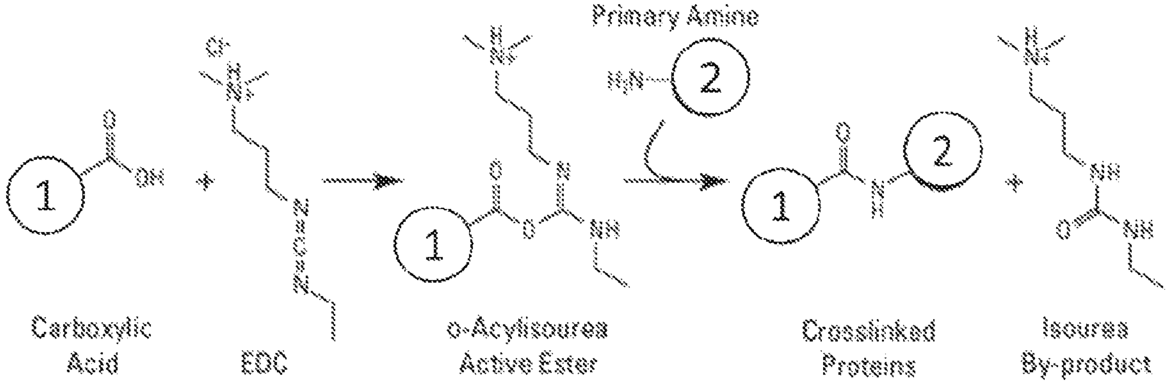
FIG. 16 is a schematic of EDC chemical cross-linking (see Example 2).
Figure 18:
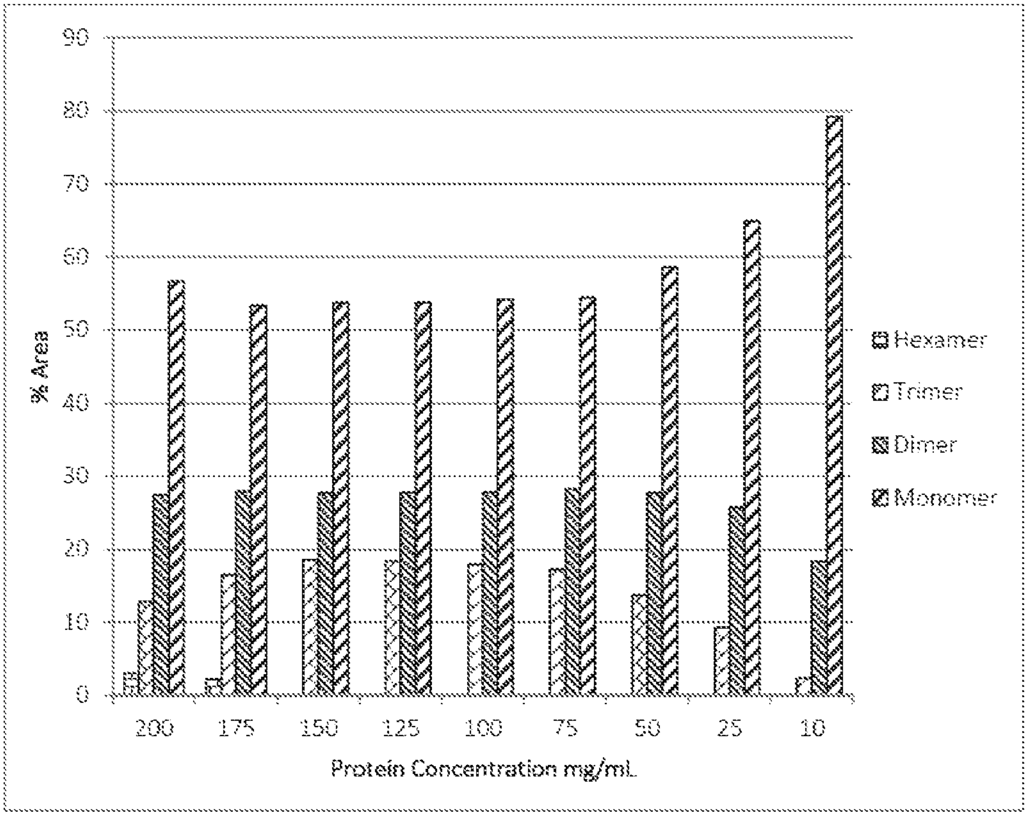
FIG. 18 shows concentration-dependent formation of antibody system oligomers by EDC chemical cross-linking of antibody AH.
Figure 19A:
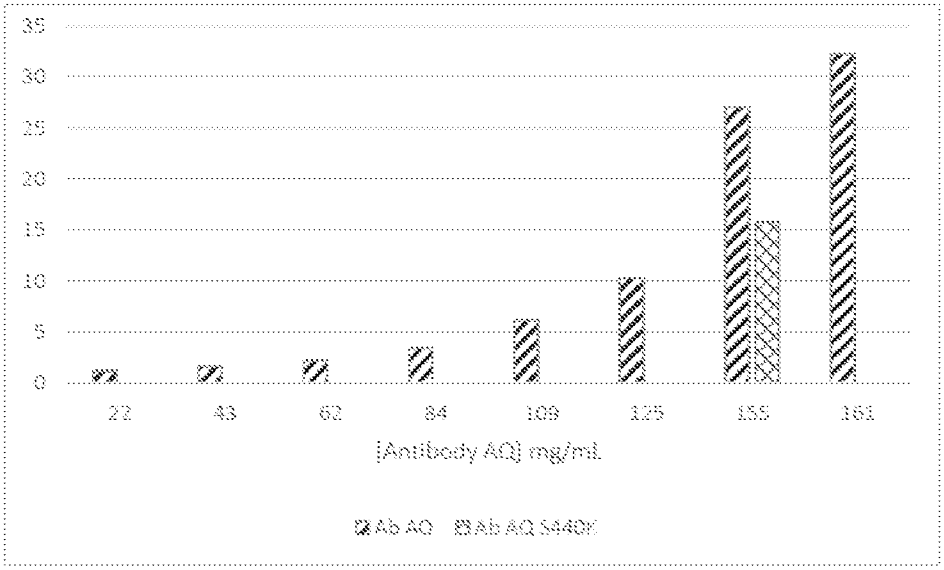
FIG. 19A shows that a S440K mutation in the Fc region reduces viscosity in antibody AQ. (Note that the concentration of the mutant is actually 150 mg/mL.)
Figure 19B:
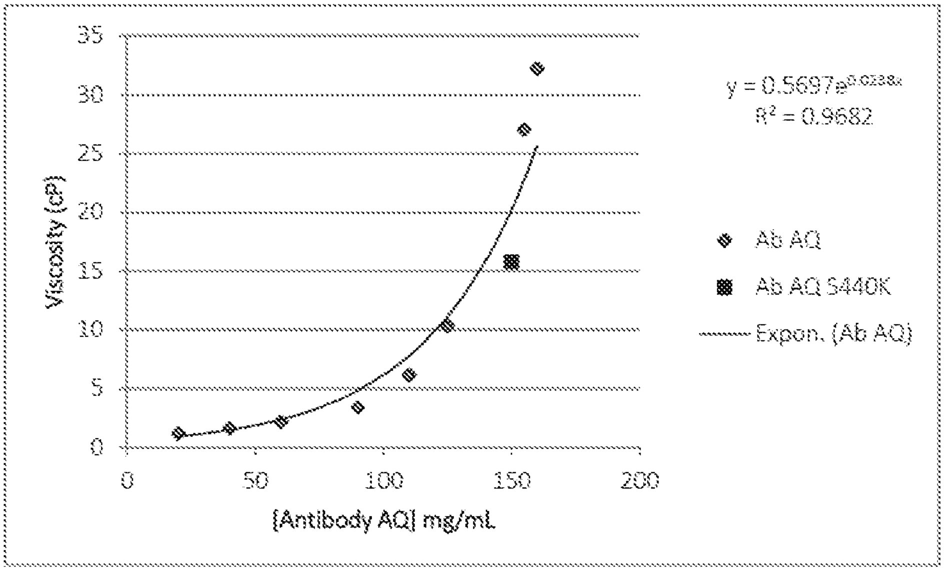
FIG. 19B is a scatter plot of the same data with an exponential fit. The diamonds in FIG. 19B denote the unmodified antibody AQ at the concentrations shown and the square shows the S440K mutant at 150 mg/mL.

- Anti-C-kit antibody (antibody BA, SEQ ID NOS: 174 and 176, encoded by nucleic acids of SEQ ID NOS: 173 and 175, respectively), anti-sclerostin antibody AH, and anti-PCSK9 antibody AK
- Anti-streptavidin IgG1 and IgG2.
- 1-ethyl-3-[3-dimethylaminopropyl] carbodiimide hydrochloride (EDC)
- Solubilization with n-methyl-2-pyrrolidone
- Size Exclusion High Performance Liquid Chromatography (SE-HPLC) with Light Scattering (LS)
- Reduced and alkylated reversed phase High Performance Liquid Chromatography (RA RP-HPLC)
- Trypsin peptide map with electro spray ionization mass spectrometry (ESI-MS)
- Cone and plate viscometer Results SE-HPLC of EDC Cross-linking of High Concentration Monoclonal Antibody Solutions Reveals Propensity to form Oligomers The compound 1-ethyl-3-[3-dimethylaminopropyl] carbodiimide hydrochloride (EDC) was used to chemically cross-link acidic residues in the antibody to primary amines in the antibody (N-terminus and/or Lys residues) and has been used in other studies to determine the regions of protein-protein interaction. The proximity of the carboxyl group to the primary amine is critical as an amide bond is formed between the two groups (FIG. 16). The cross-links that form are likely salt bridges that are present in solution. Carraway and Koshland, Jr. (1972). "Carbodiimide modification of proteins." *Methods Enzymol* 25: 616-623. A panel of antibodies was chemically cross-linked with EDC under identical solution conditions. Previous rheological studies had determined that some of the antibodies in the panel were viscous and some were not (FIG. 17). The non-viscous antibodies had small increases in dimer content but did not contain large amounts of higher order. In contrast, the viscous antibodies contained large amounts of dimer as well as higher order oligomers. A summary is provided in FIG. 17. All of the antibodies that were identified as viscous contained EDC cross-linked species that appeared to be larger than dimer. The appearance of the larger oligomeric species is concentration dependent (antibody AH is shown in FIG. 18 as an example). In order to facilitate further analysis, chemical cross-linking conditions were changed to drive the cross-linking reaction to completion. The solutions became solids after chemical cross-linking at 200 mg/mL. The solids were re-solubilized with buffer or a buffered 3% NMP solution. SE-HPLC analysis of both samples showed that the samples were similar. The buffered 3% NMP solution solubilized the protein significantly faster with more of the material going into solution. Antibody AH was re-solubilized and analyzed further as an example.

Size Analysis by SE-HPLC with Online LS

The cross-linked antibody solutions were analyzed by SE-HPLC with online light scattering to determine the size of the eluting species. SE-HPLC was conducted with online light scattering analysis of antibody AH after EDC chemical cross-linking and resolublization with 3% NMP. SE-HPLC revealed three peaks present in the UV and RI. The first peak was identified as a species with a mass of 840.5 kD. This is close to the expected mass for a hexamer of antibody AH of 873.2 kD. Another species had a mass of 494.6 kD, which is close to the predicted mass of 436.6 kD for a trimer of antibody AH. The third species showed a mass of 139.9 kD, which is close to the predicted mass of 145.5 kD for a monomer of antibody AH.

Reduced and Alkylated Reversed Phase HPLC of EDC Cross-Linked Antibody AH

The cross-linked antibody solutions were analyzed by reduced and alkylated reversed phase high performance liquid chromatography. The recovery of the majority of both light chain (LC) and heavy chain (HC) was unexpected as it was presumed that either the HC or the LC would be cross-linked to one another to form non-native LC-HC peptides or non-native LC-LC or HC-HC peptides reflecting the cross-linked oligomers observed by SEC analysis. In the case of antibody AH, the LC eluted in the same place with the exact same mass as non-cross-linked antibody AH LC. There were changes in the HC in antibody AH that are concentration dependent. There is a small amount of HC-HC cross-linked material (eluting at about 33 minutes, FIG. 21) that had an identified mass of 100 kD. At 150 mg/mL and 200 mg/mL, the distribution of HC species is similar. At lower protein concentrations, the distribution includes more of a species that elutes at about 28.5 min. The distribution of HC species correlates with the amount of oligomer present in each sample as analyzed by SEC with the 200 mg/mL sample containing the largest amount of hexamers and the 10 mg/mL sample containing very little oligomer. The pattern was observed in other viscous antibody solutions.

Example 3

Nonhuman Primate Study of Pharmacokinetics and Pharmacodynamics (PKPD) of the Anti-PCSK9 Parent Antibody AK and Low Viscosity Mutants Materials: antibody AK and its mutants. All mutations in heavy chain.

Fab Mutant: T82(72)R, R94(84)S, S95(85)R; Aho numbering (actual numbering)

Fc Mutant S(434)K (S440K in EU numbering):

Double Mutant: T82(72)R, R94(84)S, S95(85)R; S(434)K:

Four groups of 4 male cynomolgus monkeys were used in this study. Each group received 1 subcutaneous (SC) dose of 10 mg/kg as follows. Group 1 received parent antibody AK (140 mg/ml); Group 2 received Fab mutant (210 mg/ml); Group 3 received Fc mutant (210 mg/ml); Group 4: Fab/Fc mutant (210 mg/ml). Groups 1 and 2 also had diluent control SC dose. Fab mutant included the following substitutions in positions T82(72)R, R94(84)S, S95(85)R. Fc mutant included substitution in position S(434)K.

To measure viscosity at 210 mg/ml, the parent and all mutants were formulated at 210 mg/mL in 10 mM Acetate, 155 mM N-acetyl arginine (NAR), 70 mM ArgHCl, pH 5.4, 0.01% Polysorbate 80. Viscosity was measured using ARG2 cone/plate at 1000 sec-1 and 25 C. See FIG. 15.

Study Design Outline:

4 Groups of 4 Male Cynomolgus Monkeys

Each group received 1 SC dose (10 mg/kg) of:

Group 1: parent antibody AK (140 mg/ml)

Group 2: Fab mutant (210 mg/ml)

Group 3: Fc mutant (210 mg/ml)

Group 4: Fab/Fc mutant (210 mg/ml)

Groups 1 and 2 also had diluent control subcutaneous dose

Skin biopsies taken at injection site 3 days after dosing

Histopath analysis performed

Plasma LDL, HDL, total cholesterol and PK followed for 6 weeks post-dose

Study Conclusions

All 4 Homologues Produced Marked LDL Lowering

Maximal reduction 2 weeks after dosing: 1 week later than previously observed for parent The nadir of the effect was not quite as profound for the Fab/Fc mutant (~78% vs ~90%)

Return to baseline appears slightly more accelerated for the Fc mutant

PK: Mean exposures were similar (based on Cmax and AUClast) between all treatment groups (within 1.4-fold)

Fab and/or Fc mutations in anti-PCSK9 antibody AK had no significant effect on injection site reactions (ISR) or Pharmacokinetics and Pharmacodynamics (PKPD) profile in nonhuman primates (NHPs) (cynomolgus monkeys).

Fab Mutant: T82(72)R, R94(84)S, S95(85)R; Aho numbering (actual numbering).

Fc Mutant: S(434)K (S440K in EU numbering).

Example 4

Production and Characterization of Low-Viscosity Mutants of GIPR (2G10.006) Antibody AQ Cloning, Expression, Purification and High Concentration Formulation of Low Viscosity Mutants of Antibody AQ GIPR (2G10.006) AQ parent is described in U.S. Provisional Application 62/387,486 as 2G10_LC1.006 (SEQ ID NO: 74 of the cited patent application). The aforementioned US patent application is hereby incorporated by reference. Heavy chain mutant AQ (HC 1, 17, 85) with mutation sites Q1(1)E, R17(16)G, S85(75)A and light chain mutant AQ (LC 4 13 76 95 97 98) with mutation sites M4(4)L, V13 (13)L, A76(60)D, S95(77)R, Q97(79)E, S98(80)P were produced as follows. Synthetic genes for GIPR (2G10.006) (antibody AQ) low viscosity mutants were produced, digested and ligated into plasmid expression vectors. Constructs were verified by DNA sequencing. Stable cell pools were created by electroporation of a clonal CHO host cell line. The pools were cultured under selection until viability reached greater than 85%. Pools were seeding into a fed-batch production culture for 10 days and centrifuged media was harvested.

Figures 20A, 20B:
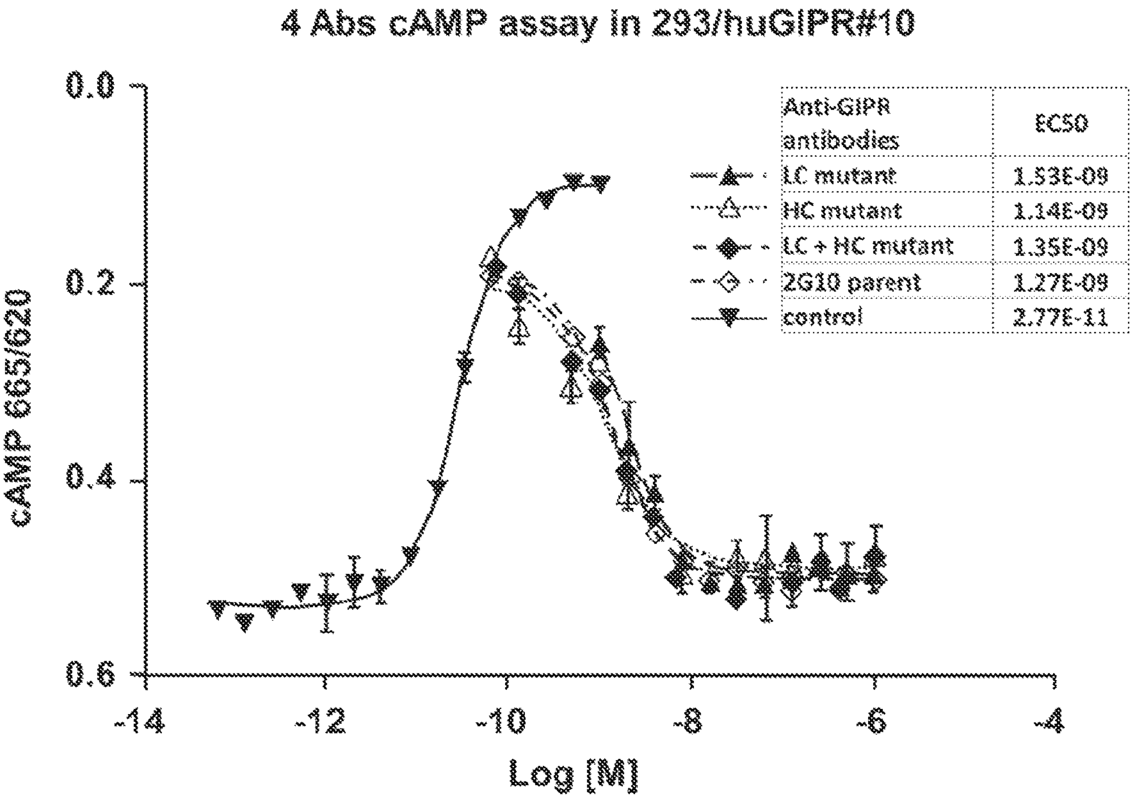
FIG. 20A is a table showing produced and characterized mutants of antibody AQ, including measured concentration and viscosity.
FIG. 20B shows cAMP response of 293/huGIPR cells expressing human GIP receptors activated by GIP and blocked by the anti-GIPR antibodies. The in vitro cAMP activity was equally unaffected by viscosity mutations. The potency remained the same within the error margin of the assay.

Harvested supernatants were sterile filtered and purified through a three column chromatography process consisting of Protein A, cation exchange, and anion exchange, similar to the process described earlier (Shukla et al. (2007), "Downstream processing of monoclonal antibodies—Application of platform approaches," *J. Chrom. B* 848: 28-39). The resulting purified pools were dialyzed into formulation buffer containing 20 mM acetate and 9% sucrose at pH 5.2 (without polysorbate), achieving a final pH of ~5.2 and concentrated to approximately 150 mg/mL above 30 kDa cutoff filter via centrifugal ultrafiltration (FIG. 20A).

Potency Measurements

Potency was measured by an assay utilizing mammalian cells 293/huGIPR expressing glucose-dependent insulinotropic polypeptide receptor (GIPR). The increasing concentrations of anti-GIPR parent AQ and the low-viscosity mutants were blocking the interaction of GIP with GIPR which induced cAMP changes monitored during the assay. An application of the assay was earlier described in Tseng C. C. et al. (1996), "Postprandial stimulation of insulin release by glucose-dependent insulinotropic polypeptide (GIP). Effect of a specific glucose-dependent insulinotropic polypeptide receptor antagonist in the rat," *J. Clin. Invest.* 98: 2440-2445.

Viscosity Measurements

Viscosity analysis of AQ and two low viscosity mutants was performed on an Anton Paar Rheometer using a CP25-1/TG spindle. All measurements were performed at 25° C., controlled by a water bath attached to the sample cup. Viscosity measurements were collected manually with increasing shear rate from 0-2000 rpm. 10 viscosity measurement results at shear rate 1000 1/s and 10 viscosity measurement results at shear rate 2000 1/s were collected for each sample and averaged to report one viscosity value per sample.

It needs to be noted that precision of viscosity measurements is much better that accuracy, because the viscosity measurements are sensitive to even minor changes in some parameters, such as the state of the viscometer, temperature in the room and some other minor parameters at the time of the measurements. Therefore, it is important to measure all samples of interest in one setting or, if samples of interest are measured in two settings, have the same reference standard in both settings.

Results

Anti-GIPR (2G10.006) antibody AQ belongs to high-viscosity germline subfamilies of heavy chain VH3|3-33 and light chain VK3|L16. Several mutations derived from FIGS. 11 and 12 were made in frames in the effort to reduce viscosity of AQ. The viscosity of the parent AQ and the two mutants measured in one viscometer setting revealed the following values: AQ—19.1 cP, AQ (HC 1, 17, 85)—15.8 cP, AQ (LC 4 13 76 95 97 98)—12.7 cP (FIG. 20). The heavy chain mutant AQ (HC 1, 17, 85) mutant was at 83% and the light chain mutant AQ (LC 4 13 76 95 97 98) was at 67% relative to the parent AQ. FIGS. 7 and 8 illustrate positions of the mutants on the viscosity versus pI plots for VH3 and VK3 family members. The in vitro cAMP activity was equally unaffected by viscosity mutations. The potency remained the same within the error margin of the in vitro cell-based assay (See FIG. 20B). To summarize, introduced mutations reduced viscosity without loss of the potency.

Example 5

GIPR Low Viscosity Mutant Light Chain V78F (LC V78F in Aho Numbering and LC V62F in Linear Numbering)

GIPR (2G10.006) antibody AQ showed a high viscosity of 23 cP at 150 mg/mL in A52Su formulation. This antibody featured a low-frequency residue V78 in Aho numbering (V62 in linear numbering) in the kappa light chain (LC V78 Aho). The frequency of occurrence of V78 is <1%, while F78 is >98% in light chain sequences related to the kappa germline. The residue LC V78 attracted attention, because it was a covariance violator. Covariance analysis allows establishing pair-wise conserved-residue positions based on the physiochemical properties of the residues in variable regions of antibodies, identifying incorrectly positioned residues (which are often non-germline residues). Covariance analysis further may suggest replacing the amino acids at the deviating positions with more common germline sequences that lead to a large conformational change uncovered by molecular-dynamics simulations (Kannan G., "Method of correlated mutational analysis to improve therapeutic antibodies," U.S. Ser. No. 61/451,929, PCT/US 2012/028596, WO 2012/125495). In an effort to eliminate the covariance violation and increase the percentage of human sequences, the LC V78F mutation was introduced in the GIPR (2G10.006) antibody AQ.

Unexpectedly, viscosity of the mutant decreased by 25%, while maintaining similar potency for human GIPR as measured in cAMP (cell-based) assays. Both sequences, the GIPR (2G10.006) AQ parent and its LC V78F mutant are described in U.S. Provisional Application 62/387,486 as 2G10 LC1.006 (SEQ ID NO: 74 of the cited application) and 2G10_LC1.003 (SEQ ID NO: 71 of the cited application), respectively. The US patent application is hereby incorporated by reference. Newly discovered in the present invention is that such substitution resulted in about 25% reduction of viscosity by LC V78F mutation. Viscosity analysis of the GIPR 2G10.006 AQ and its V78F mutant was performed at 150 mg/ml in formulation containing 20 mM acetate, 9% sucrose at pH 5.2, 0.01% polysorbate 80, 1000 shear rate and 25 C using AR-G2 Magnetic Bearing Cone and Plate Rheometer from TA Instruments—Waters LLC. Cone plate size was 20 mm in diameter, 1.988° cone angle, equipped with Steel-990918 Peltier plate and operated using the Flow Sweep procedure. The measured viscosity values were 21 cP for GIPR_2G10.006 and 15.3 cP for GIPR (2G10.003) LC V78F mutant, which is 25% decrease in viscosity.

As noted in the previous example, precision of viscosity measurements is much better that accuracy. Viscosity at 150 mg/mL with 0.01% polysorbate is typically 10% lower than without polysorbate, which was observed in case of GIPR (2G10.006). Its viscosity was 23 cP without polysorbate (as for all 43 antibodies) and 21 cP with polysorbate.

Example 6

Cynomolgus Monkey Study

The antibodies designated as AK (control, also known as AMG 145 and evolocumab) and the Fab mutant, Fc mutant, and double mutant shown in Example 3 were generated using the methodology disclosed in Examples 1 and 2. The pharmacokinetic properties of these antibodies were tested in vivo by single subcutaneous bolus injection into male cynomolgus monkeys.

Study Design

The study was conducted in male cynomolgus monkeys. The animals were 2.7 to 3.8 years old and weighted between 2.9 to 3.8 kg. The animals were acclimated to laboratory housing for 7 days before the initiation of dosing. Criteria for selection included acceptable results from the pretreatment cholesterol levels (including LDL and HDL) levels.

Before the initiation of dosing, all animals were randomized and assigned to groups using a computer-based randomization procedure.

The test and control articles were administered subcutaneously into the mid-dorsal areas to the appropriate animals once on Day 1. The injection site(s) were shaved prior to administration and marked with indelible ink. The animals were temporarily restrained for dose administration and were not sedated. The dose volume for each animal was based on the most recent body weight measurement. For Groups 1 and 2, dose solutions were administered via 2 subcutaneous injections on the back of each animal (1 with test material, 1 with diluent). Injection sites were at least 5-6 cm apart. The test material was administered on the right of the spinal column for each animal. The diluent was delivered on the left of the spinal column for each animal. For Groups 3 and 4, dose solutions were administered via a single subcutaneous injection on the back of each animal. Dose levels and volumes for each group are summarized in FIG. 21.

Blood samples were collected by venipuncture into tubes containing Potassium (K2) EDTA at various time points over the duration of the in-life portion of this study (43 days). Animals were not fasted prior to serum chemistry blood collections.

Samples were chilled following blood collections, and split for preparation of either serum or plasma. Samples were mixed gently and centrifuged. Blood samples were maintained on wet ice immediately after collection until centrifuged (1500-2000×g for approximately 10 minutes) at approximately 4° C. The resultant plasma or serum was separated and divided into 2 aliquots (primary and backup), transferred to appropriately labeled polypropylene tubes, and stored in a freezer set to maintain at −80° C. until analysis. Plasma samples were used to determine test article concentration for pharmacokinetic evaluation, serum samples were analyzed for cholesterol, HDL, and LDL.

Pharmacokinetic Evaluation

Plasma samples were analyzed for concentration of each test antibody (antibody AK, AK Fab mutant, AK S440K Fc mutant, and AK Fab/S440K double mutant) using an enzyme-linked immunosorbent assay (ELISA). The assay uses recombinant human PCSK9 as the capture reagent and a horseradish peroxidase labeled antibody to human IgG1 as the detection reagent. Standards and quality control samples (QCs) are prepared by spiking antibody AK or low viscosity homologs into 100% cynomolgus monkey K2-EDTA pool. Costar 96-well microplate wells (Corning Incorporated) are coated with recombinant human PCSK9. After a blocking step, the standards, matrix blank (NSB), QCs (QCs) and test samples are loaded into the microplate wells after pre-treating with a dilution factor of 100 in Blocker™ BLOTTO in TBS (Thermo Scientific). The antibody AK in the samples is captured by the immobilized recombinant human PCSK9 coated on the microplate. Unbound material is removed by washing the microplate wells. Following washing, mouse anti-human IgG, Ab35, HRP conjugated detection antibody is added to the microplate wells to bind the captured antibody AK. Unbound detection antibody is removed by washing the microplate wells. A one component TMB solution is added to the microplate wells for the detection of bound mouse anti-human IgG Ab35 HRP conjugate. The TMB substrate solution reacts with peroxide and, in the presence of HRP, creates a colorimetric signal that is proportional to the amount of antibody AK, or low viscosity mutant homolog, bound by the capture reagent. The color development is stopped using 2N sulfuric acid and the intensity of the color (optical density or OD) is measured at 450 nm minus 650 nm. Data are reduced using Watson version 7.4 SP3 (or later) data reduction package using a 4 parameter (Marquardt) regression model with a weighting factor of 1.

Pharmacokinetic parameters were estimated using WinNonlin pharmacokinetic software. A non-compartmental approach consistent with the subcutaneous route of administration was used for parameter estimation. All parameters were generated from individual concentrations in plasma from Day 1. The following parameters were determined Tmax (the time after dosing at which the maximum observed concentration was observed), Cmax (the maximum observed concentration measured after dosing), AUC (0-t) (the area under the concentration versus time curve from the start of dose administration to the time after dosing at which the last observed quantifiable concentration using the linear or linear/log trapezoidal method), AUC (0-t)/D (the AUC(0-t) divided by the dose administered), and RAUC (the area under the curve from T1 and T2 at steady state divided by the area under the curve from T1 to T2 during the initial dosing interval).

Results and Discussion

Figure 24A:
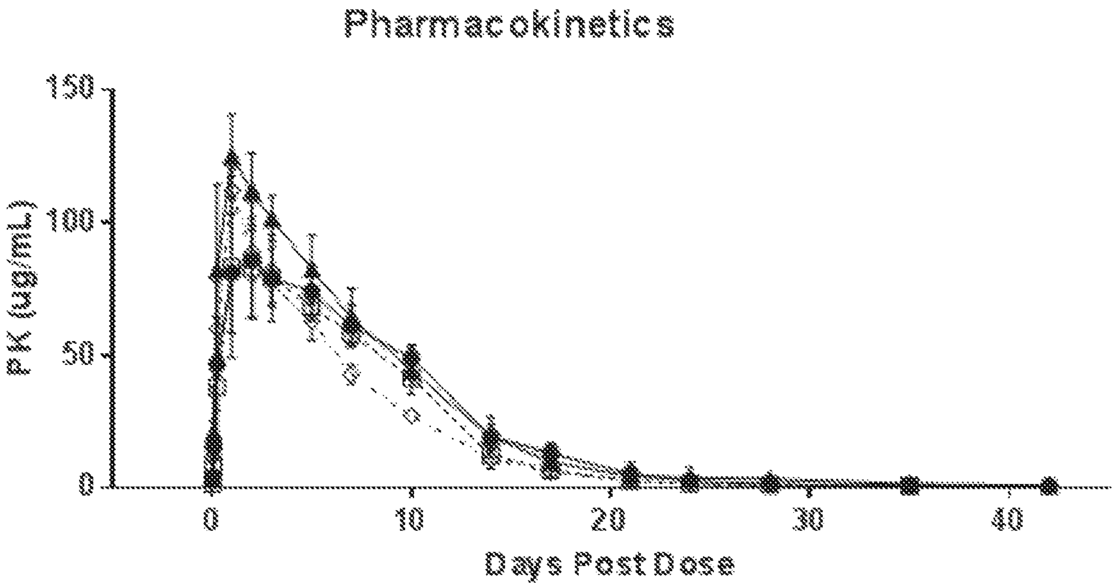
FIGS. 24A and 24B show a pharmacokinetic profile (μg/mL) with corresponding low density lipoprotein (LDL) concentration (mg/dL) profile in plasma. LDL concentrations and test article serum concentrations are presented as mean values from four animals. Solid circles with a solid line indicate the serum concentrations of the parent antibody AK. Open squares with a dashed line indicate the serum concentrations of the antibody bearing the Fab mutation. Solid triangles with a solid line indicate the serum concentrations of the antibody bearing the Fc mutation. Open diamonds with a dashed line indicate the serum concentrations of the antibody bearing both the Fab and Fc mutations. These data indicate that presence of a mutation in the Fc region that reduces viscosity of the antibody formulation results in a reduced time to Tmax and a higher Cmax. All the mutant forms of the parent antibody retain the ability to lower serum LDL-C (lower panel).
Figure 24B:
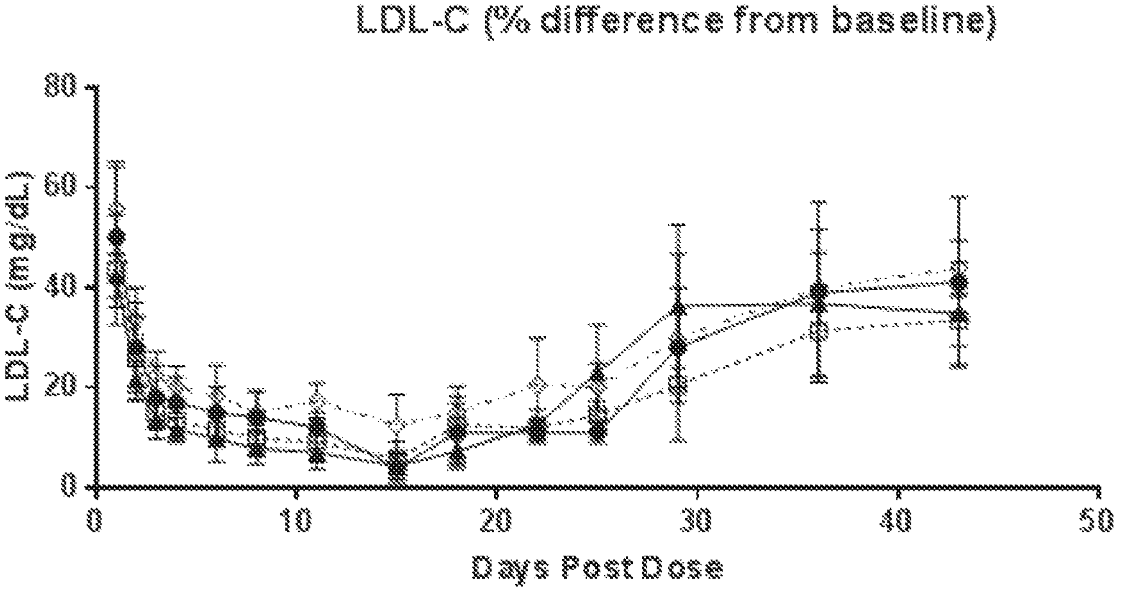

Test article concentrations plotted versus time are shown in FIGS. 24A and 24B (mean concentrations for each test article, n=4 at each time point). Pharmacokinetic parameters for the four test articles are summarized in FIG. 22. Antibodies containing the Fc mutation S440K (both antibody AK (Fc mutant) and antibody AK (Fc and Fab double mutant)) show a reduced Tmax (0.81 and 1 days respectively versus 2.5 days) and increased Cmax (125 and 112 μg/mL respectively versus 87.8 μg/mL) relative to antibody AK (control) and antibody AK (Fab mutant) indicating antibodies containing an Fc mutation that reduces viscosity are distributing more rapidly to the circulation following subcutaneous injection.

Administration of all low viscosity homologues of antibody AK resulted in expected pharmacologic mild to moderate decreases in low density lipoprotein (LDL) associated with decreased total cholesterol concentration compared to baseline (Day −6). The magnitude of decrease for total and low density lipoprotein cholesterol following administration of AK Fab mutant and AK S440K Fc mutant was generally similar to control animals with a trend toward recovery to baseline of AK S440K Fc mutant on Day 25 and AK (control) and AK Fab mutant on Day 29. The magnitude of decrease in total and low density lipoprotein cholesterol for AK Fab/S440K double mutant was generally less pronounced compared to control (antibody AK at 10 mg/kg). There were no changes in high density lipoprotein in any AK low viscosity homologue. Percentage changes in LDL-C relative to baseline are tabulated in FIG. 23 and are plotted versus time in FIGS. 24A and 24B.

ABBREVIATIONS

Abbreviated terms used throughout this specification are defined as follows.

AEI allelic expression imbalance

ANOVA analysis of variance

AUC area under the curve

BSA bovine serum albumin

DMEM Dulbecco's Modified Eagle Medium

DMSO dimethyl sulfoxide

EDC 1-ethyl-3-[3-dimethylaminopropyl] carbodiimide hydrochloride
EDTA ethylenediaminetetraacetic acid
ELISA enzyme-linked immunosorbent assay
eQTL expression quantitative trait loci
ESI-TOF electrospray ionization time of flight
FACS fluorescence-activated cell sorting
FBS fetal bovine serum
FPLC fast protein liquid chromatography
FVB a strain of mice inbred for the Friend leukemia virus 1b (Fv1b) allele
H&E Hematoxylin and eosin
HA hypoxanthine
HIC hydrophobic interaction chromatography
HPLC high performance liquid chromatography
HRP horseradish peroxidase
HUVEC human umbilical vein epithelial cell
IBD inflammatory bowel disease
IDMEM DMEM without glutamine
IFN interferon
IL interleukin
MCP monocyte chemotactic protein
MSD macromolecular structure database
PBMC peripheral blood mononuclear cell
PBS phosphate-buffered saline
PCR polymerase chain reaction
PEG polyethylene glycol
PEI polyethylenimine
QTL quantitative trait loci
RPMI media developed at Roswell Park Memorial Institute
SNP single nucleotide polymorphism
TFA trifluoroacetic acid
TMB 3,3',5,5'-Tetramethylbenzidine

What is claimed is:

1. A method of reducing the viscosity of an antigen binding protein of the VH1|1-18 germline subfamily, which comprises making viscosity-reducing substitutions $82X^1$, $94X^2$, and $95X^3$ in the VH1 amino acid sequence of the antigen binding proteins;

wherein $X^1$ is selected from R, K and H, $X^2$ is selected from S, T, N and Q and $X^3$ is selected from R, K, and H; and wherein the amino acids are numbered according to the Aho numbering system.

2. The method of claim 1, wherein the viscosity-reducing substitutions comprise 82R, 94S, and 95R.

3. The method of claim 1, further comprising modifying the VH1 sequence of an antigen binding protein comprising the VH1|1-18 germline subfamily to comprise substitution 59R.

4. The method of claim 1, which comprises modifying the Fc domain sequence to comprise one or more substitutions selected from 253A, 440K, and 439E.

5. The method of claim 4, which comprises modifying the Fc domain sequence to comprise substitutions 253A, 440K, and 439E.

6. The method of claim 1, wherein the antigen binding protein comprises a heavy chain amino acid sequence comprising SEQ ID NO: 136 except for substitutions 82R, 94S, and 95R, and a light chain amino acid sequence comprising SEQ ID NO: 134.

7. The method of claim 1, wherein the antigen binding protein comprises a heavy chain amino acid sequence comprising SEQ ID NO: 116 except for substitutions 82R, 94S, and 95R, and a light chain amino acid sequence comprising SEQ ID NO: 114.

8. The method of claim 1, wherein the antigen binding protein comprises a heavy chain amino acid sequence comprising SEQ ID NO: 140 except for substitutions 82R, 94S, and 95R, and a light chain amino acid sequence comprising SEQ ID NO: 138.

9. The method of claim 1, wherein the antigen binding protein comprises a heavy chain amino acid sequence comprising SEQ ID NO: 148 except for substitutions 82R, 94S, and 95R, and a light chain amino acid sequence comprising SEQ ID NO: 146.

10. The method of claim 1, wherein the antigen binding protein comprises a heavy chain amino acid sequence comprising SEQ ID NO: 152 except for substitutions 82R, 94S, and 95R, and a light chain amino acid sequence comprising SEQ ID NO: 150.

11. A method of treating a PCSK9-related indication in a patient, which comprises administering to the patient an antibody comprising the heavy and light chain amino acid sequences of SEQ ID NO: 136 and SEQ ID NO: 134, respectively.

12. The method of claim 11, wherein the PCSK9-related indication is hypercholesterolemia.

* * * * *

SEQUENCE LISTING

```
<160> NUMBER OF SEQ ID NOS: 383

<210> SEQ ID NO 1
<211> LENGTH: 705
<212> TYPE: DNA
<213> ORGANISM: Homo sapiens

<400> SEQUENCE: 1

atggaaaccc cggcgcagct gctgtttctg ctgctgctgt ggctgccgga taccaccggc     60

gaaattgtgt tgacgcagtc tccaggcacc ctgtctttgt ctccagggga cagagccacc    120

ctctcctgca gggccagtca gagtgttagt agcagctact tgcctggta ccagcagaaa    180

cctggccagg ctcccaggct cctcatttat ggtgcatcca gtagggccac tggcatccca    240

gacaggttca gtggcagtgg gtctgggaca gacttcactc tcaccatcag cagactggag    300

cctgaagatt ttgcagtgta ttactgtcag cagtatgata ggtcacctcg gacgttcggc    360

caagggacca aggtggaaat caaacgtacg gtggctgcac catctgtctt catcttcccg    420

ccatctgatg agcagttgaa atctggaact gcctctgttg tgtgcctgct gaataacttc    480

tatcccagag aggccaaagt acagtggaag gtggataacg ccctccaatc gggtaactcc    540

caggagagtg tcacagagca ggacagcaag gacagcacct acagcctcag cagcaccctg    600

acgctgagca aagcagacta cgagaaacac aaagtctacg cctgcgaagt cacccatcag    660

ggcctgagct cgcccgtcac aaagagcttc aacaggggag agtgt                   705


<210> SEQ ID NO 2
<211> LENGTH: 235
<212> TYPE: PRT
<213> ORGANISM: Homo sapiens

<400> SEQUENCE: 2

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Asp Arg Ala Thr Leu Ser Cys Arg Ala Ser Gln Ser
        35                  40                  45

Val Ser Ser Ser Tyr Phe Ala Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80
```

```
Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Asp Arg Ser Pro Arg Thr Phe Gly Gln Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

<210> SEQ ID NO 3
<211> LENGTH: 1389
<212> TYPE: DNA
<213> ORGANISM: Homo sapiens

<400> SEQUENCE: 3

```
atggattgga cctggcgtat tctgtttctg gtggcggcgg cgaccggcgc gcatagccag      60

gtgcagctgg tgcagtctgg ggctgaggtg aagaagcctg gggcctcagt gaaggtctcc     120

tgtaagtctt ctggatacac cttcaccggc tactatatgc actgggtgcg acaggcccct     180

ggacaagggc ttgagtggat gggatggatc aaccctaaca gtggtggcac aaactatgca     240

cagaagttta agggcagggt caccatgacc agggacacgt ccatcagcac agcctacatg     300

gagctgagca ggctgagatc tgacgacacg gccgtgtatt actgtgcgag agataagtgg     360

ctggacggct ttgactactg gggccaggga accctggtca ccgtctcctc agctagcacc     420

aagggcccat cggtcttccc cctggcgccc tgctccagga gcacctccga gagcacagcg     480

gccctgggct gcctggtcaa ggactacttc cccgaaccgg tgacggtgtc gtggaactca     540

ggcgctctga ccagcggcgt gcacaccttc ccagctgtcc tacagtcctc aggactctac     600

tccctcagca gcgtggtgac cgtgccctcc agcaacttcg gcacccagac ctacacctgc     660

aacgtagatc acaagcccag caacaccaag gtggacaaga cagttgagcg caaatgttgt     720

gtcgagtgcc caccgtgccc agcaccacct gtggcaggac cgtcagtctt cctcttcccc     780

ccaaaaccca aggacaccct catgatctcc cggacccctg aggtcacgtg cgtggtggtg     840

gacgtgagcc acgaagaccc cgaggtccag ttcaactggt acgtggacgg cgtggaggtg     900

cataatgcca agacaaagcc acgggaggag cagttcaaca gcacgttccg tgtggtcagc     960

gtcctcaccg ttgtgcacca ggactggctg aacggcaagg agtacaagtg caaggtctcc    1020

aacaaaggcc tcccagcccc catcgagaaa accatctcca aaaccaaagg gcagccccga    1080

gaaccacagg tgtacaccct gcccccatcc cgggaggaga tgaccaagaa ccaggtcagc    1140

ctgacctgcc tggtcaaagg cttctacccc agcgacatcg ccgtggagtg ggagagcaat    1200

gggcagccgg agaacaacta caagaccaca cctcccatgc tggactccga cggctccttc    1260
```

ttcctctaca gcaagctcac cgtggacaag agcaggtggc agcaggggaa cgtcttctca 1320
tgctccgtga tgcatgaggc tctgcacaac cactacacgc agaagagcct ctccctgtct 1380
ccgggtaaa 1389

<210> SEQ ID NO 4
<211> LENGTH: 463
<212> TYPE: PRT
<213> ORGANISM: Homo sapiens

<400> SEQUENCE: 4

Met Asp Trp Thr Trp Arg Ile Leu Phe Leu Val Ala Ala Ala Thr Gly
1 5 10 15

Ala His Ser Gln Val Gln Leu Val Gln Ser Gly Ala Glu Val Lys Lys
20 25 30

Pro Gly Ala Ser Val Lys Val Ser Cys Lys Ser Ser Gly Tyr Thr Phe
35 40 45

Thr Gly Tyr Tyr Met His Trp Val Arg Gln Ala Pro Gly Gln Gly Leu
50 55 60

Glu Trp Met Gly Trp Ile Asn Pro Asn Ser Gly Gly Thr Asn Tyr Ala
65 70 75 80

Gln Lys Phe Lys Gly Arg Val Thr Met Thr Arg Asp Thr Ser Ile Ser
85 90 95

Thr Ala Tyr Met Glu Leu Ser Arg Leu Arg Ser Asp Asp Thr Ala Val
100 105 110

Tyr Tyr Cys Ala Arg Asp Lys Trp Leu Asp Gly Phe Asp Tyr Trp Gly
115 120 125

Gln Gly Thr Leu Val Thr Val Ser Ser Ala Ser Thr Lys Gly Pro Ser
130 135 140

Val Phe Pro Leu Ala Pro Cys Ser Arg Ser Thr Ser Glu Ser Thr Ala
145 150 155 160

Ala Leu Gly Cys Leu Val Lys Asp Tyr Phe Pro Glu Pro Val Thr Val
165 170 175

Ser Trp Asn Ser Gly Ala Leu Thr Ser Gly Val His Thr Phe Pro Ala
180 185 190

Val Leu Gln Ser Ser Gly Leu Tyr Ser Leu Ser Ser Val Val Thr Val
195 200 205

Pro Ser Ser Asn Phe Gly Thr Gln Thr Tyr Thr Cys Asn Val Asp His
210 215 220

Lys Pro Ser Asn Thr Lys Val Asp Lys Thr Val Glu Arg Lys Cys Cys
225 230 235 240

Val Glu Cys Pro Pro Cys Pro Ala Pro Pro Val Ala Gly Pro Ser Val
245 250 255

Phe Leu Phe Pro Pro Lys Pro Lys Asp Thr Leu Met Ile Ser Arg Thr
260 265 270

Pro Glu Val Thr Cys Val Val Val Asp Val Ser His Glu Asp Pro Glu
275 280 285

Val Gln Phe Asn Trp Tyr Val Asp Gly Val Glu Val His Asn Ala Lys
290 295 300

Thr Lys Pro Arg Glu Glu Gln Phe Asn Ser Thr Phe Arg Val Val Ser
305 310 315 320

Val Leu Thr Val Val His Gln Asp Trp Leu Asn Gly Lys Glu Tyr Lys
325 330 335

Cys Lys Val Ser Asn Lys Gly Leu Pro Ala Pro Ile Glu Lys Thr Ile 340 345 350

Ser Lys Thr Lys Gly Gln Pro Arg Glu Pro Gln Val Tyr Thr Leu Pro
355 360 365

Pro Ser Arg Glu Glu Met Thr Lys Asn Gln Val Ser Leu Thr Cys Leu
370 375 380

Val Lys Gly Phe Tyr Pro Ser Asp Ile Ala Val Glu Trp Glu Ser Asn
385 390 395 400

Gly Gln Pro Glu Asn Asn Tyr Lys Thr Thr Pro Pro Met Leu Asp Ser
405 410 415

Asp Gly Ser Phe Phe Leu Tyr Ser Lys Leu Thr Val Asp Lys Ser Arg
420 425 430

Trp Gln Gln Gly Asn Val Phe Ser Cys Ser Val Met His Glu Ala Leu
435 440 445

His Asn His Tyr Thr Gln Lys Ser Leu Ser Leu Ser Pro Gly Lys
450 455 460

<210> SEQ ID NO 5
<211> LENGTH: 726
<212> TYPE: DNA
<213> ORGANISM: Homo sapiens

<400> SEQUENCE: 5
atggacatga gggtgcccgc tcagctcctg gggctcctgc tgctgtggct gagaggtgcg 60
cgctgtgata ttgtgatgac ccagactcca ctctccctgc ccgtcacccc tggagagccg 120
gcctccatct cctgcaggtc tagtcagagc ctcttgaata gtgttgatgg aagcaccaat 180
ttggactggt atctgcagaa gccagggcag tctccacagc tcctgatcta tacgctttcc 240
tatcgggcct ctggagtccc agacaggttc agtggcagtg ggtcaggcac tgacttcaca 300
ctgaaaatca gcagggtgga ggctgaggat gttggagttt attactgcat gcaacgtata 360
gagtttccgc tcactttcgg cggagggacc aaggtggaga tcaaacgtac ggtggctgca 420
ccatctgtct tcatcttccc gccatctgat gagcagttga aatctggaac tgcctctgtt 480
gtgtgcctgc tgaataactt ctatcccaga gaggccaaag tacagtggaa ggtggataac 540
gccctccaat cgggtaactc ccaggagagt gtcacagagc aggacagcaa ggacagcacc 600
tacagcctca gcagcaccct gacgctgagc aaagcagact acgagaaaca caaagtctac 660
gcctgcgaag tcacccatca gggcctgagc tcgcccgtca caaagagctt caacagggga 720
gagtgt 726

<210> SEQ ID NO 6
<211> LENGTH: 242
<212> TYPE: PRT
<213> ORGANISM: Homo sapiens

<400> SEQUENCE: 6

Met Asp Met Arg Val Pro Ala Gln Leu Leu Gly Leu Leu Leu Leu Trp
1 5 10 15

Leu Arg Gly Ala Arg Cys Asp Ile Val Met Thr Gln Thr Pro Leu Ser
20 25 30

Leu Pro Val Thr Pro Gly Glu Pro Ala Ser Ile Ser Cys Arg Ser Ser
35 40 45

Gln Ser Leu Leu Asn Ser Val Asp Gly Ser Thr Asn Leu Asp Trp Tyr
50 55 60

Leu Gln Lys Pro Gly Gln Ser Pro Gln Leu Leu Ile Tyr Thr Leu Ser
65 70 75 80

-continued

```
Tyr Arg Ala Ser Gly Val Pro Asp Arg Phe Ser Gly Ser Gly Ser Gly
                85                  90                  95

Thr Asp Phe Thr Leu Lys Ile Ser Arg Val Glu Ala Glu Asp Val Gly
            100                 105                 110

Val Tyr Tyr Cys Met Gln Arg Ile Glu Phe Pro Leu Thr Phe Gly Gly
        115                 120                 125

Gly Thr Lys Val Glu Ile Lys Arg Thr Val Ala Ala Pro Ser Val Phe
    130                 135                 140

Ile Phe Pro Pro Ser Asp Glu Gln Leu Lys Ser Gly Thr Ala Ser Val
145                 150                 155                 160

Val Cys Leu Leu Asn Asn Phe Tyr Pro Arg Glu Ala Lys Val Gln Trp
                165                 170                 175

Lys Val Asp Asn Ala Leu Gln Ser Gly Asn Ser Gln Glu Ser Val Thr
            180                 185                 190

Glu Gln Asp Ser Lys Asp Ser Thr Tyr Ser Leu Ser Ser Thr Leu Thr
        195                 200                 205

Leu Ser Lys Ala Asp Tyr Glu Lys His Lys Val Tyr Ala Cys Glu Val
    210                 215                 220

Thr His Gln Gly Leu Ser Ser Pro Val Thr Lys Ser Phe Asn Arg Gly
225                 230                 235                 240

Glu Cys


<210> SEQ ID NO 7
<211> LENGTH: 1395
<212> TYPE: DNA
<213> ORGANISM: Homo sapiens

<400> SEQUENCE: 7

atggagttgg ggctgtgctg ggttttcctt gttgctattt tagaaggtgt ccagtgtgag     60

gtgcagctgg tggagtctgg gggaggcttg gtacagcctg gggggtccct gagactctcc    120

tgtgcagcct ctggattcac cttcagtagc tatagcatga actgggtccg ccaggctcca    180

gggaaggggc tggagtgggt ttcatacatt agtagtagtg gtagttccat atactacgca    240

gactctgtga agggccgatt caccatctcc agagacaatg ccaagaactc actgtatctg    300

caaatgaaca gcctgagaga cgaggacacg gctgtgtatt actgtgcgag agagaggtac    360

tacggtgaca cgccctttga ctactggggc cagggaaccc tggtcaccgt ctctagtgcc    420

tccaccaagg gcccatcggt cttcccctg gcgccctgct ccaggagcac ctccgagagc    480

acagcggccc tgggctgcct ggtcaaggac tacttccccg aaccggtgac ggtgtcgtgg    540

aactcaggcg ctctgaccag cggcgtgcac accttcccag ctgtcctaca gtcctcagga    600

ctctactccc tcagcagcgt ggtgaccgtg ccctccagca acttcggcac ccagacctac    660

acctgcaacg tagatcacaa gcccagcaac accaaggtgg acaagacagt tgagcgcaaa    720

tgttgtgtcg agtgcccacc gtgcccagca ccacctgtgg caggaccgtc agtcttcctc    780

ttccccccaa aacccaagga caccctcatg atctcccgga cccctgaggt cacgtgcgtg    840

gtggtggacg tgagccacga agaccccgag gtccagttca actggtacgt ggacggcgtg    900

gaggtgcata atgccaagac aaagccacgg gaggagcagt tcaacagcac gttccgtgtg    960

gtcagcgtcc tcaccgttgt gcaccaggac tggctgaacg gcaaggagta caagtgcaag   1020

gtctccaaca aaggcctccc agcccccatc gagaaaacca tctccaaaac caaagggcag   1080

ccccgagaac cacaggtgta caccctgccc ccatcccggg aggagatgac caagaaccag   1140
```

-continued

```
gtcagcctga cctgcctggt caaaggcttc taccccagcg acatcgccgt ggagtgggag   1200

agcaatgggc agccggagaa caactacaag accacacctc ccatgctgga ctccgacggc   1260

tccttcttcc tctacagcaa gctcaccgtg gacaagagca ggtggcagca ggggaacgtc   1320

ttctcatgct ccgtgatgca tgaggctctg cacaaccact acacgcagaa gagcctctcc   1380

ctgtctccgg gtaaa                                                    1395


<210> SEQ ID NO 8
<211> LENGTH: 465
<212> TYPE: PRT
<213> ORGANISM: Homo sapiens

<400> SEQUENCE: 8

Met Glu Leu Gly Leu Cys Trp Val Phe Leu Val Ala Ile Leu Glu Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ser Met Asn Trp Val Arg Gln Ala Pro Gly Lys Gly Leu
    50                  55                  60

Glu Trp Val Ser Tyr Ile Ser Ser Ser Gly Ser Ser Ile Tyr Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Asp Glu Asp Thr Ala Val
            100                 105                 110

Tyr Tyr Cys Ala Arg Glu Arg Tyr Tyr Gly Asp Thr Pro Phe Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Asn Phe Gly Thr Gln Thr Tyr Thr Cys Asn Val
    210                 215                 220

Asp His Lys Pro Ser Asn Thr Lys Val Asp Lys Thr Val Glu Arg Lys
225                 230                 235                 240

Cys Cys Val Glu Cys Pro Pro Cys Pro Ala Pro Pro Val Ala Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Phe Arg Val
305                 310                 315                 320

Val Ser Val Leu Thr Val Val His Gln Asp Trp Leu Asn Gly Lys Glu
```

```
                325                 330                 335

Tyr Lys Cys Lys Val Ser Asn Lys Gly Leu Pro Ala Pro Ile Glu Lys
            340                 345                 350

Thr Ile Ser Lys Thr Lys Gly Gln Pro Arg Glu Pro Gln Val Tyr Thr
        355                 360                 365

Leu Pro Pro Ser Arg Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Met Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465


<210> SEQ ID NO 9
<211> LENGTH: 699
<212> TYPE: DNA
<213> ORGANISM: Homo sapiens

<400> SEQUENCE: 9

atgtcgccat cacaactcat tgggtttctg ctgctctggg ttccagcctc caggggtgaa      60

attgtgctga ctcagtctcc agactttcag tctgtgactc caaaggagaa agtcaccatc     120

acctgccggg ccagtcagag cattggtagt agcttacact ggtaccagca gaaaccagat     180

cagtctccaa agctcctcat caagtatgct tcccagtcct tctcaggggt cccctcgagg     240

ttcagtggca gtggatctgg gacagatttc accctcacca tcaatagcct ggaagctgaa     300

gatgctgcag cgtattactg tcatcagagt agtagtttac ctctcacttt cggcggaggg     360

accaaggtgg agatcaaacg aactgtggct gcaccatctg tcttcatctt cccgccatct     420

gatgagcagt tgaaatctgg aactgcctct gttgtgtgcc tgctgaataa cttctatccc     480

agagaggcca aagtacagtg gaaggtggat aacgccctcc aatcgggtaa ctcccaggag     540

agtgtcacag agcaggacag caaggacagc acctacagcc tcagcagcac cctgacgctg     600

agcaaagcag actacgagaa acacaaagtc tacgcctgcg aagtcaccca tcagggcctg     660

agctcgcccg tcacaaagag cttcaacagg ggagagtgt                            699


<210> SEQ ID NO 10
<211> LENGTH: 233
<212> TYPE: PRT
<213> ORGANISM: Homo sapiens

<400> SEQUENCE: 10

Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Asp Phe Gln Ser Val
            20                  25                  30

Thr Pro Lys Glu Lys Val Thr Ile Thr Cys Arg Ala Ser Gln Ser Ile
        35                  40                  45

Gly Ser Ser Leu His Trp Tyr Gln Gln Lys Pro Asp Gln Ser Pro Lys
```

-continued

```
    50                  55                  60

Leu Leu Ile Lys Tyr Ala Ser Gln Ser Phe Ser Gly Val Pro Ser Arg
65                  70                  75                  80

Phe Ser Gly Ser Gly Ser Gly Thr Asp Phe Thr Leu Thr Ile Asn Ser
                85                  90                  95

Leu Glu Ala Glu Asp Ala Ala Ala Tyr Tyr Cys His Gln Ser Ser Ser
            100                 105                 110

Leu Pro Leu Thr Phe Gly Gly Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 11
<211> LENGTH: 1389
<212> TYPE: DNA
<213> ORGANISM: Homo sapiens

<400> SEQUENCE: 11

```
atggggtcaa ccgccatcct cgccctcctc ctggctgttc tccaaggagt ctgtgccgag      60

gtgcagctga tgcagtctgg agcagaggtg aaaaagcccg gggagtctct gaagatctcc     120

tgtaagggtt ctggatacag cttttccttc cactggatcg cctgggtgcg ccagatgccc     180

gggaaaggcc tggagtggat ggggatcatc catcctggtg cctctgatac cagatacagc     240

ccgtccttcc aaggccaggt caccatctca gccgacaact ccaacagcgc cacctacctg     300

cagtggagca gcctgaaggc ctcggacacc gccatgtatt tctgtgcgag acaaagggaa     360

ctcgactact ttgactactg gggccaggga accctggtca ccgtctctag tgcctccacc     420

aagggcccat cggtcttccc cctggcgccc tgctccagga gcacctccga gagcacagcg     480

gccctgggct gcctggtcaa ggactacttc cccgaaccgg tgacggtgtc gtggaactca     540

ggcgctctga ccagcggcgt gcacaccttc ccagctgtcc tacagtcctc aggactctac     600

tccctcagca gcgtggtgac cgtgccctcc agcaacttcg gcacccagac ctacacctgc     660

aacgtagatc acaagcccag caacaccaag gtggacaaga cagttgagcg caaatgttgt     720

gtcgagtgcc caccgtgccc agcaccacct gtggcaggac cgtcagtctt cctcttcccc     780

ccaaaaccca aggacaccct catgatctcc cggacccctg aggtcacgtg cgtggtggtg     840

gacgtgagcc acgaagaccc cgaggtccag ttcaactggt acgtggacgg cgtggaggtg     900

cataatgcca agacaaagcc acgggaggag cagttcaaca gcacgttccg tgtggtcagc     960

gtcctcaccg ttgtgcacca ggactggctg aacggcaagg agtacaagtg caaggtctcc    1020

aacaaaggcc tcccagcccc catcgagaaa accatctcca aaaccaaagg gcagccccga    1080
```

gaaccacagg tgtacaccct gcccccatcc cgggaggaga tgaccaagaa ccaggtcagc 1140
ctgacctgcc tggtcaaagg cttctacccc agcgacatcg ccgtggagtg ggagagcaat 1200
gggcagccgg agaacaacta caagaccaca cctcccatgc tggactccga cggctccttc 1260
ttcctctaca gcaagctcac cgtggacaag agcaggtggc agcaggggaa cgtcttctca 1320
tgctccgtga tgcatgaggc tctgcacaac cactacacgc agaagagcct ctccctgtct 1380
ccgggtaaa 1389

<210> SEQ ID NO 12
<211> LENGTH: 463
<212> TYPE: PRT
<213> ORGANISM: Homo sapiens

<400> SEQUENCE: 12

Met Gly Ser Thr Ala Ile Leu Ala Leu Leu Leu Ala Val Leu Gln Gly
1 5 10 15

Val Cys Ala Glu Val Gln Leu Met Gln Ser Gly Ala Glu Val Lys Lys
20 25 30

Pro Gly Glu Ser Leu Lys Ile Ser Cys Lys Gly Ser Gly Tyr Ser Phe
35 40 45

Ser Phe His Trp Ile Ala Trp Val Arg Gln Met Pro Gly Lys Gly Leu
50 55 60

Glu Trp Met Gly Ile Ile His Pro Gly Ala Ser Asp Thr Arg Tyr Ser
65 70 75 80

Pro Ser Phe Gln Gly Gln Val Thr Ile Ser Ala Asp Asn Ser Asn Ser
85 90 95

Ala Thr Tyr Leu Gln Trp Ser Ser Leu Lys Ala Ser Asp Thr Ala Met
100 105 110

Tyr Phe Cys Ala Arg Gln Arg Glu Leu Asp Tyr Phe Asp Tyr Trp Gly
115 120 125

Gln Gly Thr Leu Val Thr Val Ser Ser Ala Ser Thr Lys Gly Pro Ser
130 135 140

Val Phe Pro Leu Ala Pro Cys Ser Arg Ser Thr Ser Glu Ser Thr Ala
145 150 155 160

Ala Leu Gly Cys Leu Val Lys Asp Tyr Phe Pro Glu Pro Val Thr Val
165 170 175

Ser Trp Asn Ser Gly Ala Leu Thr Ser Gly Val His Thr Phe Pro Ala
180 185 190

Val Leu Gln Ser Ser Gly Leu Tyr Ser Leu Ser Ser Val Val Thr Val
195 200 205

Pro Ser Ser Asn Phe Gly Thr Gln Thr Tyr Thr Cys Asn Val Asp His
210 215 220

Lys Pro Ser Asn Thr Lys Val Asp Lys Thr Val Glu Arg Lys Cys Cys
225 230 235 240

Val Glu Cys Pro Pro Cys Pro Ala Pro Pro Val Ala Gly Pro Ser Val
245 250 255

Phe Leu Phe Pro Pro Lys Pro Lys Asp Thr Leu Met Ile Ser Arg Thr
260 265 270

Pro Glu Val Thr Cys Val Val Val Asp Val Ser His Glu Asp Pro Glu
275 280 285

Val Gln Phe Asn Trp Tyr Val Asp Gly Val Glu Val His Asn Ala Lys
290 295 300

Thr Lys Pro Arg Glu Glu Gln Phe Asn Ser Thr Phe Arg Val Val Ser
305 310 315 320

-continued

```
Val Leu Thr Val Val His Gln Asp Trp Leu Asn Gly Lys Glu Tyr Lys
                325                 330                 335

Cys Lys Val Ser Asn Lys Gly Leu Pro Ala Pro Ile Glu Lys Thr Ile
            340                 345                 350

Ser Lys Thr Lys Gly Gln Pro Arg Glu Pro Gln Val Tyr Thr Leu Pro
        355                 360                 365

Pro Ser Arg Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
    450                 455                 460


<210> SEQ ID NO 13
<211> LENGTH: 708
<212> TYPE: DNA
<213> ORGANISM: Homo sapiens

<400> SEQUENCE: 13

atggacatga gggtccccgc tcagctcctg gggctcctgc tgctgtggct gagaggtgcg      60

cgctgtgata tccagatgac ccaatcccct tctagtctgt ccgcttctgt gggcgacagg     120

gttacaataa cttgcaaagc gagccaggac atcaacaaat atgtggcttg gtatcagcaa     180

aaacccggca aggcaccaaa attgctcatt tattacacgt catggctcca gcctggtgta     240

cctagcaggt tttccggctc cggctcaggt accgacttta ctttcactat ctcctcactg     300

cagccggagg acattgccac atactactgt ctccaatatg ataacttgtt gtatactttt     360

gggcaaggaa ctaagctcga gatcaaacgt acggtggctg caccatctgt cttcatcttc     420

ccgccatctg atgagcagtt gaaatctgga actgcctctg ttgtgtgcct gctgaataac     480

ttctatccca gagaggccaa agtacagtgg aaggtggata acgccctcca atcgggtaac     540

tcccaggaga gtgtcacaga gcaggacagc aaggacagca cctacagcct cagcagcacc     600

ctgacgctga gcaaagcaga ctacgagaaa cacaaagtct acgcctgcga agtcacccat     660

cagggcctga gctcgcccgt cacaaagagc ttcaacaggg gagagtgt                  708


<210> SEQ ID NO 14
<211> LENGTH: 236
<212> TYPE: PRT
<213> ORGANISM: Homo sapiens

<400> SEQUENCE: 14

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Lys Ala Ser
        35                  40                  45

Gln Asp Ile Asn Lys Tyr Val Ala Trp Tyr Gln Gln Lys Pro Gly Lys
    50                  55                  60
```

```
Ala Pro Lys Leu Leu Ile Tyr Tyr Thr Ser Trp Leu Gln Pro Gly Val
65                  70                  75                  80

Pro Ser Arg Phe Ser Gly Ser Gly Ser Gly Thr Asp Phe Thr Phe Thr
                85                  90                  95

Ile Ser Ser Leu Gln Pro Glu Asp Ile Ala Thr Tyr Tyr Cys Leu Gln
            100                 105                 110

Tyr Asp Asn Leu Leu Tyr Thr Phe Gly Gln Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 15
<211> LENGTH: 1401
<212> TYPE: DNA
<213> ORGANISM: Homo sapiens

<400> SEQUENCE: 15

```
atggacatga gggtgcccgc tcagctcctg gggctcctgc tgctgtggct gagaggtgcg     60

cgctgtgagg ttcagcttgt ggagtctggc ggcggcctgg tgcagccagg cggttcactc    120

aggctgagct gtgctgcatc agggttcacc ttcagccgtt actggatgaa ctgggtgcgg    180

caagcacccg ggaaaggcct ggagtgggtg gctcagattc gcttgaaaag tgacaattat    240

gccactcact atgcagaaag cgtgaagggg cgctttacaa tttctagaga caacgccaaa    300

aactcactgt acctgcagat gaacagcctc agagctgagg atacagctgt gtattattgt    360

actgaggggc tcgactattg ggacagggc acgacagtga ccgtctctag tgcctccacc    420

aagggcccat cggtcttccc cctggcaccc tcctccaaga gcacctctgg gggcacagcg    480

gccctgggct gcctggtcaa ggactacttc cccgaaccgg tgacggtgtc gtggaactca    540

ggcgccctga ccagcggcgt gcacaccttc ccggctgtcc tacagtcctc aggactctac    600

tccctcagca gcgtggtgac cgtgccctcc agcagcttgg gcacccagac ctacatctgc    660

aacgtgaatc acaagcccag caacaccaag gtggacaaga aagttgagcc caaatcttgt    720

gacaaaactc acacatgccc accgtgccca gcacctgaac tcctgggggg accgtcagtc    780

ttcctcttcc ccccaaaacc caaggacacc ctcatgatct cccggacccc tgaggtcaca    840

tgcgtggtgg tggacgtgag ccacgaagac cctgaggtca agttcaactg gtacgtggac    900

ggcgtggagg tgcataatgc caagacaaag ccgcgggagg agcagtacaa cagcacgtac    960

cgtgtggtca gcgtcctcac cgtcctgcac caggactggc tgaatggcaa ggagtacaag   1020

tgcaaggtct ccaacaaagc cctcccagcc cccatcgaga aaaccatctc caaagccaaa   1080

gggcagcccc gagaaccaca ggtgtacacc ctgcccccat cccgggagga gatgaccaag   1140
```

-continued

```
aaccaggtca gcctgacctg cctggtcaaa ggcttctatc ccagcgacat cgccgtggag   1200

tgggagagca atgggcagcc ggagaacaac tacaagacca cgcctcccgt gctggactcc   1260

gacggctcct tcttcctcta tagcaagctc accgtggaca agagcaggtg gcagcagggg   1320

aacgtcttct catgctccgt gatgcatgag gctctgcaca accactacac gcagaagagc   1380

ctctccctgt ctccgggtaa a                                              1401


<210> SEQ ID NO 16
<211> LENGTH: 467
<212> TYPE: PRT
<213> ORGANISM: Homo sapiens

<400> SEQUENCE: 16

Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Arg Tyr Trp Met Asn Trp Val Arg Gln Ala Pro Gly
    50                  55                  60

Lys Gly Leu Glu Trp Val Ala Gln Ile Arg Leu Lys Ser Asp Asn Tyr
65                  70                  75                  80

Ala Thr His Tyr Ala Glu Ser Val Lys Gly Arg Phe Thr Ile Ser Arg
                85                  90                  95

Asp Asn Ala Lys Asn Ser Leu Tyr Leu Gln Met Asn Ser Leu Arg Ala
            100                 105                 110

Glu Asp Thr Ala Val Tyr Tyr Cys Thr Glu Gly Leu Asp Tyr Trp Gly
        115                 120                 125

Gln Gly Thr Thr Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320
```

```
Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465


<210> SEQ ID NO 17
<211> LENGTH: 708
<212> TYPE: DNA
<213> ORGANISM: Homo sapiens

<400> SEQUENCE: 17

atggacatga gggtcctcgc tcagctcctg gggctcctgc tgctctgttt cccaggtgcc      60

agatgtgaca tccagatgac ccagtctcca tcctcactgt ctgcatctgt aggagacaga     120

gtcaccatca cttgtcgggc gagtcagggt attagcaact ggttagcctg gtatcagcag     180

aaaccagaga aagcccctaa gtccctgatc tatgctgcat ccagtttgca aagtggggtc     240

ccatcaaggt tcagcggcag tggatctggg acagatttca ctctcaccat cagcagcctg     300

cagcctgaag attttgcaac ttattactgc caacagtatg atagttaccc tcggacgttc     360

ggccaaggga ccaaggtgga aatcaaacga actgtggctg caccatctgt cttcatcttc     420

ccgccatctg atgagcagtt gaaatctgga actgcctctg ttgtgtgcct gctgaataac     480

ttctatccca gagaggccaa agtacagtgg aaggtggata acgccctcca atcgggtaac     540

tcccaggaga gtgtcacaga gcaggacagc aaggacagca cctacagcct cagcagcacc     600

ctgacgctga gcaaagcaga ctacgagaaa cacaaagtct acgcctgcga agtcacccat     660

cagggcctga gctcgcccgt cacaaagagc ttcaacaggg gagagtgt                  708


<210> SEQ ID NO 18
<211> LENGTH: 236
<212> TYPE: PRT
<213> ORGANISM: Homo sapiens

<400> SEQUENCE: 18

Met Asp Met Arg Val Leu Ala Gln Leu Leu Gly Leu Leu Leu Leu Cys
1               5                   10                  15

Phe Pro Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45
```

```
Gln Gly Ile Ser Asn Trp Leu Ala Trp Tyr Gln Gln Lys Pro Glu Lys
    50                  55                  60

Ala Pro Lys Ser Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Tyr Asp Ser Tyr Pro Arg Thr Phe Gly Gln Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 19
<211> LENGTH: 1398
<212> TYPE: DNA
<213> ORGANISM: Homo sapiens

<400> SEQUENCE: 19

```
atggagttgg ggctgaactg ggttttcctt gttgctattt tagaaggtgt ccactgtgag     60

gtgcagctgg tggagtctgg gggaggcttg gtccagcctg gggggtccct gagactctcc    120

tgtgcagctt ctggatttac ctttagtagt tattggatga gttgggtccg ccaggctcca    180

gggaaagggc tggagtgggt ggcctacata aagcaagatg gaaatgagaa atactatgtg    240

gactctgtga agggccgatt caccatctcc agagacaacg ccaagaactc attgtatctg    300

caaatgaaca gcctgagagc cgaggacacg gctgtgtatt actgtgcgag ggaagggata    360

ctttggttcg gggacttacc gacgttctgg ggccagggaa ccctggtcac cgtctctagt    420

gcctccacca agggcccatc ggtcttcccc ctggcgccct gctccaggag cacctccgag    480

agcacagcgg ccctgggctg cctggtcaag gactacttcc ccgaaccggt gacggtgtcg    540

tggaactcag gcgctctgac cagcggcgtg cacaccttcc cagctgtcct acagtcctca    600

ggactctact ccctcagcag cgtggtgacc gtgccctcca gcaacttcgg cacccagacc    660

tacacctgca acgtagatca caagcccagc aacaccaagg tggacaagac agttgagcgc    720

aaatgttgtg tcgagtgccc accgtgccca gcaccacctg tggcaggacc gtcagtcttc    780

ctcttccccc caaaacccaa ggacaccctc atgatctccc ggacccctga ggtcacgtgc    840

gtggtggtgg acgtgagcca cgaagacccc gaggtccagt tcaactggta cgtggacggc    900

gtggaggtgc ataatgccaa gacaaagcca cgggaggagc agttcaacag cacgttccgt    960

gtggtcagcg tcctcaccgt tgtgcaccag gactggctga acggcaagga gtacaagtgc   1020

aaggtctcca acaaaggcct cccagccccc atcgagaaaa ccatctccaa aaccaaaggg   1080
```

cagccccgag aaccacaggt gtacaccctg cccccatccc gggaggagat gaccaagaac 1140
caggtcagcc tgacctgcct ggtcaaaggc ttctacccca gcgacatcgc cgtggagtgg 1200
gagagcaatg ggcagccgga gaacaactac aagaccacac ctcccatgct ggactccgac 1260
ggctccttct tcctctacag caagctcacc gtggacaaga gcaggtggca gcaggggaac 1320
gtcttctcat gctccgtgat gcatgaggct ctgcacaacc actacacgca gaagagcctc 1380
tccctgtctc cgggtaaa 1398

<210> SEQ ID NO 20
<211> LENGTH: 466
<212> TYPE: PRT
<213> ORGANISM: Homo sapiens

<400> SEQUENCE: 20

Met Glu Leu Gly Leu Asn Trp Val Phe Leu Val Ala Ile Leu Glu Gly
1 5 10 15

Val His Cys Glu Val Gln Leu Val Glu Ser Gly Gly Gly Leu Val Gln
20 25 30

Pro Gly Gly Ser Leu Arg Leu Ser Cys Ala Ala Ser Gly Phe Thr Phe
35 40 45

Ser Ser Tyr Trp Met Ser Trp Val Arg Gln Ala Pro Gly Lys Gly Leu
50 55 60

Glu Trp Val Ala Tyr Ile Lys Gln Asp Gly Asn Glu Lys Tyr Tyr Val
65 70 75 80

Asp Ser Val Lys Gly Arg Phe Thr Ile Ser Arg Asp Asn Ala Lys Asn
85 90 95

Ser Leu Tyr Leu Gln Met Asn Ser Leu Arg Ala Glu Asp Thr Ala Val
100 105 110

Tyr Tyr Cys Ala Arg Glu Gly Ile Leu Trp Phe Gly Asp Leu Pro Thr
115 120 125

Phe Trp Gly Gln Gly Thr Leu Val Thr Val Ser Ser Ala Ser Thr Lys
130 135 140

Gly Pro Ser Val Phe Pro Leu Ala Pro Cys Ser Arg Ser Thr Ser Glu
145 150 155 160

Ser Thr Ala Ala Leu Gly Cys Leu Val Lys Asp Tyr Phe Pro Glu Pro
165 170 175

Val Thr Val Ser Trp Asn Ser Gly Ala Leu Thr Ser Gly Val His Thr
180 185 190

Phe Pro Ala Val Leu Gln Ser Ser Gly Leu Tyr Ser Leu Ser Ser Val
195 200 205

Val Thr Val Pro Ser Ser Asn Phe Gly Thr Gln Thr Tyr Thr Cys Asn
210 215 220

Val Asp His Lys Pro Ser Asn Thr Lys Val Asp Lys Thr Val Glu Arg
225 230 235 240

Lys Cys Cys Val Glu Cys Pro Pro Cys Pro Ala Pro Pro Val Ala Gly
245 250 255

Pro Ser Val Phe Leu Phe Pro Pro Lys Pro Lys Asp Thr Leu Met Ile
260 265 270

Ser Arg Thr Pro Glu Val Thr Cys Val Val Val Asp Val Ser His Glu
275 280 285

Asp Pro Glu Val Gln Phe Asn Trp Tyr Val Asp Gly Val Glu Val His
290 295 300

Asn Ala Lys Thr Lys Pro Arg Glu Glu Gln Phe Asn Ser Thr Phe Arg

```
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465


<210> SEQ ID NO 21
<211> LENGTH: 723
<212> TYPE: DNA
<213> ORGANISM: Homo sapiens

<400> SEQUENCE: 21

atggacatga ggctccctgc tcagctcctg gggctgctaa tgctctgggt cccaggatcc      60

agtggggatg ttctgatgac tcagtctcca ctctccctgc ccgtcaccct tggacagccg     120

gcctccatct cctgcaggtc tagtcaaagc atcgtacaca gtaacggaaa cacctacttg     180

gagtggtatc tgcagaggcc aggccaatct ccaaagctcc taatttataa ggtttctaac     240

cggttctctg gggtcccaga cagattcagc ggcagtgggt caggcactga tttcacactg     300

aaaatcagca gggtggaggc tgaggatgtt ggggtttatt actgcttcca aggtagccac     360

gttcctctga cgttcggcgc agggaccaag ctggaaatca aacggactgt ggctgcacca     420

tctgtcttca tcttcccgcc atctgatgag cagttgaaat ctggaactgc ctctgttgtg     480

tgcctgctga ataacttcta tcccagagag gccaaagtac agtggaaggt ggataacgcc     540

ctccaatcgg gtaactccca ggagagtgtc acagagcagg acagcaagga cagcacctac     600

agcctcagca gcaccctgac gctgagcaaa gcagactacg agaaacacaa agtctacgcc     660

tgcgaagtca cccatcaggg cctgagctcg cccgtcacaa agagcttcaa caggggagag     720

tgt                                                                   723


<210> SEQ ID NO 22
<211> LENGTH: 241
<212> TYPE: PRT
<213> ORGANISM: Homo sapiens

<400> SEQUENCE: 22

Met Asp Met Arg Leu Pro Ala Gln Leu Leu Gly Leu Leu Met Leu Trp
1               5                   10                  15

Val Pro Gly Ser Ser Gly Asp Val Leu Met Thr Gln Ser Pro Leu Ser
            20                  25                  30
```

```
Leu Pro Val Thr Leu Gly Gln Pro Ala Ser Ile Ser Cys Arg Ser Ser
        35                  40                  45

Gln Ser Ile Val His Ser Asn Gly Asn Thr Tyr Leu Glu Trp Tyr Leu
    50                  55                  60

Gln Arg Pro Gly Gln Ser Pro Lys Leu Leu Ile Tyr Lys Val Ser Asn
65                  70                  75                  80

Arg Phe Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Val Gly Val
            100                 105                 110

Tyr Tyr Cys Phe Gln Gly Ser His Val Pro Leu Thr Phe Gly Ala Gly
        115                 120                 125

Thr Lys Leu Glu Ile Lys Arg Thr Val Ala Ala Pro Ser Val Phe Ile
    130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys


<210> SEQ ID NO 23
<211> LENGTH: 1410
<212> TYPE: DNA
<213> ORGANISM: Homo sapiens

<400> SEQUENCE: 23

atggacacac tttgctccac gctcctgctg ctgaccatcc cttcatgggt cttgtcccag      60

gtcaccttga aggagtctgg tcctgcgctg gtgaaaccca cacagaccct cacgctgacc     120

tgcaccttct ctgggttctc actccgcact agtggaatgg gcgtgggctg gatccgtcag     180

cccccaggaa aggccctgga gtggcttgcc cacatttggt gggatgatga taagagctac     240

aacccatctc tgaagagcca gctcaccatc tctaaggaca cctccaaaaa ccaggtggtc     300

cttacaatga ccaacatgga ccctgtggac acagccacat attactgtgc acgcagaaac     360

tattactacg acgactactt cgcctactgg ggccagggca ccctggtcac cgtctctagt     420

gcctccacca agggcccatc ggtcttcccc ctggcaccct cctccaagag cacctctggg     480

ggcacagcgg ccctgggctg cctggtcaag gactacttcc ccgaaccggt gacggtgtcg     540

tggaactcag gcgccctgac cagcggcgtg cacaccttcc cggctgtcct acagtcctca     600

ggactctact ccctcagcag cgtggtgacc gtgccctcca gcagcttggg cacccagacc     660

tacatctgca acgtgaatca caagcccagc aacaccaagg tggacaagaa agttgagccc     720

aaatcttgtg acaaaactca cacatgccca ccgtgcccag cacctgaact cctgggggga     780

ccgtcagtct tcctcttccc cccaaaaccc aaggacaccc tcatgatctc ccggacccct     840

gaggtcacat gcgtggtggt ggacgtgagc cacgaagacc ctgaggtcaa gttcaactgg     900
```

```
tacgtggacg gcgtggaggt gcataatgcc aagacaaagc cgcgggagga gcagtacaac    960

agcacgtacc gtgtggtcag cgtcctcacc gtcctgcacc aggactggct gaatggcaag   1020

gagtacaagt gcaaggtctc caacaaagcc ctcccagccc ccatcgagaa aaccatctcc   1080

aaagccaaag ggcagccccg agaaccacag gtgtacaccc tgcccccatc ccgggatgag   1140

ctgaccaaga accaggtcag cctgacctgc ctggtcaaag gcttctatcc cagcgacatc   1200

gccgtggagt gggagagcaa tgggcagccg gagaacaact acaagaccac gcctcccgtg   1260

ctggactccg acggctcctt cttcctctat agcaagctca ccgtggacaa gagcaggtgg   1320

cagcagggga acgtcttctc atgctccgtg atgcatgagg ctctgcacaa ccactacacg   1380

cagaagagcc tctccctgtc tccgggtaaa                                    1410
```

```
<210> SEQ ID NO 24
<211> LENGTH: 470
<212> TYPE: PRT
<213> ORGANISM: Homo sapiens

<400> SEQUENCE: 24

Met Asp Thr Leu Cys Ser Thr Leu Leu Leu Leu Thr Ile Pro Ser Trp
1               5                   10                  15

Val Leu Ser Gln Val Thr Leu Lys Glu Ser Gly Pro Ala Leu Val Lys
            20                  25                  30

Pro Thr Gln Thr Leu Thr Leu Thr Cys Thr Phe Ser Gly Phe Ser Leu
        35                  40                  45

Arg Thr Ser Gly Met Gly Val Gly Trp Ile Arg Gln Pro Pro Gly Lys
    50                  55                  60

Ala Leu Glu Trp Leu Ala His Ile Trp Trp Asp Asp Asp Lys Ser Tyr
65                  70                  75                  80

Asn Pro Ser Leu Lys Ser Gln Leu Thr Ile Ser Lys Asp Thr Ser Lys
                85                  90                  95

Asn Gln Val Val Leu Thr Met Thr Asn Met Asp Pro Val Asp Thr Ala
            100                 105                 110

Thr Tyr Tyr Cys Ala Arg Arg Asn Tyr Tyr Tyr Asp Asp Tyr Phe Ala
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
```

-continued

```
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470


<210> SEQ ID NO 25
<211> LENGTH: 705
<212> TYPE: DNA
<213> ORGANISM: Homo sapiens

<400> SEQUENCE: 25

atggaaaccc cggcgcagct gctgtttctg ctgctgctgt ggctgccgga taccaccggc      60

gaaattgtgt tgacgcagtc tccaggcacc ctgtctttgt ctccagggga aagagccacc     120

ctctcctgca gggccagtca gagtgttagc agcagctact tcgcctggta ccaacagaaa     180

cctggccagg ctcccaggct cctcatctat ggtacatcca gcagggccac tggcatccca     240

gacaggttca gtggcagtgg gtctgggaca gacttcactc tcaccgtcag cagactggag     300

cctgaggatt ttgcagtgta ttactgtcag cagtatgata ggtcacctcg gacgttcggc     360

caagggacca aggtggaaat caaacgtacg gtggctgcac catctgtctt catcttcccg     420

ccatctgatg agcagttgaa atctggaact gcctctgttg tgtgcctgct gaataacttc     480

tatcccagag aggccaaagt acagtggaag gtggataacg ccctccaatc gggtaactcc     540

caggagagtg tcacagagca ggacagcaag gacagcacct acagcctcag cagcaccctg     600

acgctgagca aagcagacta cgagaaacac aaagtctacg cctgcgaagt cacccatcag     660

ggcctgagct cgcccgtcac aaagagcttc aacaggggag agtgt                    705


<210> SEQ ID NO 26
<211> LENGTH: 235
<212> TYPE: PRT
<213> ORGANISM: Homo sapiens

<400> SEQUENCE: 26

Met Glu Thr Pro Ala Gln Leu Leu Phe Leu Leu Leu Leu Trp Leu Pro
```

-continued

```
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Ser Ser Tyr Phe Ala Trp Tyr Gln Gln Lys Pro Gly Gln Ala
    50                  55                  60

Pro Arg Leu Leu Ile Tyr Gly Thr Ser Ser Arg Ala Thr Gly Ile Pro
65                  70                  75                  80

Asp Arg Phe Ser Gly Ser Gly Ser Gly Thr Asp Phe Thr Leu Thr Val
                85                  90                  95

Ser Arg Leu Glu Pro Glu Asp Phe Ala Val Tyr Tyr Cys Gln Gln Tyr
            100                 105                 110

Asp Arg Ser Pro Arg Thr Phe Gly Gln Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

<210> SEQ ID NO 27
<211> LENGTH: 1389
<212> TYPE: DNA
<213> ORGANISM: Homo sapiens

<400> SEQUENCE: 27

```
atggattgga cctggcgtat tctgtttctg gtggcggcgg cgaccggcgc gcatagccag      60

gtgcagttgg tgcagtctgg ggctgcggtg aagaagcctg gggcctcagt gaaggtctcc     120

tgcaaggctt ctggatacac cttcaccggc tactatatac actgggtgcg acaggcccct     180

ggacaagggc ttgagtggat gggatggatc aaccctaaca gtggtggcac aaactatgca     240

caaaagtttc agggcagggt caccatgacc agggacacgt ccatcagcac agcctccatg     300

gaactgagca ggctgagatc tgacgacacg gccgtttatt tctgtgcgag agatcggtgg     360

ctggatgctt ttgatatctg gggccaaggg acaatggtca ccgtctcttc tgctagcacc     420

aagggcccat cggtcttccc cctggcgccc tgctccagga gcacctccga gagcacagcg     480

gccctgggct gcctggtcaa ggactacttc cccgaaccgg tgacggtgtc gtggaactca     540

ggcgctctga ccagcggcgt gcacaccttc ccagctgtcc tacagtcctc aggactctac     600

tccctcagca gcgtggtgac cgtgccctcc agcaacttcg gcacccagac ctacacctgc     660

aacgtagatc acaagcccag caacaccaag gtggacaaga cagttgagcg caaatgttgt     720

gtcgagtgcc caccgtgccc agcaccacct gtggcaggac cgtcagtctt cctcttcccc     780

ccaaaaccca aggacaccct catgatctcc cggacccctg aggtcacgtg cgtggtggtg     840
```

-continued

```
gacgtgagcc acgaagaccc cgaggtccag ttcaactggt acgtggacgg cgtggaggtg    900

cataatgcca agacaaagcc acgggaggag cagttcaaca gcacgttccg tgtggtcagc    960

gtcctcaccg ttgtgcacca ggactggctg aacggcaagg agtacaagtg caaggtctcc   1020

aacaaaggcc tcccagcccc catcgagaaa accatctcca aaaccaaagg gcagccccga   1080

gaaccacagg tgtacaccct gcccccatcc cgggaggaga tgaccaagaa ccaggtcagc   1140

ctgacctgcc tggtcaaagg cttctacccc agcgacatcg ccgtggagtg ggagagcaat   1200

gggcagccgg agaacaacta caagaccaca cctcccatgc tggactccga cggctccttc   1260

ttcctctaca gcaagctcac cgtggacaag agcaggtggc agcaggggaa cgtcttctca   1320

tgctccgtga tgcatgaggc tctgcacaac cactacacgc agaagagcct ctccctgtct   1380

ccgggtaaa                                                           1389


<210> SEQ ID NO 28
<211> LENGTH: 463
<212> TYPE: PRT
<213> ORGANISM: Homo sapiens

<400> SEQUENCE: 28

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Ala Val Lys Lys
            20                  25                  30

Pro Gly Ala Ser Val Lys Val Ser Cys Lys Ala Ser Gly Tyr Thr Phe
        35                  40                  45

Thr Gly Tyr Tyr Ile His Trp Val Arg Gln Ala Pro Gly Gln Gly Leu
    50                  55                  60

Glu Trp Met Gly Trp Ile Asn Pro Asn Ser Gly Gly Thr Asn Tyr Ala
65                  70                  75                  80

Gln Lys Phe Gln Gly Arg Val Thr Met Thr Arg Asp Thr Ser Ile Ser
                85                  90                  95

Thr Ala Ser Met Glu Leu Ser Arg Leu Arg Ser Asp Asp Thr Ala Val
            100                 105                 110

Tyr Phe Cys Ala Arg Asp Arg Trp Leu Asp Ala Phe Asp Ile Trp Gly
        115                 120                 125

Gln Gly Thr Met Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
            260                 265                 270
```

```
Pro Glu Val Thr Cys Val Val Val Asp Val Ser His Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
                325                 330                 335

Cys Lys Val Ser Asn Lys Gly Leu Pro Ala Pro Ile Glu Lys Thr Ile
            340                 345                 350

Ser Lys Thr Lys Gly Gln Pro Arg Glu Pro Gln Val Tyr Thr Leu Pro
        355                 360                 365

Pro Ser Arg Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
    450                 455                 460
```

<210> SEQ ID NO 29
<211> LENGTH: 705
<212> TYPE: DNA
<213> ORGANISM: Homo sapiens

<400> SEQUENCE: 29

```
atggaaaccc cagctcagct tctcttcctc ctgctactct ggctcccaga taccaccgga     60

gaaattgtgt tgacgcagtc tccaggcacc ctgtctttgt ctccagggga aagagccacc    120

ctctcctgca gggccagtca gagtgttagc agcggctact taacctggta ccagcagaaa    180

cctggccagg ctcccagact cctcatctat ggtgcatcca gcagggccac tggcatccca    240

gacaggttca gtggcagtgg gtctgggacg gacttcactc tcaccatcag cagactggag    300

cctgaagatt ttgcagtgta ttactgtcag cagtatggta actcactgag caggtttggc    360

caggggacca agctggagat caaacgtacg gtggctgcac catctgtctt catcttcccg    420

ccatctgatg agcagttgaa atctggaact gcctctgttg tgtgcctgct gaataacttc    480

tatcccagag aggccaaagt acagtggaag gtggataacg ccctccaatc gggtaactcc    540

caggagagtg tcacagagca ggacagcaag gacagcacct acagcctcag cagcaccctg    600

acgctgagca aagcagacta cgagaaacac aaagtctacg cctgcgaagt cacccatcag    660

ggcctgagct cgcccgtcac aaagagcttc aacaggggag agtgt                    705
```

<210> SEQ ID NO 30
<211> LENGTH: 235
<212> TYPE: PRT
<213> ORGANISM: Homo sapiens

<400> SEQUENCE: 30

```
Met Glu Thr Pro Ala Gln Leu Leu Phe Leu Leu Leu Leu Trp Leu Pro
1               5                   10                  15
```

-continued

```
Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Ser Gly Tyr Leu Thr Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Asn Ser Leu Ser Arg Phe Gly Gln Gly Thr Lys Leu Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235


<210> SEQ ID NO 31
<211> LENGTH: 1422
<212> TYPE: DNA
<213> ORGANISM: Homo sapiens

<400> SEQUENCE: 31

atggacatga gggtgcccgc tcagctcctg gggctcctgc tgctgtggct gagaggtgcg      60

cgctgtcagg tgcagctggt ggagtctggg ggaggcgtgg tccagcctgg gaggtccctg     120

agactctcct gtgcagcgtc tggattcacc ttcagtagct atggcatgca ctgggtccgc     180

caggctccag gcaaggggct ggagtgggtg gcagttatat ggtatgatgg aagtaataaa     240

tactatgcag actccgtgaa gggccgattc atcatctcca gagataaatc caagaacacg     300

ctgtatctgc aaatgaacag cctgagagcc gaggacacgg ctgtgtatta ctgtgcgaga     360

gcggggggta tagcagcagc tggcctctac tactactacg gtatggacgt ctggggccaa     420

gggaccacgg tcaccgtctc tagtgcctcc accaagggcc catcggtctt ccccctggcg     480

ccctgctcca ggagcacctc cgagagcaca gcggccctgg gctgcctggt caaggactac     540

ttccccgaac cggtgacggt gtcgtggaac tcaggcgctc tgaccagcgg cgtgcacacc     600

ttcccagctg tcctacagtc ctcaggactc tactccctca gcagcgtggt gaccgtgccc     660

tccagcaact tcggcaccca gacctacacc tgcaacgtag atcacaagcc cagcaacacc     720

aaggtggaca agacagttga gcgcaaatgt tgtgtcgagt gcccaccgtg cccagcacca     780

cctgtggcag gaccgtcagt cttcctcttc cccccaaaac ccaaggacac cctcatgatc     840
```

```
tcccggaccc ctgaggtcac gtgcgtggtg gtggacgtga gccacgaaga ccccgaggtc    900

cagttcaact ggtacgtgga cggcgtggag gtgcataatg ccaagacaaa gccacgggag    960

gagcagttca acagcacgtt ccgtgtggtc agcgtcctca ccgttgtgca ccaggactgg   1020

ctgaacggca aggagtacaa gtgcaaggtc tccaacaaag gcctcccagc ccccatcgag   1080

aaaaccatct ccaaaaccaa agggcagccc cgagaaccac aggtgtacac cctgccccca   1140

tcccgggagg agatgaccaa gaaccaggtc agcctgacct gcctggtcaa aggcttctac   1200

cccagcgaca tcgccgtgga gtgggagagc aatgggcagc cggagaacaa ctacaagacc   1260

acacctccca tgctggactc cgacggctcc ttcttcctct acagcaagct caccgtggac   1320

aagagcaggt ggcagcaggg gaacgtcttc tcatgctccg tgatgcatga ggctctgcac   1380

aaccactaca cgcagaagag cctctccctg tctccgggta aa                      1422
```

<210> SEQ ID NO 32
<211> LENGTH: 474
<212> TYPE: PRT
<213> ORGANISM: Homo sapiens

<400> SEQUENCE: 32

```
Met Asp Met Arg Val Pro Ala Gln Leu Leu Gly Leu Leu Leu Leu Trp
1               5                   10                  15

Leu Arg Gly Ala Arg Cys Gln Val Gln Leu Val Glu Ser Gly Gly Gly
            20                  25                  30

Val Val Gln Pro Gly Arg Ser Leu Arg Leu Ser Cys Ala Ala Ser Gly
        35                  40                  45

Phe Thr Phe Ser Ser Tyr Gly Met His Trp Val Arg Gln Ala Pro Gly
    50                  55                  60

Lys Gly Leu Glu Trp Val Ala Val Ile Trp Tyr Asp Gly Ser Asn Lys
65                  70                  75                  80

Tyr Tyr Ala Asp Ser Val Lys Gly Arg Phe Ile Ile Ser Arg Asp Lys
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Arg Ala Gly Gly Ile Ala Ala Ala Gly
        115                 120                 125

Leu Tyr Tyr Tyr Tyr Gly Met Asp Val Trp Gly Gln Gly Thr Thr Val
    130                 135                 140

Thr Val Ser Ser Ala Ser Thr Lys Gly Pro Ser Val Phe Pro Leu Ala
145                 150                 155                 160

Pro Cys Ser Arg Ser Thr Ser Glu Ser Thr Ala Ala Leu Gly Cys Leu
                165                 170                 175

Val Lys Asp Tyr Phe Pro Glu Pro Val Thr Val Ser Trp Asn Ser Gly
            180                 185                 190

Ala Leu Thr Ser Gly Val His Thr Phe Pro Ala Val Leu Gln Ser Ser
        195                 200                 205

Gly Leu Tyr Ser Leu Ser Ser Val Val Thr Val Pro Ser Ser Asn Phe
    210                 215                 220

Gly Thr Gln Thr Tyr Thr Cys Asn Val Asp His Lys Pro Ser Asn Thr
225                 230                 235                 240

Lys Val Asp Lys Thr Val Glu Arg Lys Cys Cys Val Glu Cys Pro Pro
                245                 250                 255

Cys Pro Ala Pro Pro Val Ala Gly Pro Ser Val Phe Leu Phe Pro Pro
            260                 265                 270
```

```
Lys Pro Lys Asp Thr Leu Met Ile Ser Arg Thr Pro Glu Val Thr Cys
        275                 280                 285

Val Val Val Asp Val Ser His Glu Asp Pro Glu Val Gln Phe Asn Trp
    290                 295                 300

Tyr Val Asp Gly Val Glu Val His Asn Ala Lys Thr Lys Pro Arg Glu
305                 310                 315                 320

Glu Gln Phe Asn Ser Thr Phe Arg Val Val Ser Val Leu Thr Val Val
                325                 330                 335

His Gln Asp Trp Leu Asn Gly Lys Glu Tyr Lys Cys Lys Val Ser Asn
            340                 345                 350

Lys Gly Leu Pro Ala Pro Ile Glu Lys Thr Ile Ser Lys Thr Lys Gly
        355                 360                 365

Gln Pro Arg Glu Pro Gln Val Tyr Thr Leu Pro Pro Ser Arg Glu Glu
    370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Met Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470
```

<210> SEQ ID NO 33
<211> LENGTH: 806
<212> TYPE: DNA
<213> ORGANISM: Homo sapiens

<400> SEQUENCE: 33

```
atgacatcca ctttgccttt ctctccacag gtgtccactc ccaggtccaa gtttaaacgg     60

atctctagcg aattccctct agagtcgact agaccaccat ggacatgagg gtgcccgctc    120

agctcctggg gctcctgctg ctgtggctga gaggtgcgcg ctgttcttct gagctgactc    180

aggaccctac tgtgtctgtg gccttgggac agacagtcaa aatcacatgc caaggagaca    240

gcctcagaag tttttatgca agctggtacc agcagaagcc aggacaggcc cctgtacttg    300

tcttctatgg taaaaacaac cggccctcag ggatcccaga ccgattctct ggctccagct    360

caggaaacac agcttccttg accatcactg gggctcaggc ggaagatgag gctgactatt    420

attgtaattc ccgggacagc agtgtttacc atctggtact cggcggaggg accaagctga    480

ccgtcctagg tcagcccaag gccaacccca ctgtcactct gttcccgccc tcctctgagg    540

agctccaagc caacaaggcc acactagtgt gtctgatcag tgacttctac ccgggagctg    600

tgacagtggc ctggaaggca gatggcagcc ccgtcaaggc gggagtggag accaccaaac    660

cctccaaaca gagcaacaac aagtacgcgg ccagcagcta cctgagcctg acgcccgagc    720

agtggaagtc ccacagaagc tacagctgcc aggtcacgca tgaagggagc accgtggaga    780

agacagtggc ccctacagaa tgttca                                         806
```

<210> SEQ ID NO 34
<211> LENGTH: 236
<212> TYPE: PRT

<213> ORGANISM: Homo sapiens

<400> SEQUENCE: 34

```
Met Asp Met Arg Val Pro Ala Gln Leu Leu Gly Leu Leu Leu Leu Trp
1               5                   10                  15

Leu Arg Gly Ala Arg Cys Ser Ser Glu Leu Thr Gln Asp Pro Thr Val
            20                  25                  30

Ser Val Ala Leu Gly Gln Thr Val Lys Ile Thr Cys Gln Gly Asp Ser
        35                  40                  45

Leu Arg Ser Phe Tyr Ala Ser Trp Tyr Gln Gln Lys Pro Gly Gln Ala
    50                  55                  60

Pro Val Leu Val Phe Tyr Gly Lys Asn Asn Arg Pro Ser Gly Ile Pro
65                  70                  75                  80

Asp Arg Phe Ser Gly Ser Ser Ser Gly Asn Thr Ala Ser Leu Thr Ile
                85                  90                  95

Thr Gly Ala Gln Ala Glu Asp Glu Ala Asp Tyr Tyr Cys Asn Ser Arg
            100                 105                 110

Asp Ser Ser Val Tyr His Leu Val Leu Gly Gly Gly Thr Lys Leu Thr
        115                 120                 125

Val Leu Gly Gln Pro Lys Ala Asn Pro Thr Val Thr Leu Phe Pro Pro
    130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Gly
                165                 170                 175

Ser Pro Val Lys Ala Gly Val Glu Thr Thr Lys Pro Ser Lys Gln Ser
            180                 185                 190

Asn Asn Lys Tyr Ala Ala Ser Ser Tyr Leu Ser Leu Thr Pro Glu Gln
        195                 200                 205

Trp Lys Ser His Arg Ser Tyr Ser Cys Gln Val Thr His Glu Gly Ser
    210                 215                 220

Thr Val Glu Lys Thr Val Ala Pro Thr Glu Cys Ser
225                 230                 235
```

<210> SEQ ID NO 35
<211> LENGTH: 1434
<212> TYPE: DNA
<213> ORGANISM: Homo sapiens

<400> SEQUENCE: 35

```
atggacatga gggtgcccgc tcagctcctg gggctcctgc tgctgtggct gagaggtgcg      60

cgctgtcagg tgcagttggt gcagtctggg gctgaggtga agaagcctgg ggcctcagtg     120

aaggtctcct gcaaggcttc tggatacacc ttcaccggct actatatgca ctgggtgcga     180

caggcccctg gacaagggct tgagtggatg ggatggatca accctaacag tggtggcaca     240

aactatgcac agaagtttca gggcagggtc accatgacca gggacacgtc catcagcaca     300

gcctacatgg agctgagcag gctgagatct gacgacacgg ccgtgtattt ctgtgcgaga     360

gatcaaatga gtattattat gcttcgggga gtttttcccc cttactatta cggtatggac     420

gtctggggcc aagggaccac ggtcaccgtc tctagtgcct ccaccaaggg cccatcggtc     480

ttccccctgg cgccctgctc caggagcacc tccgagagca cagcggccct gggctgcctg     540

gtcaaggact acttccccga accggtgacg gtgtcgtgga actcaggcgc tctgaccagc     600

ggcgtgcaca ccttcccagc tgtcctacag tcctcaggac tctactccct cagcagcgtg     660
```

-continued

```
gtgaccgtgc cctccagcaa cttcggcacc cagacctaca cctgcaacgt agatcacaag    720

cccagcaaca ccaaggtgga caagacagtt gagcgcaaat gttgtgtcga gtgcccaccg    780

tgcccagcac cacctgtggc aggaccgtca gtcttcctct tccccccaaa acccaaggac    840

accctcatga tctcccggac ccctgaggtc acgtgcgtgg tggtggacgt gagccacgaa    900

gaccccgagg tccagttcaa ctggtacgtg gacggcgtgg aggtgcataa tgccaagaca    960

aagccacggg aggagcagtt caacagcacg ttccgtgtgg tcagcgtcct caccgttgtg   1020

caccaggact ggctgaacgg caaggagtac aagtgcaagg tctccaacaa aggcctccca   1080

gcccccatcg agaaaaccat ctccaaaacc aaagggcagc cccgagaacc acaggtgtac   1140

accctgcccc catcccggga ggagatgacc aagaaccagg tcagcctgac ctgcctggtc   1200

aaaggcttct accccagcga catcgccgtg gagtgggaga gcaatgggca gccggagaac   1260

aactacaaga ccacacctcc catgctggac tccgacggct ccttcttcct ctacagcaag   1320

ctcaccgtgg acaagagcag gtggcagcag gggaacgtct tctcatgctc cgtgatgcat   1380

gaggctctgc acaaccacta cacgcagaag agcctctccc tgtctccggg taaa         1434
```

<210> SEQ ID NO 36
<211> LENGTH: 478
<212> TYPE: PRT
<213> ORGANISM: Homo sapiens

<400> SEQUENCE: 36

```
Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Gly Tyr Tyr Met His Trp Val Arg Gln Ala Pro Gly
    50                  55                  60

Gln Gly Leu Glu Trp Met Gly Trp Ile Asn Pro Asn Ser Gly Gly Thr
65                  70                  75                  80

Asn Tyr Ala Gln Lys Phe Gln Gly Arg Val Thr Met Thr Arg Asp Thr
                85                  90                  95

Ser Ile Ser Thr Ala Tyr Met Glu Leu Ser Arg Leu Arg Ser Asp Asp
            100                 105                 110

Thr Ala Val Tyr Phe Cys Ala Arg Asp Gln Met Ser Ile Ile Met Leu
        115                 120                 125

Arg Gly Val Phe Pro Pro Tyr Tyr Tyr Gly Met Asp Val Trp Gly Gln
    130                 135                 140

Gly Thr Thr Val Thr Val Ser Ser Ala Ser Thr Lys Gly Pro Ser Val
145                 150                 155                 160

Phe Pro Leu Ala Pro Cys Ser Arg Ser Thr Ser Glu Ser Thr Ala Ala
                165                 170                 175

Leu Gly Cys Leu Val Lys Asp Tyr Phe Pro Glu Pro Val Thr Val Ser
            180                 185                 190

Trp Asn Ser Gly Ala Leu Thr Ser Gly Val His Thr Phe Pro Ala Val
        195                 200                 205

Leu Gln Ser Ser Gly Leu Tyr Ser Leu Ser Ser Val Val Thr Val Pro
    210                 215                 220

Ser Ser Asn Phe Gly Thr Gln Thr Tyr Thr Cys Asn Val Asp His Lys
225                 230                 235                 240
```

-continued

```
Pro Ser Asn Thr Lys Val Asp Lys Thr Val Glu Arg Lys Cys Cys Val
                245                 250                 255

Glu Cys Pro Pro Cys Pro Ala Pro Pro Val Ala Gly Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser His Glu Asp Pro Glu Val
    290                 295                 300

Gln Phe Asn Trp Tyr Val Asp Gly Val Glu Val His Asn Ala Lys Thr
305                 310                 315                 320

Lys Pro Arg Glu Glu Gln Phe Asn Ser Thr Phe Arg Val Val Ser Val
                325                 330                 335

Leu Thr Val Val His Gln Asp Trp Leu Asn Gly Lys Glu Tyr Lys Cys
            340                 345                 350

Lys Val Ser Asn Lys Gly Leu Pro Ala Pro Ile Glu Lys Thr Ile Ser
        355                 360                 365

Lys Thr Lys Gly Gln Pro Arg Glu Pro Gln Val Tyr Thr Leu Pro Pro
    370                 375                 380

Ser Arg Glu Glu Met Thr Lys Asn Gln Val Ser Leu Thr Cys Leu Val
385                 390                 395                 400

Lys Gly Phe Tyr Pro Ser Asp Ile Ala Val Glu Trp Glu Ser Asn Gly
                405                 410                 415

Gln Pro Glu Asn Asn Tyr Lys Thr Thr Pro Pro Met Leu Asp Ser Asp
            420                 425                 430

Gly Ser Phe Phe Leu Tyr Ser Lys Leu Thr Val Asp Lys Ser Arg Trp
        435                 440                 445

Gln Gln Gly Asn Val Phe Ser Cys Ser Val Met His Glu Ala Leu His
    450                 455                 460

Asn His Tyr Thr Gln Lys Ser Leu Ser Leu Ser Pro Gly Lys
465                 470                 475
```

<210> SEQ ID NO 37
<211> LENGTH: 723
<212> TYPE: DNA
<213> ORGANISM: Homo sapiens

<400> SEQUENCE: 37

```
atggacatga gggtgcccgc tcagctcctg gggctcctgc tgctgtggct gagaggtgcc      60

agatgtgata ttgtgatgac tcagtctcca ctctccctgc ccgtcacccc tggagagccg     120

gcctccatct cctgcaggtc tagtcagagc ctcctgcata gtaatggata caactatttg     180

gattggtacc tgcagaagcc agggcagtct ccacagctcc tgatctattt gggttctaat     240

cgggcctccg gggtccctga caggttcagt ggcagtggat caggcacaga ttttacactg     300

aaaatcagca gagtggaggc tgaggatgtt ggggtttatt actgcatgca agctctacaa     360

actccgctca ctttcggcgg agggaccaag gtagagatca aacggactgt ggctgcacca     420

tctgtcttca tcttcccgcc atctgatgag cagttgaaat ctggaactgc ctctgttgtg     480

tgcctgctga ataacttcta tcccagagag gccaaagtac agtggaaggt ggataacgcc     540

ctccaatcgg gtaactccca ggagagtgtc acagagcagg acagcaagga cagcacctac     600

agcctcagca gcaccctgac gctgagcaaa gcagactacg agaaacacaa agtctacgcc     660

tgcgaagtca cccatcaggg cctgagctcg cccgtcacaa agagcttcaa caggggagag     720

tgt                                                                   723
```

<210> SEQ ID NO 38
<211> LENGTH: 241
<212> TYPE: PRT
<213> ORGANISM: Homo sapiens

<400> SEQUENCE: 38

```
Met Asp Met Arg Val Pro Ala Gln Leu Leu Gly Leu Leu Leu Leu Trp
1               5                   10                  15

Leu Arg Gly Ala Arg Cys Asp Ile Val Met Thr Gln Ser Pro Leu Ser
            20                  25                  30

Leu Pro Val Thr Pro Gly Glu Pro Ala Ser Ile Ser Cys Arg Ser Ser
        35                  40                  45

Gln Ser Leu Leu His Ser Asn Gly Tyr Asn Tyr Leu Asp Trp Tyr Leu
    50                  55                  60

Gln Lys Pro Gly Gln Ser Pro Gln Leu Leu Ile Tyr Leu Gly Ser Asn
65                  70                  75                  80

Arg Ala Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Val Gly Val
            100                 105                 110

Tyr Tyr Cys Met Gln Ala Leu Gln Thr Pro Leu Thr Phe Gly Gly Gly
        115                 120                 125

Thr Lys Val Glu Ile Lys Arg Thr Val Ala Ala Pro Ser Val Phe Ile
    130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys
```

<210> SEQ ID NO 39
<211> LENGTH: 1425
<212> TYPE: DNA
<213> ORGANISM: Homo sapiens

<400> SEQUENCE: 39

```
atggacatga gggtgcccgc tcagctcctg gggctcctgc tgctgtggct gagaggtgcc      60

agatgtgagg tgcagctggt ggagtctggg ggaggcttgg tccagcctgg ggggtccctg     120

agactctcct gtgcagcctc cggattcacc tttagtagct attggatgag ctgggtccgc     180

caggctccag ggaaggggct ggagtgggtg gccagcataa aacaagatgg aagtgagaaa     240

tactatgtgg actctgtgaa gggccgattc accatctcca gagacaacgc caggaactca     300

ctgtatctgc aaatgaacag cctgagagcc gaggacacgg ctgtgtatta ctgtgcgaga     360

gatcttgtat taatggtgta tgatatagac tactactact acggtatgga cgtctggggc     420

caagggacca cggtcaccgt ctcctcagcc tccaccaagg gcccatcggt cttccccctg     480
```

-continued

```
gcgccctgct ccaggagcac ctccgagagc acagcggccc tgggctgcct ggtcaaggac    540

tacttccccg aaccggtgac ggtgtcgtgg aactcaggcg ctctgaccag cggcgtgcac    600

accttcccag ctgtcctaca gtcctcagga ctctactccc tcagcagcgt ggtgaccgtg    660

ccctccagca acttcggcac ccagacctac acctgcaacg tagatcacaa gcccagcaac    720

accaaggtgg acaagacagt tgagcgcaaa tgttgtgtcg agtgcccacc gtgcccagca    780

ccacctgtgg caggaccgtc agtcttcctc ttccccccaa aacccaagga caccctcatg    840

atctcccgga cccctgaggt cacgtgcgtg gtggtggacg tgagccacga agaccccgag    900

gtccagttca actggtacgt ggacggcgtg gaggtgcata atgccaagac aaagccacgg    960

gaggagcagt tcaacagcac gttccgtgtg gtcagcgtcc tcaccgttgt gcaccaggac   1020

tggctgaacg gcaaggagta caagtgcaag gtctccaaca aaggcctccc agcccccatc   1080

gagaaaacca tctccaaaac caaagggcag ccccgagaac cacaggtgta caccctgccc   1140

ccatcccggg aggagatgac caagaaccag gtcagcctga cctgcctggt caaaggcttc   1200

taccccagcg acatcgccgt ggagtgggag agcaatgggc agccggagaa caactacaag   1260

accacacctc ccatgctgga ctccgacggc tccttcttcc tctacagcaa gctcaccgtg   1320

gacaagagca ggtggcagca ggggaacgtc ttctcatgct ccgtgatgca tgaggctctg   1380

cacaaccact acacgcagaa gagcctctcc ctgtctccgg gtaaa                   1425
```

<210> SEQ ID NO 40
<211> LENGTH: 475
<212> TYPE: PRT
<213> ORGANISM: Homo sapiens

<400> SEQUENCE: 40

```
Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Trp Met Ser Trp Val Arg Gln Ala Pro Gly
    50                  55                  60

Lys Gly Leu Glu Trp Val Ala Ser Ile Lys Gln Asp Gly Ser Glu Lys
65                  70                  75                  80

Tyr Tyr Val Asp Ser Val Lys Gly Arg Phe Thr Ile Ser Arg Asp Asn
                85                  90                  95

Ala Arg Asn Ser Leu Tyr Leu Gln Met Asn Ser Leu Arg Ala Glu Asp
            100                 105                 110

Thr Ala Val Tyr Tyr Cys Ala Arg Asp Leu Val Leu Met Val Tyr Asp
        115                 120                 125

Ile Asp Tyr Tyr Tyr Tyr Gly Met Asp Val Trp Gly Gln Gly Thr Thr
    130                 135                 140

Val Thr Val Ser Ser Ala Ser Thr Lys Gly Pro Ser Val Phe Pro Leu
145                 150                 155                 160

Ala Pro Cys Ser Arg Ser Thr Ser Glu Ser Thr Ala Ala Leu Gly Cys
                165                 170                 175

Leu Val Lys Asp Tyr Phe Pro Glu Pro Val Thr Val Ser Trp Asn Ser
            180                 185                 190

Gly Ala Leu Thr Ser Gly Val His Thr Phe Pro Ala Val Leu Gln Ser
        195                 200                 205
```

-continued

```
Ser Gly Leu Tyr Ser Leu Ser Ser Val Val Thr Val Pro Ser Ser Asn
    210                 215                 220

Phe Gly Thr Gln Thr Tyr Thr Cys Asn Val Asp His Lys Pro Ser Asn
225                 230                 235                 240

Thr Lys Val Asp Lys Thr Val Glu Arg Lys Cys Cys Val Glu Cys Pro
                245                 250                 255

Pro Cys Pro Ala Pro Pro Val Ala Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Gln Phe Asn
    290                 295                 300

Trp Tyr Val Asp Gly Val Glu Val His Asn Ala Lys Thr Lys Pro Arg
305                 310                 315                 320

Glu Glu Gln Phe Asn Ser Thr Phe Arg Val Val Ser Val Leu Thr Val
                325                 330                 335

Val His Gln Asp Trp Leu Asn Gly Lys Glu Tyr Lys Cys Lys Val Ser
            340                 345                 350

Asn Lys Gly Leu Pro Ala Pro Ile Glu Lys Thr Ile Ser Lys Thr Lys
        355                 360                 365

Gly Gln Pro Arg Glu Pro Gln Val Tyr Thr Leu Pro Pro Ser Arg Glu
    370                 375                 380

Glu Met Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Met Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475
```

<210> SEQ ID NO 41
<211> LENGTH: 723
<212> TYPE: DNA
<213> ORGANISM: Homo sapiens

<400> SEQUENCE: 41

```
atggacatga gggtgcccgc tcagctcctg gggctcctgc tgctgtggct gagaggtgcc     60

agatgtgata ttgtgatgac tcagtctcca ctctccctgc ccgtcacccc tggagagccg    120

gcctccatct cctgcaggtc tagtcagagc ctcctgcata gtaatgggta caactatttg    180

gattggtacc tgcagaagcc agggcagtct ccacagctcc tgatctattt gggttctaat    240

cgggcctccg gggtccctga caggttcagt ggcagtggat caggcacaca tcttacactg    300

aaaatcagca gagtggaggc tgaggatgtt ggagtttatt actgcatgca aactctacaa    360

actccgctca ctttcggcgg agggaccaag gtagagatca aacggactgt ggctgcacca    420

tctgtcttca tcttcccgcc atctgatgag cagttgaaat ctggaactgc ctctgttgtg    480

tgcctgctga ataacttcta tcccagagag gccaaagtac agtggaaggt ggataacgcc    540

ctccaatcgg gtaactccca ggagagtgtc acagagcagg acagcaagga cagcacctac    600
```

```
agcctcagca gcaccctgac gctgagcaaa gcagactacg agaaacacaa agtctacgcc    660

tgcgaagtca cccatcaggg cctgagctcg cccgtcacaa agagcttcaa caggggagag    720

tgt                                                                  723


<210> SEQ ID NO 42
<211> LENGTH: 241
<212> TYPE: PRT
<213> ORGANISM: Homo sapiens

<400> SEQUENCE: 42

Met Asp Met Arg Val Pro Ala Gln Leu Leu Gly Leu Leu Leu Leu Trp
1               5                   10                  15

Leu Arg Gly Ala Arg Cys Asp Ile Val Met Thr Gln Ser Pro Leu Ser
            20                  25                  30

Leu Pro Val Thr Pro Gly Glu Pro Ala Ser Ile Ser Cys Arg Ser Ser
        35                  40                  45

Gln Ser Leu Leu His Ser Asn Gly Tyr Asn Tyr Leu Asp Trp Tyr Leu
    50                  55                  60

Gln Lys Pro Gly Gln Ser Pro Gln Leu Leu Ile Tyr Leu Gly Ser Asn
65                  70                  75                  80

Arg Ala Ser Gly Val Pro Asp Arg Phe Ser Gly Ser Gly Ser Gly Thr
                85                  90                  95

His Leu Thr Leu Lys Ile Ser Arg Val Glu Ala Glu Asp Val Gly Val
            100                 105                 110

Tyr Tyr Cys Met Gln Thr Leu Gln Thr Pro Leu Thr Phe Gly Gly Gly
        115                 120                 125

Thr Lys Val Glu Ile Lys Arg Thr Val Ala Ala Pro Ser Val Phe Ile
    130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys


<210> SEQ ID NO 43
<211> LENGTH: 1425
<212> TYPE: DNA
<213> ORGANISM: Homo sapiens

<400> SEQUENCE: 43

atggacatga gggtgcccgc tcagctcctg gggctcctgc tgctgtggct gagaggtgcc     60

agatgtgagg tgcagctggt ggagtctggg ggaggcttgg tccagcctgg ggggtccctg    120

agactctcct gtgcagcctc cggattcacc tttagtaact attggatgag ctgggtccgc    180

caggctccag ggaaggggct ggagtgggtg gccagcataa aacaagatgg aagtgagaaa    240

tactatgtgg actctgtgaa gggccgattc gccatctcca gagacaacgc caagaactca    300
```

-continued

```
ctgtttctgc aaatgaacag cctgagagcc gaggacacgg ctgtgtatta ctgtgcgaga    360

gatcttgtac taatggtgta tgatatagac tactactact acggtatgga cgtctggggc    420

caagggacca cggtcaccgt ctcctcagcc tccaccaagg gcccatcggt cttccccctg    480

gcgccctgct ccaggagcac ctccgagagc acagcggccc tgggctgcct ggtcaaggac    540

tacttccccg aaccggtgac ggtgtcgtgg aactcaggcg ctctgaccag cggcgtgcac    600

accttcccag ctgtcctaca gtcctcagga ctctactccc tcagcagcgt ggtgaccgtg    660

ccctccagca acttcggcac ccagacctac acctgcaacg tagatcacaa gcccagcaac    720

accaaggtgg acaagacagt tgagcgcaaa tgttgtgtcg agtgcccacc gtgcccagca    780

ccacctgtgg caggaccgtc agtcttcctc ttccccccaa aacccaagga caccctcatg    840

atctcccgga cccctgaggt cacgtgcgtg gtggtggacg tgagccacga agaccccgag    900

gtccagttca actggtacgt ggacggcgtg gaggtgcata atgccaagac aaagccacgg    960

gaggagcagt tcaacagcac gttccgtgtg gtcagcgtcc tcaccgttgt gcaccaggac   1020

tggctgaacg gcaaggagta caagtgcaag gtctccaaca aaggcctccc agcccccatc   1080

gagaaaacca tctccaaaac caaagggcag ccccgagaac cacaggtgta caccctgccc   1140

ccatcccggg aggagatgac caagaaccag gtcagcctga cctgcctggt caaaggcttc   1200

taccccagcg acatcgccgt ggagtgggag agcaatgggc agccggagaa caactacaag   1260

accacacctc ccatgctgga ctccgacggc tccttcttcc tctacagcaa gctcaccgtg   1320

gacaagagca ggtggcagca ggggaacgtc ttctcatgct ccgtgatgca tgaggctctg   1380

cacaaccact acacgcagaa gagcctctcc ctgtctccgg gtaaa                   1425
```

<210> SEQ ID NO 44
<211> LENGTH: 475
<212> TYPE: PRT
<213> ORGANISM: Homo sapiens

<400> SEQUENCE: 44

```
Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Asn Tyr Trp Met Ser Trp Val Arg Gln Ala Pro Gly
    50                  55                  60

Lys Gly Leu Glu Trp Val Ala Ser Ile Lys Gln Asp Gly Ser Glu Lys
65                  70                  75                  80

Tyr Tyr Val Asp Ser Val Lys Gly Arg Phe Ala Ile Ser Arg Asp Asn
                85                  90                  95

Ala Lys Asn Ser Leu Phe Leu Gln Met Asn Ser Leu Arg Ala Glu Asp
            100                 105                 110

Thr Ala Val Tyr Tyr Cys Ala Arg Asp Leu Val Leu Met Val Tyr Asp
        115                 120                 125

Ile Asp Tyr Tyr Tyr Tyr Gly Met Asp Val Trp Gly Gln Gly Thr Thr
    130                 135                 140

Val Thr Val Ser Ser Ala Ser Thr Lys Gly Pro Ser Val Phe Pro Leu
145                 150                 155                 160

Ala Pro Cys Ser Arg Ser Thr Ser Glu Ser Thr Ala Ala Leu Gly Cys
                165                 170                 175
```

-continued

```
Leu Val Lys Asp Tyr Phe Pro Glu Pro Val Thr Val Ser Trp Asn Ser
            180                 185                 190

Gly Ala Leu Thr Ser Gly Val His Thr Phe Pro Ala Val Leu Gln Ser
        195                 200                 205

Ser Gly Leu Tyr Ser Leu Ser Ser Val Val Thr Val Pro Ser Ser Asn
    210                 215                 220

Phe Gly Thr Gln Thr Tyr Thr Cys Asn Val Asp His Lys Pro Ser Asn
225                 230                 235                 240

Thr Lys Val Asp Lys Thr Val Glu Arg Lys Cys Cys Val Glu Cys Pro
                245                 250                 255

Pro Cys Pro Ala Pro Pro Val Ala Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Gln Phe Asn
    290                 295                 300

Trp Tyr Val Asp Gly Val Glu Val His Asn Ala Lys Thr Lys Pro Arg
305                 310                 315                 320

Glu Glu Gln Phe Asn Ser Thr Phe Arg Val Val Ser Val Leu Thr Val
                325                 330                 335

Val His Gln Asp Trp Leu Asn Gly Lys Glu Tyr Lys Cys Lys Val Ser
            340                 345                 350

Asn Lys Gly Leu Pro Ala Pro Ile Glu Lys Thr Ile Ser Lys Thr Lys
        355                 360                 365

Gly Gln Pro Arg Glu Pro Gln Val Tyr Thr Leu Pro Pro Ser Arg Glu
    370                 375                 380

Glu Met Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Met Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475
```

<210> SEQ ID NO 45
<211> LENGTH: 705
<212> TYPE: DNA
<213> ORGANISM: Homo sapiens

<400> SEQUENCE: 45

```
atgacttgtt ctccactgct gctgactctg ctgattcatt gtactggttc ttgggcgcag      60

tctgtgttga cgcagccgcc ctcagtgtct gcggccccag gacagaaggt caccatctcc     120

tgctctggaa gcagctccaa cattgggaat aattatgtat cctggtacca gcagctccca     180

ggaacagccc ccaaactcct catttatgac aataataagc gaccctcagg gattcctgac     240

cgattctctg gctccaagtc tggcacgtca accaccctgg gcatcaccgg actccagact     300

ggggacgagg ccgattatta ctgcggaaca tgggatagcc gcctgagtgc tgtggttttc     360

ggcggaggga ccaagctgac cgtcctaggt cagcccaagg ccaaccccac tgtcactctg     420
```

ttcccgccct cctctgagga gctccaagcc aacaaggcca cactagtgtg tctgatcagt 480
gacttctacc cgggagctgt gacagtggcc tggaaggcag atggcagccc cgtcaaggcg 540
ggagtggaga ccaccaaacc ctccaaacag agcaacaaca agtacgcggc cagcagctac 600
ctgagcctga cgcccgagca gtggaagtcc cacagaagct acagctgcca ggtcacgcat 660
gaagggagca ccgtggagaa gacagtggcc cctacagaat gttca 705

<210> SEQ ID NO 46
<211> LENGTH: 235
<212> TYPE: PRT
<213> ORGANISM: Homo sapiens

<400> SEQUENCE: 46

Met Thr Cys Ser Pro Leu Leu Leu Thr Leu Leu Ile His Cys Thr Gly
1 5 10 15

Ser Trp Ala Gln Ser Val Leu Thr Gln Pro Pro Ser Val Ser Ala Ala
20 25 30

Pro Gly Gln Lys Val Thr Ile Ser Cys Ser Gly Ser Ser Ser Asn Ile
35 40 45

Gly Asn Asn Tyr Val Ser Trp Tyr Gln Gln Leu Pro Gly Thr Ala Pro
50 55 60

Lys Leu Leu Ile Tyr Asp Asn Asn Lys Arg Pro Ser Gly Ile Pro Asp
65 70 75 80

Arg Phe Ser Gly Ser Lys Ser Gly Thr Ser Thr Thr Leu Gly Ile Thr
85 90 95

Gly Leu Gln Thr Gly Asp Glu Ala Asp Tyr Tyr Cys Gly Thr Trp Asp
100 105 110

Ser Arg Leu Ser Ala Val Val Phe Gly Gly Gly Thr Lys Leu Thr Val
115 120 125

Leu Gly Gln Pro Lys Ala Asn Pro Thr Val Thr Leu Phe Pro Pro Ser
130 135 140

Ser Glu Glu Leu Gln Ala Asn Lys Ala Thr Leu Val Cys Leu Ile Ser
145 150 155 160

Asp Phe Tyr Pro Gly Ala Val Thr Val Ala Trp Lys Ala Asp Gly Ser
165 170 175

Pro Val Lys Ala Gly Val Glu Thr Thr Lys Pro Ser Lys Gln Ser Asn
180 185 190

Asn Lys Tyr Ala Ala Ser Ser Tyr Leu Ser Leu Thr Pro Glu Gln Trp
195 200 205

Lys Ser His Arg Ser Tyr Ser Cys Gln Val Thr His Glu Gly Ser Thr
210 215 220

Val Glu Lys Thr Val Ala Pro Thr Glu Cys Ser
225 230 235

<210> SEQ ID NO 47
<211> LENGTH: 1425
<212> TYPE: DNA
<213> ORGANISM: Homo sapiens

<400> SEQUENCE: 47
atggaatttg gtctgtcttg ggtatttctg gttgctctgc tgcgtggcgt gcagtgccag 60
gtgcagctgg tggaatctgg gggaggcgtg gtccagcctg ggaggtccct gagactctcc 120
tgtgcagcct ctggattcac cttcagtagc tttggcatgc actgggtccg ccaggctcca 180
ggcaaggggc tggagtgggt ggcagttata tcatttgatg gaagtattaa gtattctgta 240

-continued

```
gactccgtga agggccgatt caccatctcc agagacaatt caaagaacac gctgtttctg    300

caaatgaaca gcctgcgagc cgaggacacg gctgtgtatt actgtgcgag agatcggctc    360

aattactatg atagtagtgg ttattatcac tacaaatact acggtatggc cgtctggggc    420

caagggacca cggtcaccgt ctctagtgcc tccaccaagg gcccatcggt cttccccctg    480

gcgccctgct ccaggagcac ctccgagagc acagcggccc tgggctgcct ggtcaaggac    540

tacttccccg aaccggtgac ggtgtcgtgg aactcaggcg ctctgaccag cggcgtgcac    600

accttcccag ctgtcctaca gtcctcagga ctctactccc tcagcagcgt ggtgaccgtg    660

ccctccagca acttcggcac ccagacctac acctgcaacg tagatcacaa gcccagcaac    720

accaaggtgg acaagacagt tgagcgcaaa tgttgtgtcg agtgcccacc gtgcccagca    780

ccacctgtgg caggaccgtc agtcttcctc ttccccccaa aacccaagga caccctcatg    840

atctcccgga cccctgaggt cacgtgcgtg gtggtggacg tgagccacga agaccccgag    900

gtccagttca actggtacgt ggacggcgtg gaggtgcata atgccaagac aaagccacgg    960

gaggagcagt tcaacagcac gttccgtgtg gtcagcgtcc tcaccgttgt gcaccaggac   1020

tggctgaacg gcaaggagta caagtgcaag gtctccaaca aaggcctccc agcccccatc   1080

gagaaaacca tctccaaaac caaagggcag ccccgagaac cacaggtgta caccctgccc   1140

ccatcccggg aggagatgac caagaaccag gtcagcctga cctgcctggt caaaggcttc   1200

taccccagcg acatcgccgt ggagtgggag agcaatgggc agccggagaa caactacaag   1260

accacacctc ccatgctgga ctccgacggc tccttcttcc tctacagcaa gctcaccgtg   1320

gacaagagca ggtggcagca ggggaacgtc ttctcatgct ccgtgatgca tgaggctctg   1380

cacaaccact acacgcagaa gagcctctcc ctgtctccgg gtaaa                    1425
```

<210> SEQ ID NO 48
<211> LENGTH: 475
<212> TYPE: PRT
<213> ORGANISM: Homo sapiens

<400> SEQUENCE: 48

```
Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Phe Gly Met His Trp Val Arg Gln Ala Pro Gly Lys Gly Leu
    50                  55                  60

Glu Trp Val Ala Val Ile Ser Phe Asp Gly Ser Ile Lys Tyr Ser Val
65                  70                  75                  80

Asp Ser Val Lys Gly Arg Phe Thr Ile Ser Arg Asp Asn Ser Lys Asn
                85                  90                  95

Thr Leu Phe Leu Gln Met Asn Ser Leu Arg Ala Glu Asp Thr Ala Val
            100                 105                 110

Tyr Tyr Cys Ala Arg Asp Arg Leu Asn Tyr Tyr Asp Ser Ser Gly Tyr
        115                 120                 125

Tyr His Tyr Lys Tyr Tyr Gly Met Ala Val Trp Gly Gln Gly Thr Thr
    130                 135                 140

Val Thr Val Ser Ser Ala Ser Thr Lys Gly Pro Ser Val Phe Pro Leu
145                 150                 155                 160

Ala Pro Cys Ser Arg Ser Thr Ser Glu Ser Thr Ala Ala Leu Gly Cys
```

```
                165                 170                 175

Leu Val Lys Asp Tyr Phe Pro Glu Pro Val Thr Val Ser Trp Asn Ser
            180                 185                 190

Gly Ala Leu Thr Ser Gly Val His Thr Phe Pro Ala Val Leu Gln Ser
        195                 200                 205

Ser Gly Leu Tyr Ser Leu Ser Ser Val Val Thr Val Pro Ser Ser Asn
    210                 215                 220

Phe Gly Thr Gln Thr Tyr Thr Cys Asn Val Asp His Lys Pro Ser Asn
225                 230                 235                 240

Thr Lys Val Asp Lys Thr Val Glu Arg Lys Cys Cys Val Glu Cys Pro
                245                 250                 255

Pro Cys Pro Ala Pro Pro Val Ala Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Gln Phe Asn
    290                 295                 300

Trp Tyr Val Asp Gly Val Glu Val His Asn Ala Lys Thr Lys Pro Arg
305                 310                 315                 320

Glu Glu Gln Phe Asn Ser Thr Phe Arg Val Val Ser Val Leu Thr Val
                325                 330                 335

Val His Gln Asp Trp Leu Asn Gly Lys Glu Tyr Lys Cys Lys Val Ser
            340                 345                 350

Asn Lys Gly Leu Pro Ala Pro Ile Glu Lys Thr Ile Ser Lys Thr Lys
        355                 360                 365

Gly Gln Pro Arg Glu Pro Gln Val Tyr Thr Leu Pro Pro Ser Arg Glu
    370                 375                 380

Glu Met Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Met Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475
```

<210> SEQ ID NO 49
<211> LENGTH: 702
<212> TYPE: DNA
<213> ORGANISM: Homo sapiens

<400> SEQUENCE: 49

```
atggacatga gggtgcccgc tcagctcctg gggctcctgc tgctgtggct gagaggtgcc     60

agatgttatg agctgactca gccaccctca gtgtccgtgt ccccaggaca gacagccacc    120

atcacctgct ctggagataa attgggggaa agatatgcgt cttggtatca gcagaggcca    180

ggccagtccc ctgtactggt catctatcaa gatatcaagc ggccctcagg gatccctgag    240

cgattctctg gctccaactc tgggaacaca gccactctga ccatcagcgg gacccaggct    300

atggatgagg ctgactattt ctgtcaggcg tggtacagca gcaccaatgt gcttttcggc    360
```

-continued ggagggacca agctgaccgt cctaggtcag cccaaggctg ccccctcggt cactctgttc 420
ccgccctcct ctgaggagct tcaagccaac aaggccacac tggtgtgtct cataagtgac 480
ttctacccgg gagccgtgac agtggcctgg aaggcagata gcagccccgt caaggcggga 540
gtggagacca ccacaccctc caaacaaagc aacaacaagt acgcggccag cagctatctg 600
agcctgacgc ctgagcagtg gaagtcccac agaagctaca gctgccaggt cacgcatgaa 660
gggagcaccg tggagaagac agtggcccct acagaatgtt ca 702

<210> SEQ ID NO 50
<211> LENGTH: 234
<212> TYPE: PRT
<213> ORGANISM: Homo sapiens

<400> SEQUENCE: 50

Met Asp Met Arg Val Pro Ala Gln Leu Leu Gly Leu Leu Leu Leu Trp
1 5 10 15

Leu Arg Gly Ala Arg Cys Tyr Glu Leu Thr Gln Pro Pro Ser Val Ser
20 25 30

Val Ser Pro Gly Gln Thr Ala Thr Ile Thr Cys Ser Gly Asp Lys Leu
35 40 45

Gly Glu Arg Tyr Ala Ser Trp Tyr Gln Gln Arg Pro Gly Gln Ser Pro
50 55 60

Val Leu Val Ile Tyr Gln Asp Ile Lys Arg Pro Ser Gly Ile Pro Glu
65 70 75 80

Arg Phe Ser Gly Ser Asn Ser Gly Asn Thr Ala Thr Leu Thr Ile Ser
85 90 95

Gly Thr Gln Ala Met Asp Glu Ala Asp Tyr Phe Cys Gln Ala Trp Tyr
100 105 110

Ser Ser Thr Asn Val Leu Phe Gly Gly Gly Thr Lys Leu Thr Val Leu
115 120 125

Gly Gln Pro Lys Ala Ala Pro Ser Val Thr Leu Phe Pro Pro Ser Ser
130 135 140

Glu Glu Leu Gln Ala Asn Lys Ala Thr Leu Val Cys Leu Ile Ser Asp
145 150 155 160

Phe Tyr Pro Gly Ala Val Thr Val Ala Trp Lys Ala Asp Ser Ser Pro
165 170 175

Val Lys Ala Gly Val Glu Thr Thr Thr Pro Ser Lys Gln Ser Asn Asn
180 185 190

Lys Tyr Ala Ala Ser Ser Tyr Leu Ser Leu Thr Pro Glu Gln Trp Lys
195 200 205

Ser His Arg Ser Tyr Ser Cys Gln Val Thr His Glu Gly Ser Thr Val
210 215 220

Glu Lys Thr Val Ala Pro Thr Glu Cys Ser
225 230

<210> SEQ ID NO 51
<211> LENGTH: 1398
<212> TYPE: DNA
<213> ORGANISM: Homo sapiens

<400> SEQUENCE: 51
atggagtttg ggctgagctg ggttttcctc gttgctcttt taagaggtgt ccagtgtcag 60
gtgcagctgg tggagtctgg gggaggcgtg gtccagcctg ggaggtccct gagactctcc 120
tgtgcagcgt ctggattcac cttcagtagc tatggcatgc actgggtccg ccaggctcca 180

-continued

```
ggcaaggggc tggagtgggt ggcagttata tggtatgctg aaagtaataa atactacgca    240

gactccgtga agggccgatt caccatctcc agagacaatt ccaagaacac gctgtatctg    300

caaatgaaca gcctgagagc cgaggacacg gctgtgtatt actgtgcgag agcccaggag    360

ggtatagccc ctgacgcttt tgatatctgg ggccaaggaa caatggtcac cgtctcttca    420

gcctccacca agggcccatc ggtcttcccc ctggcgccct gctccaggag cacctccgag    480

agcacagcgg ccctgggctg cctggtcaag gactacttcc ccgaaccggt gacggtgtcg    540

tggaactcag gcgctctgac cagcggcgtg cacaccttcc cagctgtcct acagtcctca    600

ggactctact ccctcagcag cgtggtgacc gtgccctcca gcaacttcgg cacccagacc    660

tacacctgca acgtagatca caagcccagc aacaccaagg tggacaagac agttgagcgc    720

aaatgttgtg tcgagtgccc accgtgccca gcaccacctg tggcaggacc gtcagtcttc    780

ctcttccccc caaaacccaa ggacaccctc atgatctccc ggacccctga ggtcacgtgc    840

gtggtggtgg acgtgagcca cgaagacccc gaggtccagt tcaactggta cgtggacggc    900

gtggaggtgc ataatgccaa gacaaagcca cgggaggagc agttcaacag cacgttccgt    960

gtggtcagcg tcctcaccgt tgtgcaccag gactggctga acggcaagga gtacaagtgc   1020

aaggtctcca acaaaggcct cccagccccc atcgagaaaa ccatctccaa aaccaaaggg   1080

cagccccgag aaccacaggt gtacaccctg cccccatccc gggaggagat gaccaagaac   1140

caggtcagcc tgacctgcct ggtcaaaggc ttctacccca gcgacatcgc cgtggagtgg   1200

gagagcaatg ggcagccgga gaacaactac aagaccacac ctcccatgct ggactccgac   1260

ggctccttct tcctctacag caagctcacc gtggacaaga gcaggtggca gcaggggaac   1320

gtcttctcat gctccgtgat gcatgaggct ctgcacaacc actacacgca gaagagcctc   1380

tccctgtctc cgggtaaa                                                  1398


<210> SEQ ID NO 52
<211> LENGTH: 466
<212> TYPE: PRT
<213> ORGANISM: Homo sapiens

<400> SEQUENCE: 52

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ala Val Ile Trp Tyr Ala Glu Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Ala Gln Glu Gly Ile Ala Pro Asp Ala Phe Asp
        115                 120                 125

Ile Trp Gly Gln Gly Thr Met Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160
```

```
Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465
```

<210> SEQ ID NO 53
<211> LENGTH: 702
<212> TYPE: DNA
<213> ORGANISM: Homo sapiens

<400> SEQUENCE: 53

```
atggggtcaa ccgccatcct tggcctcctc ctggctgtcc tgcagggagg gcgcgccgaa      60

attgtgttga cgcagtctcc aggcaccctg tctttgtctc caggggaaag agccaccctc     120

tcctgcaggg ccagtcagag tgttagcagc agctacttag cctggcacca gcagaaacct     180

ggccaggctc ccaggctcct catctatggt gcatccagca gggccactgg catcccagac     240

aggttcagtg gcagtgggtc tgggacagac ttcactctca ccatcagcag actggagcct     300
```

-continued

```
gaagattttg cagtgtatta ctgtcagcag tatggtagct caccgtggac gttcggccaa    360

gggaccaagg tggaaatcaa acgtacggtg gctgcaccat ctgtcttcat cttcccgcca    420

tctgatgagc agttgaaatc tggaactgcc tctgttgtgt gcctgctgaa taacttctat    480

cccagagagg ccaaagtaca gtggaaggtg gataacgccc tccaatcggg taactcccag    540

gagagtgtca cagagcagga cagcaaggac agcacctaca gcctcagcag caccctgacg    600

ctgagcaaag cagactacga gaaacacaaa gtctacgcct gcgaagtcac ccatcagggc    660

ctgagctcgc ccgtcacaaa gagcttcaac aggggagagt gt                       702
```

```
<210> SEQ ID NO 54
<211> LENGTH: 234
<212> TYPE: PRT
<213> ORGANISM: Homo sapiens

<400> SEQUENCE: 54

Met Gly Ser Thr Ala Ile Leu Gly Leu Leu Leu Ala Val Leu Gln Gly
1               5                   10                  15

Gly Arg Ala Glu Ile Val Leu Thr Gln Ser Pro Gly Thr Leu Ser Leu
            20                  25                  30

Ser Pro Gly Glu Arg Ala Thr Leu Ser Cys Arg Ala Ser Gln Ser Val
        35                  40                  45

Ser Ser Ser Tyr Leu Ala Trp His Gln Gln Lys Pro Gly Gln Ala Pro
    50                  55                  60

Arg Leu Leu Ile Tyr Gly Ala Ser Ser Arg Ala Thr Gly Ile Pro Asp
65                  70                  75                  80

Arg Phe Ser Gly Ser Gly Ser Gly Thr Asp Phe Thr Leu Thr Ile Ser
                85                  90                  95

Arg Leu Glu Pro Glu Asp Phe Ala Val Tyr Tyr Cys Gln Gln Tyr Gly
            100                 105                 110

Ser Ser Pro Trp Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230


<210> SEQ ID NO 55
<211> LENGTH: 1389
<212> TYPE: DNA
<213> ORGANISM: Homo sapiens

<400> SEQUENCE: 55

atggggtcaa ccgccatcct tggcctcctc ctggctgtcc tgcagggagg gcgcgccgag     60

gtgcagctat tggagtctgg gggaggcttg gtacagcctg gggggtccct gagactctcc    120
```

-continued

```
tgtgcagcct ctggattcac ctttagcacc tatgtcatga gctgggtccg ccaggctcca    180

gggaaggggc tggagtgggt ctcaagtatt agtggtagtg gtcttggctc atactacgca    240

gactccgtga agggccggtt caccatctcc agagacaatt ccaagaacac gctgtatctg    300

caaatgaaca gcctgagagc cgaggacacg gccgtatatt actgtgcgaa agaggcccat    360

cggggggccct ttgactactg gggccaggga accctggtca ccgtctcctc agctagcacc    420

aagggcccat cggtcttccc cctggcgccc tgctccagga gcacctccga gagcacagcg    480

gccctgggct gcctggtcaa ggactacttc cccgaaccgg tgacggtgtc gtggaactca    540

ggcgctctga ccagcggcgt gcacaccttc ccagctgtcc tacagtcctc aggactctac    600

tccctcagca gcgtggtgac cgtgccctcc agcaacttcg gcacccagac ctacacctgc    660

aacgtagatc acaagcccag caacaccaag gtggacaaga cagttgagcg caaatgttgt    720

gtcgagtgcc caccgtgccc agcaccacct gtggcaggac cgtcagtctt cctcttcccc    780

ccaaaaccca aggacaccct catgatctcc cggacccctg aggtcacgtg cgtggtggtg    840

gacgtgagcc acgaagaccc cgaggtccag ttcaactggt acgtggacgg cgtggaggtg    900

cataatgcca agacaaagcc acgggaggag cagttcaaca gcacgttccg tgtggtcagc    960

gtcctcaccg ttgtgcacca ggactggctg aacggcaagg agtacaagtg caaggtctcc   1020

aacaaaggcc tcccagcccc catcgagaaa accatctcca aaaccaaagg gcagccccga   1080

gaaccacagg tgtacaccct gcccccatcc cgggaggaga tgaccaagaa ccaggtcagc   1140

ctgacctgcc tggtcaaagg cttctacccc agcgacatcg ccgtggagtg ggagagcaat   1200

gggcagccgg agaacaacta caagaccaca cctcccatgc tggactccga cggctccttc   1260

ttcctctaca gcaagctcac cgtggacaag agcaggtggc agcaggggaa cgtcttctca   1320

tgctccgtga tgcatgaggc tctgcacaac cactacacgc agaagagcct ctccctgtct   1380

ccgggtaaa                                                           1389
```

<210> SEQ ID NO 56
<211> LENGTH: 463
<212> TYPE: PRT
<213> ORGANISM: Homo sapiens

<400> SEQUENCE: 56

```
Met Gly Ser Thr Ala Ile Leu Gly Leu Leu Leu Ala Val Leu Gln Gly
1               5                   10                  15

Gly Arg Ala Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Thr Tyr Val Met Ser Trp Val Arg Gln Ala Pro Gly Lys Gly Leu
    50                  55                  60

Glu Trp Val Ser Ser Ile Ser Gly Ser Gly Leu Gly Ser Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Glu Ala His Arg Gly Pro Phe Asp Tyr Trp Gly
        115                 120                 125

Gln Gly Thr Leu Val Thr Val Ser Ser Ala Ser Thr Lys Gly Pro Ser
    130                 135                 140
```

```
Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
                325                 330                 335

Cys Lys Val Ser Asn Lys Gly Leu Pro Ala Pro Ile Glu Lys Thr Ile
            340                 345                 350

Ser Lys Thr Lys Gly Gln Pro Arg Glu Pro Gln Val Tyr Thr Leu Pro
        355                 360                 365

Pro Ser Arg Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
    450                 455                 460
```

<210> SEQ ID NO 57
<211> LENGTH: 721
<212> TYPE: DNA
<213> ORGANISM: Homo sapiens

<400> SEQUENCE: 57

```
atgaggctcc ttgctcagct tctggggctg ctaatgctct gggtccctgg atccagtggg     60

gatattgtga tgacccagac tccactctcc tcacctgtca cccttggaca gccggcctcc    120

atctcctgca ggtctagtca aagcctcgta cacagtgatg gaaacaccta cttgagttgg    180

cttcagcaga ggccaggcca gcctccaaga ctcctaattt ataagaaatt taaccggttc    240

tctggggtcc cagacagatt cagtggcagt ggggcaggga cagatttcac actgaaaatc    300

agcagggtgg aagctgagga tgtcggggtt tattactgca tgcaagctac acaaattcct    360
```

ctcactttcg gccctgggac caaagtggat atcaaacgaa ctgtggctgc accatctgtc 420
ttcatcttcc cgccatctga tgagcagttg aaatctggaa ctgcctctgt tgtgtgcctg 480
ctgaataact tctatcccag agaggccaaa gtacagtgga aggtggataa cgccctccaa 540
tcgggtaact cccaggagag tgtcacagag caggacagca aggacagcac ctacagcctc 600
agcagcaccc tgacgctgag caaagcagac tacgagaaac acaaagtcta cgcctgcgaa 660
gtcacccatc agggcctgag ctcgcccgtc acaaagagct tcaacagggg agagtgttga 720
g 721

<210> SEQ ID NO 58
<211> LENGTH: 239
<212> TYPE: PRT
<213> ORGANISM: Homo sapiens

<400> SEQUENCE: 58

Met Arg Leu Leu Ala Gln Leu Leu Gly Leu Leu Met Leu Trp Val Pro
1 5 10 15

Gly Ser Ser Gly Asp Ile Val Met Thr Gln Thr Pro Leu Ser Ser Pro
20 25 30

Val Thr Leu Gly Gln Pro Ala Ser Ile Ser Cys Arg Ser Ser Gln Ser
35 40 45

Leu Val His Ser Asp Gly Asn Thr Tyr Leu Ser Trp Leu Gln Gln Arg
50 55 60

Pro Gly Gln Pro Pro Arg Leu Leu Ile Tyr Lys Lys Phe Asn Arg Phe
65 70 75 80

Ser Gly Val Pro Asp Arg Phe Ser Gly Ser Gly Ala Gly Thr Asp Phe
85 90 95

Thr Leu Lys Ile Ser Arg Val Glu Ala Glu Asp Val Gly Val Tyr Tyr
100 105 110

Cys Met Gln Ala Thr Gln Ile Pro Leu Thr Phe Gly Pro Gly Thr Lys
115 120 125

Val Asp Ile Lys Arg Thr Val Ala Ala Pro Ser Val Phe Ile Phe Pro
130 135 140

Pro Ser Asp Glu Gln Leu Lys Ser Gly Thr Ala Ser Val Val Cys Leu
145 150 155 160

Leu Asn Asn Phe Tyr Pro Arg Glu Ala Lys Val Gln Trp Lys Val Asp
165 170 175

Asn Ala Leu Gln Ser Gly Asn Ser Gln Glu Ser Val Thr Glu Gln Asp
180 185 190

Ser Lys Asp Ser Thr Tyr Ser Leu Ser Ser Thr Leu Thr Leu Ser Lys
195 200 205

Ala Asp Tyr Glu Lys His Lys Val Tyr Ala Cys Glu Val Thr His Gln
210 215 220

Gly Leu Ser Ser Pro Val Thr Lys Ser Phe Asn Arg Gly Glu Cys
225 230 235

<210> SEQ ID NO 59
<211> LENGTH: 1416
<212> TYPE: DNA
<213> ORGANISM: Homo sapiens

<400> SEQUENCE: 59
atggagtttg ggctgagctg ggttttcctc gttgctcttt taagaggtgt ccagtgtcag 60
gtgcagctgg tggagtctgg gggaggcgtg gtccagcctg ggaggtccct gagactctcc 120

```
tgtgcagcgt ctggattcac cttcagtttc tatggcatgc actgggtccg ccaggctcca    180

ggcaaggggc tggagtgggt ggcagttata tggtatgatg gaagtaataa atactatgca    240

gactccgtga agggccgatt caccatctcc agagacaatt ccaagaacac gctgtatctg    300

caaatgaaca gcctgagagc cgaggacacg gctgtgtatt actgtgcgag agggggttat    360

gattacgttt gggggagtta tcgccgtaac tccgactttg actactgggg ccagggaacc    420

ctggtcaccg tctctagtgc ctccaccaag ggcccatcgg tcttcccct ggcgccctgc    480

tccaggagca cctccgagag cacagcggcc ctgggctgcc tggtcaagga ctacttcccc    540

gaaccggtga cggtgtcgtg gaactcaggc gctctgacca gcggcgtgca caccttccca    600

gctgtcctac agtcctcagg actctactcc ctcagcagcg tggtgaccgt gccctccagc    660

aacttcggca cccagaccta cacctgcaac gtagatcaca agcccagcaa caccaaggtg    720

gacaagacag ttgagcgcaa atgttgtgtc gagtgcccac cgtgcccagc accacctgtg    780

gcaggaccgt cagtcttcct cttcccccca aaacccaagg acaccctcat gatctcccgg    840

acccctgagg tcacgtgcgt ggtggtggac gtgagccacg aagaccccga ggtccagttc    900

aactggtacg tggacggcgt ggaggtgcat aatgccaaga caaagccacg ggaggagcag    960

ttcaacagca cgttccgtgt ggtcagcgtc ctcaccgttg tgcaccagga ctggctgaac   1020

ggcaaggagt acaagtgcaa ggtctccaac aaaggcctcc cagcccccat cgagaaaacc   1080

atctccaaaa ccaaagggca gccccgagaa ccacaggtgt acaccctgcc cccatcccgg   1140

gaggagatga ccaagaacca ggtcagcctg acctgcctgg tcaaaggctt ctaccccagc   1200

gacatcgccg tggagtggga gagcaatggg cagccggaga acaactacaa gaccacacct   1260

cccatgctgg actccgacgg ctccttcttc ctctacagca agctcaccgt ggacaagagc   1320

aggtggcagc aggggaacgt cttctcatgc tccgtgatgc atgaggctct gcacaaccac   1380

tacacgcaga agagcctctc cctgtctccg ggtaaa                             1416

<210> SEQ ID NO 60
<211> LENGTH: 472
<212> TYPE: PRT
<213> ORGANISM: Homo sapiens

<400> SEQUENCE: 60

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Phe Tyr Gly Met His Trp Val Arg Gln Ala Pro Gly Lys Gly Leu
    50                  55                  60

Glu Trp Val Ala Val Ile Trp Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Gly Gly Tyr Asp Tyr Val Trp Gly Ser Tyr Arg
        115                 120                 125

Arg Asn Ser Asp Phe Asp Tyr Trp Gly Gln Gly Thr Leu Val Thr Val
    130                 135                 140
```

-continued

```
Ser Ser Ala Ser Thr Lys Gly Pro Ser Val Phe Pro Leu Ala Pro Cys
145                 150                 155                 160

Ser Arg Ser Thr Ser Glu Ser Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Asn Phe Gly Thr
    210                 215                 220

Gln Thr Tyr Thr Cys Asn Val Asp His Lys Pro Ser Asn Thr Lys Val
225                 230                 235                 240

Asp Lys Thr Val Glu Arg Lys Cys Cys Val Glu Cys Pro Pro Cys Pro
                245                 250                 255

Ala Pro Pro Val Ala Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Gln Phe Asn Trp Tyr Val
    290                 295                 300

Asp Gly Val Glu Val His Asn Ala Lys Thr Lys Pro Arg Glu Glu Gln
305                 310                 315                 320

Phe Asn Ser Thr Phe Arg Val Val Ser Val Leu Thr Val Val His Gln
                325                 330                 335

Asp Trp Leu Asn Gly Lys Glu Tyr Lys Cys Lys Val Ser Asn Lys Gly
            340                 345                 350

Leu Pro Ala Pro Ile Glu Lys Thr Ile Ser Lys Thr Lys Gly Gln Pro
        355                 360                 365

Arg Glu Pro Gln Val Tyr Thr Leu Pro Pro Ser Arg Glu Glu Met Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Met Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys
465                 470
```

<210> SEQ ID NO 61
<211> LENGTH: 705
<212> TYPE: DNA
<213> ORGANISM: Homo sapiens

<400> SEQUENCE: 61

```
atggaagccc cagctcagct tctcttcctc ctgctactct ggctcccaga taccactgga      60

gaaatagtga tgacgcagtc tccagccacc ctgtctgtgt ctccagggga aagagccacc     120

ctctcctgca gggccagtca gagtgttgac agcaacttag cctggtaccg gcagaaacct     180

ggccaggctc ccaggctcct catctatggt gcatccacca gggccactgg tatcccagcc     240
```

```
aggttcagtg gcagtgggtc tgggactgag ttcactctca ccatcagcag cctgcagtct    300

gaagattttg cagtttatta ctgtcagcag tatattaact ggcctccgat caccttcggc    360

caagggacac gactggagat taaacgaact gtggctgcac catctgtctt catcttcccg    420

ccatctgatg agcagttgaa atctggaact gcctctgttg tgtgcctgct gaataacttc    480

tatcccagag aggccaaagt acagtggaag gtggataacg ccctccaatc gggtaactcc    540

caggagagtg tcacagagca ggacagcaag gacagcacct acagcctcag cagcaccctg    600

acgctgagca aagcagacta cgagaaacac aaagtctacg cctgcgaagt cacccatcag    660

ggcctgagct cgcccgtcac aaagagcttc aacaggggag agtgt                    705


<210> SEQ ID NO 62
<211> LENGTH: 235
<212> TYPE: PRT
<213> ORGANISM: Homo sapiens

<400> SEQUENCE: 62

Met Glu Ala Pro Ala Gln Leu Leu Phe Leu Leu Leu Leu Trp Leu Pro
1               5                   10                  15

Asp Thr Thr Gly Glu Ile Val Met Thr Gln Ser Pro Ala Thr Leu Ser
            20                  25                  30

Val Ser Pro Gly Glu Arg Ala Thr Leu Ser Cys Arg Ala Ser Gln Ser
        35                  40                  45

Val Asp Ser Asn Leu Ala Trp Tyr Arg Gln Lys Pro Gly Gln Ala Pro
    50                  55                  60

Arg Leu Leu Ile Tyr Gly Ala Ser Thr Arg Ala Thr Gly Ile Pro Ala
65                  70                  75                  80

Arg Phe Ser Gly Ser Gly Ser Gly Thr Glu Phe Thr Leu Thr Ile Ser
                85                  90                  95

Ser Leu Gln Ser Glu Asp Phe Ala Val Tyr Tyr Cys Gln Gln Tyr Ile
            100                 105                 110

Asn Trp Pro Pro Ile Thr Phe Gly Gln Gly Thr Arg Leu Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235


<210> SEQ ID NO 63
<211> LENGTH: 1395
<212> TYPE: DNA
<213> ORGANISM: Homo sapiens

<400> SEQUENCE: 63

atgaaacacc tgtggttctt ccttctcctg gtggcagctc ccagatgggt cctgtcccag     60
```

```
gtgcagctgc aggagtcggg cccaggactg gtgaagcctt cggagaccct gtccctcacc    120

tgcactgtct ctggtggctc catcagtatt tactactgga gctggatccg gcagccccca    180

gggaagggac tggagtggat tgggtatgtc tattacagtg ggagcaccaa ttacaacccc    240

tccctcaaga gtcgagtcac catatcagta gacacgtcca agaaccagtt ctccctgaag    300

ctgaactctg tgaccgctgc ggacacggcc gtgtattact gtgcgagagg gggatacgat    360

ttttggagtg gttattttga ctactggggc cagggaaccc tggtcaccgt ctctagtgcc    420

tccaccaagg gcccatcggt cttccccctg gcgccctgct ccaggagcac ctccgagagc    480

acagcggccc tgggctgcct ggtcaaggac tacttccccg aaccggtgac ggtgtcgtgg    540

aactcaggcg ctctgaccag cggcgtgcac accttcccag ctgtcctaca gtcctcagga    600

ctctactccc tcagcagcgt ggtgaccgtg ccctccagca acttcggcac ccagacctac    660

acctgcaacg tagatcacaa gcccagcaac accaaggtgg acaagacagt tgagcgcaaa    720

tgttgtgtcg agtgcccacc gtgcccagca ccacctgtgg caggaccgtc agtcttcctc    780

ttccccccaa aacccaagga caccctcatg atctcccgga cccctgaggt cacgtgcgtg    840

gtggtggacg tgagccacga agaccccgag gtccagttca actggtacgt ggacggcgtg    900

gaggtgcata atgccaagac aaagccacgg gaggagcagt tcaacagcac gttccgtgtg    960

gtcagcgtcc tcaccgttgt gcaccaggac tggctgaacg gcaaggagta caagtgcaag   1020

gtctccaaca aaggcctccc agcccccatc gagaaaacca tctccaaaac caaagggcag   1080

ccccgagaac cacaggtgta caccctgccc ccatcccggg aggagatgac caagaaccag   1140

gtcagcctga cctgcctggt caaaggcttc taccccagcg acatcgccgt ggagtgggag   1200

agcaatgggc agccggagaa caactacaag accacacctc ccatgctgga ctccgacggc   1260

tccttcttcc tctacagcaa gctcaccgtg gacaagagca ggtggcagca ggggaacgtc   1320

ttctcatgct ccgtgatgca tgaggctctg cacaaccact acacgcagaa gagcctctcc   1380

ctgtctccgg gtaaa                                                    1395
```

<210> SEQ ID NO 64
<211> LENGTH: 465
<212> TYPE: PRT
<213> ORGANISM: Homo sapiens

<400> SEQUENCE: 64

```
Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Gly Ser Ile
        35                  40                  45

Ser Ile Tyr Tyr Trp Ser Trp Ile Arg Gln Pro Pro Gly Lys Gly Leu
    50                  55                  60

Glu Trp Ile Gly Tyr Val Tyr Tyr Ser Gly Ser Thr Asn Tyr Asn Pro
65                  70                  75                  80

Ser Leu Lys Ser Arg Val Thr Ile Ser Val Asp Thr Ser Lys Asn Gln
                85                  90                  95

Phe Ser Leu Lys Leu Asn Ser Val Thr Ala Ala Asp Thr Ala Val Tyr
            100                 105                 110

Tyr Cys Ala Arg Gly Gly Tyr Asp Phe Trp Ser Gly Tyr Phe Asp Tyr
        115                 120                 125
```

```
Trp Gly Gln Gly Thr Leu Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Asn Phe Gly Thr Gln Thr Tyr Thr Cys Asn Val
    210                 215                 220

Asp His Lys Pro Ser Asn Thr Lys Val Asp Lys Thr Val Glu Arg Lys
225                 230                 235                 240

Cys Cys Val Glu Cys Pro Pro Cys Pro Ala Pro Pro Val Ala Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Phe Arg Val
305                 310                 315                 320

Val Ser Val Leu Thr Val Val His Gln Asp Trp Leu Asn Gly Lys Glu
                325                 330                 335

Tyr Lys Cys Lys Val Ser Asn Lys Gly Leu Pro Ala Pro Ile Glu Lys
            340                 345                 350

Thr Ile Ser Lys Thr Lys Gly Gln Pro Arg Glu Pro Gln Val Tyr Thr
        355                 360                 365

Leu Pro Pro Ser Arg Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Met Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465
```

<210> SEQ ID NO 65
<211> LENGTH: 723
<212> TYPE: DNA
<213> ORGANISM: Homo sapiens

<400> SEQUENCE: 65

```
atggtgctgc agacccaggt gtttattagc ctgctgctgt ggattagcgg cgcgtatggc      60

gacatcgtgc tgacccagtc tccagactcc ctggctgtgt ctctgggcga gagggccacc     120

atcaactgca agtccagcca gagtatttta tacagctcca gcaatgagaa cttcttaact     180
```

```
tggtaccagc agaaaccagg acagcctcct aagctgctca tttactgggc atctacccgg    240

gaatccgggg tccctgaccg attcagtggc agcgggtctg ggacagattt cactctcacc    300

atcagcagcc tgcagcctga agatgtggca gtttattact gtcagcaata ttttagtgtt    360

tttcggacgt tcggccaagg gaccagggtg gaaatcaaac gtacggtggc tgcaccatct    420

gtcttcatct tcccgccatc tgatgagcag ttgaaatctg gaactgcctc tgttgtgtgc    480

ctgctgaata acttctatcc cagagaggcc aaagtacagt ggaaggtgga taacgccctc    540

caatcgggta actcccagga gagtgtcaca gagcaggaca gcaaggacag cacctacagc    600

ctcagcagca ccctgacgct gagcaaagca gactacgaga aacacaaagt ctacgcctgc    660

gaagtcaccc atcagggcct gagctcgccc gtcacaaaga gcttcaacag gggagagtgt    720

tag                                                                 723
```

<210> SEQ ID NO 66
<211> LENGTH: 240
<212> TYPE: PRT
<213> ORGANISM: Homo sapiens

<400> SEQUENCE: 66

```
Met Val Leu Gln Thr Gln Val Phe Ile Ser Leu Leu Leu Trp Ile Ser
1               5                   10                  15

Gly Ala Tyr Gly Asp Ile Val Leu Thr Gln Ser Pro Asp Ser Leu Ala
            20                  25                  30

Val Ser Leu Gly Glu Arg Ala Thr Ile Asn Cys Lys Ser Ser Gln Ser
        35                  40                  45

Ile Leu Tyr Ser Ser Ser Asn Glu Asn Phe Leu Thr Trp Tyr Gln Gln
    50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Pro Glu Asp Val Ala Val Tyr
            100                 105                 110

Tyr Cys Gln Gln Tyr Phe Ser Val Phe Arg Thr Phe Gly Gln Gly Thr
        115                 120                 125

Arg Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

<210> SEQ ID NO 67
<211> LENGTH: 1395
<212> TYPE: DNA
<213> ORGANISM: Homo sapiens

<400> SEQUENCE: 67
atggattgga cctggcgtat tctgtttctg gtggcggcgg cgaccggcgc gcatagccag 60
gtgcagctgg tgcagtctgg ggctgaggtg aagaagcctg gggcctcagt gaaggtctcc 120
tgcaaggctt ctggatacac cttcaccggc tactatatac actgggtgcg acaggcccct 180
ggacaagggc ttgagtggat gggatggatc aaccctaaca gtggtggcac aaactctgca 240
cagaagtttc ggggcagggt caccatgacc agggacacgt ccatcagcac agcctacatg 300
gagctgagca ggctgagatc tgacgacacg gccgtgtatt actgtgcgcg agagggtgga 360
tacagctatg gttactttga ctactggggc cagggaaccc tggtcaccgt ctcctcagct 420
agcaccaagg gcccatcggt cttccccctg gcgccctgct ccaggagcac ctccgagagc 480
acagcggccc tgggctgcct ggtcaaggac tacttccccg aaccggtgac ggtgtcgtgg 540
aactcaggcg ctctgaccag cggcgtgcac accttcccag ctgtcctaca gtcctcagga 600
ctctactccc tcagcagcgt ggtgaccgtg ccctccagca acttcggcac ccagacctac 660
acctgcaacg tagatcacaa gcccagcaac accaaggtgg acaagacagt tgagcgcaaa 720
tgttgtgtcg agtgcccacc gtgcccagca ccacctgtgg caggaccgtc agtcttcctc 780
ttccccccaa aacccaagga caccctcatg atctcccgga cccctgaggt cacgtgcgtg 840
gtggtggacg tgagccacga agaccccgag gtccagttca actggtacgt ggacggcgtg 900
gaggtgcata atgccaagac aaagccacgg gaggagcagt tcaacagcac gttccgtgtg 960
gtcagcgtcc tcaccgttgt gcaccaggac tggctgaacg gcaaggagta caagtgcaag 1020
gtctccaaca aaggcctccc agcccccatc gagaaaacca tctccaaaac caaagggcag 1080
ccccgagaac cacaggtgta caccctgccc ccatcccggg aggagatgac caagaaccag 1140
gtcagcctga cctgcctggt caaaggcttc taccccagcg acatcgccgt ggagtgggag 1200
agcaatgggc agccggagaa caactacaag accacacctc ccatgctgga ctccgacggc 1260
tccttcttcc tctacagcaa gctcaccgtg gacaagagca ggtggcagca ggggaacgtc 1320
ttctcatgct ccgtgatgca tgaggctctg cacaaccact acacgcagaa gagcctctcc 1380
ctgtctccgg gtaaa 1395

<210> SEQ ID NO 68
<211> LENGTH: 465
<212> TYPE: PRT
<213> ORGANISM: Homo sapiens

<400> SEQUENCE: 68

Met Asp Trp Thr Trp Arg Ile Leu Phe Leu Val Ala Ala Ala Thr Gly
1 5 10 15

Ala His Ser Gln Val Gln Leu Val Gln Ser Gly Ala Glu Val Lys Lys
20 25 30

Pro Gly Ala Ser Val Lys Val Ser Cys Lys Ala Ser Gly Tyr Thr Phe
35 40 45

Thr Gly Tyr Tyr Ile His Trp Val Arg Gln Ala Pro Gly Gln Gly Leu
50 55 60

Glu Trp Met Gly Trp Ile Asn Pro Asn Ser Gly Gly Thr Asn Ser Ala
65 70 75 80

Gln Lys Phe Arg Gly Arg Val Thr Met Thr Arg Asp Thr Ser Ile Ser
85 90 95

Thr Ala Tyr Met Glu Leu Ser Arg Leu Arg Ser Asp Asp Thr Ala Val
100 105 110

```
Tyr Tyr Cys Ala Arg Glu Gly Gly Tyr Ser Tyr Gly Tyr Phe Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Asn Phe Gly Thr Gln Thr Tyr Thr Cys Asn Val
    210                 215                 220

Asp His Lys Pro Ser Asn Thr Lys Val Asp Lys Thr Val Glu Arg Lys
225                 230                 235                 240

Cys Cys Val Glu Cys Pro Pro Cys Pro Ala Pro Pro Val Ala Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Phe Arg Val
305                 310                 315                 320

Val Ser Val Leu Thr Val Val His Gln Asp Trp Leu Asn Gly Lys Glu
                325                 330                 335

Tyr Lys Cys Lys Val Ser Asn Lys Gly Leu Pro Ala Pro Ile Glu Lys
            340                 345                 350

Thr Ile Ser Lys Thr Lys Gly Gln Pro Arg Glu Pro Gln Val Tyr Thr
        355                 360                 365

Leu Pro Pro Ser Arg Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Met Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465
```

<210> SEQ ID NO 69
<211> LENGTH: 708
<212> TYPE: DNA
<213> ORGANISM: Homo sapiens

<400> SEQUENCE: 69

```
atggacatga gggtccccgc tcagctcctg gggctcctgc tgctctggtt cccaggtgcc     60
```

```
aggtgtgaca tccagatgac ccagtctcca tcctccctgt ctgcatctgt aggagacaga    120

gtcaccatca cttgccgggc aagtcagggc attagaaatg atttaggctg gtatcagcag    180

aaaccaggga aagcccctaa gcgcctgatc tatgctgcat ccagtttgca aagtggggtc    240

ccatcaaggt tcagcggcag tggatctggg acagaattca ctctcacaat cagcagtgtg    300

cagcctgaag attttgtaac ttattactgt ctacagcata atagtaaccc tctcactttc    360

ggcggaggga ccaaggtgga gatcaaacga actgtggctg caccatctgt cttcatcttc    420

ccgccatctg atgagcagtt gaaatctgga actgcctctg ttgtgtgcct gctgaataac    480

ttctatccca gagaggccaa agtacagtgg aaggtggata acgccctcca atcgggtaac    540

tcccaggaga gtgtcacaga gcaggacagc aaggacagca cctacagcct cagcagcacc    600

ctgacgctga gcaaagcaga ctacgagaaa cacaaagtct acgcctgcga agtcacccat    660

cagggcctga gctcgcccgt cacaaagagc ttcaacaggg gagagtgt                 708
```

<210> SEQ ID NO 70
<211> LENGTH: 236
<212> TYPE: PRT
<213> ORGANISM: Homo sapiens

<400> SEQUENCE: 70

```
Met Asp Met Arg Val Pro Ala Gln Leu Leu Gly Leu Leu Leu Leu Trp
1               5                   10                  15

Phe Pro Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Arg Asn Asp Leu Gly Trp Tyr Gln Gln Lys Pro Gly Lys
    50                  55                  60

Ala Pro Lys Arg Leu Ile Tyr Ala Ala Ser Ser Leu Gln Ser Gly Val
65                  70                  75                  80

Pro Ser Arg Phe Ser Gly Ser Gly Ser Gly Thr Glu Phe Thr Leu Thr
                85                  90                  95

Ile Ser Ser Val Gln Pro Glu Asp Phe Val Thr Tyr Tyr Cys Leu Gln
            100                 105                 110

His Asn Ser Asn Pro Leu Thr Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 71
<211> LENGTH: 1419

<212> TYPE: DNA
<213> ORGANISM: Homo sapiens

<400> SEQUENCE: 71

```
atggagtttg ggctgagctg ggttttcctc gttgctcttt taagaggtgt ccagtgtcag     60
gtgcagctgg tggagtctgg gggaggcgtg gtccagcctg ggaggtccct gagactctcc    120
tgtgcagcgt ctggattcac cttcagtagc tatggcatgc actgggtccg ccaggctcca    180
ggcaaggggc tggagtgggt ggcagttatg tggtatgatg gaagtaataa agactatgta    240
gactccgtga agggccgatt caccatctcc agagacaatt ccaagaacac gctgtatctg    300
caaatgaacc gcctgagagc cgaggacacg gctgtgtatt actgtgcgag agaaaaagat    360
cattacgaca ttttgactgg ttataactac tactacggtc tggacgtctg gggccaaggg    420
accacggtca ccgtctcctc agcctccacc aagggcccat cggtcttccc cctggcgccc    480
tgctccagga gcacctccga gagcacagcg gccctgggct gcctggtcaa ggactacttc    540
cccgaaccgg tgacggtgtc gtggaactca ggcgctctga ccagcggcgt gcacaccttc    600
ccagctgtcc tacagtcctc aggactctac tccctcagca gcgtggtgac cgtgccctcc    660
agcaacttcg gcacccagac ctacacctgc aacgtagatc acaagcccag caacaccaag    720
gtggacaaga cagttgagcg caaatgttgt gtcgagtgcc caccgtgccc agcaccacct    780
gtggcaggac cgtcagtctt cctcttcccc ccaaaaccca aggacaccct catgatctcc    840
cggacccctg aggtcacgtg cgtggtggtg gacgtgagcc acgaagaccc cgaggtccag    900
ttcaactggt acgtggacgg cgtggaggtg cataatgcca agacaaagcc acgggaggag    960
cagttcaaca gcacgttccg tgtggtcagc gtcctcaccg ttgtgcacca ggactggctg   1020
aacggcaagg agtacaagtg caaggtctcc aacaaaggcc tcccagcccc catcgagaaa   1080
accatctcca aaaccaaagg gcagccccga gaaccacagg tgtacaccct gcccccatcc   1140
cgggaggaga tgaccaagaa ccaggtcagc ctgacctgcc tggtcaaagg cttctacccc   1200
agcgacatcg ccgtggagtg ggagagcaat gggcagccgg agaacaacta caagaccaca   1260
cctcccatgc tggactccga cggctccttc ttcctctaca gcaagctcac cgtggacaag   1320
agcaggtggc agcaggggaa cgtcttctca tgctccgtga tgcatgaggc tctgcacaac   1380
cactacacgc agaagagcct ctccctgtct ccgggtaaa                          1419
```

<210> SEQ ID NO 72
<211> LENGTH: 473
<212> TYPE: PRT
<213> ORGANISM: Homo sapiens

<400> SEQUENCE: 72

```
Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ala Val Met Trp Tyr Asp Gly Ser Asn Lys Asp Tyr Val
65                  70                  75                  80

Asp Ser Val Lys Gly Arg Phe Thr Ile Ser Arg Asp Asn Ser Lys Asn
                85                  90                  95
```

```
Thr Leu Tyr Leu Gln Met Asn Arg Leu Arg Ala Glu Asp Thr Ala Val
            100                 105                 110

Tyr Tyr Cys Ala Arg Glu Lys Asp His Tyr Asp Ile Leu Thr Gly Tyr
        115                 120                 125

Asn Tyr Tyr Tyr Gly Leu Asp Val Trp Gly Gln Gly Thr Thr Val Thr
    130                 135                 140

Val Ser Ser Ala Ser Thr Lys Gly Pro Ser Val Phe Pro Leu Ala Pro
145                 150                 155                 160

Cys Ser Arg Ser Thr Ser Glu Ser Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Asn Phe Gly
    210                 215                 220

Thr Gln Thr Tyr Thr Cys Asn Val Asp His Lys Pro Ser Asn Thr Lys
225                 230                 235                 240

Val Asp Lys Thr Val Glu Arg Lys Cys Cys Val Glu Cys Pro Pro Cys
                245                 250                 255

Pro Ala Pro Pro Val Ala Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Gln Phe Asn Trp Tyr
    290                 295                 300

Val Asp Gly Val Glu Val His Asn Ala Lys Thr Lys Pro Arg Glu Glu
305                 310                 315                 320

Gln Phe Asn Ser Thr Phe Arg Val Val Ser Val Leu Thr Val Val His
                325                 330                 335

Gln Asp Trp Leu Asn Gly Lys Glu Tyr Lys Cys Lys Val Ser Asn Lys
            340                 345                 350

Gly Leu Pro Ala Pro Ile Glu Lys Thr Ile Ser Lys Thr Lys Gly Gln
        355                 360                 365

Pro Arg Glu Pro Gln Val Tyr Thr Leu Pro Pro Ser Arg Glu Glu Met
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Met Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470
```

<210> SEQ ID NO 73
<211> LENGTH: 705
<212> TYPE: DNA
<213> ORGANISM: Homo sapiens

<400> SEQUENCE: 73

```
atggaaaccc cggcgcagct gctgtttctg ctgctgctgt ggctgccgga taccaccggc     60

gaaattgtgt tgacgcagtc tccaggcacc ctgtctttgt ctccagggga aagagccacc    120

ctctcctgca gggccagtca gtatattagc aacacctatt tagcctggtt ccagcagaaa    180

cctggccagg ctcccaggct cctcatctat ggtgcagcca ccagggccac tggcatccca    240

gacaggttca gtggcagtgg gtctgggaca gacttcactt tcaccatcag cagactggag    300

cctgaagatt ttgcagtgta ttactgtcag cagtatggta gctcaccgtg gacgttcggc    360

caagggacca cggtggaaat caaacgtacg gtggctgcac catctgtctt catcttcccg    420

ccatctgatg agcagttgaa atctggaact gcctctgttg tgtgcctgct gaataacttc    480

tatcccagag aggccaaagt acagtggaag gtggataacg ccctccaatc gggtaactcc    540

caggagagtg tcacagagca ggacagcaag gacagcacct acagcctcag cagcaccctg    600

acgctgagca aagcagacta cgagaaacac aaagtctacg cctgcgaagt cacccatcag    660

ggcctgagct cgcccgtcac aaagagcttc aacaggggag agtgt                   705
```

<210> SEQ ID NO 74
<211> LENGTH: 235
<212> TYPE: PRT
<213> ORGANISM: Homo sapiens

<400> SEQUENCE: 74

```
Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Tyr
        35                  40                  45

Ile Ser Asn Thr Tyr Leu Ala Trp Phe Gln Gln Lys Pro Gly Gln Ala
    50                  55                  60

Pro Arg Leu Leu Ile Tyr Gly Ala Ala Thr Arg Ala Thr Gly Ile Pro
65                  70                  75                  80

Asp Arg Phe Ser Gly Ser Gly Ser Gly Thr Asp Phe Thr Phe Thr Ile
                85                  90                  95

Ser Arg Leu Glu Pro Glu Asp Phe Ala Val Tyr Tyr Cys Gln Gln Tyr
            100                 105                 110

Gly Ser Ser Pro Trp Thr Phe Gly Gln Gly Thr Thr Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

<210> SEQ ID NO 75
<211> LENGTH: 1389
<212> TYPE: DNA
<213> ORGANISM: Homo sapiens

<400> SEQUENCE: 75
atggattgga cctggcgtat tctgtttctg gtggcggcgg cgaccggcgc gcatagccag 60
gtgcagttgg tgcagtctgg ggctgaggtg aagaagcctg gggcctcagt gaaggtctcc 120
tgcaaggctt ctggatacac cttcaccggc tactatatgc actgggtgcg acaggcccct 180
ggacaagggc ttgagtggat gggatggatc aaccctaaca gtggtggcac aaactatgca 240
cagaggtttc ggggcagggt caccatgacc agggacacgt ccatcagcac agcctacatg 300
gaactgagca ggctgagatc tgacgacacg gccgtgtatt actgtgcgag agccccgtat 360
gactggacct ttgactactg gggccaggga accctggtca ccgtctcctc agctagcacc 420
aagggcccat cggtcttccc cctggcgccc tgctccagga gcacctccga gagcacagcg 480
gccctgggct gcctggtcaa ggactacttc cccgaaccgg tgacggtgtc gtggaactca 540
ggcgctctga ccagcggcgt gcacaccttc ccagctgtcc tacagtcctc aggactctac 600
tccctcagca gcgtggtgac cgtgccctcc agcaacttcg gcacccagac ctacacctgc 660
aacgtagatc acaagcccag caacaccaag gtggacaaga cagttgagcg caaatgttgt 720
gtcgagtgcc caccgtgccc agcaccacct gtggcaggac cgtcagtctt cctcttcccc 780
ccaaaaccca aggacaccct catgatctcc cggacccctg aggtcacgtg cgtggtggtg 840
gacgtgagcc acgaagaccc cgaggtccag ttcaactggt acgtggacgg cgtggaggtg 900
cataatgcca agacaaagcc acgggaggag cagttcaaca gcacgttccg tgtggtcagc 960
gtcctcaccg ttgtgcacca ggactggctg aacggcaagg agtacaagtg caaggtctcc 1020
aacaaaggcc tcccagcccc catcgagaaa accatctcca aaaccaaagg gcagccccga 1080
gaaccacagg tgtacaccct gcccccatcc cgggaggaga tgaccaagaa ccaggtcagc 1140
ctgacctgcc tggtcaaagg cttctacccc agcgacatcg ccgtggagtg ggagagcaat 1200
gggcagccgg agaacaacta caagaccaca cctcccatgc tggactccga cggctccttc 1260
ttcctctaca gcaagctcac cgtggacaag agcaggtggc agcaggggaa cgtcttctca 1320
tgctccgtga tgcatgaggc tctgcacaac cactacacgc agaagagcct ctccctgtct 1380
ccgggtaaa 1389

<210> SEQ ID NO 76
<211> LENGTH: 463
<212> TYPE: PRT
<213> ORGANISM: Homo sapiens

<400> SEQUENCE: 76

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Gly Tyr Tyr Met His Trp Val Arg Gln Ala Pro Gly Gln Gly Leu
    50                  55                  60

Glu Trp Met Gly Trp Ile Asn Pro Asn Ser Gly Gly Thr Asn Tyr Ala
65                  70                  75                  80

Gln Arg Phe Arg Gly Arg Val Thr Met Thr Arg Asp Thr Ser Ile Ser

```
                85                  90                  95

Thr Ala Tyr Met Glu Leu Ser Arg Leu Arg Ser Asp Asp Thr Ala Val
            100                 105                 110

Tyr Tyr Cys Ala Arg Ala Pro Tyr Asp Trp Thr Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
                325                 330                 335

Cys Lys Val Ser Asn Lys Gly Leu Pro Ala Pro Ile Glu Lys Thr Ile
            340                 345                 350

Ser Lys Thr Lys Gly Gln Pro Arg Glu Pro Gln Val Tyr Thr Leu Pro
        355                 360                 365

Pro Ser Arg Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
    450                 455                 460
```

<210> SEQ ID NO 77
<211> LENGTH: 708
<212> TYPE: DNA
<213> ORGANISM: Homo sapiens

<400> SEQUENCE: 77

-continued

```
atggacatga gggtgcccgc tcagctcctg gggctcctgc tgctgtggct gagaggtgcg      60

cgctgtgaca tccagatgac ccagtctcca tcttccgtgt ctgcatctgt aggagacaga     120

gtcaccatca cttgtcgggc gagtcagggt attagcaact ggttagcctg gtatcagcag     180

aaaccaggga cagcccctaa actcctgatc tatgctgcat ccagtttgca aagtggggtc     240

ccatcaaggt tcagcggcag tggatctggg acagatttca ctctcaccat cagcagcctg     300

cagcctgaag attttgcaac ttactattgt caacaggcta acagtttccc attcactttc     360

ggccctggga ccaaagtgga tatcaaacgt acggtggctg caccatctgt cttcatcttc     420

ccgccatctg atgagcagtt gaaatctgga actgcctctg ttgtgtgcct gctgaataac     480

ttctatccca gagaggccaa agtacagtgg aaggtggata acgccctcca atcgggtaac     540

tcccaggaga gtgtcacaga gcaggacagc aaggacagca cctacagcct cagcagcacc     600

ctgacgctga gcaaagcaga ctacgagaaa cacaaagtct acgcctgcga agtcacccat     660

cagggcctga gctcgcccgt cacaaagagc ttcaacaggg gagagtgt                  708
```

<210> SEQ ID NO 78
<211> LENGTH: 236
<212> TYPE: PRT
<213> ORGANISM: Homo sapiens

<400> SEQUENCE: 78

```
Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Val Ser Ala Ser Val Gly Asp Arg Val Thr Ile Thr Cys Arg Ala Ser
        35                  40                  45

Gln Gly Ile Ser Asn Trp Leu Ala Trp Tyr Gln Gln Lys Pro Gly Thr
    50                  55                  60

Ala Pro Lys Leu Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Ala Asn Ser Phe Pro Phe Thr Phe Gly Pro Gly Thr Lys Val Asp Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 79

<211> LENGTH: 1407
<212> TYPE: DNA
<213> ORGANISM: Homo sapiens

<400> SEQUENCE: 79
atggacatga gggtgcccgc tcagctcctg gggctcctgc tgctgtggct gagaggtgcg 60
cgctgtcagg tgcagttggt gcagtctggg actgaggtga agaagcctgg ggcctcaatg 120
aaggtttcct gcaaggcatc tggatacacc ttcaccagct attatatgca ctgggtgcga 180
caggcccctg gacaagggct tgagtggatg ggaataatca accctagtgg tgatagcaca 240
agctacgcac agaagttcca gggcagagtc accatgacca gggacacgtc cacgaacaca 300
gtctacatgg agctgagcag cctgagatct gaggacacgg ccatgtatta ctgtgcgaga 360
gatgtagagg ttcggggaat ttctcacttt gactactggg gccagggaac cctggtcacc 420
gtctctagtg cctccaccaa gggcccatcg gtcttccccc tggcgccctg ctccaggagc 480
acctccgaga gcacagcggc cctgggctgc ctggtcaagg actacttccc cgaaccggtg 540
acggtgtcgt ggaactcagg cgctctgacc agcggcgtgc acaccttccc agctgtccta 600
cagtcctcag gactctactc cctcagcagc gtggtgaccg tgccctccag caacttcggc 660
acccagacct acacctgcaa cgtagatcac aagcccagca acaccaaggt ggacaagaca 720
gttgagcgca aatgttgtgt cgagtgccca ccgtgcccag caccacctgt ggcaggaccg 780
tcagtcttcc tcttcccccc aaaacccaag gacaccctca tgatctcccg gacccctgag 840
gtcacgtgcg tggtggtgga cgtgagccac gaagaccccg aggtccagtt caactggtac 900
gtggacggcg tggaggtgca taatgccaag acaaagccac gggaggagca gttcaacagc 960
acgttccgtg tggtcagcgt cctcaccgtt gtgcaccagg actggctgaa cggcaaggag 1020
tacaagtgca aggtctccaa caaaggcctc ccagccccca tcgagaaaac catctccaaa 1080
accaaagggc agccccgaga accacaggtg tacaccctgc ccccatcccg ggaggagatg 1140
accaagaacc aggtcagcct gacctgcctg gtcaaaggct tctaccccag cgacatcgcc 1200
gtggagtggg agagcaatgg gcagccggag aacaactaca agaccacacc tcccatgctg 1260
gactccgacg gctccttctt cctctacagc aagctcaccg tggacaagag caggtggcag 1320
caggggaacg tcttctcatg ctccgtgatg catgaggctc tgcacaacca ctacacgcag 1380
aagagcctct ccctgtctcc gggtaaa 1407

<210> SEQ ID NO 80
<211> LENGTH: 469
<212> TYPE: PRT
<213> ORGANISM: Homo sapiens

<400> SEQUENCE: 80

Met Asp Met Arg Val Pro Ala Gln Leu Leu Gly Leu Leu Leu Leu Trp
1 5 10 15

Leu Arg Gly Ala Arg Cys Gln Val Gln Leu Val Gln Ser Gly Thr Glu
20 25 30

Val Lys Lys Pro Gly Ala Ser Met Lys Val Ser Cys Lys Ala Ser Gly
35 40 45

Tyr Thr Phe Thr Ser Tyr Tyr Met His Trp Val Arg Gln Ala Pro Gly
50 55 60

Gln Gly Leu Glu Trp Met Gly Ile Ile Asn Pro Ser Gly Asp Ser Thr
65 70 75 80

Ser Tyr Ala Gln Lys Phe Gln Gly Arg Val Thr Met Thr Arg Asp Thr
85 90 95

-continued

```
Ser Thr Asn Thr Val Tyr Met Glu Leu Ser Ser Leu Arg Ser Glu Asp
            100                 105                 110

Thr Ala Met Tyr Tyr Cys Ala Arg Asp Val Glu Val Arg Gly Ile Ser
        115                 120                 125

His Phe Asp Tyr Trp Gly Gln Gly Thr Leu Val Thr Val Ser Ser Ala
    130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Asn Phe Gly Thr Gln Thr Tyr
    210                 215                 220

Thr Cys Asn Val Asp His Lys Pro Ser Asn Thr Lys Val Asp Lys Thr
225                 230                 235                 240

Val Glu Arg Lys Cys Cys Val Glu Cys Pro Pro Cys Pro Ala Pro Pro
                245                 250                 255

Val Ala Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Gln Phe Asn Trp Tyr Val Asp Gly Val
    290                 295                 300

Glu Val His Asn Ala Lys Thr Lys Pro Arg Glu Glu Gln Phe Asn Ser
305                 310                 315                 320

Thr Phe Arg Val Val Ser Val Leu Thr Val Val His Gln Asp Trp Leu
                325                 330                 335

Asn Gly Lys Glu Tyr Lys Cys Lys Val Ser Asn Lys Gly Leu Pro Ala
            340                 345                 350

Pro Ile Glu Lys Thr Ile Ser Lys Thr Lys Gly Gln Pro Arg Glu Pro
        355                 360                 365

Gln Val Tyr Thr Leu Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Met Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465
```

<210> SEQ ID NO 81
<211> LENGTH: 714
<212> TYPE: DNA
<213> ORGANISM: Homo sapiens -continued

<400> SEQUENCE: 81

```
atgggatgga gctgtatcat cctcttcttg gtagcaacag ctacaggtgt ccactccgac     60

atccagctga cccagtctcc atcatctctg agcgcatctg ttggagatag ggtcactatg    120

agctgtaagt ccagtcaaag tgttttatac agtgcaaatc acaagaacta cttggcctgg    180

taccagcaga aaccagggaa agcacctaaa ctgctgatct actgggcatc cactagggaa    240

tctggtgtcc cttcgcgatt ctctggcagc ggatctggga cagattttac tttcaccatc    300

agctctcttc aaccagaaga cattgcaaca tattattgtc accaatacct ctcctcgtgg    360

acgttcggtg gagggaccaa ggtgcagatc aaacgaactg tggctgcacc atctgtcttc    420

atcttcccgc catctgatga gcagttgaaa tctggaactg cctctgttgt gtgcctgctg    480

aataacttct atcccagaga ggccaaagta cagtggaagg tggataacgc cctccaatcg    540

ggtaactccc aggagagtgt cacagagcag gacagcaagg acagcaccta cagcctcagc    600

agcaccctga cgctgagcaa agcagactac gagaaacaca aagtctacgc ctgcgaagtc    660

acccatcagg gcctgagctc gcccgtcaca aagagcttca acaggggaga gtgt          714
```

<210> SEQ ID NO 82
<211> LENGTH: 238
<212> TYPE: PRT
<213> ORGANISM: Homo sapiens

<400> SEQUENCE: 82

```
Met Gly Trp Ser Cys Ile Ile Leu Phe Leu Val Ala Thr Ala Thr Gly
1               5                   10                  15

Val His Ser Asp Ile Gln Leu Thr Gln Ser Pro Ser Ser Leu Ser Ala
            20                  25                  30

Ser Val Gly Asp Arg Val Thr Met Ser Cys Lys Ser Ser Gln Ser Val
        35                  40                  45

Leu Tyr Ser Ala Asn His Lys Asn Tyr Leu Ala Trp Tyr Gln Gln Lys
    50                  55                  60

Pro Gly Lys Ala Pro Lys Leu Leu Ile Tyr Trp Ala Ser Thr Arg Glu
65                  70                  75                  80

Ser Gly Val Pro Ser Arg Phe Ser Gly Ser Gly Ser Gly Thr Asp Phe
                85                  90                  95

Thr Phe Thr Ile Ser Ser Leu Gln Pro Glu Asp Ile Ala Thr Tyr Tyr
            100                 105                 110

Cys His Gln Tyr Leu Ser Ser Trp Thr Phe Gly Gly Gly Thr Lys Val
        115                 120                 125

Gln Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 83
<211> LENGTH: 1395
<212> TYPE: DNA
<213> ORGANISM: Homo sapiens

<400> SEQUENCE: 83

```
atgggatgga gctgtatcat cctcttcttg gtagcaacag ctacaggtgt ccactcccag      60

gtccagctgg tccaatcagg ggctgaagtc aagaaacctg ggtcatcagt gaaggtctcc     120

tgcaaggctt ctggctacac ctttactagc tactggctgc actgggtcag gcaggcacct     180

ggacagggtc tggaatggat tggatacatt aatcctagga atgattatac tgagtacaat     240

cagaacttca aggacaaggc cacaataact gcagacgaat ccaccaatac agcctacatg     300

gagctgagca gcctgaggtc tgaggacacg gcattttatt tttgtgcaag aagggatatt     360

actacgttct actggggcca aggcaccacg gtcaccgtct cctcagcctc caccaagggc     420

ccatcggtct tccccctggc accctcctcc aagagcacct ctgggggcac agcggccctg     480

ggctgcctgg tcaaggacta cttccccgaa ccggtgacgg tgtcgtggaa ctcaggcgcc     540

ctgaccagcg gcgtgcacac cttcccggct gtcctacagt cctcaggact ctactccctc     600

agcagcgtgg tgaccgtgcc ctccagcagc ttgggcaccc agacctacat ctgcaacgtg     660

aatcacaagc ccagcaacac caaggtggac aagagagttg agcccaaatc ttgtgacaaa     720

actcacacat gcccaccgtg cccagcacct gaactcctgg ggggaccgtc agtcttcctc     780

ttccccccaa aacccaagga caccctcatg atctcccgga cccctgaggt cacatgcgtg     840

gtggtggacg tgagccacga agaccctgag gtcaagttca actggtacgt ggacggcgtg     900

gaggtgcata atgccaagac aaagccgcgg gaggagcagt acaacagcac gtaccgtgtg     960

gtcagcgtcc tcaccgtcct gcaccaggac tggctgaatg gcaaggagta caagtgcaag    1020

gtctccaaca aagccctccc agcccccatc gagaaaacca tctccaaagc caaagggcag    1080

ccccgagaac cacaggtgta caccctgccc ccatcccggg aggagatgac caagaaccag    1140

gtcagcctga cctgcctggt caaaggcttc tatcccagcg acatcgccgt ggagtgggag    1200

agcaatgggc agccggagaa caactacaag accacgcctc ccgtgctgga ctccgacggc    1260

tccttcttcc tctatagcaa gctcaccgtg gacaagagca ggtggcagca ggggaacgtc    1320

ttctcatgct ccgtgatgca tgaggctctg cacaaccact acacgcagaa gagcctctcc    1380

ctgtctccgg gtaaa                                                     1395
```

<210> SEQ ID NO 84
<211> LENGTH: 465
<212> TYPE: PRT
<213> ORGANISM: Homo sapiens

<400> SEQUENCE: 84

```
Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr Ser Tyr Trp Leu His Trp Val Arg Gln Ala Pro Gly Gln Gly Leu
    50                  55                  60

Glu Trp Ile Gly Tyr Ile Asn Pro Arg Asn Asp Tyr Thr Glu Tyr Asn
65                  70                  75                  80
```

```
Gln Asn Phe Lys Asp Lys Ala Thr Ile Thr Ala Asp Glu Ser Thr Asn
                85                  90                  95

Thr Ala Tyr Met Glu Leu Ser Ser Leu Arg Ser Glu Asp Thr Ala Phe
            100                 105                 110

Tyr Phe Cys Ala Arg Arg Asp Ile Thr Thr Phe Tyr Trp Gly Gln Gly
        115                 120                 125

Thr Thr Val Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Arg Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465
```

<210> SEQ ID NO 85
<211> LENGTH: 705
<212> TYPE: DNA

<213> ORGANISM: Homo sapiens

<400> SEQUENCE: 85
atggaaaccc cagctcagct tctcttcctc ctgctactct ggctcccaga taccaccgga 60
gaaattgtgt tgacgcagtc tccaggcacc ctgtctttgt ctccagggga aagagccacc 120
ctctcctgca gggccagtca gagtgttagc agcagctact tagcctggta ccagcagaaa 180
cctggccagg ctcccaggct cctcatatat ggtgcatcca gcagggccac tggcatccca 240
gacaggttca gtggcagtgg gtctgggaca gacttcactc tcaccatcag cagactggag 300
cctgaagatt ttgcagtgta ttactgtcag cggtctggtg gctcatcatt cactttcggc 360
cctgggacca aagtggatat caaacgaact gtggctgcac catctgtctt catcttcccg 420
ccatctgatg agcagttgaa atctggaact gcctctgttg tgtgcctgct gaataacttc 480
tatcccagag aggccaaagt acagtggaag gtggataacg ccctccaatc gggtaactcc 540
caggagagtg tcacagagca ggacagcaag gacagcacct acagcctcag cagcaccctg 600
acgctgagca aagcagacta cgagaaacac aaagtctacg cctgcgaagt cacccatcag 660
ggcctgagct cgcccgtcac aaagagcttc aacaggggag agtgt 705

<210> SEQ ID NO 86
<211> LENGTH: 235
<212> TYPE: PRT
<213> ORGANISM: Homo sapiens

<400> SEQUENCE: 86

Met Glu Thr Pro Ala Gln Leu Leu Phe Leu Leu Leu Leu Trp Leu Pro
1 5 10 15

Asp Thr Thr Gly Glu Ile Val Leu Thr Gln Ser Pro Gly Thr Leu Ser
20 25 30

Leu Ser Pro Gly Glu Arg Ala Thr Leu Ser Cys Arg Ala Ser Gln Ser
35 40 45

Val Ser Ser Ser Tyr Leu Ala Trp Tyr Gln Gln Lys Pro Gly Gln Ala
50 55 60

Pro Arg Leu Leu Ile Tyr Gly Ala Ser Ser Arg Ala Thr Gly Ile Pro
65 70 75 80

Asp Arg Phe Ser Gly Ser Gly Ser Gly Thr Asp Phe Thr Leu Thr Ile
85 90 95

Ser Arg Leu Glu Pro Glu Asp Phe Ala Val Tyr Tyr Cys Gln Arg Ser
100 105 110

Gly Gly Ser Ser Phe Thr Phe Gly Pro Gly Thr Lys Val Asp Ile Lys
115 120 125

Arg Thr Val Ala Ala Pro Ser Val Phe Ile Phe Pro Pro Ser Asp Glu
130 135 140

Gln Leu Lys Ser Gly Thr Ala Ser Val Val Cys Leu Leu Asn Asn Phe
145 150 155 160

Tyr Pro Arg Glu Ala Lys Val Gln Trp Lys Val Asp Asn Ala Leu Gln
165 170 175

Ser Gly Asn Ser Gln Glu Ser Val Thr Glu Gln Asp Ser Lys Asp Ser
180 185 190

Thr Tyr Ser Leu Ser Ser Thr Leu Thr Leu Ser Lys Ala Asp Tyr Glu
195 200 205

Lys His Lys Val Tyr Ala Cys Glu Val Thr His Gln Gly Leu Ser Ser
210 215 220

Pro Val Thr Lys Ser Phe Asn Arg Gly Glu Cys 225 230 235

<210> SEQ ID NO 87
<211> LENGTH: 1398
<212> TYPE: DNA
<213> ORGANISM: Homo sapiens

<400> SEQUENCE: 87
atggggtcaa ccgccatcct cgccctcctc ctggctgttc tccaaggagt ctgtgccgag 60
gtgcagctgg tacagtctgg agcagaggtg aaaaagcccg gggagtctct gaagatctcc 120
tgtaagggtt ctggatacaa ctttaccagc tactggatcg gctgggtgcg ccagatgccc 180
gggaaaggcc tggagttgat ggggatcatc tatcctggtg actctgatac cagatacagc 240
ccgtccttcc aaggccaggt caccatctca gccgacaagt ccatcagcac cgcctacctg 300
cagtggagca gcctgaaggc ctcggacacc gccatgtatt actgtggttc ggggagctac 360
ttttacttcg atctctgggg ccgtggcacc ctggtcaccg tctctagtgc ctccaccaag 420
ggcccatcgg tcttcccct ggcaccctcc tccaagagca cctctggggg cacagcggcc 480
ctgggctgcc tggtcaagga ctacttcccc gaaccggtga cggtgtcgtg gaactcaggc 540
gccctgacca gcggcgtgca caccttcccg gctgtcctac agtcctcagg actctactcc 600
ctcagcagcg tggtgaccgt gccctccagc agcttgggca cccagaccta catctgcaac 660
gtgaatcaca agcccagcaa caccaaggtg gacaagaaag ttgagcccaa atcttgtgac 720
aaaactcaca catgcccacc gtgcccagca cctgaactcc tggggggacc gtcagtcttc 780
ctcttccccc caaaacccaa ggacaccctc atgatctccc ggacccctga ggtcacatgc 840
gtggtggtgg acgtgagcca cgaagaccct gaggtcaagt tcaactggta cgtggacggc 900
gtggaggtgc ataatgccaa gacaaagccg cgggaggagc agtacaacag cacgtaccgt 960
gtggtcagcg tcctcaccgt cctgcaccag gactggctga atggcaagga gtacaagtgc 1020
aaggtctcca acaaagccct cccagccccc atcgagaaaa ccatctccaa agccaaaggg 1080
cagccccgag aaccacaggt gtacaccctg cccccatccc gggatgagct gaccaagaac 1140
caggtcagcc tgacctgcct ggtcaaaggc ttctatccca gcgacatcgc cgtggagtgg 1200
gagagcaatg ggcagccgga gaacaactac aagaccacgc ctcccgtgct ggactccgac 1260
ggctccttct tcctctatag caagctcacc gtggacaaga gcaggtggca gcaggggaac 1320
gtcttctcat gctccgtgat gcatgaggct ctgcacaacc actacacgca gaagagcctc 1380
tccctgtctc cgggtaaa 1398

<210> SEQ ID NO 88
<211> LENGTH: 466
<212> TYPE: PRT
<213> ORGANISM: Homo sapiens

<400> SEQUENCE: 88

Met Gly Ser Thr Ala Ile Leu Ala Leu Leu Leu Ala Val Leu Gln Gly
1 5 10 15

Val Cys Ala Glu Val Gln Leu Val Gln Ser Gly Ala Glu Val Lys Lys
20 25 30

Pro Gly Glu Ser Leu Lys Ile Ser Cys Lys Gly Ser Gly Tyr Asn Phe
35 40 45

Thr Ser Tyr Trp Ile Gly Trp Val Arg Gln Met Pro Gly Lys Gly Leu
50 55 60

Glu Leu Met Gly Ile Ile Tyr Pro Gly Asp Ser Asp Thr Arg Tyr Ser

```
65                  70                  75                  80

Pro Ser Phe Gln Gly Gln Val Thr Ile Ser Ala Asp Lys Ser Ile Ser
                85                  90                  95

Thr Ala Tyr Leu Gln Trp Ser Ser Leu Lys Ala Ser Asp Thr Ala Met
            100                 105                 110

Tyr Tyr Cys Gly Ser Gly Ser Tyr Phe Tyr Phe Asp Leu Trp Gly Arg
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Asp Glu Leu Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465
```

<210> SEQ ID NO 89

<211> LENGTH: 723
<212> TYPE: DNA
<213> ORGANISM: Homo sapiens

<400> SEQUENCE: 89
atggacatga gggtgcccgc tcagctcctg gggctcctgc tgctgtggct gagaggtgcg 60
cgctgtgata ttgtgatgac tcagtctcca ctctccctgc ccgtcacccc tggagagccg 120
gcctccatct cctgcaggtc tagtcagagc ctcctgcata gtcatggata caactatttg 180
gattggtacc tgcagaagcc agggcagtct ccacagctcc tgatctattt gggttctaat 240
cgggcctccg gggtccctga caggttcagt ggcagtggat caggcacaga ttttacactg 300
aaaatcagca gagtggaggc tgaggatgtt ggggtttatt actgcatgca aggtacacac 360
tggcctccga cttttggcca ggggaccaag ctggagatca aacgtacggt ggctgcacca 420
tctgtcttca tcttcccgcc atctgatgag cagttgaaat ctggaactgc ctctgttgtg 480
tgcctgctga ataacttcta tcccagagag gccaaagtac agtggaaggt ggataacgcc 540
ctccaatcgg gtaactccca ggagagtgtc acagagcagg acagcaagga cagcacctac 600
agcctcagca gcaccctgac gctgagcaaa gcagactacg agaaacacaa agtctacgcc 660
tgcgaagtca cccatcaggg cctgagctcg cccgtcacaa agagcttcaa caggggagag 720
tgt 723

<210> SEQ ID NO 90
<211> LENGTH: 241
<212> TYPE: PRT
<213> ORGANISM: Homo sapiens

<400> SEQUENCE: 90

Met Asp Met Arg Val Pro Ala Gln Leu Leu Gly Leu Leu Leu Leu Trp
1 5 10 15

Leu Arg Gly Ala Arg Cys Asp Ile Val Met Thr Gln Ser Pro Leu Ser
20 25 30

Leu Pro Val Thr Pro Gly Glu Pro Ala Ser Ile Ser Cys Arg Ser Ser
35 40 45

Gln Ser Leu Leu His Ser His Gly Tyr Asn Tyr Leu Asp Trp Tyr Leu
50 55 60

Gln Lys Pro Gly Gln Ser Pro Gln Leu Leu Ile Tyr Leu Gly Ser Asn
65 70 75 80

Arg Ala Ser Gly Val Pro Asp Arg Phe Ser Gly Ser Gly Ser Gly Thr
85 90 95

Asp Phe Thr Leu Lys Ile Ser Arg Val Glu Ala Glu Asp Val Gly Val
100 105 110

Tyr Tyr Cys Met Gln Gly Thr His Trp Pro Pro Thr Phe Gly Gln Gly
115 120 125

Thr Lys Leu Glu Ile Lys Arg Thr Val Ala Ala Pro Ser Val Phe Ile
130 135 140

Phe Pro Pro Ser Asp Glu Gln Leu Lys Ser Gly Thr Ala Ser Val Val
145 150 155 160

Cys Leu Leu Asn Asn Phe Tyr Pro Arg Glu Ala Lys Val Gln Trp Lys
165 170 175

Val Asp Asn Ala Leu Gln Ser Gly Asn Ser Gln Glu Ser Val Thr Glu
180 185 190

Gln Asp Ser Lys Asp Ser Thr Tyr Ser Leu Ser Ser Thr Leu Thr Leu
195 200 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys

<210> SEQ ID NO 91
<211> LENGTH: 1410
<212> TYPE: DNA
<213> ORGANISM: Homo sapiens

<400> SEQUENCE: 91
atggacatga gggtgcccgc tcagctcctg gggctcctgc tgctgtggct gagaggtgcg 60
cgctgtgagg tccagctggt gcagtctggg ggaggcgtgg tccagcctgg gaggtccctg 120
agactctcct gtgcagcgtc tggattcacc ttcagtagct atggcatgca ctgggtccgc 180
caggctccag gcaaggggct ggagtgggtt tcatacatta gtagtagtgg tagtaccata 240
tactacgcag actctgtgaa gggccgattc accatctcca gggacaacgc caagaactca 300
ctatatctgc aaatgaacag cctgagagcc gaggacacgg ccgtgtatta ctgtgcgaga 360
gatctgttag attacgatct gttgactggt tatggctact ggggccaggg aaccctggtc 420
accgtctcta gtgcctccac caagggccca tcggtcttcc ccctggcgcc ctgctccagg 480
agcacctccg agagcacagc ggccctgggc tgcctggtca aggactactt ccccgaaccg 540
gtgacggtgt cgtggaactc aggcgctctg accagcggcg tgcacacctt cccagctgtc 600
ctacagtcct caggactcta ctccctcagc agcgtggtga ccgtgccctc cagcaacttc 660
ggcacccaga cctacacctg caacgtagat cacaagccca gcaacaccaa ggtggacaag 720
acagttgagc gcaaatgttg tgtcgagtgc ccaccgtgcc cagcaccacc tgtggcagga 780
ccgtcagtct tcctcttccc cccaaaaccc aaggacaccc tcatgatctc ccggacccct 840
gaggtcacgt gcgtggtggt ggacgtgagc cacgaagacc ccgaggtcca gttcaactgg 900
tacgtggacg gcgtggaggt gcataatgcc aagacaaagc cacgggagga gcagttcaac 960
agcacgttcc gtgtggtcag cgtcctcacc gttgtgcacc aggactggct gaacggcaag 1020
gagtacaagt gcaaggtctc caacaaaggc ctcccagccc ccatcgagaa aaccatctcc 1080
aaaaccaaag ggcagccccg agaaccacag gtgtacaccc tgcccccatc ccgggaggag 1140
atgaccaaga accaggtcag cctgacctgc ctggtcaaag gcttctaccc cagcgacatc 1200
gccgtggagt gggagagcaa tgggcagccg gagaacaact acaagaccac acctcccatg 1260
ctggactccg acggctcctt cttcctctac agcaagctca ccgtggacaa gagcaggtgg 1320
cagcagggga acgtcttctc atgctccgtg atgcatgagg ctctgcacaa ccactacacg 1380
cagaagagcc tctccctgtc tccgggtaaa 1410

<210> SEQ ID NO 92
<211> LENGTH: 470
<212> TYPE: PRT
<213> ORGANISM: Homo sapiens

<400> SEQUENCE: 92

Met Asp Met Arg Val Pro Ala Gln Leu Leu Gly Leu Leu Leu Leu Trp
1               5                   10                  15

Leu Arg Gly Ala Arg Cys Glu Val Gln Leu Val Gln Ser Gly Gly Gly
            20                  25                  30

Val Val Gln Pro Gly Arg Ser Leu Arg Leu Ser Cys Ala Ala Ser Gly

-continued

```
        35                  40                  45

Phe Thr Phe Ser Ser Tyr Gly Met His Trp Val Arg Gln Ala Pro Gly
    50                  55                  60

Lys Gly Leu Glu Trp Val Ser Tyr Ile Ser Ser Ser Gly Ser Thr Ile
65                  70                  75                  80

Tyr Tyr Ala Asp Ser Val Lys Gly Arg Phe Thr Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Val Tyr Tyr Cys Ala Arg Asp Leu Leu Asp Tyr Asp Leu Leu
        115                 120                 125

Thr Gly Tyr Gly Tyr Trp Gly Gln Gly Thr Leu Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Asn Phe Gly Thr Gln Thr
    210                 215                 220

Tyr Thr Cys Asn Val Asp His Lys Pro Ser Asn Thr Lys Val Asp Lys
225                 230                 235                 240

Thr Val Glu Arg Lys Cys Cys Val Glu Cys Pro Pro Cys Pro Ala Pro
                245                 250                 255

Pro Val Ala Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Gln Phe Asn Trp Tyr Val Asp Gly
    290                 295                 300

Val Glu Val His Asn Ala Lys Thr Lys Pro Arg Glu Glu Gln Phe Asn
305                 310                 315                 320

Ser Thr Phe Arg Val Val Ser Val Leu Thr Val Val His Gln Asp Trp
                325                 330                 335

Leu Asn Gly Lys Glu Tyr Lys Cys Lys Val Ser Asn Lys Gly Leu Pro
            340                 345                 350

Ala Pro Ile Glu Lys Thr Ile Ser Lys Thr Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Met Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460
```

```
Ser Leu Ser Pro Gly Lys
465                 470


<210> SEQ ID NO 93
<211> LENGTH: 705
<212> TYPE: DNA
<213> ORGANISM: Homo sapiens

<400> SEQUENCE: 93

atggaaaccc cagcgcagct tctcttcctc ctgctactct ggctcccaga taccaccgga     60

gaaattgtgt tgacgcagtc tccaggcacc ctgtctttgt ctccagggga aagagccacc    120

ctctcctgca gggccagtca gggtattagt agaagctact tagcctggta ccagcagaaa    180

cctggccagg ctcccagcct cctcatctat ggtgcatcca gcagggccac tggcatccca    240

gacaggttca gtggcagtgg gtctgggaca gacttcactc tcaccatcag cagactggag    300

cctgaagatt ttgcagtgta ttactgtcaa caatttggta gttcaccgtg gacgttcggc    360

caagggacca aggtggaaat caaacgaact gtggctgcac catctgtctt catcttcccg    420

ccatctgatg agcagttgaa atctggaact gctagcgttg tgtgcctgct gaataacttc    480

tatcccagag aggccaaagt acagtggaag gtggataacg ccctccaatc gggtaactcc    540

caggagagtg tcacagagca ggacagcaag gacagcacct acagcctcag cagcaccctg    600

acgctgagca aagcagacta cgagaaacac aaagtctacg cctgcgaagt cacccatcag    660

ggcctgagct cgcccgtcac aaagagcttc aacaggggag agtgt                    705


<210> SEQ ID NO 94
<211> LENGTH: 235
<212> TYPE: PRT
<213> ORGANISM: Homo sapiens

<400> SEQUENCE: 94

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Gly
        35                  40                  45

Ile Ser Arg Ser Tyr Leu Ala Trp Tyr Gln Gln Lys Pro Gly Gln Ala
    50                  55                  60

Pro Ser Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Phe
            100                 105                 110

Gly Ser Ser Pro Trp Thr Phe Gly Gln Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190
```

```
Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

<210> SEQ ID NO 95
<211> LENGTH: 1413
<212> TYPE: DNA
<213> ORGANISM: Homo sapiens

<400> SEQUENCE: 95

```
atgaagcatc tgtggttctt cctcctgctg gtggcagctc ccagatgggt cctgtcccag      60

gtgcagctgc aggagtcggg cccaggactg gtgaagcctt cacagaccct gtccctcacc     120

tgcactgtct ctggtggctc catcagcagt ggtgattact tctggagctg gatccgccag     180

ctcccaggga agggcctgga gtggattggg cacatccata acagtgggac cacctactac     240

aatccgtccc tcaagagtcg agttaccata tcagtagaca cgtctaagaa gcagttctcc     300

ctgaggctga gttctgtgac tgccgcggac acggccgtat attactgtgc gagagatcga     360

gggggtgact actactatgg tatggacgtc tggggccaag ggaccacggt caccgtctcc     420

tcagcctcca ccaagggccc atccgtcttc cccctggcac cctcctccaa gagcacctct     480

gggggcacag cggccctggg ctgcctggtc aaggactact tccccgaacc ggtgacggtg     540

tcgtggaact caggcgccct gaccagcggc gtgcacacct tcccggctgt cctacagtcc     600

tcaggactct actccctcag cagcgtggtg accgtgccct ccagcagctt gggcacccag     660

acctacatct gcaacgtgaa tcacaagccc agcaacacca aggtggacaa gagagttgag     720

cccaaatctt gtgacaaaac tcacacatgc ccaccgtgcc cagcacctga actcctgggg     780

ggaccgtcag tcttcctctt ccccccaaaa cccaaggaca ccctcatgat ctcccggacc     840

cctgaggtca catgcgtggt ggtggacgtg agccacgaag accctgaggt caagttcaac     900

tggtacgtgg acggcgtgga ggtgcataat gccaagacaa agccgcggga ggagcagtac     960

aacagcacgt accgtgtggt cagcgtcctc accgtcctgc accaggactg gctgaatggc    1020

aaggagtaca agtgcaaggt ctccaacaaa gccctcccag cccccatcga gaaaaccatc    1080

tccaaagcca aagggcagcc ccgagaacca caggtgtaca ccctgccccc atcccgggag    1140

gagatgacca agaaccaggt cagcctgacc tgcctggtca aaggcttcta tcccagcgac    1200

atcgccgtgg agtgggagag caatgggcag ccggagaaca actacaagac cacgcctccc    1260

gtgctggact ccgacggctc cttcttcctc tatagcaagc tcaccgtgga caagagcagg    1320

tggcagcagg ggaacgtctt ctcatgctcc gtgatgcatg aggctctgca caaccactac    1380

acgcagaaga gcctctccct gtctccgggt aaa                                 1413
```

<210> SEQ ID NO 96
<211> LENGTH: 471
<212> TYPE: PRT
<213> ORGANISM: Homo sapiens

<400> SEQUENCE: 96

```
Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30
```

-continued

```
Pro Ser Gln Thr Leu Ser Leu Thr Cys Thr Val Ser Gly Gly Ser Ile
        35                  40                  45

Ser Ser Gly Asp Tyr Phe Trp Ser Trp Ile Arg Gln Leu Pro Gly Lys
    50                  55                  60

Gly Leu Glu Trp Ile Gly His Ile His Asn Ser Gly Thr Thr Tyr Tyr
65                  70                  75                  80

Asn Pro Ser Leu Lys Ser Arg Val Thr Ile Ser Val Asp Thr Ser Lys
                85                  90                  95

Lys Gln Phe Ser Leu Arg Leu Ser Ser Val Thr Ala Ala Asp Thr Ala
            100                 105                 110

Val Tyr Tyr Cys Ala Arg Asp Arg Gly Gly Asp Tyr Tyr Tyr Gly Met
        115                 120                 125

Asp Val Trp Gly Gln Gly Thr Thr Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445
```

```
Cys Ser Val Met His Glu Ala Leu His Asn His Tyr Thr Gln Lys Ser
    450                 455                 460

Leu Ser Leu Ser Pro Gly Lys
465                 470


<210> SEQ ID NO 97
<211> LENGTH: 708
<212> TYPE: DNA
<213> ORGANISM: Homo sapiens

<400> SEQUENCE: 97

atggacatga gggtccctgc tcagctcctg gggctcctgc tgctctggct ctcaggtgcc      60

agatgtgaca tccagatgac ccagtctcca tcctccctgt ctgcatctgt aggagacaga     120

gtcaccatca cttgccaggc gagtcaggac atcagcaact atttaaattg gtatcagcag     180

aaaccaggga aagcccctaa actcctgatc tacgatgcat ccaatttgga aacaggggtc     240

ccatcaaggt tcagtggaag tggatctggg acagatttta ctttcaccat cagcagcctg     300

cagcctgaag atattgcaac atatttctgt caacactttg atcatctccc gctcgctttc     360

ggcggaggga ccaaggtgga gatcaaacga actgtggctg caccatctgt cttcatcttc     420

ccgccatctg atgagcagtt gaaatctgga actgcctctg ttgtgtgcct gctgaataac     480

ttctatccca gagaggccaa agtacagtgg aaggtggata acgccctcca atcgggtaac     540

tcccaggaga gtgtcacaga gcaggacagc aaggacagca cctacagcct cagcagcacc     600

ctgacgctga gcaaagcaga ctacgagaaa cacaaagtct acgcctgcga agtcacccat     660

cagggcctga gctcgcccgt cacaaagagc ttcaacaggg gagagtgt                  708


<210> SEQ ID NO 98
<211> LENGTH: 236
<212> TYPE: PRT
<213> ORGANISM: Homo sapiens

<400> SEQUENCE: 98

Met Asp Met Arg Val Pro Ala Gln Leu Leu Gly Leu Leu Leu Leu Trp
1               5                   10                  15

Leu Ser Gly Ala Arg Cys Asp Ile Gln Met Thr Gln Ser Pro Ser Ser
            20                  25                  30

Leu Ser Ala Ser Val Gly Asp Arg Val Thr Ile Thr Cys Gln Ala Ser
        35                  40                  45

Gln Asp Ile Ser Asn Tyr Leu Asn Trp Tyr Gln Gln Lys Pro Gly Lys
    50                  55                  60

Ala Pro Lys Leu Leu Ile Tyr Asp Ala Ser Asn Leu Glu Thr Gly Val
65                  70                  75                  80

Pro Ser Arg Phe Ser Gly Ser Gly Ser Gly Thr Asp Phe Thr Phe Thr
                85                  90                  95

Ile Ser Ser Leu Gln Pro Glu Asp Ile Ala Thr Tyr Phe Cys Gln His
            100                 105                 110

Phe Asp His Leu Pro Leu Ala Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175
```

```
Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235


<210> SEQ ID NO 99
<211> LENGTH: 1392
<212> TYPE: DNA
<213> ORGANISM: Homo sapiens

<400> SEQUENCE: 99

atgaaacacc tgtggttctt cctcctcctg gtggcagctc ccagatgggt cctgtcccag      60

gtacagctgc aggagtcggg cccaggactg gtgaagcctt cggagaccct gtccctcacc     120

tgcactgtct ctggtggctc cgtcagcagt ggtgattact actggacctg gatccggcag     180

tccccaggga agggactgga gtggattgga cacatctatt acagtgggaa caccaattat     240

aacccctccc tcaagagtcg actcaccata tcaattgaca cgtccaagac tcagttctcc     300

ctgaagctga gttctgtgac cgctgcggac acggccattt attactgtgt gcgagatcga     360

gtgactggtg cttttgatat ctggggccaa gggacaatgg tcaccgtctc ttcagctagc     420

accaagggcc catcggtctt ccccctggcg ccctgctcca ggagcacctc cgagagcaca     480

gcggccctgg gctgcctggt caaggactac ttccccgaac cggtgacggt gtcgtggaac     540

tcaggcgctc tgaccagcgg cgtgcacacc ttcccagctg tcctacagtc ctcaggactc     600

tactccctca gcagcgtggt gaccgtgccc tccagcaact tcggcaccca gacctacacc     660

tgcaacgtag atcacaagcc cagcaacacc aaggtggaca agacagttga gcgcaaatgt     720

tgtgtcgagt gcccaccgtg cccagcacca cctgtggcag gaccgtcagt cttcctcttc     780

cccccaaaac ccaaggacac cctcatgatc tcccggaccc ctgaggtcac gtgcgtggtg     840

gtggacgtga gccacgaaga ccccgaggtc cagttcaact ggtacgtgga cggcgtggag     900

gtgcataatg ccaagacaaa gccacgggag gagcagttca acagcacgtt ccgtgtggtc     960

agcgtcctca ccgttgtgca ccaggactgg ctgaacggca aggagtacaa gtgcaaggtc    1020

tccaacaaag gcctcccagc ccccatcgag aaaaccatct ccaaaaccaa agggcagccc    1080

cgagaaccac aggtgtacac cctgccccca tcccgggagg agatgaccaa gaaccaggtc    1140

agcctgacct gcctggtcaa aggcttctac cccagcgaca tcgccgtgga gtgggagagc    1200

aatgggcagc cggagaacaa ctacaagacc acacctccca tgctggactc cgacggctcc    1260

ttcttcctct acagcaagct caccgtggac aagagcaggt ggcagcaggg gaacgtcttc    1320

tcatgctccg tgatgcatga ggctctgcac aaccactaca cgcagaagag cctctccctg    1380

tctccgggta aa                                                        1392


<210> SEQ ID NO 100
<211> LENGTH: 464
<212> TYPE: PRT
<213> ORGANISM: Homo sapiens

<400> SEQUENCE: 100

Met Lys His Leu Trp Phe Phe Leu Leu Leu Val Ala Ala Pro Arg Trp
1               5                   10                  15
```

-continued

```
Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Gly Ser Val
        35                  40                  45

Ser Ser Gly Asp Tyr Tyr Trp Thr Trp Ile Arg Gln Ser Pro Gly Lys
    50                  55                  60

Gly Leu Glu Trp Ile Gly His Ile Tyr Tyr Ser Gly Asn Thr Asn Tyr
65                  70                  75                  80

Asn Pro Ser Leu Lys Ser Arg Leu Thr Ile Ser Ile Asp Thr Ser Lys
                85                  90                  95

Thr Gln Phe Ser Leu Lys Leu Ser Ser Val Thr Ala Ala Asp Thr Ala
            100                 105                 110

Ile Tyr Tyr Cys Val Arg Asp Arg Val Thr Gly Ala Phe Asp Ile Trp
        115                 120                 125

Gly Gln Gly Thr Met Val Thr Val Ser Ser Ala Ser Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Asn Phe Gly Thr Gln Thr Tyr Thr Cys Asn Val Asp
    210                 215                 220

His Lys Pro Ser Asn Thr Lys Val Asp Lys Thr Val Glu Arg Lys Cys
225                 230                 235                 240

Cys Val Glu Cys Pro Pro Cys Pro Ala Pro Pro Val Ala Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Gln Phe Asn Trp Tyr Val Asp Gly Val Glu Val His Asn Ala
    290                 295                 300

Lys Thr Lys Pro Arg Glu Glu Gln Phe Asn Ser Thr Phe Arg Val Val
305                 310                 315                 320

Ser Val Leu Thr Val Val His Gln Asp Trp Leu Asn Gly Lys Glu Tyr
                325                 330                 335

Lys Cys Lys Val Ser Asn Lys Gly Leu Pro Ala Pro Ile Glu Lys Thr
            340                 345                 350

Ile Ser Lys Thr Lys Gly Gln Pro Arg Glu Pro Gln Val Tyr Thr Leu
        355                 360                 365

Pro Pro Ser Arg Glu Glu Met Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Met Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
```

```
        435                 440                 445

Leu His Asn His Tyr Thr Gln Lys Ser Leu Ser Leu Ser Pro Gly Lys
    450                 455                 460
```

<210> SEQ ID NO 101
<211> LENGTH: 708
<212> TYPE: DNA
<213> ORGANISM: Homo sapiens

<400> SEQUENCE: 101

```
atggaaaccc cagcgcagct tctcttcctc ctgctactct ggctcccaga taccgctagc      60

gaaattgtgt tgacgcagtc tccaggcacc ctgtctttgt ctccagggga aagagccacc     120

ctctcctgca gggccagtca gagtgttagc aacagctact tagcctggta ccagcagaaa     180

cctggccagg ctcccaggct cctcatctat ggtgcatcca gcagggcccc tggcatccca     240

gacaggttca gtggcagtgg gtctgggaca gacttcactc tcaccatcag cagactggag     300

cctgaagatt ttgcagtgta ttactgtcag cagtatgatc actcagcagg gtggacgttc     360

ggccaaggga ccaaggtgga gatcaaacgt acggtggctg caccatctgt cttcatcttc     420

ccgccatctg atgagcagtt gaaatctgga actgcctctg ttgtgtgcct gctgaataac     480

ttctatccca gagaggccaa agtacagtgg aaggtggata acgccctcca atcgggtaac     540

tcccaggaga gtgtcacaga gcaggacagc aaggacagca cctacagcct cagcagcacc     600

ctgacgctga gcaaagcaga ctacgagaaa cacaaagtct acgcctgcga agtcacccat     660

cagggcctga gctcgcccgt cacaaagagc ttcaacaggg gagagtgt                  708
```

<210> SEQ ID NO 102
<211> LENGTH: 236
<212> TYPE: PRT
<213> ORGANISM: Homo sapiens

<400> SEQUENCE: 102

```
Met Glu Thr Pro Ala Gln Leu Leu Phe Leu Leu Leu Leu Trp Leu Pro
1               5                   10                  15

Asp Thr Ala Ser Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Asn Ser Tyr Leu Ala Trp Tyr Gln Gln Lys Pro Gly Gln Ala
    50                  55                  60

Pro Arg Leu Leu Ile Tyr Gly Ala Ser Ser Arg Ala Pro Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Asp His Ser Ala Gly Trp Thr Phe Gly Gln Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
```

```
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 103
<211> LENGTH: 1680
<212> TYPE: DNA
<213> ORGANISM: Homo sapiens

<400> SEQUENCE: 103

```
atggggtcaa ccgccatcct tggcctcctc ctggctgttc tccaaggagt cgctagcgag     60
gttcagctgg tggagtctgg gggaggcttg gtacagcctg gggggtccct gagactctcc    120
tgtgcagcct ctggattcac cttcagtaga aatgctatgt tctgggttcg ccaggctcca    180
ggaaaaggtc tggagtgggt atcaggtatt ggtactggtg gtgccacaag ctatgcagac    240
tccgtgaagg gccgattcac catctccaga gacaatgcca agaactcctt gtatcttcaa    300
atgaacagcc tgagagccga ggacacggct gtgtattact gtgcaagagg gaggtactac    360
ttcccgtggt ggggccaggg aaccctggtc accgtctcct cagcctccac caagggccca    420
tcggtcttcc ccctggcgcc ctgctccagg agcacctccg agagcacagc ggccctgggc    480
tgcctggtca aggactactt ccccgaaccg gtgacggtgt cgtggaactc aggcgctctg    540
accagcggcg tgcacacctt cccggctgtc ctacagtcct caggactcta ctccctcagc    600
agcgtggtga ccgtgccctc cagcaacttc ggcacccaga cctacacctg caacgtagat    660
cacaagccca gcaacaccaa ggtggacaag acagttggtg agaggccagc tcagggaggg    720
agggtgtctg ctggaagcca ggctcagccc tcctgcctgg acgcaccccg gctgtgcagc    780
cccagcccag ggcagcaagg caggccccat ctgtctcctc acccggaggc ctctgcccgc    840
cccactcatg ctcagggaga gggtcttctg gctttttcca ccaggctcca ggcaggcaca    900
ggctgggtgc ccctacccca ggcccttcac acacaggggc aggtgcttgg ctcagacctg    960
ccaaaagcca tatccgggag gaccctgccc ctgaccgagc gcaaatgttg tgtcgagtgc   1020
ccaccgtgcc cagcaccacc tgtggcagga ccgtcagtct tcctcttccc cccaaaaccc   1080
aaggacaccc tcatgatctc ccggacccct gaggtcacgt gcgtggtggt ggacgtgagc   1140
cacgaagacc ccgaggtcca gttcaactgg tacgtggacg gcgtggaggt gcataatgcc   1200
aagacaaagc cacgggagga gcagttcaac agcacgttcc gtgtggtcag cgtcctcacc   1260
gtcgtgcacc aggactggct gaacggcaag gagtacaagt gcaaggtctc caacaaaggc   1320
ctcccagccc ccatcgagaa aaccatctcc aaaaccaaag ggcagccccg agaaccacag   1380
gtgtacaccc tgcccccatc ccgggaggag atgaccaaga accaggtcag cctgacctgc   1440
ctggtcaaag gcttctaccc cagcgacatc gccgtggagt gggagagcaa tgggcagccg   1500
gagaacaact acaagaccac acctcccatg ctggactccg acggctcctt cttcctctac   1560
agcaagctca ccgtggacaa gagcaggtgg cagcagggga acgtcttctc atgctccgtg   1620
atgcatgagg ctctgcacaa ccactacacg cagaagagcc tctccctgtc tccgggtaaa   1680
```

<210> SEQ ID NO 104
<211> LENGTH: 460
<212> TYPE: PRT

<213> ORGANISM: Homo sapiens

<400> SEQUENCE: 104

```
Met Gly Ser Thr Ala Ile Leu Gly Leu Leu Leu Ala Val Leu Gln Gly
1               5                   10                  15

Val Ala Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Arg Asn Ala Met Phe Trp Val Arg Gln Ala Pro Gly Lys Gly Leu
    50                  55                  60

Glu Trp Val Ser Gly Ile Gly Thr Gly Gly Ala Thr Ser Tyr Ala Asp
65                  70                  75                  80

Ser Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Thr Ala Val Tyr
            100                 105                 110

Tyr Cys Ala Arg Gly Arg Tyr Tyr Phe Pro Trp Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Asn Phe Gly Thr Gln Thr Tyr Thr Cys Asn Val Asp His Lys Pro Ser
    210                 215                 220

Asn Thr Lys Val Asp Lys Thr Val Glu Arg Lys Cys Cys Val Glu Cys
225                 230                 235                 240

Pro Pro Cys Pro Ala Pro Pro Val Ala Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Gln Phe
        275                 280                 285

Asn Trp Tyr Val Asp Gly Val Glu Val His Asn Ala Lys Thr Lys Pro
    290                 295                 300

Arg Glu Glu Gln Phe Asn Ser Thr Phe Arg Val Val Ser Val Leu Thr
305                 310                 315                 320

Val Val His Gln Asp Trp Leu Asn Gly Lys Glu Tyr Lys Cys Lys Val
                325                 330                 335

Ser Asn Lys Gly Leu Pro Ala Pro Ile Glu Lys Thr Ile Ser Lys Thr
            340                 345                 350

Lys Gly Gln Pro Arg Glu Pro Gln Val Tyr Thr Leu Pro Pro Ser Arg
        355                 360                 365

Glu Glu Met Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400
```

-continued

```
Glu Asn Asn Tyr Lys Thr Thr Pro Pro Met Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460


<210> SEQ ID NO 105
<211> LENGTH: 702
<212> TYPE: DNA
<213> ORGANISM: Homo sapiens

<400> SEQUENCE: 105

atggaaaccc cagcgcagct tctcttcctc ctgctactct ggctcccaga taccaccgga      60

gaaattgtgt tgacgcagtc tccaggcacc ctgtctttgt ctccagggga aagagccacc     120

ctctcctgca gggccagtca gagtgttagc agcagctact tagcctggta ccagcagaaa     180

cctggccagg ctcccaggct cctcatctat ggtgcatccc gcagggccac tggcatccca     240

gacaggttca gtggcagtgg gtctgggaca gacttcactc tcaccatcag cagactggag     300

cctgaagatt ttgcagtgta ttactgtcag cggtatggta gctcacacac ttttggccag     360

gggaccaagc tggagatcag ccgaactgtg gctgcaccat ctgtcttcat cttcccgcca     420

tctgatgagc agttgaaatc tggaactgcc tctgttgtgt gcctgctgaa taacttctat     480

cccagagagg ccaaagtaca gtggaaggtg gataacgccc tccaatcggg taactcccag     540

gagagtgtca cagagcagga cagcaaggac agcacctaca gcctcagcag caccctgacg     600

ctgagcaaag cagactacga gaaacacaaa gtctacgcct gcgaagtcac ccatcagggc     660

ctgagctcgc ccgtcacaaa gagcttcaac aggggagagt gt                        702


<210> SEQ ID NO 106
<211> LENGTH: 234
<212> TYPE: PRT
<213> ORGANISM: Homo sapiens

<400> SEQUENCE: 106

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Ser Ser Tyr Leu Ala Trp Tyr Gln Gln Lys Pro Gly Gln Ala
    50                  55                  60

Pro Arg Leu Leu Ile Tyr Gly Ala Ser Arg Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Arg Tyr
            100                 105                 110

Gly Ser Ser His Thr Phe Gly Gln Gly Thr Lys Leu Glu Ile Ser Arg
        115                 120                 125

Thr Val Ala Ala Pro Ser Val Phe Ile Phe Pro Pro Ser Asp Glu Gln
    130                 135                 140
```

Leu Lys Ser Gly Thr Ala Ser Val Val Cys Leu Leu Asn Asn Phe Tyr
145 150 155 160

Pro Arg Glu Ala Lys Val Gln Trp Lys Val Asp Asn Ala Leu Gln Ser
165 170 175

Gly Asn Ser Gln Glu Ser Val Thr Glu Gln Asp Ser Lys Asp Ser Thr
180 185 190

Tyr Ser Leu Ser Ser Thr Leu Thr Leu Ser Lys Ala Asp Tyr Glu Lys
195 200 205

His Lys Val Tyr Ala Cys Glu Val Thr His Gln Gly Leu Ser Ser Pro
210 215 220

Val Thr Lys Ser Phe Asn Arg Gly Glu Cys
225 230

<210> SEQ ID NO 107
<211> LENGTH: 1401
<212> TYPE: DNA
<213> ORGANISM: Homo sapiens

<400> SEQUENCE: 107
atggggtcaa ccgccatcct cgccctcctc ctggctgttc tccaaggagt ctgtgccgag 60
gtgcagctgg tgcagtctgg agcagaggtg aaaaagcccg gggagtctct gaagatctcc 120
tgtaaggttt ctggatactt ctttaccacc tactggatcg gctgggtgcg ccagatgccc 180
gggaaaggcc tggagtatat ggggatcatc tatcctggtg actctgatac cagatacagc 240
ccgtccttcc aaggccaggt caccatctca gccgacaagt ccatcagcac cgcctacctg 300
cagtggagca gcctgaaggc ctcggacacc gccatgtatt actgtgcgag agggggtaac 360
tggaactgct ttgactactg gggccaggga accctggtca ccgtctcctc agcctccacc 420
aagggcccat cggtcttccc cctggcaccc tcctccaaga gcacctctgg gggcacagcg 480
gccctgggct gcctggtcaa ggactacttc cccgaaccgg tgacggtgtc gtggaactca 540
ggcgccctga ccagcggcgt gcacaccttc ccggctgtcc tacagtcctc aggactctac 600
tccctcagca gcgtggtgac cgtgccctcc agcagcttgg gcacccagac ctacatctgc 660
aacgtgaatc acaagcccag caacaccaag gtggacaaga gagttgagcc caaatcttgt 720
gacaaaactc acacatgccc accgtgccca gcacctgaac tcctgggggg accgtcagtc 780
ttcctcttcc ccccaaaacc caaggacacc ctcatgatct cccggacccc tgaggtcaca 840
tgcgtggtgg tggacgtgag ccacgaagac cctgaggtca agttcaactg gtacgtggac 900
ggcgtggagg tgcataatgc caagacaaag ccgcgggagg agcagtacaa cagcacgtac 960
cgtgtggtca gcgtcctcac cgtcctgcac caggactggc tgaatggcaa ggagtacaag 1020
tgcaaggtct ccaacaaagc cctcccagcc cccatcgaga aaaccatctc caaagccaaa 1080
gggcagcccc gagaaccaca ggtgtacacc ctgcccccat cccgggatga gctgaccaag 1140
aaccaggtca gcctgacctg cctggtcaaa ggcttctatc ccagcgacat cgccgtggag 1200
tgggagagca atgggcagcc ggagaacaac tacaagacca cgcctcccgt gctggactcc 1260
gacggctcct tcttcctcta cagcaagctc accgtggaca agagcaggtg gcagcagggg 1320
aacgtcttct catgctccgt gatgcatgag gctctgcaca accactacac gcagaagagc 1380
ctctccctgt ctccgggtaa a 1401

<210> SEQ ID NO 108
<211> LENGTH: 467
<212> TYPE: PRT
<213> ORGANISM: Homo sapiens

<400> SEQUENCE: 108

Met Gly Ser Thr Ala Ile Leu Ala Leu Leu Leu Ala Val Leu Gln Gly
1 5 10 15

Val Cys Ala Glu Val Gln Leu Val Gln Ser Gly Ala Glu Val Lys Lys
20 25 30

Pro Gly Glu Ser Leu Lys Ile Ser Cys Lys Val Ser Gly Tyr Phe Phe
35 40 45

Thr Thr Tyr Trp Ile Gly Trp Val Arg Gln Met Pro Gly Lys Gly Leu
50 55 60

Glu Tyr Met Gly Ile Ile Tyr Pro Gly Asp Ser Asp Thr Arg Tyr Ser
65 70 75 80

Pro Ser Phe Gln Gly Gln Val Thr Ile Ser Ala Asp Lys Ser Ile Ser
85 90 95

Thr Ala Tyr Leu Gln Trp Ser Ser Leu Lys Ala Ser Asp Thr Ala Met
100 105 110

Tyr Tyr Cys Ala Arg Gly Gly Asn Trp Asn Cys Phe Asp Tyr Trp Gly
115 120 125

Gln Gly Thr Leu Val Thr Val Ser Ser Ala Ser Thr Lys Gly Pro Ser
130 135 140

Val Phe Pro Leu Ala Pro Ser Ser Lys Ser Thr Ser Gly Gly Thr Ala
145 150 155 160

Ala Leu Gly Cys Leu Val Lys Asp Tyr Phe Pro Glu Pro Val Thr Val
165 170 175

Ser Trp Asn Ser Gly Ala Leu Thr Ser Gly Val His Thr Phe Pro Ala
180 185 190

Val Leu Gln Ser Ser Gly Leu Tyr Ser Leu Ser Ser Val Val Thr Val
195 200 205

Pro Ser Ser Ser Leu Gly Thr Gln Thr Tyr Ile Cys Asn Val Asn His
210 215 220

Lys Pro Ser Asn Thr Lys Val Asp Lys Arg Val Glu Pro Lys Ser Cys
225 230 235 240

Asp Lys Thr His Thr Cys Pro Pro Cys Pro Ala Pro Glu Leu Leu Gly
245 250 255

Gly Pro Ser Val Phe Leu Phe Pro Pro Lys Pro Lys Asp Thr Leu Met
260 265 270

Ile Ser Arg Thr Pro Glu Val Thr Cys Val Val Val Asp Val Ser His
275 280 285

Glu Asp Pro Glu Val Lys Phe Asn Trp Tyr Val Asp Gly Val Glu Val
290 295 300

His Asn Ala Lys Thr Lys Pro Arg Glu Glu Gln Tyr Asn Ser Thr Tyr
305 310 315 320

Arg Val Val Ser Val Leu Thr Val Leu His Gln Asp Trp Leu Asn Gly
325 330 335

Lys Glu Tyr Lys Cys Lys Val Ser Asn Lys Ala Leu Pro Ala Pro Ile
340 345 350

Glu Lys Thr Ile Ser Lys Ala Lys Gly Gln Pro Arg Glu Pro Gln Val
355 360 365

Tyr Thr Leu Pro Pro Ser Arg Asp Glu Leu Thr Lys Asn Gln Val Ser
370 375 380

Leu Thr Cys Leu Val Lys Gly Phe Tyr Pro Ser Asp Ile Ala Val Glu
385 390 395 400

Trp Glu Ser Asn Gly Gln Pro Glu Asn Asn Tyr Lys Thr Thr Pro Pro

```
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465


<210> SEQ ID NO 109
<211> LENGTH: 723
<212> TYPE: DNA
<213> ORGANISM: Homo sapiens

<400> SEQUENCE: 109

atggacatga gggtgcccgc tcagctcctg gggctcctgc tgctgtggct gagaggtgcc      60

agatgtgatg ttgtgatgac tcagtctcca ctctccctgc ccgtcacccc tggagagccg     120

gcctccatct cctgcaggtc tagtcagagc ctcctgcata gtaatggata caactatttg     180

gattggtacc tgcagaagcc agggcagtct ccacagctcc tgatctattt gggttctaat     240

cgggcctccg gggtccctga caggttcagt ggcagtggat caggcacaga ttttacactg     300

aaaatcagca gggtggaggc tgaggatgtt ggggtttatt actgcatgca aggtacacac     360

tggcctctga cgttcggcca agggaccaag gtggagatca aacgaactgt ggctgcacca     420

tctgtcttca tcttcccgcc atctgatgag cagttgaaat ctggaactgc ctctgttgtg     480

tgcctgctga ataacttcta tcccagagag gccaaagtac agtggaaggt ggataacgcc     540

ctccaatcgg gtaactccca ggagagtgtc acagagcagg acagcaagga cagcacctac     600

agcctcagca gcaccctgac gctgagcaaa gcagactacg agaaacacaa agtctacgcc     660

tgcgaagtca cccatcaggg cctgagctcg cccgtcacaa agagcttcaa caggggagag     720

tgt                                                                   723


<210> SEQ ID NO 110
<211> LENGTH: 241
<212> TYPE: PRT
<213> ORGANISM: Homo sapiens

<400> SEQUENCE: 110

Met Asp Met Arg Val Pro Ala Gln Leu Leu Gly Leu Leu Leu Leu Trp
1               5                   10                  15

Leu Arg Gly Ala Arg Cys Asp Val Val Met Thr Gln Ser Pro Leu Ser
            20                  25                  30

Leu Pro Val Thr Pro Gly Glu Pro Ala Ser Ile Ser Cys Arg Ser Ser
        35                  40                  45

Gln Ser Leu Leu His Ser Asn Gly Tyr Asn Tyr Leu Asp Trp Tyr Leu
    50                  55                  60

Gln Lys Pro Gly Gln Ser Pro Gln Leu Leu Ile Tyr Leu Gly Ser Asn
65                  70                  75                  80

Arg Ala Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Val Gly Val
            100                 105                 110

Tyr Tyr Cys Met Gln Gly Thr His Trp Pro Leu Thr Phe Gly Gln Gly
        115                 120                 125
```

```
Thr Lys Val Glu Ile Lys Arg Thr Val Ala Ala Pro Ser Val Phe Ile
    130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys


<210> SEQ ID NO 111
<211> LENGTH: 1413
<212> TYPE: DNA
<213> ORGANISM: Homo sapiens

<400> SEQUENCE: 111

atggacatga gggtgcccgc tcagctcctg gggctcctgc tgctgtggct gagaggtgcc      60

agatgtcagg tgcagctgca ggagtcgggc ccaggactgg tgaagccttc ggggaccctg     120

tccctcacct gcgctgtctc tggtggctcc atcagcagta gtaactggtg gagttgggtc     180

cgccagcccc cagggaaggg gctggagtgg attggggaaa tctatcatag tgggagcacc     240

aactacaacc cgtccctcaa gagtcgagtc accatatcag tagacaagtc caagaaccag     300

ttctccctga agctgagctc tgtgaccgcc gcggacacgg ccgtgtatta ctgtgcgaga     360

tggaccgggc gtactgatgc ttttgatatc tggggccaag ggacaatggt caccgtctct     420

agtgcctcca ccaagggccc atcggtcttc cccctggcac cctcctccaa gagcacctct     480

gggggcacag cggccctggg ctgcctggtc aaggactact tccccgaacc ggtgacggtg     540

tcgtggaact caggcgccct gaccagcggc gtgcacacct tcccggctgt cctacagtcc     600

tcaggactct actccctcag cagcgtggtg accgtgccct ccagcagctt gggcacccag     660

acctacatct gcaacgtgaa tcacaagccc agcaacacca aggtggacaa gaaagttgag     720

cccaaatctt gtgacaaaac tcacacatgc ccaccgtgcc cagcacctga actcctgggg     780

ggaccgtcag tcttcctctt ccccccaaaa cccaaggaca ccctcatgat ctcccggacc     840

cctgaggtca catgcgtggt ggtggacgtg agccacgaag accctgaggt caagttcaac     900

tggtacgtgg acggcgtgga ggtgcataat gccaagacaa agccgcggga ggagcagtac     960

aacagcacgt accgtgtggt cagcgtcctc accgtcctgc accaggactg gctgaatggc    1020

aaggagtaca agtgcaaggt ctccaacaaa gccctcccag cccccatcga gaaaaccatc    1080

tccaaagcca aagggcagcc ccgagaacca caggtgtaca ccctgccccc atcccgggat    1140

gagctgacca agaaccaggt cagcctgacc tgcctggtca aaggcttcta tcccagcgac    1200

atcgccgtgg agtgggagag caatgggcag ccggagaaca actacaagac cacgcctccc    1260

gtgctggact ccgacggctc cttcttcctc tatagcaagc tcaccgtgga caagagcagg    1320

tggcagcagg ggaacgtctt ctcatgctcc gtgatgcatg aggctctgca caaccactac    1380

acgcagaaga gcctctccct gtctccgggt aaa                                 1413
```

<210> SEQ ID NO 112
<211> LENGTH: 471
<212> TYPE: PRT
<213> ORGANISM: Homo sapiens

<400> SEQUENCE: 112

```
Met Asp Met Arg Val Pro Ala Gln Leu Leu Gly Leu Leu Leu Leu Trp
1               5                   10                  15

Leu Arg Gly Ala Arg Cys Gln Val Gln Leu Gln Glu Ser Gly Pro Gly
            20                  25                  30

Leu Val Lys Pro Ser Gly Thr Leu Ser Leu Thr Cys Ala Val Ser Gly
        35                  40                  45

Gly Ser Ile Ser Ser Ser Asn Trp Trp Ser Trp Val Arg Gln Pro Pro
    50                  55                  60

Gly Lys Gly Leu Glu Trp Ile Gly Glu Ile Tyr His Ser Gly Ser Thr
65                  70                  75                  80

Asn Tyr Asn Pro Ser Leu Lys Ser Arg Val Thr Ile Ser Val Asp Lys
                85                  90                  95

Ser Lys Asn Gln Phe Ser Leu Lys Leu Ser Ser Val Thr Ala Ala Asp
            100                 105                 110

Thr Ala Val Tyr Tyr Cys Ala Arg Trp Thr Gly Arg Thr Asp Ala Phe
        115                 120                 125

Asp Ile Trp Gly Gln Gly Thr Met Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
```

-continued

```
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470


<210> SEQ ID NO 113
<211> LENGTH: 702
<212> TYPE: DNA
<213> ORGANISM: Homo sapiens

<400> SEQUENCE: 113

atggaagcgc cggcgcagct tctcttcctc ctgctactct ggctcccaga taccactgga      60

gaaatagtga tgacgcagtc tccagccacc ctgtctgtgt ctcctgggga aagagccacc     120

ctctcctgca gggccagtca gagtgttagc agcaacttag cctggttcca gcagaaacct     180

ggccaggctc ccaggcccct catctatgat gcatccacca gggccactgg tgtcccagcc     240

aggttcagtg gcagtgggtc tgggacagac ttcactctca ccatcagcag cctgcagtct     300

gaagattttg cagtttatta ctgtcagcag tatgataact ggccgctcac tttcggcgga     360

gggaccaagg tggagatcaa acgtacggtg gctgcaccat ctgtcttcat cttcccgcca     420

tctgatgagc agttgaaatc tggaactgcc tctgttgtgt gcctgctgaa taacttctat     480

cccagagagg ccaaagtaca gtggaaggtg gataacgccc tccaatcggg taactcccag     540

gagagtgtca cagagcagga cagcaaggac agcacctaca gcctcagcag caccctgacg     600

ctgagcaaag cagactacga gaaacacaaa gtctacgcct gcgaagtcac ccatcagggc     660

ctgagctcgc ccgtcacaaa gagcttcaac aggggagagt gt                        702


<210> SEQ ID NO 114
<211> LENGTH: 234
<212> TYPE: PRT
<213> ORGANISM: Homo sapiens

<400> SEQUENCE: 114

Met Glu Ala Pro Ala Gln Leu Leu Phe Leu Leu Leu Leu Trp Leu Pro
1               5                   10                  15

Asp Thr Thr Gly Glu Ile Val Met Thr Gln Ser Pro Ala Thr Leu Ser
            20                  25                  30

Val Ser Pro Gly Glu Arg Ala Thr Leu Ser Cys Arg Ala Ser Gln Ser
        35                  40                  45

Val Ser Ser Asn Leu Ala Trp Phe Gln Gln Lys Pro Gly Gln Ala Pro
    50                  55                  60

Arg Pro Leu Ile Tyr Asp Ala Ser Thr Arg Ala Thr Gly Val Pro Ala
65                  70                  75                  80

Arg Phe Ser Gly Ser Gly Ser Gly Thr Asp Phe Thr Leu Thr Ile Ser
                85                  90                  95

Ser Leu Gln Ser Glu Asp Phe Ala Val Tyr Tyr Cys Gln Gln Tyr Asp
```

-continued

```
            100                 105                 110

Asn Trp Pro Leu Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 115
<211> LENGTH: 1383
<212> TYPE: DNA
<213> ORGANISM: Homo sapiens

<400> SEQUENCE: 115

```
atggagtgga cctggagggt ccttttcttg gtggcagcag caacaggtgc ccactcccag     60

gttcagctgg tgcagtctgg agctgaggtg aagaagcctg gggcctcagt gaaggtctcc    120

tgcaaggctt ctggttacac ctttaccaga tatggtatca gctgggtgcg acaggcccct    180

ggacaagggc ttgagtggat gggatggatc agcacttaca gtggtaacac aaactatgca    240

cagaagctcc agggcagagt caccatgacc acagacacat ccacgagcac agcctacatg    300

gagctgagga gcctgagatc tgacgacacg gccgtgtatt actgtgcgag acggcagctt    360

tactttgact actggggcca gggaaccctg gtcaccgtct cctcagctag caccaagggc    420

ccatcggtct tccccctggc gccctgctcc aggagcacct ccgagagcac agcggccctg    480

ggctgcctgg tcaaggacta cttccccgaa ccggtgacgg tgtcgtggaa ctcaggcgct    540

ctgaccagcg gcgtgcacac cttcccagct gtcctacagt cctcaggact ctactccctc    600

agcagcgtgg tgaccgtgcc ctccagcaac ttcggcaccc agacctacac ctgcaacgta    660

gatcacaagc ccagcaacac caaggtggac aagacagttg agcgcaaatg ttgtgtcgag    720

tgcccaccgt gcccagcacc acctgtggca ggaccgtcag tcttcctctt ccccccaaaa    780

cccaaggaca ccctcatgat ctcccggacc cctgaggtca cgtgcgtggt ggtggacgtg    840

agccacgaag accccgaggt ccagttcaac tggtacgtgg acggcgtgga ggtgcataat    900

gccaagacaa agccacggga ggagcagttc aacagcacgt tccgtgtggt cagcgtcctc    960

accgttgtgc accaggactg gctgaacggc aaggagtaca agtgcaaggt ctccaacaaa   1020

ggcctcccag cccccatcga gaaaaccatc tccaaaacca aagggcagcc ccgagaacca   1080

caggtgtaca ccctgccccc atcccgggag gagatgacca agaaccaggt cagcctgacc   1140

tgcctggtca aaggcttcta ccccagcgac atcgccgtgg agtgggagag caatgggcag   1200

ccggagaaca actacaagac cacacctccc atgctggact ccgacggctc cttcttcctc   1260

tacagcaagc tcaccgtgga caagagcagg tggcagcagg ggaacgtctt ctcatgctcc   1320

gtgatgcatg aggctctgca caaccactac acgcagaaga gcctctccct gtctccgggt   1380
```

aaa 1383

<210> SEQ ID NO 116
<211> LENGTH: 461
<212> TYPE: PRT
<213> ORGANISM: Homo sapiens

<400> SEQUENCE: 116

Met Glu Trp Thr Trp Arg Val Leu Phe Leu Val Ala Ala Ala Thr Gly
1 5 10 15

Ala His Ser Gln Val Gln Leu Val Gln Ser Gly Ala Glu Val Lys Lys
20 25 30

Pro Gly Ala Ser Val Lys Val Ser Cys Lys Ala Ser Gly Tyr Thr Phe
35 40 45

Thr Arg Tyr Gly Ile Ser Trp Val Arg Gln Ala Pro Gly Gln Gly Leu
50 55 60

Glu Trp Met Gly Trp Ile Ser Thr Tyr Ser Gly Asn Thr Asn Tyr Ala
65 70 75 80

Gln Lys Leu Gln Gly Arg Val Thr Met Thr Thr Asp Thr Ser Thr Ser
85 90 95

Thr Ala Tyr Met Glu Leu Arg Ser Leu Arg Ser Asp Asp Thr Ala Val
100 105 110

Tyr Tyr Cys Ala Arg Arg Gln Leu Tyr Phe Asp Tyr Trp Gly Gln Gly
115 120 125

Thr Leu Val Thr Val Ser Ser Ala Ser Thr Lys Gly Pro Ser Val Phe
130 135 140

Pro Leu Ala Pro Cys Ser Arg Ser Thr Ser Glu Ser Thr Ala Ala Leu
145 150 155 160

Gly Cys Leu Val Lys Asp Tyr Phe Pro Glu Pro Val Thr Val Ser Trp
165 170 175

Asn Ser Gly Ala Leu Thr Ser Gly Val His Thr Phe Pro Ala Val Leu
180 185 190

Gln Ser Ser Gly Leu Tyr Ser Leu Ser Ser Val Val Thr Val Pro Ser
195 200 205

Ser Asn Phe Gly Thr Gln Thr Tyr Thr Cys Asn Val Asp His Lys Pro
210 215 220

Ser Asn Thr Lys Val Asp Lys Thr Val Glu Arg Lys Cys Cys Val Glu
225 230 235 240

Cys Pro Pro Cys Pro Ala Pro Pro Val Ala Gly Pro Ser Val Phe Leu
245 250 255

Phe Pro Pro Lys Pro Lys Asp Thr Leu Met Ile Ser Arg Thr Pro Glu
260 265 270

Val Thr Cys Val Val Val Asp Val Ser His Glu Asp Pro Glu Val Gln
275 280 285

Phe Asn Trp Tyr Val Asp Gly Val Glu Val His Asn Ala Lys Thr Lys
290 295 300

Pro Arg Glu Glu Gln Phe Asn Ser Thr Phe Arg Val Val Ser Val Leu
305 310 315 320

Thr Val Val His Gln Asp Trp Leu Asn Gly Lys Glu Tyr Lys Cys Lys
325 330 335

Val Ser Asn Lys Gly Leu Pro Ala Pro Ile Glu Lys Thr Ile Ser Lys
340 345 350

Thr Lys Gly Gln Pro Arg Glu Pro Gln Val Tyr Thr Leu Pro Pro Ser
355 360 365

-continued

```
Arg Glu Glu Met Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Met Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
    450                 455                 460
```

<210> SEQ ID NO 117
<211> LENGTH: 717
<212> TYPE: DNA
<213> ORGANISM: Homo sapiens

<400> SEQUENCE: 117

```
atgaggctcc ctgctcagct cctggggctg ctaatgctct ggatacctgg atccagtgca      60

gatattgtga tgacccagac tccactctct ctgtccgtca cccctggaca gccggcctcc     120

atctcctgca agtctggtca gagcctcctg catagtgatg gaaagaccta tttgtattgg     180

tacctgcaga agccaggcca gcctccacag ttcctgatct atgaagtttc caaccggttc     240

tctagagtgc cagataggtt cagtggcagc gggtcaggga cagatttcac actgagaatc     300

agccgggtgg aggctgagga tgttggaatt tattactgca tgcaaagtat acagcttccg     360

tggacgttcg gccaagggac ccaggtggaa atcaaacgaa ctgtggctgc accatctgtc     420

ttcatcttcc cgccatctga tgagcagttg aaatctggaa ctgcctctgt tgtgtgcctg     480

ctgaataact tctatcccag agaggccaaa gtacagtgga aggtggataa cgccctccaa     540

tcgggtaact cccaggagag tgtcacagag caggacagca aggacagcac ctacagcctc     600

agcagcaccc tgacgctgag caaagcagac tacgagaaac acaaagtcta cgcctgcgaa     660

gtcacccatc agggcctgag ctcgcccgtc acaaagagct tcaacagggg agagtgt        717
```

<210> SEQ ID NO 118
<211> LENGTH: 239
<212> TYPE: PRT
<213> ORGANISM: Homo sapiens

<400> SEQUENCE: 118

```
Met Arg Leu Pro Ala Gln Leu Leu Gly Leu Leu Met Leu Trp Ile Pro
1               5                   10                  15

Gly Ser Ser Ala Asp Ile Val Met Thr Gln Thr Pro Leu Ser Leu Ser
            20                  25                  30

Val Thr Pro Gly Gln Pro Ala Ser Ile Ser Cys Lys Ser Gly Gln Ser
        35                  40                  45

Leu Leu His Ser Asp Gly Lys Thr Tyr Leu Tyr Trp Tyr Leu Gln Lys
    50                  55                  60

Pro Gly Gln Pro Pro Gln Phe Leu Ile Tyr Glu Val Ser Asn Arg Phe
65                  70                  75                  80

Ser Arg Val Pro Asp Arg Phe Ser Gly Ser Gly Ser Gly Thr Asp Phe
                85                  90                  95

Thr Leu Arg Ile Ser Arg Val Glu Ala Glu Asp Val Gly Ile Tyr Tyr
            100                 105                 110
```

```
Cys Met Gln Ser Ile Gln Leu Pro Trp Thr Phe Gly Gln Gly Thr Gln
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235


<210> SEQ ID NO 119
<211> LENGTH: 1377
<212> TYPE: DNA
<213> ORGANISM: Homo sapiens

<400> SEQUENCE: 119

atggagtttg ggctgagctg ggttttcctc gttgctcttt taagaggtgt ccagtgtcag     60

gtgcagctgg tggagtctgg gggaggcgtg gtccagcctg ggaggtccct gagactctcc    120

tgtgcagcct ctggattcac cttcagtggc tatggcatgc actgggtccg ccaggctcca    180

ggcaaggggc tggagtgggt ggcagttata tcatatgatg gaaatgataa atactatgca    240

gactccgtga agggccgatt caccatctcc agagacaatg ccaagaacac gctgtatctg    300

caaatgaaca gcctgagagc tgaggacacg gctgtgtatt actgtgcgag agagctacgg    360

gtcctctggg gccagggaac cctggtcacc gtctctagtg cctccaccaa gggcccatcg    420

gtcttccccc tggcgccctg ctccaggagc acctccgaga gcacagcggc cctgggctgc    480

ctggtcaagg actacttccc cgaaccggtg acggtgtcgt ggaactcagg cgctctgacc    540

agcggcgtgc acaccttccc agctgtccta cagtcctcag gactctactc cctcagcagc    600

gtggtgaccg tgccctccag caacttcggc acccagacct acacctgcaa cgtagatcac    660

aagcccagca acaccaaggt ggacaagaca gttgagcgca aatgttgtgt cgagtgccca    720

ccgtgcccag caccacctgt ggcaggaccg tcagtcttcc tcttcccccc aaaacccaag    780

gacaccctca tgatctcccg gacccctgag gtcacgtgcg tggtggtgga cgtgagccac    840

gaagaccccg aggtccagtt caactggtac gtggacggcg tggaggtgca taatgccaag    900

acaaagccac gggaggagca gttcaacagc acgttccgtg tggtcagcgt cctcaccgtt    960

gtgcaccagg actggctgaa cggcaaggag tacaagtgca aggtctccaa caaaggcctc   1020

ccagccccca tcgagaaaac catctccaaa accaaagggc agccccgaga accacaggtg   1080

tacaccctgc ccccatcccg ggaggagatg accaagaacc aggtcagcct gacctgcctg   1140

gtcaaaggct tctaccccag cgacatcgcc gtggagtggg agagcaatgg gcagccggag   1200

aacaactaca agaccacacc tcccatgctg gactccgacg gctccttctt cctctacagc   1260

aagctcaccg tggacaagag caggtggcag caggggaacg tcttctcatg ctccgtgatg   1320

catgaggctc tgcacaacca ctacacgcag aagagcctct ccctgtctcc gggtaaa      1377
```

<210> SEQ ID NO 120
<211> LENGTH: 459
<212> TYPE: PRT
<213> ORGANISM: Homo sapiens

<400> SEQUENCE: 120

```
Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Gly Tyr Gly Met His Trp Val Arg Gln Ala Pro Gly Lys Gly Leu
    50                  55                  60

Glu Trp Val Ala Val Ile Ser Tyr Asp Gly Asn Asp Lys Tyr Tyr Ala
65                  70                  75                  80

Asp Ser Val Lys Gly Arg Phe Thr Ile Ser Arg Asp Asn Ala Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Glu Leu Arg Val Leu Trp Gly Gln Gly Thr Leu
        115                 120                 125

Val Thr Val Ser Ser Ala Ser Thr Lys Gly Pro Ser Val Phe Pro Leu
    130                 135                 140

Ala Pro Cys Ser Arg Ser Thr Ser Glu Ser Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
            180                 185                 190

Ser Gly Leu Tyr Ser Leu Ser Ser Val Val Thr Val Pro Ser Ser Asn
        195                 200                 205

Phe Gly Thr Gln Thr Tyr Thr Cys Asn Val Asp His Lys Pro Ser Asn
    210                 215                 220

Thr Lys Val Asp Lys Thr Val Glu Arg Lys Cys Cys Val Glu Cys Pro
225                 230                 235                 240

Pro Cys Pro Ala Pro Pro Val Ala Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Gln Phe Asn
        275                 280                 285

Trp Tyr Val Asp Gly Val Glu Val His Asn Ala Lys Thr Lys Pro Arg
    290                 295                 300

Glu Glu Gln Phe Asn Ser Thr Phe Arg Val Val Ser Val Leu Thr Val
305                 310                 315                 320

Val His Gln Asp Trp Leu Asn Gly Lys Glu Tyr Lys Cys Lys Val Ser
                325                 330                 335

Asn Lys Gly Leu Pro Ala Pro Ile Glu Lys Thr Ile Ser Lys Thr Lys
            340                 345                 350

Gly Gln Pro Arg Glu Pro Gln Val Tyr Thr Leu Pro Pro Ser Arg Glu
        355                 360                 365

Glu Met Thr Lys Asn Gln Val Ser Leu Thr Cys Leu Val Lys Gly Phe
    370                 375                 380
```

Tyr Pro Ser Asp Ile Ala Val Glu Trp Glu Ser Asn Gly Gln Pro Glu
385 390 395 400

Asn Asn Tyr Lys Thr Thr Pro Pro Met Leu Asp Ser Asp Gly Ser Phe
405 410 415

Phe Leu Tyr Ser Lys Leu Thr Val Asp Lys Ser Arg Trp Gln Gln Gly
420 425 430

Asn Val Phe Ser Cys Ser Val Met His Glu Ala Leu His Asn His Tyr
435 440 445

Thr Gln Lys Ser Leu Ser Leu Ser Pro Gly Lys
450 455

<210> SEQ ID NO 121
<211> LENGTH: 705
<212> TYPE: DNA
<213> ORGANISM: Homo sapiens

<400> SEQUENCE: 121
atggacatga gggtgcccgc tcagctcctg gggctcctgc tgctgtggct gagaggtgcc 60
agatgtgaca tccagatgac ccagtctcca tcctccctgt ctgcatctgt aggtgaccgt 120
gtcaccatca cttgccgcgc aagtcaggat attagcagct atttaaattg gtatcagcag 180
aaaccaggga aagcccctaa gctcctgatc tattctactt cccgtttgaa tagtggggtc 240
ccatcacgct tcagtggcag tggctctggg acagatttca ctctcaccat cagcagtctg 300
caacctgaag attttgcaac ttactactgt caacaggata ttaaacaccc tacgttcggt 360
caaggcacca aggtggagat caaacgtacg gtggctgcac catctgtctt catcttcccg 420
ccatctgatg agcagttgaa atctggaact gcctctgttg tgtgcctgct gaataacttc 480
tatcccagag aggccaaagt acagtggaag gtggataacg ccctccaatc gggtaactcc 540
caggagagtg tcacagagca ggacagcaag gacagcacct acagcctcag cagcaccctg 600
acgctgagca aagcagacta cgagaaacac aaagtctacg cctgcgaagt cacccatcag 660
ggcctgagct cgcccgtcac aaagagcttc aacaggggag agtgt 705

<210> SEQ ID NO 122
<211> LENGTH: 235
<212> TYPE: PRT
<213> ORGANISM: Homo sapiens

<400> SEQUENCE: 122

Met Asp Met Arg Val Pro Ala Gln Leu Leu Gly Leu Leu Leu Leu Trp
1 5 10 15

Leu Arg Gly Ala Arg Cys Asp Ile Gln Met Thr Gln Ser Pro Ser Ser
20 25 30

Leu Ser Ala Ser Val Gly Asp Arg Val Thr Ile Thr Cys Arg Ala Ser
35 40 45

Gln Asp Ile Ser Ser Tyr Leu Asn Trp Tyr Gln Gln Lys Pro Gly Lys
50 55 60

Ala Pro Lys Leu Leu Ile Tyr Ser Thr Ser Arg Leu Asn Ser Gly Val
65 70 75 80

Pro Ser Arg Phe Ser Gly Ser Gly Ser Gly Thr Asp Phe Thr Leu Thr
85 90 95

Ile Ser Ser Leu Gln Pro Glu Asp Phe Ala Thr Tyr Tyr Cys Gln Gln
100 105 110

Asp Ile Lys His Pro Thr Phe Gly Gln Gly Thr Lys Val Glu Ile Lys
115 120 125

```
Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235


<210> SEQ ID NO 123
<211> LENGTH: 1395
<212> TYPE: DNA
<213> ORGANISM: Homo sapiens

<400> SEQUENCE: 123

atggactgga cctggaggat cctcttcttg gtggcagcag ccacaggagc ccactccgag      60

gtgcagctgg tgcagtctgg ggctgaggtg aagaagcctg ggtcctcggt gaaggtctcc     120

tgcaaggctt ctggttttac cttcaccgac tatattatgc actgggtgcg tcaggcccct     180

ggtcaagggc ttgagtggat gggctatatc aacccttata atgatgacac cgaatacaac     240

gagaagttca agggccgtgt cacgattacc gcggacaaat ccacgagcac agcctacatg     300

gagctgagca gcctgcgctc tgaggacacg gccgtgtatt actgtgcgcg ttcgatttat     360

tactacgatg ccccgtttgc ttactggggc caagggactc tggtcaccgt ctctagtgcc     420

tccaccaagg gcccatcggt cttccccctg gcgccctgct ccaggagcac ctccgagagc     480

acagcggccc tgggctgcct ggtcaaggac tacttccccg aaccggtgac ggtgtcgtgg     540

aactcaggcg ctctgaccag cggcgtgcac accttcccag ctgtcctaca gtcctcagga     600

ctctactccc tcagcagcgt ggtgaccgtg ccctccagca acttcggcac ccagacctac     660

acctgcaacg tagatcacaa gcccagcaac accaaggtgg acaagacagt tgagcgcaaa     720

tgttgtgtcg agtgcccacc gtgcccagca ccacctgtgg caggaccgtc agtcttcctc     780

ttccccccaa aacccaagga caccctcatg atctcccgga cccctgaggt cacgtgcgtg     840

gtggtggacg tgagccacga agaccccgag gtccagttca actggtacgt ggacggcgtg     900

gaggtgcata atgccaagac aaagccacgg gaggagcagt tcaacagcac gttccgtgtg     960

gtcagcgtcc tcaccgttgt gcaccaggac tggctgaacg gcaaggagta caagtgcaag    1020

gtctccaaca aaggcctccc agcccccatc gagaaaacca tctccaaaac caaagggcag    1080

ccccgagaac cacaggtgta caccctgccc ccatcccggg aggagatgac caagaaccag    1140

gtcagcctga cctgcctggt caaaggcttc taccccagcg acatcgccgt ggagtgggag    1200

agcaatgggc agccggagaa caactacaag accacacctc ccatgctgga ctccgacggc    1260

tccttcttcc tctacagcaa gctcaccgtg gacaagagca ggtggcagca ggggaacgtc    1320

ttctcatgct ccgtgatgca tgaggctctg cacaaccact acacgcagaa gagcctctcc    1380

ctgtctccgg gtaaa                                                     1395
```

<210> SEQ ID NO 124
<211> LENGTH: 465
<212> TYPE: PRT
<213> ORGANISM: Homo sapiens

<400> SEQUENCE: 124

```
Met Asp Trp Thr Trp Arg Ile Leu Phe Leu Val Ala Ala Ala Thr Gly
1               5                   10                  15

Ala His Ser Glu Val Gln Leu Val Gln Ser Gly Ala Glu Val Lys Lys
            20                  25                  30

Pro Gly Ser Ser Val Lys Val Ser Cys Lys Ala Ser Gly Phe Thr Phe
        35                  40                  45

Thr Asp Tyr Ile Met His Trp Val Arg Gln Ala Pro Gly Gln Gly Leu
    50                  55                  60

Glu Trp Met Gly Tyr Ile Asn Pro Tyr Asn Asp Asp Thr Glu Tyr Asn
65                  70                  75                  80

Glu Lys Phe Lys Gly Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Ser Ile Tyr Tyr Tyr Asp Ala Pro Phe Ala Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Asn Phe Gly Thr Gln Thr Tyr Thr Cys Asn Val
    210                 215                 220

Asp His Lys Pro Ser Asn Thr Lys Val Asp Lys Thr Val Glu Arg Lys
225                 230                 235                 240

Cys Cys Val Glu Cys Pro Pro Cys Pro Ala Pro Pro Val Ala Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Phe Arg Val
305                 310                 315                 320

Val Ser Val Leu Thr Val Val His Gln Asp Trp Leu Asn Gly Lys Glu
                325                 330                 335

Tyr Lys Cys Lys Val Ser Asn Lys Gly Leu Pro Ala Pro Ile Glu Lys
            340                 345                 350

Thr Ile Ser Lys Thr Lys Gly Gln Pro Arg Glu Pro Gln Val Tyr Thr
        355                 360                 365

Leu Pro Pro Ser Arg Glu Glu Met Thr Lys Asn Gln Val Ser Leu Thr
    370                 375                 380
```

-continued

```
Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Met Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465


<210> SEQ ID NO 125
<211> LENGTH: 699
<212> TYPE: DNA
<213> ORGANISM: Homo sapiens

<400> SEQUENCE: 125

atggggtcaa ccgccatcct tggcctcctc ctggctgtcc tgcagggagg gcgcgcctcc     60

tatgtgctga ctcagccacc ctcggtgtca gtggccccag gacagacggc caggattacc    120

tgtgggggaa acaaccttgg aagtaaaagt gtgcactggt accagcagaa gccaggccag    180

gcccctgtgc tggtcgtcta tgatgatagc gaccggccct catggatccc tgagcgattc    240

tctggctcca actctgggaa cacggccacc ctgaccatca gcaggggcga agccggggat    300

gaggccgact attactgtca ggtgtgggat agtagtagtg atcatgtggt attcggcgga    360

gggaccaagc tgaccgtcct aggccaaccg aaagcggcgc cctcggtcac tctgttcccg    420

ccctcctctg aggagcttca agccaacaag gccacactgg tgtgtctcat aagtgacttc    480

tacccgggag ccgtgacagt ggcctggaag gcagatagca gccccgtcaa ggcgggagtg    540

gagaccacca caccctccaa acaaagcaac aacaagtacg cggccagcag ctatctgagc    600

ctgacgcctg agcagtggaa gtcccacaga agctacagct gccaggtcac gcatgaaggg    660

agcaccgtgg agaagacagt ggcccctaca gaatgttca                            699


<210> SEQ ID NO 126
<211> LENGTH: 233
<212> TYPE: PRT
<213> ORGANISM: Homo sapiens

<400> SEQUENCE: 126

Met Gly Ser Thr Ala Ile Leu Gly Leu Leu Leu Ala Val Leu Gln Gly
1               5                   10                  15

Gly Arg Ala Ser Tyr Val Leu Thr Gln Pro Pro Ser Val Ser Val Ala
            20                  25                  30

Pro Gly Gln Thr Ala Arg Ile Thr Cys Gly Gly Asn Asn Leu Gly Ser
        35                  40                  45

Lys Ser Val His Trp Tyr Gln Gln Lys Pro Gly Gln Ala Pro Val Leu
    50                  55                  60

Val Val Tyr Asp Asp Ser Asp Arg Pro Ser Trp Ile Pro Glu Arg Phe
65                  70                  75                  80

Ser Gly Ser Asn Ser Gly Asn Thr Ala Thr Leu Thr Ile Ser Arg Gly
                85                  90                  95

Glu Ala Gly Asp Glu Ala Asp Tyr Tyr Cys Gln Val Trp Asp Ser Ser
            100                 105                 110
```

-continued

```
Ser Asp His Val Val Phe Gly Gly Gly Thr Lys Leu Thr Val Leu Gly
        115                 120                 125

Gln Pro Lys Ala Ala Pro Ser Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230
```

<210> SEQ ID NO 127
<211> LENGTH: 1401
<212> TYPE: DNA
<213> ORGANISM: Homo sapiens

<400> SEQUENCE: 127

```
atggggtcaa ccgccatcct tggcctcctc ctggctgtcc tgcagggagg gcgcgcccag     60

atgcagctgg tggagtctgg gggaggcgtg gtccagcctg ggaggtccct gagactctcc    120

tgtgcagcgt ctggattcac cttcagaacc tatggcatgc actgggtccg ccaggctcca    180

ggcaagggac tggagtgggt ggcagttata tggtatgatg gaagtaataa acactatgca    240

gactccgtga agggccgatt caccatcacc agagacaatt ccaagaacac tctgaatctg    300

caaatgaaca gcctgagagc cgaggacacg gctgtgtatt actgtgcgag agcccctcag    360

tgggagctag ttcatgaagc ttttgatatc tggggccaag ggacaatggt caccgtctct    420

tcagctagca ccaagggccc atcggtcttc cccctggcgc cctgctccag gagcacctcc    480

gagagcacag cggccctggg ctgcctggtc aaggactact tccccgaacc ggtgacggtg    540

tcgtggaact caggcgctct gaccagcggc gtgcacacct tcccagctgt cctacagtcc    600

tcaggactct actccctcag cagcgtggtg accgtgccct ccagcaactt cggcacccag    660

acctacacct gcaacgtaga tcacaagccc agcaacacca aggtggacaa gacagttgag    720

cgcaaatgtt gtgtcgagtg cccaccgtgc ccagcaccac ctgtggcagg accgtcagtc    780

ttcctcttcc ccccaaaacc caaggacacc ctcatgatct cccggacccc tgaggtcacg    840

tgcgtggtgg tggacgtgag ccacgaagac cccgaggtcc agttcaactg gtacgtggac    900

ggcgtggagg tgcataatgc caagacaaag ccacgggagg agcagttcaa cagcacgttc    960

cgtgtggtca gcgtcctcac cgttgtgcac caggactggc tgaacggcaa ggagtacaag   1020

tgcaaggtct ccaacaaagg cctcccagcc cccatcgaga aaaccatctc caaaaccaaa   1080

gggcagcccc gagaaccaca ggtgtacacc ctgcccccat cccgggagga gatgaccaag   1140

aaccaggtca gcctgacctg cctggtcaaa ggcttctacc ccagcgacat cgccgtggag   1200

tgggagagca atgggcagcc ggagaacaac tacaagacca cacctcccat gctggactcc   1260

gacggctcct tcttcctcta cagcaagctc accgtggaca agagcaggtg gcagcagggg   1320

aacgtcttct catgctccgt gatgcatgag gctctgcaca accactacac gcagaagagc   1380

ctctccctgt ctccgggtaa a                                             1401
```

<210> SEQ ID NO 128
<211> LENGTH: 467
<212> TYPE: PRT
<213> ORGANISM: Homo sapiens

<400> SEQUENCE: 128

Met Gly Ser Thr Ala Ile Leu Gly Leu Leu Leu Ala Val Leu Gln Gly
1 5 10 15

Gly Arg Ala Gln Met Gln Leu Val Glu Ser Gly Gly Gly Val Val Gln
20 25 30

Pro Gly Arg Ser Leu Arg Leu Ser Cys Ala Ala Ser Gly Phe Thr Phe
35 40 45

Arg Thr Tyr Gly Met His Trp Val Arg Gln Ala Pro Gly Lys Gly Leu
50 55 60

Glu Trp Val Ala Val Ile Trp Tyr Asp Gly Ser Asn Lys His Tyr Ala
65 70 75 80

Asp Ser Val Lys Gly Arg Phe Thr Ile Thr Arg Asp Asn Ser Lys Asn
85 90 95

Thr Leu Asn Leu Gln Met Asn Ser Leu Arg Ala Glu Asp Thr Ala Val
100 105 110

Tyr Tyr Cys Ala Arg Ala Pro Gln Trp Glu Leu Val His Glu Ala Phe
115 120 125

Asp Ile Trp Gly Gln Gly Thr Met Val Thr Val Ser Ser Ala Ser Thr
130 135 140

Lys Gly Pro Ser Val Phe Pro Leu Ala Pro Cys Ser Arg Ser Thr Ser
145 150 155 160

Glu Ser Thr Ala Ala Leu Gly Cys Leu Val Lys Asp Tyr Phe Pro Glu
165 170 175

Pro Val Thr Val Ser Trp Asn Ser Gly Ala Leu Thr Ser Gly Val His
180 185 190

Thr Phe Pro Ala Val Leu Gln Ser Ser Gly Leu Tyr Ser Leu Ser Ser
195 200 205

Val Val Thr Val Pro Ser Ser Asn Phe Gly Thr Gln Thr Tyr Thr Cys
210 215 220

Asn Val Asp His Lys Pro Ser Asn Thr Lys Val Asp Lys Thr Val Glu
225 230 235 240

Arg Lys Cys Cys Val Glu Cys Pro Pro Cys Pro Ala Pro Pro Val Ala
245 250 255

Gly Pro Ser Val Phe Leu Phe Pro Pro Lys Pro Lys Asp Thr Leu Met
260 265 270

Ile Ser Arg Thr Pro Glu Val Thr Cys Val Val Val Asp Val Ser His
275 280 285

Glu Asp Pro Glu Val Gln Phe Asn Trp Tyr Val Asp Gly Val Glu Val
290 295 300

His Asn Ala Lys Thr Lys Pro Arg Glu Glu Gln Phe Asn Ser Thr Phe
305 310 315 320

Arg Val Val Ser Val Leu Thr Val Val His Gln Asp Trp Leu Asn Gly
325 330 335

Lys Glu Tyr Lys Cys Lys Val Ser Asn Lys Gly Leu Pro Ala Pro Ile
340 345 350

Glu Lys Thr Ile Ser Lys Thr Lys Gly Gln Pro Arg Glu Pro Gln Val
355 360 365

Tyr Thr Leu Pro Pro Ser Arg Glu Glu Met Thr Lys Asn Gln Val Ser

```
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Met Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465


<210> SEQ ID NO 129
<211> LENGTH: 702
<212> TYPE: DNA
<213> ORGANISM: Homo sapiens

<400> SEQUENCE: 129

atgggtgtgc ctactcatct cctgggtttg ttgctgctct ggattacaca tgccatatgt      60

gatatccgga tgacacagtc tccagcttcc ctgtctgcat ctctgggaga aactgtcaac     120

atcgaatgtc tagcaagtga ggacatttac agtgatttag catggtatca gcagaagcca     180

gggaaatctc ctcagctcct gatctataat gcaaatagct tgcaaaatgg ggtcccttca     240

cggtttagtg gcagtggatc tggcacacag tattctctaa aaataaacag cctgcaatct     300

gaagatgtcg cgacttattt ctgtcaacaa tataacaatt atcctccgac gttcggtgga     360

ggcaccaagc tggaattgaa acgggctgat gctgcaccaa ctgtatctat cttcccacca     420

tccacggaac agttagcaac tggaggtgcc tcagtcgtgt gcctcatgaa caacttctat     480

cccagagaca tcagtgtcaa gtggaagatt gatggcactg aacgacgaga tggtgtcctg     540

gacagtgtta ctgatcagga cagcaaagac agcacgtaca gcatgagcag caccctctcg     600

ttgaccaagg ctgactatga aagtcataac ctctatacct gtgaggttgt tcataagaca     660

tcatcctcac ccgtcgtcaa gagcttcaac aggaatgagt gt                        702


<210> SEQ ID NO 130
<211> LENGTH: 234
<212> TYPE: PRT
<213> ORGANISM: Homo sapiens

<400> SEQUENCE: 130

Met Gly Val Pro Thr His Leu Leu Gly Leu Leu Leu Leu Trp Ile Thr
1               5                   10                  15

His Ala Ile Cys Asp Ile Arg Met Thr Gln Ser Pro Ala Ser Leu Ser
            20                  25                  30

Ala Ser Leu Gly Glu Thr Val Asn Ile Glu Cys Leu Ala Ser Glu Asp
        35                  40                  45

Ile Tyr Ser Asp Leu Ala Trp Tyr Gln Gln Lys Pro Gly Lys Ser Pro
    50                  55                  60

Gln Leu Leu Ile Tyr Asn Ala Asn Ser Leu Gln Asn Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Ser Glu Asp Val Ala Thr Tyr Phe Cys Gln Gln Tyr Asn
```

```
            100                 105                 110

Asn Tyr Pro Pro Thr Phe Gly Gly Gly Thr Lys Leu Glu Leu Lys Arg
        115                 120                 125

Ala Asp Ala Ala Pro Thr Val Ser Ile Phe Pro Pro Ser Thr Glu Gln
    130                 135                 140

Leu Ala Thr Gly Gly Ala Ser Val Val Cys Leu Met Asn Asn Phe Tyr
145                 150                 155                 160

Pro Arg Asp Ile Ser Val Lys Trp Lys Ile Asp Gly Thr Glu Arg Arg
                165                 170                 175

Asp Gly Val Leu Asp Ser Val Thr Asp Gln Asp Ser Lys Asp Ser Thr
            180                 185                 190

Tyr Ser Met Ser Ser Thr Leu Ser Leu Thr Lys Ala Asp Tyr Glu Ser
        195                 200                 205

His Asn Leu Tyr Thr Cys Glu Val Val His Lys Thr Ser Ser Ser Pro
    210                 215                 220

Val Val Lys Ser Phe Asn Arg Asn Glu Cys
225                 230


<210> SEQ ID NO 131
<211> LENGTH: 1395
<212> TYPE: DNA
<213> ORGANISM: Homo sapiens

<400> SEQUENCE: 131

atggacatca ggctcagctt ggctttcctt gtccttttca taaaaggtgt ccagtgtgag     60

gtacagctgg tggagtctgg cggaggattg gtacagcctg caaactccct gaaactctcc    120

tgtgcagcct caggattcac tttcagtgac tatgccatgg cctgggtccg ccagtctcca    180

aagaagggtc tggagtgggt cgcaaccatt atttatgatg gtagtagcac ttactatcga    240

gactccgtga agggccgatt cactatctcc agagataatg caaaaagcac cctatacctg    300

caaatggaca gtctgaggtc tgaggacacg gccacttatt actgtgcaac aggtctgggt    360

atagctacgg actactttga ttactggggc caaggagtcc tggtcacagt ctcctcagct    420

gaaacaacag ccccatctgt ctatccactg gctcctggaa ctgctctcaa aagtaactcc    480

atggtgaccc tgggatgcct ggtcaagggc tatttccctg agccagtcac cgtgacctgg    540

aactctggag ccctgtccag cggtgtgcac accttcccag ctgtcctgca gtctgggctc    600

tacactctca ccagctcagt gactgtaccc tccagcacct ggcccagcca gaccgtcacc    660

tgcaacgtag cccacccggc cagcagcacc aaggtggaca agaaaattgt gcccagaaac    720

tgtggaggtg attgcaagcc ttgtatatgt acaggctcag aagtatcatc tgtcttcatc    780

ttccccccaa agcccaaaga tgtgctcacc atcactctga ctcctaaggt cacgtgtgtt    840

gtggtagaca ttagccagga cgatcccgag gtccatttca gctggtttgt agatgacgtg    900

gaagtccaca cagctcagac tcgaccacca gaggagcagt tcaacagcac tttccgctca    960

gtcagtgaac tccccatcct gcaccaggac tggctcaatg gcaggacgtt cagatgcaag   1020

gtcaccagtg cagctttccc atcccccatc gagaaaacca tctccaaacc cgaaggcaga   1080

acacaagttc cgcatgtata caccatgtca cctaccaagg aagagatgac ccagaatgaa   1140

gtcagtatca cctgcatggt aaaaggcttc tatcccccag acatttatgt ggagtggcag   1200

atgaacgggc agccacagga aaactacaag aacactccac ctacgatgga cacagatggg   1260

agttacttcc tctacagcaa gctcaatgtg aagaaggaaa aatggcagca gggaaacacg   1320

ttcacgtgtt ctgtgctgca tgaaggcctg cacaaccacc atactgagaa gagtctctcc   1380
```

```
cactctccgg gtaaa                                                    1395


<210> SEQ ID NO 132
<211> LENGTH: 465
<212> TYPE: PRT
<213> ORGANISM: Homo sapiens

<400> SEQUENCE: 132

Met Asp Ile Arg Leu Ser Leu Ala Phe Leu Val Leu Phe Ile Lys Gly
1               5                   10                  15

Val Gln Cys Glu Val Gln Leu Val Glu Ser Gly Gly Gly Leu Val Gln
            20                  25                  30

Pro Ala Asn Ser Leu Lys Leu Ser Cys Ala Ala Ser Gly Phe Thr Phe
        35                  40                  45

Ser Asp Tyr Ala Met Ala Trp Val Arg Gln Ser Pro Lys Lys Gly Leu
    50                  55                  60

Glu Trp Val Ala Thr Ile Ile Tyr Asp Gly Ser Ser Thr Tyr Tyr Arg
65                  70                  75                  80

Asp Ser Val Lys Gly Arg Phe Thr Ile Ser Arg Asp Asn Ala Lys Ser
                85                  90                  95

Thr Leu Tyr Leu Gln Met Asp Ser Leu Arg Ser Glu Asp Thr Ala Thr
            100                 105                 110

Tyr Tyr Cys Ala Thr Gly Leu Gly Ile Ala Thr Asp Tyr Phe Asp Tyr
        115                 120                 125

Trp Gly Gln Gly Val Leu Val Thr Val Ser Ser Ala Glu Thr Thr Ala
    130                 135                 140

Pro Ser Val Tyr Pro Leu Ala Pro Gly Thr Ala Leu Lys Ser Asn Ser
145                 150                 155                 160

Met Val Thr Leu Gly Cys Leu Val Lys Gly Tyr Phe Pro Glu Pro Val
                165                 170                 175

Thr Val Thr Trp Asn Ser Gly Ala Leu Ser Ser Gly Val His Thr Phe
            180                 185                 190

Pro Ala Val Leu Gln Ser Gly Leu Tyr Thr Leu Thr Ser Ser Val Thr
        195                 200                 205

Val Pro Ser Ser Thr Trp Pro Ser Gln Thr Val Thr Cys Asn Val Ala
    210                 215                 220

His Pro Ala Ser Ser Thr Lys Val Asp Lys Lys Ile Val Pro Arg Asn
225                 230                 235                 240

Cys Gly Gly Asp Cys Lys Pro Cys Ile Cys Thr Gly Ser Glu Val Ser
                245                 250                 255

Ser Val Phe Ile Phe Pro Pro Lys Pro Lys Asp Val Leu Thr Ile Thr
            260                 265                 270

Leu Thr Pro Lys Val Thr Cys Val Val Val Asp Ile Ser Gln Asp Asp
        275                 280                 285

Pro Glu Val His Phe Ser Trp Phe Val Asp Asp Val Glu Val His Thr
    290                 295                 300

Ala Gln Thr Arg Pro Pro Glu Glu Gln Phe Asn Ser Thr Phe Arg Ser
305                 310                 315                 320

Val Ser Glu Leu Pro Ile Leu His Gln Asp Trp Leu Asn Gly Arg Thr
                325                 330                 335

Phe Arg Cys Lys Val Thr Ser Ala Ala Phe Pro Ser Pro Ile Glu Lys
            340                 345                 350

Thr Ile Ser Lys Pro Glu Gly Arg Thr Gln Val Pro His Val Tyr Thr
        355                 360                 365
```

Met Ser Pro Thr Lys Glu Glu Met Thr Gln Asn Glu Val Ser Ile Thr
    370                 375                 380

Cys Met Val Lys Gly Phe Tyr Pro Pro Asp Ile Tyr Val Glu Trp Gln
385                 390                 395                 400

Met Asn Gly Gln Pro Gln Glu Asn Tyr Lys Asn Thr Pro Pro Thr Met
                405                 410                 415

Asp Thr Asp Gly Ser Tyr Phe Leu Tyr Ser Lys Leu Asn Val Lys Lys
            420                 425                 430

Glu Lys Trp Gln Gln Gly Asn Thr Phe Thr Cys Ser Val Leu His Glu
        435                 440                 445

Gly Leu His Asn His His Thr Glu Lys Ser Leu Ser His Ser Pro Gly
    450                 455                 460

Lys
465

<210> SEQ ID NO 133
<211> LENGTH: 711
<212> TYPE: DNA
<213> ORGANISM: Homo sapiens

<400> SEQUENCE: 133
atggacatga gggtgcccgc tcagctcctg gggctcctgc tgctgtggct gagaggtgcc 60
agatgtgagt ctgccctgac tcagcctgcc tccgtgtctg ggtctcctgg acagtcgatc 120
accatctcct gcactggaac cagcagtgac gttggtggtt ataactctgt ctcctggtac 180
caacagcacc caggcaaagc ccccaaactc atgatttatg aggtcagtaa tcggccctca 240
ggggtttcta atcgcttctc tggctccaag tctggcaaca cggcctccct gaccatctct 300
gggctccagg ctgaggacga ggctgattat tactgcaatt catatacaag caccagcatg 360
gtattcggcg gagggaccaa gctgaccgtc ctaggtcagc ccaaggctgc cccctcggtc 420
actctgttcc cgccctcctc tgaggagctt caagccaaca aggccacact ggtgtgtctc 480
ataagtgact tctacccggg agccgtgaca gtggcctgga aggcagatag cagccccgtc 540
aaggcgggag tggagaccac cacaccctcc aaacaaagca acaacaagta cgcggccagc 600
agctatctga gcctgacgcc tgagcagtgg aagtcccaca gaagctacag ctgccaggtc 660
acgcatgaag ggagcaccgt ggagaagaca gtggccccta cagaatgttc a 711

<210> SEQ ID NO 134
<211> LENGTH: 237
<212> TYPE: PRT
<213> ORGANISM: Homo sapiens

<400> SEQUENCE: 134

Met Asp Met Arg Val Pro Ala Gln Leu Leu Gly Leu Leu Leu Leu Trp
1               5                   10                  15

Leu Arg Gly Ala Arg Cys Glu Ser Ala Leu Thr Gln Pro Ala Ser Val
            20                  25                  30

Ser Gly Ser Pro Gly Gln Ser Ile Thr Ile Ser Cys Thr Gly Thr Ser
        35                  40                  45

Ser Asp Val Gly Gly Tyr Asn Ser Val Ser Trp Tyr Gln Gln His Pro
    50                  55                  60

Gly Lys Ala Pro Lys Leu Met Ile Tyr Glu Val Ser Asn Arg Pro Ser
65                  70                  75                  80

Gly Val Ser Asn Arg Phe Ser Gly Ser Lys Ser Gly Asn Thr Ala Ser
                85                  90                  95

```
Leu Thr Ile Ser Gly Leu Gln Ala Glu Asp Glu Ala Asp Tyr Tyr Cys
            100                 105                 110

Asn Ser Tyr Thr Ser Thr Ser Met Val Phe Gly Gly Gly Thr Lys Leu
        115                 120                 125

Thr Val Leu Gly Gln Pro Lys Ala Ala Pro Ser Val Thr Leu Phe Pro
    130                 135                 140

Pro Ser Ser Glu Glu Leu Gln Ala Asn Lys Ala Thr Leu Val Cys Leu
145                 150                 155                 160

Ile Ser Asp Phe Tyr Pro Gly Ala Val Thr Val Ala Trp Lys Ala Asp
                165                 170                 175

Ser Ser Pro Val Lys Ala Gly Val Glu Thr Thr Thr Pro Ser Lys Gln
            180                 185                 190

Ser Asn Asn Lys Tyr Ala Ala Ser Ser Tyr Leu Ser Leu Thr Pro Glu
        195                 200                 205

Gln Trp Lys Ser His Arg Ser Tyr Ser Cys Gln Val Thr His Glu Gly
    210                 215                 220

Ser Thr Val Glu Lys Thr Val Ala Pro Thr Glu Cys Ser
225                 230                 235
```

<210> SEQ ID NO 135
<211> LENGTH: 1380
<212> TYPE: DNA
<213> ORGANISM: Homo sapiens

<400> SEQUENCE: 135

```
atggactgga cctggaggat ccttttcttg gtggcagcag ccacaggtgt ccactccgag     60

gttcagctgg tgcagtctgg agctgaggtg aagaagcctg gggcctcagt gaaggtctcc    120

tgcaaggctt ctggttacac cttaaccagc tatggtatca gctgggtgcg acaggcccct    180

ggacaagggc ttgagtggat gggatgggtc agtttttata atggtaacac aaactatgca    240

cagaagctcc agggcagagg caccatgacc acagacccat ccacgagcac agcctacatg    300

gagctgagga gcctgagatc tgacgacacg gccgtgtatt actgtgcgag aggctacggt    360

atggacgtct ggggccaagg gaccacggtc accgtctcct ctgcctccac caagggccca    420

tcggtcttcc ccctggcgcc ctgctccagg agcacctccg agagcacagc ggccctgggc    480

tgcctggtca aggactactt ccccgaaccg gtgacggtgt cgtggaactc aggcgctctg    540

accagcggcg tgcacacctt cccagctgtc ctacagtcct caggactcta ctccctcagc    600

agcgtggtga ccgtgccctc cagcaacttc ggcacccaga cctacacctg caacgtagat    660

cacaagccca gcaacaccaa ggtggacaag acagttgagc gcaaatgttg tgtcgagtgc    720

ccaccgtgcc cagcaccacc tgtggcagga ccgtcagtct tcctcttccc cccaaaaccc    780

aaggacaccc tcatgatctc ccggacccct gaggtcacgt gcgtggtggt ggacgtgagc    840

cacgaagacc ccgaggtcca gttcaactgg tacgtggacg gcgtggaggt gcataatgcc    900

aagacaaagc cacgggagga gcagttcaac agcacgttcc gtgtggtcag cgtcctcacc    960

gttgtgcacc aggactggct gaacggcaag gagtacaagt gcaaggtctc caacaaaggc   1020

ctcccagccc ccatcgagaa aaccatctcc aaaaccaaag ggcagccccg agaaccacag   1080

gtgtacaccc tgcccccatc ccgggaggag atgaccaaga accaggtcag cctgacctgc   1140

ctggtcaaag gcttctaccc cagcgacatc gccgtggagt gggagagcaa tgggcagccg   1200

gagaacaact acaagaccac acctcccatg ctggactccg acggctcctt cttcctctac   1260

agcaagctca ccgtggacaa gagcaggtgg cagcagggga acgtcttctc atgctccgtg   1320
```

atgcatgagg ctctgcacaa ccactacacg cagaagagcc tctccctgtc tccgggtaaa 1380

<210> SEQ ID NO 136
<211> LENGTH: 460
<212> TYPE: PRT
<213> ORGANISM: Homo sapiens

<400> SEQUENCE: 136

Met Asp Trp Thr Trp Arg Ile Leu Phe Leu Val Ala Ala Ala Thr Gly
1               5                   10                  15

Val His Ser Glu Val Gln Leu Val Gln Ser Gly Ala Glu Val Lys Lys
            20                  25                  30

Pro Gly Ala Ser Val Lys Val Ser Cys Lys Ala Ser Gly Tyr Thr Leu
        35                  40                  45

Thr Ser Tyr Gly Ile Ser Trp Val Arg Gln Ala Pro Gly Gln Gly Leu
    50                  55                  60

Glu Trp Met Gly Trp Val Ser Phe Tyr Asn Gly Asn Thr Asn Tyr Ala
65                  70                  75                  80

Gln Lys Leu Gln Gly Arg Gly Thr Met Thr Thr Asp Pro Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Gly Tyr Gly Met Asp Val Trp Gly Gln Gly Thr
        115                 120                 125

Thr Val Thr Val Ser Ser Ala Ser Thr Lys Gly Pro Ser Val Phe Pro
    130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Asn Phe Gly Thr Gln Thr Tyr Thr Cys Asn Val Asp His Lys Pro Ser
    210                 215                 220

Asn Thr Lys Val Asp Lys Thr Val Glu Arg Lys Cys Cys Val Glu Cys
225                 230                 235                 240

Pro Pro Cys Pro Ala Pro Pro Val Ala Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Gln Phe
        275                 280                 285

Asn Trp Tyr Val Asp Gly Val Glu Val His Asn Ala Lys Thr Lys Pro
    290                 295                 300

Arg Glu Glu Gln Phe Asn Ser Thr Phe Arg Val Val Ser Val Leu Thr
305                 310                 315                 320

Val Val His Gln Asp Trp Leu Asn Gly Lys Glu Tyr Lys Cys Lys Val
                325                 330                 335

Ser Asn Lys Gly Leu Pro Ala Pro Ile Glu Lys Thr Ile Ser Lys Thr
            340                 345                 350

Lys Gly Gln Pro Arg Glu Pro Gln Val Tyr Thr Leu Pro Pro Ser Arg
        355                 360                 365

```
Glu Glu Met Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Met Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460


<210> SEQ ID NO 137
<211> LENGTH: 693
<212> TYPE: DNA
<213> ORGANISM: Homo sapiens

<400> SEQUENCE: 137

atggcatgga tccctctctt cctcggcgtc cttgcttact gcacaggatc cgtggcctcc      60

tatgaggtga ctcaggcacc ctcagtgtcc gtgtccccag gacagacagc cagcatcacc     120

tgctctggag ataaattggg ggataaatat gcttgttggt atcagcagaa gccaggccag     180

tcccctgtgc tggtcatcta tcaagatagc aagcggccct cagggatccc tgagcgattc     240

tctggctcca actctggaaa cacagccact ctgaccatca gcgggaccca ggctatggat     300

gaggctgact attactgtca ggcgtgggac agcagcactg cggtattcgg cggagggacc     360

aagctgaccg tcctaggtca gcccaaggct gccccctcgg tcactctgtt cccgccctcc     420

tctgaggagc ttcaagccaa caaggccaca ctggtgtgtc tcataagtga cttctacccg     480

ggagccgtga cagtggcctg gaaggcagat agcagccccg tcaaggcggg agtggagacc     540

accacaccct ccaaacaaag caacaacaag tacgcggcca gcagctatct gagcctgacg     600

cctgagcagt ggaagtccca cagaagctac agctgccagg tcacgcatga agggagcacc     660

gtggagaaga cagtggcccc tacagaatgt tca                                  693


<210> SEQ ID NO 138
<211> LENGTH: 231
<212> TYPE: PRT
<213> ORGANISM: Homo sapiens

<400> SEQUENCE: 138

Met Ala Trp Ile Pro Leu Phe Leu Gly Val Leu Ala Tyr Cys Thr Gly
1               5                   10                  15

Ser Val Ala Ser Tyr Glu Val Thr Gln Ala Pro Ser Val Ser Val Ser
            20                  25                  30

Pro Gly Gln Thr Ala Ser Ile Thr Cys Ser Gly Asp Lys Leu Gly Asp
        35                  40                  45

Lys Tyr Ala Cys Trp Tyr Gln Gln Lys Pro Gly Gln Ser Pro Val Leu
    50                  55                  60

Val Ile Tyr Gln Asp Ser Lys Arg Pro Ser Gly Ile Pro Glu Arg Phe
65                  70                  75                  80

Ser Gly Ser Asn Ser Gly Asn Thr Ala Thr Leu Thr Ile Ser Gly Thr
                85                  90                  95

Gln Ala Met Asp Glu Ala Asp Tyr Tyr Cys Gln Ala Trp Asp Ser Ser
            100                 105                 110
```

```
Thr Ala Val Phe Gly Gly Gly Thr Lys Leu Thr Val Leu Gly Gln Pro
        115                 120                 125

Lys Ala Ala Pro Ser Val Thr Leu Phe Pro Pro Ser Ser Glu Glu Leu
    130                 135                 140

Gln Ala Asn Lys Ala Thr Leu Val Cys Leu Ile Ser Asp Phe Tyr Pro
145                 150                 155                 160

Gly Ala Val Thr Val Ala Trp Lys Ala Asp Ser Ser Pro Val Lys Ala
                165                 170                 175

Gly Val Glu Thr Thr Thr Pro Ser Lys Gln Ser Asn Asn Lys Tyr Ala
            180                 185                 190

Ala Ser Ser Tyr Leu Ser Leu Thr Pro Glu Gln Trp Lys Ser His Arg
        195                 200                 205

Ser Tyr Ser Cys Gln Val Thr His Glu Gly Ser Thr Val Glu Lys Thr
    210                 215                 220

Val Ala Pro Thr Glu Cys Ser
225                 230


<210> SEQ ID NO 139
<211> LENGTH: 1401
<212> TYPE: DNA
<213> ORGANISM: Homo sapiens

<400> SEQUENCE: 139

atggactgga cctggagcat ccttttcttg gtggcagcag caacaggtgc ccactcccag      60

gttcagctgg tgcagtctgg agctgaggtg aagaagcctg gggcctcagt gaaggtctcc     120

tgcaaggctt ctggttacac ctttaccagt tatggtctca gctgggtgcg acaggcccct     180

ggacaagggc ttgagtggat gggatggatc atcccttaca atggtaacac aaactctgca     240

cagaaactcc agggcagagt caccatgacc acagacacat ccacgagcac agcctacatg     300

gagctgagga gcctgagatc tgacgacacg gccgtgtatt tctgtgcgag agacagggac     360

tacggtgtca attatgatgc ttttgatatc tggggccaag ggacaatggt caccgtctct     420

tcagcctcca ccaagggccc atcggtcttc cccctggcgc cctgctccag gagcacctcc     480

gagagcacag cggccctggg ctgcctggtc aaggactact tccccgaacc ggtgacggtg     540

tcgtggaact caggcgctct gaccagcggc gtgcacacct tcccagctgt cctacagtcc     600

tcaggactct actccctcag cagcgtggtg accgtgccct ccagcaactt cggcacccag     660

acctacacct gcaacgtaga tcacaagccc agcaacacca aggtggacaa gacagttgag     720

cgcaaatgtt gtgtcgagtg cccaccgtgc ccagcaccac ctgtggcagg accgtcagtc     780

ttcctcttcc ccccaaaacc caaggacacc ctcatgatct cccggacccc tgaggtcacg     840

tgcgtggtgg tggacgtgag ccacgaagac cccgaggtcc agttcaactg gtacgtggac     900

ggcgtggagg tgcataatgc caagacaaag ccacgggagg agcagttcaa cagcacgttc     960

cgtgtggtca gcgtcctcac cgttgtgcac caggactggc tgaacggcaa ggagtacaag    1020

tgcaaggtct ccaacaaagg cctcccagcc cccatcgaga aaaccatctc caaaaccaaa    1080

gggcagcccc gagaaccaca ggtgtacacc ctgcccccat cccgggagga gatgaccaag    1140

aaccaggtca gcctgacctg cctggtcaaa ggcttctacc ccagcgacat cgccgtggag    1200

tgggagagca atgggcagcc ggagaacaac tacaagacca cacctcccat gctggactcc    1260

gacggctcct tcttcctcta cagcaagctc accgtggaca agagcaggtg gcagcagggg    1320

aacgtcttct catgctccgt gatgcatgag gctctgcaca accactacac gcagaagagc    1380
```

ctctccctgt ctccgggtaa a 1401

<210> SEQ ID NO 140
<211> LENGTH: 467
<212> TYPE: PRT
<213> ORGANISM: Homo sapiens

<400> SEQUENCE: 140

```
Met Asp Trp Thr Trp Ser Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Gly Leu Ser Trp Val Arg Gln Ala Pro Gly Gln Gly Leu
    50                  55                  60

Glu Trp Met Gly Trp Ile Ile Pro Tyr Asn Gly Asn Thr Asn Ser Ala
65                  70                  75                  80

Gln Lys Leu Gln Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Phe Cys Ala Arg Asp Arg Asp Tyr Gly Val Asn Tyr Asp Ala Phe
        115                 120                 125

Asp Ile Trp Gly Gln Gly Thr Met Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Asn Phe Gly Thr Gln Thr Tyr Thr Cys
    210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Phe
305                 310                 315                 320

Arg Val Val Ser Val Leu Thr Val Val His Gln Asp Trp Leu Asn Gly
                325                 330                 335

Lys Glu Tyr Lys Cys Lys Val Ser Asn Lys Gly Leu Pro Ala Pro Ile
            340                 345                 350

Glu Lys Thr Ile Ser Lys Thr Lys Gly Gln Pro Arg Glu Pro Gln Val
        355                 360                 365
```

```
Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Met Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465


<210> SEQ ID NO 141
<211> LENGTH: 705
<212> TYPE: DNA
<213> ORGANISM: Homo sapiens

<400> SEQUENCE: 141

atggcctggg ctccactact tctcaccctc ctcgctcact gcacaggttc ttgggccaat      60

tttatgctga ctcagcccca ctctgtgtcg gagtctccgg ggaagacggt ggccatctcc     120

tgcacccgca acagtggcag cattgccagc aactctgtgc agtggtacca gcagcgcccg     180

ggcagttccc ccaccactgt gatctttgag gataaccaaa gaccctctgg ggtccctgat     240

cggttctctg gctccatcga cagctcctcc aactctgcct ccctcaccat ctctggtctg     300

aagactgagg acgaggctga ctactactgt cagtcttatg atagcaacaa ttgggtgttc     360

ggcggaggga ccaaactgac cgtcctaggt cagcccaagg ccaaccccac tgtcactctg     420

ttcccgccct cctctgagga gctccaagcc aacaaggcca cactagtgtg tctgatcagt     480

gacttctacc cgggagctgt gacagtggcc tggaaggcag atggcagccc cgtcaaggcg     540

ggagtggaga ccaccaaacc ctccaaacag agcaacaaca agtacgcggc cagcagctac     600

ctgagcctga cgcccgagca gtggaagtcc cacagaagct acagctgcca ggtcacgcat     660

gaagggagca ccgtggagaa gacagtggcc cctacagaat gttca                     705


<210> SEQ ID NO 142
<211> LENGTH: 235
<212> TYPE: PRT
<213> ORGANISM: Homo sapiens

<400> SEQUENCE: 142

Met Ala Trp Ala Pro Leu Leu Leu Thr Leu Leu Ala His Cys Thr Gly
1               5                   10                  15

Ser Trp Ala Asn Phe Met Leu Thr Gln Pro His Ser Val Ser Glu Ser
            20                  25                  30

Pro Gly Lys Thr Val Ala Ile Ser Cys Thr Arg Asn Ser Gly Ser Ile
        35                  40                  45

Ala Ser Asn Ser Val Gln Trp Tyr Gln Gln Arg Pro Gly Ser Ser Pro
    50                  55                  60

Thr Thr Val Ile Phe Glu Asp Asn Gln Arg Pro Ser Gly Val Pro Asp
65                  70                  75                  80

Arg Phe Ser Gly Ser Ile Asp Ser Ser Ser Asn Ser Ala Ser Leu Thr
                85                  90                  95
```

```
Ile Ser Gly Leu Lys Thr Glu Asp Glu Ala Asp Tyr Tyr Cys Gln Ser
            100                 105                 110

Tyr Asp Ser Asn Asn Trp Val Phe Gly Gly Gly Thr Lys Leu Thr Val
        115                 120                 125

Leu Gly Gln Pro Lys Ala Asn Pro Thr Val Thr Leu Phe Pro Pro Ser
    130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Gly Ser
                165                 170                 175

Pro Val Lys Ala Gly Val Glu Thr Thr Lys Pro Ser Lys Gln Ser Asn
            180                 185                 190

Asn Lys Tyr Ala Ala Ser Ser Tyr Leu Ser Leu Thr Pro Glu Gln Trp
        195                 200                 205

Lys Ser His Arg Ser Tyr Ser Cys Gln Val Thr His Glu Gly Ser Thr
    210                 215                 220

Val Glu Lys Thr Val Ala Pro Thr Glu Cys Ser
225                 230                 235


<210> SEQ ID NO 143
<211> LENGTH: 1410
<212> TYPE: DNA
<213> ORGANISM: Homo sapiens

<400> SEQUENCE: 143

atggagtttg ggctgagctg ggttttcctc gttgctcttt taagaggtgt ccagtgtcag      60

gtgcagctgg tggagtctgg gggaggcgtg gtccagcctg ggaggtccct gagactctcc     120

tgtgcagcgt ctggattcac cttcagtagc tatgtcatgc actgggtccg ccaggctcca     180

ggcaaggggc tggagtgggt ggctgttata tggtatgatg gaagtaataa atactatgca     240

gactccgtga agggccgatt caccatctcc agagacaatt ccaagaacac gctgtatctg     300

caaatgaaca gcctgagagc cgaggacacg gctgtgtatt actgtgcgag agaggggtat     360

gactacggtg aagactacta ctactacggt atggacgtct ggggccaagg gaccacggtc     420

accgtctcta gtgcctccac caagggccca tcggtcttcc ccctggcgcc ctgctccagg     480

agcacctccg agagcacagc ggccctgggc tgcctggtca aggactactt ccccgaaccg     540

gtgacggtgt cgtggaactc aggcgctctg accagcggcg tgcacacctt cccagctgtc     600

ctacagtcct caggactcta ctccctcagc agcgtggtga ccgtgccctc cagcaacttc     660

ggcacccaga cctacacctg caacgtagat cacaagccca gcaacaccaa ggtggacaag     720

acagttgagc gcaaatgttg tgtcgagtgc ccaccgtgcc cagcaccacc tgtggcagga     780

ccgtcagtct tcctcttccc cccaaaaccc aaggacaccc tcatgatctc ccggacccct     840

gaggtcacgt gcgtggtggt ggacgtgagc cacgaagacc ccgaggtcca gttcaactgg     900

tacgtggacg gcgtggaggt gcataatgcc aagacaaagc cacgggagga gcagttcaac     960

agcacgttcc gtgtggtcag cgtcctcacc gttgtgcacc aggactggct gaacggcaag    1020

gagtacaagt gcaaggtctc caacaaaggc ctcccagccc ccatcgagaa aaccatctcc    1080

aaaaccaaag ggcagccccg agaaccacag gtgtacaccc tgcccccatc ccgggaggag    1140

atgaccaaga accaggtcag cctgacctgc ctggtcaaag gcttctaccc cagcgacatc    1200

gccgtggagt gggagagcaa tgggcagccg gagaacaact acaagaccac acctcccatg    1260

ctggactccg acggctcctt cttcctctac agcaagctca ccgtggacaa gagcaggtgg    1320
```

```
cagcagggga acgtcttctc atgctccgtg atgcatgagg ctctgcacaa ccactacacg   1380

cagaagagcc tctccctgtc tccgggtaaa                                    1410


<210> SEQ ID NO 144
<211> LENGTH: 470
<212> TYPE: PRT
<213> ORGANISM: Homo sapiens

<400> SEQUENCE: 144

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Val Met His Trp Val Arg Gln Ala Pro Gly Lys Gly Leu
    50                  55                  60

Glu Trp Val Ala Val Ile Trp Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Glu Gly Tyr Asp Tyr Gly Glu Asp Tyr Tyr Tyr
        115                 120                 125

Tyr Gly Met Asp Val Trp Gly Gln Gly Thr Thr Val Thr Val Ser Ser
    130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Asn Phe Gly Thr Gln Thr
    210                 215                 220

Tyr Thr Cys Asn Val Asp His Lys Pro Ser Asn Thr Lys Val Asp Lys
225                 230                 235                 240

Thr Val Glu Arg Lys Cys Cys Val Glu Cys Pro Pro Cys Pro Ala Pro
                245                 250                 255

Pro Val Ala Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Gln Phe Asn Trp Tyr Val Asp Gly
    290                 295                 300

Val Glu Val His Asn Ala Lys Thr Lys Pro Arg Glu Glu Gln Phe Asn
305                 310                 315                 320

Ser Thr Phe Arg Val Val Ser Val Leu Thr Val Val His Gln Asp Trp
                325                 330                 335

Leu Asn Gly Lys Glu Tyr Lys Cys Lys Val Ser Asn Lys Gly Leu Pro
            340                 345                 350

Ala Pro Ile Glu Lys Thr Ile Ser Lys Thr Lys Gly Gln Pro Arg Glu
```

```
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Met Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470
```

<210> SEQ ID NO 145
<211> LENGTH: 708
<212> TYPE: DNA
<213> ORGANISM: Homo sapiens

<400> SEQUENCE: 145

```
atggacatga gggtccccgc tcagctcctg gggctcctgc tactctggct ccgaggtgcc     60

agatgtgaca tccagatgac ccagtctcca tcctccctct ccgcatccgt aggcgaccgc    120

gtaaccataa catgtagagc atctcaagat atttccaact atttgaattg gtaccaacaa    180

aaacccggca aagcacctaa actcctcatt tactatacat caagactcct ctccggcgtt    240

ccatcacgat tctcaggctc cggctccggc acagatttca cactcactat ttcctccctc    300

caaccagaag attttgcaac ctattactgt caacaaggcg atacactccc atacacattc    360

ggcggcggca caaaagttga aattaaacgt acggtggctg caccatctgt cttcatcttc    420

ccgccatctg atgagcagtt gaaatctgga actgcctctg ttgtgtgcct gctgaataac    480

ttctatccca gagaggccaa agtacagtgg aaggtggata acgccctcca atcgggtaac    540

tcccaggaga gtgtcacaga gcaggacagc aaggacagca cctacagcct cagcagcacc    600

ctgacgctga gcaaagcaga ctacgagaaa cacaaagtct acgcctgcga agtcacccat    660

cagggcctga gctcgcccgt cacaaagagc ttcaacaggg gagagtgt                 708
```

<210> SEQ ID NO 146
<211> LENGTH: 236
<212> TYPE: PRT
<213> ORGANISM: Homo sapiens

<400> SEQUENCE: 146

```
Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Asp Ile Ser Asn Tyr Leu Asn Trp Tyr Gln Gln Lys Pro Gly Lys
    50                  55                  60

Ala Pro Lys Leu Leu Ile Tyr Tyr Thr Ser Arg Leu Leu Ser Gly Val
65                  70                  75                  80

Pro Ser Arg Phe Ser Gly Ser Gly Ser Gly Thr Asp Phe Thr Leu Thr
```

```
                85                  90                  95

Ile Ser Ser Leu Gln Pro Glu Asp Phe Ala Thr Tyr Tyr Cys Gln Gln
            100                 105                 110

Gly Asp Thr Leu Pro Tyr Thr Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

```
<210> SEQ ID NO 147
<211> LENGTH: 1404
<212> TYPE: DNA
<213> ORGANISM: Homo sapiens

<400> SEQUENCE: 147

atggactgga cctggaggat cctcttcttg gtggcagcag ccacaggagc ccactccgag      60

gtgcagctgg tgcagagcgg cgccgaggta aaaaaaccag gagcaagcgt taaagtttct     120

tgtaaagcaa gcggatatac atttacagat tacaacatgc attgggtaag acaagcgcca     180

ggacaaggat tggaatggat gggcgaaatt aaccctaata gtggaggagc aggctacaat     240

caaaaattca aagggagagt tacaatgaca acagacacaa gcacttcaac agcatatatg     300

gaactgcgat cacttagaag cgacgataca gctgtatact attgcgcacg acttgggtat     360

gatgatatat atgatgactg gtatttcgat gtttggggcc agggaacaac agttaccgtc     420

tctagtgcct ccaccaaggg cccatcggtc ttccccctgg cgccctgctc caggagcacc     480

tccgagagca cagcggccct gggctgcctg gtcaaggact acttccccga accggtgacg     540

gtgtcgtgga actcaggcgc tctgaccagc ggcgtgcaca ccttcccagc tgtcctacag     600

tcctcaggac tctactccct cagcagcgtg gtgaccgtgc cctccagcaa cttcggcacc     660

cagacctaca cctgcaacgt agatcacaag cccagcaaca ccaaggtgga caagacagtt     720

gagcgcaaat gttgtgtcga gtgcccaccg tgcccagcac cacctgtggc aggaccgtca     780

gtcttcctct tccccccaaa acccaaggac accctcatga tctcccggac ccctgaggtc     840

acgtgcgtgg tggtggacgt gagccacgaa gaccccgagg tccagttcaa ctggtacgtg     900

gacggcgtgg aggtgcataa tgccaagaca aagccacggg aggagcagtt caacagcacg     960

ttccgtgtgg tcagcgtcct caccgttgtg caccaggact ggctgaacgg caaggagtac    1020

aagtgcaagg tctccaacaa aggcctccca gcccccatcg agaaaaccat ctccaaaacc    1080

aaagggcagc cccgagaacc acaggtgtac accctgcccc catcccggga ggagatgacc    1140

aagaaccagg tcagcctgac ctgcctggtc aaaggcttct accccagcga catcgccgtg    1200

gagtgggaga gcaatgggca gccggagaac aactacaaga ccacacctcc catgctggac    1260
```

tccgacggct ccttcttcct ctacagcaag ctcaccgtgg acaagagcag gtggcagcag 1320
gggaacgtct tctcatgctc cgtgatgcat gaggctctgc acaaccacta cacgcagaag 1380
agcctctccc tgtctccggg taaa 1404

<210> SEQ ID NO 148
<211> LENGTH: 468
<212> TYPE: PRT
<213> ORGANISM: Homo sapiens

<400> SEQUENCE: 148

Met Asp Trp Thr Trp Arg Ile Leu Phe Leu Val Ala Ala Ala Thr Gly
1 5 10 15

Ala His Ser Glu Val Gln Leu Val Gln Ser Gly Ala Glu Val Lys Lys
20 25 30

Pro Gly Ala Ser Val Lys Val Ser Cys Lys Ala Ser Gly Tyr Thr Phe
35 40 45

Thr Asp Tyr Asn Met His Trp Val Arg Gln Ala Pro Gly Gln Gly Leu
50 55 60

Glu Trp Met Gly Glu Ile Asn Pro Asn Ser Gly Gly Ala Gly Tyr Asn
65 70 75 80

Gln Lys Phe Lys Gly Arg Val Thr Met Thr Thr Asp Thr Ser Thr Ser
85 90 95

Thr Ala Tyr Met Glu Leu Arg Ser Leu Arg Ser Asp Asp Thr Ala Val
100 105 110

Tyr Tyr Cys Ala Arg Leu Gly Tyr Asp Asp Ile Tyr Asp Asp Trp Tyr
115 120 125

Phe Asp Val Trp Gly Gln Gly Thr Thr Val Thr Val Ser Ser Ala Ser
130 135 140

Thr Lys Gly Pro Ser Val Phe Pro Leu Ala Pro Cys Ser Arg Ser Thr
145 150 155 160

Ser Glu Ser Thr Ala Ala Leu Gly Cys Leu Val Lys Asp Tyr Phe Pro
165 170 175

Glu Pro Val Thr Val Ser Trp Asn Ser Gly Ala Leu Thr Ser Gly Val
180 185 190

His Thr Phe Pro Ala Val Leu Gln Ser Ser Gly Leu Tyr Ser Leu Ser
195 200 205

Ser Val Val Thr Val Pro Ser Ser Asn Phe Gly Thr Gln Thr Tyr Thr
210 215 220

Cys Asn Val Asp His Lys Pro Ser Asn Thr Lys Val Asp Lys Thr Val
225 230 235 240

Glu Arg Lys Cys Cys Val Glu Cys Pro Pro Cys Pro Ala Pro Pro Val
245 250 255

Ala Gly Pro Ser Val Phe Leu Phe Pro Pro Lys Pro Lys Asp Thr Leu
260 265 270

Met Ile Ser Arg Thr Pro Glu Val Thr Cys Val Val Val Asp Val Ser
275 280 285

His Glu Asp Pro Glu Val Gln Phe Asn Trp Tyr Val Asp Gly Val Glu
290 295 300

Val His Asn Ala Lys Thr Lys Pro Arg Glu Glu Gln Phe Asn Ser Thr
305 310 315 320

Phe Arg Val Val Ser Val Leu Thr Val Val His Gln Asp Trp Leu Asn
325 330 335

Gly Lys Glu Tyr Lys Cys Lys Val Ser Asn Lys Gly Leu Pro Ala Pro
340 345 350

```
Ile Glu Lys Thr Ile Ser Lys Thr Lys Gly Gln Pro Arg Glu Pro Gln
        355                 360                 365

Val Tyr Thr Leu Pro Pro Ser Arg Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Met Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465


<210> SEQ ID NO 149
<211> LENGTH: 720
<212> TYPE: DNA
<213> ORGANISM: Homo sapiens

<400> SEQUENCE: 149

atggtgttgc agacccaggt cttcatttct ctgttgctct ggatctctgg tgcctacggg      60

gacatcgtga tgacccagtc tccagactcc ctggctgtgt ctctgggcga gagggccacc     120

atcaactgca agtccagcca gagtgtttta gacagctccg acaataagaa ctacttagct     180

tggtaccagc agaaaccagg acagcctcct aagctgctca tttactgggc atctaaccgg     240

gaatccgggg tccctgaccg attcagtggc agcgggtctg ggacagattt cactctcacc     300

atcagcagcc tgcaggctga agatgtggca gtttattact gtcagcaata ttatagtgat     360

ccattcactt tcggccctgg gaccaaagtg gatatcaaac gtacggtggc tgcaccatct     420

gtcttcatct tcccgccatc tgatgagcag ttgaaatctg gaactgcctc tgttgtgtgc     480

ctgctgaata acttctatcc cagagaggcc aaagtacagt ggaaggtgga taacgccctc     540

caatcgggta actcccagga gagtgtcaca gagcaggaca gcaaggacag cacctacagc     600

ctcagcagca ccctgacgct gagcaaagca gactacgaga aacacaaagt ctacgcctgc     660

gaagtcaccc atcagggcct gagctcgccc gtcacaaaga gcttcaacag gggagagtgt     720


<210> SEQ ID NO 150
<211> LENGTH: 240
<212> TYPE: PRT
<213> ORGANISM: Homo sapiens

<400> SEQUENCE: 150

Met Val Leu Gln Thr Gln Val Phe Ile Ser Leu Leu Leu Trp Ile Ser
1               5                   10                  15

Gly Ala Tyr Gly Asp Ile Val Met Thr Gln Ser Pro Asp Ser Leu Ala
            20                  25                  30

Val Ser Leu Gly Glu Arg Ala Thr Ile Asn Cys Lys Ser Ser Gln Ser
        35                  40                  45

Val Leu Asp Ser Ser Asp Asn Lys Asn Tyr Leu Ala Trp Tyr Gln Gln
    50                  55                  60

Lys Pro Gly Gln Pro Pro Lys Leu Leu Ile Tyr Trp Ala Ser Asn Arg
65                  70                  75                  80
```

-continued

```
Glu Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110

Tyr Cys Gln Gln Tyr Tyr Ser Asp Pro Phe Thr Phe Gly Pro Gly Thr
        115                 120                 125

Lys Val Asp Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240


<210> SEQ ID NO 151
<211> LENGTH: 1395
<212> TYPE: DNA
<213> ORGANISM: Homo sapiens

<400> SEQUENCE: 151

atggactgga cctggagcat ccttttcttg gtggcagcac caacaggtgc ccactcccag     60

gttcagctgg tgcagtctgg agctgaggtg aagaagcctg gggcctcagt gaaggtctcc    120

tgcaaggctt ctggttacac ctttaccagc tatggtatca gctgggtgcg acaggcccct    180

ggacaagggc ttgagtggat gggatggatc agcgcttaca atggtaacac aaactatgca    240

cagaagctcc agggcagagt caccatgacc acagacacat ccacgagcac agcctacatg    300

gagctgagga gcctgagatc tgacgacacg gccgtgtatt actgtgcgag agagtcgtgg    360

ttcggggagg tattctttga ctactggggc cagggaaccc tggtcaccgt ctcctcagct    420

agcaccaagg gcccatcggt cttccccctg gcgccctgct ccaggagcac ctccgagagc    480

acagcggccc tgggctgcct ggtcaaggac tacttccccg aaccggtgac ggtgtcgtgg    540

aactcaggcg ctctgaccag cggcgtgcac accttcccag ctgtcctaca gtcctcagga    600

ctctactccc tcagcagcgt ggtgaccgtg ccctccagca acttcggcac ccagacctac    660

acctgcaacg tagatcacaa gcccagcaac accaaggtgg acaagacagt tgagcgcaaa    720

tgttgtgtcg agtgcccacc gtgcccagca ccacctgtgg caggaccgtc agtcttcctc    780

ttccccccaa aacccaagga caccctcatg atctcccgga cccctgaggt cacgtgcgtg    840

gtggtggacg tgagccacga agaccccgag gtccagttca actggtacgt ggacggcgtg    900

gaggtgcata atgccaagac aaagccacgg gaggagcagt tcaacagcac gttccgtgtg    960

gtcagcgtcc tcaccgttgt gcaccaggac tggctgaacg gcaaggagta caagtgcaag   1020

gtctccaaca aaggcctccc agcccccatc gagaaaacca tctccaaaac caaagggcag   1080

ccccgagaac cacaggtgta caccctgccc ccatcccggg aggagatgac caagaaccag   1140

gtcagcctga cctgcctggt caaaggcttc taccccagcg acatcgccgt ggagtgggag   1200
```

-continued

```
agcaatgggc agccggagaa caactacaag accacacctc ccatgctgga ctccgacggc   1260

tccttcttcc tctacagcaa gctcaccgtg gacaagagca ggtggcagca ggggaacgtc   1320

ttctcatgct ccgtgatgca tgaggctctg cacaaccact acacgcagaa gagcctctcc   1380

ctgtctccgg gtaaa                                                    1395
```

```
<210> SEQ ID NO 152
<211> LENGTH: 465
<212> TYPE: PRT
<213> ORGANISM: Homo sapiens

<400> SEQUENCE: 152

Met Asp Trp Thr Trp Ser Ile Leu Phe Leu Val Ala Ala Pro Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Gly Ile Ser Trp Val Arg Gln Ala Pro Gly Gln Gly Leu
    50                  55                  60

Glu Trp Met Gly Trp Ile Ser Ala Tyr Asn Gly Asn Thr Asn Tyr Ala
65                  70                  75                  80

Gln Lys Leu Gln Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Glu Ser Trp Phe Gly Glu Val Phe Phe Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Cys Ser Arg Ser Thr Ser Glu Ser
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Asn Phe Gly Thr Gln Thr Tyr Thr Cys Asn Val
    210                 215                 220

Asp His Lys Pro Ser Asn Thr Lys Val Asp Lys Thr Val Glu Arg Lys
225                 230                 235                 240

Cys Cys Val Glu Cys Pro Pro Cys Pro Ala Pro Pro Val Ala Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Phe Arg Val
305                 310                 315                 320

Val Ser Val Leu Thr Val Val His Gln Asp Trp Leu Asn Gly Lys Glu
                325                 330                 335
```

```
Tyr Lys Cys Lys Val Ser Asn Lys Gly Leu Pro Ala Pro Ile Glu Lys
            340                 345                 350

Thr Ile Ser Lys Thr Lys Gly Gln Pro Arg Glu Pro Gln Val Tyr Thr
        355                 360                 365

Leu Pro Pro Ser Arg Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Met Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465


<210> SEQ ID NO 153
<211> LENGTH: 708
<212> TYPE: DNA
<213> ORGANISM: Homo sapiens

<400> SEQUENCE: 153

atggacatga gggtgcccgc tcagctcctg gggctcctgc tgctgtggct gagaggtgcg      60

cgctgtgaca tccagatgac ccagtctcca tcttccgtgt ctgcatctgt aggagacaga     120

gtcaccatca cttgtcgggc gagtcagggt attagcagct ggttagcctg gtatcaacag     180

aaaccaggga aagcccctaa gctcctgatc tatggtgcat ccaatttgga aagtggggtc     240

ccatcaaggt tcagcggcag tggatctggg acagatttca ctctcaccat cagcagcctg     300

cagcctgaag attttgcaaa ttactattgt caacaggcta acagtttccc gtggacgttc     360

ggccaaggga ccaaggtgga aatcaaacgt acggtggctg caccatctgt cttcatcttc     420

ccgccatctg atgagcagtt gaaatctgga actgcctctg ttgtgtgcct gctgaataac     480

ttctatccca gagaggccaa agtacagtgg aaggtggata acgccctcca atcgggtaac     540

tcccaggaga gtgtcacaga gcaggacagc aaggacagca cctacagcct cagcagcacc     600

ctgacgctga gcaaagcaga ctacgagaaa cacaaagtct acgcctgcga agtcacccat     660

cagggcctga gctcgcccgt cacaaagagc ttcaacaggg gagagtgt                  708


<210> SEQ ID NO 154
<211> LENGTH: 236
<212> TYPE: PRT
<213> ORGANISM: Homo sapiens

<400> SEQUENCE: 154

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Val Ser Ala Ser Val Gly Asp Arg Val Thr Ile Thr Cys Arg Ala Ser
        35                  40                  45

Gln Gly Ile Ser Ser Trp Leu Ala Trp Tyr Gln Gln Lys Pro Gly Lys
    50                  55                  60
```

```
Ala Pro Lys Leu Leu Ile Tyr Gly Ala Ser Asn Leu Glu Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Asn Tyr Tyr Cys Gln Gln
            100                 105                 110

Ala Asn Ser Phe Pro Trp Thr Phe Gly Gln Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235


<210> SEQ ID NO 155
<211> LENGTH: 1398
<212> TYPE: DNA
<213> ORGANISM: Homo sapiens

<400> SEQUENCE: 155

atggacatga gggtgcccgc tcagctcctg gggctcctgc tgctgtggct gagaggtgcg     60

cgctgtcagg tccagctggt acagtctggg gctgaggtga agaagcctgg ggcctcagtg    120

aaggtctcct gcaaggtttc cggatacacc ctcagtgatt tatccatcca ctgggtgcga    180

caggctcctg gaaaagggct tgagtggatg ggaggttttg atcctcaaga tggtgaaaca    240

atctacgcac agaagttcca gggcagagtc accatgaccg aggacacatc tacagacaca    300

gcctacatgg agctgagcag cctgaaatct gaggacacgg ccgtgtatta ctgcgcaacg    360

gggagcagct cgtcctggtt cgacccctgg ggccagggaa ccctggtcac cgtctctagt    420

gcctccacca agggcccatc ggtcttcccc ctggcgccct gctccaggag cacctccgag    480

agcacagcgg ccctgggctg cctggtcaag gactacttcc ccgaaccggt gacggtgtcg    540

tggaactcag gcgctctgac cagcggcgtg cacaccttcc cagctgtcct acagtcctca    600

ggactctact ccctcagcag cgtggtgacc gtgccctcca gcaacttcgg cacccagacc    660

tacacctgca acgtagatca caagcccagc aacaccaagg tggacaagac agttgagcgc    720

aaatgttgtg tcgagtgccc accgtgccca gcaccacctg tggcaggacc gtcagtcttc    780

ctcttccccc caaaacccaa ggacaccctc atgatctccc ggacccctga ggtcacgtgc    840

gtggtggtgg acgtgagcca cgaagacccc gaggtccagt tcaactggta cgtggacggc    900

gtggaggtgc ataatgccaa gacaaagcca cgggaggagc agttcaacag cacgttccgt    960

gtggtcagcg tcctcaccgt tgtgcaccag gactggctga acggcaagga gtacaagtgc   1020

aaggtctcca acaaaggcct cccagccccc atcgagaaaa ccatctccaa aaccaaaggg   1080

cagccccgag aaccacaggt gtacaccctg cccccatccc gggaggagat gaccaagaac   1140
```

-continued caggtcagcc tgacctgcct ggtcaaaggc ttctacccca gcgacatcgc cgtggagtgg 1200
gagagcaatg ggcagccgga gaacaactac aagaccacac ctcccatgct ggactccgac 1260
ggctccttct tcctctacag caagctcacc gtggacaaga gcaggtggca gcaggggaac 1320
gtcttctcat gctccgtgat gcatgaggct ctgcacaacc actacacgca gaagagcctc 1380
tccctgtctc cgggtaaa 1398

<210> SEQ ID NO 156
<211> LENGTH: 466
<212> TYPE: PRT
<213> ORGANISM: Homo sapiens

<400> SEQUENCE: 156

Met Asp Met Arg Val Pro Ala Gln Leu Leu Gly Leu Leu Leu Leu Trp
1 5 10 15

Leu Arg Gly Ala Arg Cys Gln Val Gln Leu Val Gln Ser Gly Ala Glu
20 25 30

Val Lys Lys Pro Gly Ala Ser Val Lys Val Ser Cys Lys Val Ser Gly
35 40 45

Tyr Thr Leu Ser Asp Leu Ser Ile His Trp Val Arg Gln Ala Pro Gly
50 55 60

Lys Gly Leu Glu Trp Met Gly Gly Phe Asp Pro Gln Asp Gly Glu Thr
65 70 75 80

Ile Tyr Ala Gln Lys Phe Gln Gly Arg Val Thr Met Thr Glu Asp Thr
85 90 95

Ser Thr Asp Thr Ala Tyr Met Glu Leu Ser Ser Leu Lys Ser Glu Asp
100 105 110

Thr Ala Val Tyr Tyr Cys Ala Thr Gly Ser Ser Ser Ser Trp Phe Asp
115 120 125

Pro Trp Gly Gln Gly Thr Leu Val Thr Val Ser Ser Ala Ser Thr Lys
130 135 140

Gly Pro Ser Val Phe Pro Leu Ala Pro Cys Ser Arg Ser Thr Ser Glu
145 150 155 160

Ser Thr Ala Ala Leu Gly Cys Leu Val Lys Asp Tyr Phe Pro Glu Pro
165 170 175

Val Thr Val Ser Trp Asn Ser Gly Ala Leu Thr Ser Gly Val His Thr
180 185 190

Phe Pro Ala Val Leu Gln Ser Ser Gly Leu Tyr Ser Leu Ser Ser Val
195 200 205

Val Thr Val Pro Ser Ser Asn Phe Gly Thr Gln Thr Tyr Thr Cys Asn
210 215 220

Val Asp His Lys Pro Ser Asn Thr Lys Val Asp Lys Thr Val Glu Arg
225 230 235 240

Lys Cys Cys Val Glu Cys Pro Pro Cys Pro Ala Pro Pro Val Ala Gly
245 250 255

Pro Ser Val Phe Leu Phe Pro Pro Lys Pro Lys Asp Thr Leu Met Ile
260 265 270

Ser Arg Thr Pro Glu Val Thr Cys Val Val Val Asp Val Ser His Glu
275 280 285

Asp Pro Glu Val Gln Phe Asn Trp Tyr Val Asp Gly Val Glu Val His
290 295 300

Asn Ala Lys Thr Lys Pro Arg Glu Glu Gln Phe Asn Ser Thr Phe Arg
305 310 315 320

Val Val Ser Val Leu Thr Val Val His Gln Asp Trp Leu Asn Gly Lys

```
                325                 330                 335

Glu Tyr Lys Cys Lys Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465
```

<210> SEQ ID NO 157
<211> LENGTH: 702
<212> TYPE: DNA
<213> ORGANISM: Homo sapiens

<400> SEQUENCE: 157

```
atggagaccc ctgcccagct gctgttcctg ctgctgctgt ggctgcccga cacaaccggc     60

gaaatcgtca tgacacagag ccctgccaca ctgtccgtga gccctggaga gagggctacc    120

ctgagctgca gggcttccca gagcgtgagc agcaacctgg cctggtacca acagaagcct    180

ggccaggccc ctaggctgct gatctacggc gctgctacca gggccaccgg tattcctgcc    240

agggtgtccg gctccggatc cggcaccgag tttaccctga ccatcagcag cctgcagagc    300

gaggacttcg ccgtgtacta ctgtcagcaa tacaacaact ggcccctgac ctttggcggc    360

ggcaccaagg tggagatcaa gaggacagtg gccgccccca gcgtgttcat cttccctccc    420

agcgacgagc agctgaagag cggcaccgcc agcgtggtgt gtctgctgaa caacttctac    480

cccagggagg ccaaggtgca gtggaaggtg gacaacgccc tgcagtccgg caactcccag    540

gagtccgtga ccgagcagga ctccaaggac tccacctact ccctgtcctc caccctgacc    600

ctgtccaagg ccgactacga gaagcacaag gtgtacgcct gcgaggtgac ccaccagggc    660

ctgtcctccc ctgtgaccaa gagcttcaac aggggcgagt gc                        702
```

<210> SEQ ID NO 158
<211> LENGTH: 234
<212> TYPE: PRT
<213> ORGANISM: Homo sapiens

<400> SEQUENCE: 158

```
Met Glu Thr Pro Ala Gln Leu Leu Phe Leu Leu Leu Leu Trp Leu Pro
1               5                   10                  15

Asp Thr Thr Gly Glu Ile Val Met Thr Gln Ser Pro Ala Thr Leu Ser
            20                  25                  30

Val Ser Pro Gly Glu Arg Ala Thr Leu Ser Cys Arg Ala Ser Gln Ser
        35                  40                  45

Val Ser Ser Asn Leu Ala Trp Tyr Gln Gln Lys Pro Gly Gln Ala Pro
```

```
    50                  55                  60

Arg Leu Leu Ile Tyr Gly Ala Ala Thr Arg Ala Thr Gly Ile Pro Ala
65                  70                  75                  80

Arg Val Ser Gly Ser Gly Ser Gly Thr Glu Phe Thr Leu Thr Ile Ser
                85                  90                  95

Ser Leu Gln Ser Glu Asp Phe Ala Val Tyr Tyr Cys Gln Gln Tyr Asn
            100                 105                 110

Asn Trp Pro Leu Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230


<210> SEQ ID NO 159
<211> LENGTH: 1416
<212> TYPE: DNA
<213> ORGANISM: Homo sapiens

<400> SEQUENCE: 159

atggatatgc gggtccctgc tcagctgctg ggactgctgc tgctgtggct gaggggcgcc      60

aggtgtcagg tgcagctggt cgaaagcgga ggaggagtgg tgcagcccgg aaggtccctg     120

aggctgtcct gcgccgctag cggcttcacc ttttccaact acggcatgca ctgggtgagg     180

caagcccctg gagagggcct ggaatgggtg gctgctatct ggttcgacgc cagcgacaag     240

tactatgccg acgctgtgaa gggccggttc accatcagca gggacaacag caagaacacc     300

ctctacctgc agatgaacag cctccgggcc gaggacaccg ctgtctatta ctgtgccagg     360

gaccaggcca tcttcggagt ggtccccgat tactggggcc agggaaccct ggtgaccgtg     420

tcctccgctt ccacaaaggg acctagcgtg ttccctctgg cccctagcag caagtccaca     480

agcggaggaa cagccgccct gggctgtctc gtgaaggact attttcccga gcccgtgacc     540

gtgtcctgga actccggagc cctgacctcc ggcgtgcata cattccccgc tgtcctgcag     600

tccagcggcc tctactccct gtcctccgtg gtcaccgtgc ctagcagcag cctgggcacc     660

cagacataca tctgcaacgt caaccacaag ccttccaaca ccaaggtgga caagaaggtg     720

gagcccaagt cctgtgacaa gacccacacc tgtcctccct gtcctgctcc tgagctgctg     780

ggaggcccct ccgtcttcct gttccctccc aagcccaagg acaccctgat gatctccagg     840

acccctgaag tgacatgtgt ggtggtggat gtgagccacg aagatcccga ggtgaagttc     900

aactggtacg tggacggcgt ggaggtgcac aacgctaaaa caaagccctg cgaggagcag     960

tacggatcca cctacaggtg cgtgtccgtg ctcaccgtgc tccatcagga ctggctgaac    1020

ggaaaagagt acaagtgcaa agtcagcaat aaggccctgc ccgcccctat cgagaaaacc    1080
```

atcagcaagg ccaaaggcca gcccagggag cctcaggtgt ataccctgcc tccctccagg 1140
gaggagatga ccaagaacca ggtgagcctg acctgcctcg tgaagggctt ttatccctcc 1200
gacatcgctg tggagtggga gagcaatggc cagcctgaaa acaactacaa aaccaccccc 1260
cctgtgctgg atagcgacgg cagcttcttc ctctactcca agctgaccgt cgataagtcc 1320
cggtggcagc agggcaacgt gtttagctgc agcgtgatgc acgaagccct gcataaccac 1380
tacacccaga agagcctgag cctcagcccc ggaaag 1416

<210> SEQ ID NO 160
<211> LENGTH: 472
<212> TYPE: PRT
<213> ORGANISM: Homo sapiens

<400> SEQUENCE: 160

Met Asp Met Arg Val Pro Ala Gln Leu Leu Gly Leu Leu Leu Leu Trp
1 5 10 15

Leu Arg Gly Ala Arg Cys Gln Val Gln Leu Val Glu Ser Gly Gly Gly
20 25 30

Val Val Gln Pro Gly Arg Ser Leu Arg Leu Ser Cys Ala Ala Ser Gly
35 40 45

Phe Thr Phe Ser Asn Tyr Gly Met His Trp Val Arg Gln Ala Pro Gly
50 55 60

Glu Gly Leu Glu Trp Val Ala Ala Ile Trp Phe Asp Ala Ser Asp Lys
65 70 75 80

Tyr Tyr Ala Asp Ala Val Lys Gly Arg Phe Thr Ile Ser Arg Asp Asn
85 90 95

Ser Lys Asn Thr Leu Tyr Leu Gln Met Asn Ser Leu Arg Ala Glu Asp
100 105 110

Thr Ala Val Tyr Tyr Cys Ala Arg Asp Gln Ala Ile Phe Gly Val Val
115 120 125

Pro Asp Tyr Trp Gly Gln Gly Thr Leu Val Thr Val Ser Ser Ala Ser
130 135 140

Thr Lys Gly Pro Ser Val Phe Pro Leu Ala Pro Ser Ser Lys Ser Thr
145 150 155 160

Ser Gly Gly Thr Ala Ala Leu Gly Cys Leu Val Lys Asp Tyr Phe Pro
165 170 175

Glu Pro Val Thr Val Ser Trp Asn Ser Gly Ala Leu Thr Ser Gly Val
180 185 190

His Thr Phe Pro Ala Val Leu Gln Ser Ser Gly Leu Tyr Ser Leu Ser
195 200 205

Ser Val Val Thr Val Pro Ser Ser Ser Leu Gly Thr Gln Thr Tyr Ile
210 215 220

Cys Asn Val Asn His Lys Pro Ser Asn Thr Lys Val Asp Lys Lys Val
225 230 235 240

Glu Pro Lys Ser Cys Asp Lys Thr His Thr Cys Pro Pro Cys Pro Ala
245 250 255

Pro Glu Leu Leu Gly Gly Pro Ser Val Phe Leu Phe Pro Pro Lys Pro
260 265 270

Lys Asp Thr Leu Met Ile Ser Arg Thr Pro Glu Val Thr Cys Val Val
275 280 285

Val Asp Val Ser His Glu Asp Pro Glu Val Lys Phe Asn Trp Tyr Val
290 295 300

Asp Gly Val Glu Val His Asn Ala Lys Thr Lys Pro Cys Glu Glu Gln
305 310 315 320

```
Tyr Gly Ser Thr Tyr Arg Cys Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Glu Glu Met Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys
465                 470
```

<210> SEQ ID NO 161
<211> LENGTH: 702
<212> TYPE: DNA
<213> ORGANISM: Homo sapiens

<400> SEQUENCE: 161

```
atggagaccc ctgcccagct gctgttcctg ctgctgctgt ggctgcccga cacaaccggc      60

gaaatcgtcc tgacacagag ccctgccaca ctgtccctga gccctggaga gagggctacc     120

ctgagctgca gggcttccca gagcgtgagc agcaacctgg cctggtacca acagaagcct     180

ggccaggccc ctaggctgct gatctacggc gctgctacca gggccaccgg tattcctgac     240

agggtgtccg gctccggatc cggcaccgag tttaccctga ccatcagccg cctggagccc     300

gaggacttcg ccgtgtacta ctgtcagcaa tacaacaact ggcccctgac ctttggcggc     360

ggcaccaagg tggagatcaa gaggacagtg gccgcccca gcgtgttcat cttccctccc     420

agcgacgagc agctgaagag cggcaccgcc agcgtggtgt gtctgctgaa caacttctac     480

cccagggagg ccaaggtgca gtggaaggtg gacaacgccc tgcagtccgg caactcccag     540

gagtccgtga ccgagcagga ctccaaggac tccacctact ccctgtcctc caccctgacc     600

ctgtccaagg ccgactacga gaagcacaag gtgtacgcct gcgaggtgac ccaccagggc     660

ctgtcctccc ctgtgaccaa gagcttcaac aggggcgagt gc                        702
```

<210> SEQ ID NO 162
<211> LENGTH: 234
<212> TYPE: PRT
<213> ORGANISM: Homo sapiens

<400> SEQUENCE: 162

```
Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45
```

```
Val Ser Ser Asn Leu Ala Trp Tyr Gln Gln Lys Pro Gly Gln Ala Pro
    50                  55                  60

Arg Leu Leu Ile Tyr Gly Ala Ala Thr Arg Ala Thr Gly Ile Pro Asp
65                  70                  75                  80

Arg Val Ser Gly Ser Gly Ser Gly Thr Glu Phe Thr Leu Thr Ile Ser
                85                  90                  95

Arg Leu Glu Pro Glu Asp Phe Ala Val Tyr Tyr Cys Gln Gln Tyr Asn
            100                 105                 110

Asn Trp Pro Leu Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230


<210> SEQ ID NO 163
<211> LENGTH: 1416
<212> TYPE: DNA
<213> ORGANISM: Homo sapiens

<400> SEQUENCE: 163

atggatatgc gggtccctgc tcagctgctg ggactgctgc tgctgtggct gaggggcgcc      60

aggtgtgagg tgcagctggt cgaaagcgga ggaggagtgg tgcagcccgg agggtccctg     120

aggctgtcct gcgccgctag cggcttcacc ttttccaact acggcatgca ctgggtgagg     180

caagccccctg gagagggcct ggaatgggtg gctgctatct ggttcgacgc cagcgacaag    240

tactatgccg acgctgtgaa gggccggttc accatcagca gggacaacgc caagaacacc     300

ctctacctgc agatgaacag cctccgggcc gaggacaccg ctgtctatta ctgtgccagg     360

gaccaggcca tcttcggagt ggtccccgat tactggggcc agggaaccct ggtgaccgtg     420

tcctccgctt ccacaaaggg acctagcgtg ttccctctgg cccctagcag caagtccaca     480

agcggaggaa cagccgccct gggctgtctc gtgaaggact attttcccga gcccgtgacc     540

gtgtcctgga actccggagc cctgacctcc ggcgtgcata cattccccgc tgtcctgcag     600

tccagcggcc tctactccct gtcctccgtg gtcaccgtgc ctagcagcag cctgggcacc     660

cagacataca tctgcaacgt caaccacaag ccttccaaca ccaaggtgga caagaaggtg     720

gagcccaagt cctgtgacaa gacccacacc tgtcctccct gtcctgctcc tgagctgctg     780

ggaggcccct ccgtcttcct gttccctccc aagcccaagg acaccctgat gatctccagg     840

acccctgaag tgacatgtgt ggtggtggat gtgagccacg aagatcccga ggtgaagttc     900

aactggtacg tggacggcgt ggaggtgcac aacgctaaaa caaagccctg cgaggagcag     960

tacggatcca cctacaggtg cgtgtccgtg ctcaccgtgc tccatcagga ctggctgaac    1020
```

-continued

```
ggaaaagagt acaagtgcaa agtcagcaat aaggccctgc ccgcccctat cgagaaaacc   1080

atcagcaagg ccaaaggcca gcccagggag cctcaggtgt ataccctgcc tccctccagg   1140

gaggagatga ccaagaacca ggtgagcctg acctgcctcg tgaagggctt ttatccctcc   1200

gacatcgctg tggagtggga gagcaatggc cagcctgaaa acaactacaa aaccaccccc   1260

cctgtgctgg atagcgacgg cagcttcttc ctctactcca agctgaccgt cgataagtcc   1320

cggtggcagc agggcaacgt gtttagctgc agcgtgatgc acgaagccct gcataaccac   1380

tacacccaga agagcctgag cctcagcccc ggaaag                             1416
```

<210> SEQ ID NO 164
<211> LENGTH: 472
<212> TYPE: PRT
<213> ORGANISM: Homo sapiens

<400> SEQUENCE: 164

```
Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
            20                  25                  30

Val Val Gln Pro Gly Gly Ser Leu Arg Leu Ser Cys Ala Ala Ser Gly
        35                  40                  45

Phe Thr Phe Ser Asn Tyr Gly Met His Trp Val Arg Gln Ala Pro Gly
    50                  55                  60

Glu Gly Leu Glu Trp Val Ala Ala Ile Trp Phe Asp Ala Ser Asp Lys
65                  70                  75                  80

Tyr Tyr Ala Asp Ala Val Lys Gly Arg Phe Thr Ile Ser Arg Asp Asn
                85                  90                  95

Ala Lys Asn Thr Leu Tyr Leu Gln Met Asn Ser Leu Arg Ala Glu Asp
            100                 105                 110

Thr Ala Val Tyr Tyr Cys Ala Arg Asp Gln Ala Ile Phe Gly Val Val
        115                 120                 125

Pro Asp Tyr Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300
```

-continued

```
Asp Gly Val Glu Val His Asn Ala Lys Thr Lys Pro Cys Glu Glu Gln
305                 310                 315                 320

Tyr Gly Ser Thr Tyr Arg Cys Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Glu Glu Met Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys
465                 470


<210> SEQ ID NO 165
<211> LENGTH: 717
<212> TYPE: DNA
<213> ORGANISM: Homo sapiens

<400> SEQUENCE: 165

atgaggctcc ctgctcagct cctggggctg ctaatgctct gggtccctgg atccagtggg      60

gatattgtga tgacccagac tccactctcc tcacctgtca cccttggaca gccggcctcc     120

atctcctgca ggtctagtca aagcctcgta cacagtgatg gaaacaccta cttgaattgg     180

cttcagcaga ggccaggcca gcctccaaga ctcctaattt ataagatttc taaccggttc     240

tctggggtcc cagacagatt cactggcagt ggggcaggga cagatttcac actgaaaatc     300

agcagggtgg aagctgagga tgtcggggtt tatacctgca tgcaagttac acaatttcct     360

ctcaccttcg gccaagggac acgactggag attaaacgaa ctgtggctgc accatctgtc     420

ttcatcttcc cgccatctga tgagcagttg aaatctggaa ctgcctctgt tgtgtgcctg     480

ctgaataact tctatcccag agaggccaaa gtacagtgga aggtggataa cgccctccaa     540

tcgggtaact cccaggagag tgtcacagag caggacagca aggacagcac ctacagcctc     600

agcagcaccc tgacgctgag caaagcagac tacgagaaac acaaagtcta cgcctgcgaa     660

gtcacccatc agggcctgag ctcgcccgtc acaaagagct tcaacagggg agagtgt        717


<210> SEQ ID NO 166
<211> LENGTH: 239
<212> TYPE: PRT
<213> ORGANISM: Homo sapiens

<400> SEQUENCE: 166

Met Arg Leu Pro Ala Gln Leu Leu Gly Leu Leu Met Leu Trp Val Pro
1               5                   10                  15

Gly Ser Ser Gly Asp Ile Val Met Thr Gln Thr Pro Leu Ser Ser Pro
            20                  25                  30
```

```
Val Thr Leu Gly Gln Pro Ala Ser Ile Ser Cys Arg Ser Ser Gln Ser
        35                  40                  45

Leu Val His Ser Asp Gly Asn Thr Tyr Leu Asn Trp Leu Gln Gln Arg
    50                  55                  60

Pro Gly Gln Pro Pro Arg Leu Leu Ile Tyr Lys Ile Ser Asn Arg Phe
65                  70                  75                  80

Ser Gly Val Pro Asp Arg Phe Thr Gly Ser Gly Ala Gly Thr Asp Phe
                85                  90                  95

Thr Leu Lys Ile Ser Arg Val Glu Ala Glu Asp Val Gly Val Tyr Thr
            100                 105                 110

Cys Met Gln Val Thr Gln Phe Pro Leu Thr Phe Gly Gln Gly Thr Arg
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

<210> SEQ ID NO 167
<211> LENGTH: 1410
<212> TYPE: DNA
<213> ORGANISM: Homo sapiens

<400> SEQUENCE: 167

```
atggacacac tttgctacac actcctgctg ctgaccaccc cttcctgggt cttgtcccag     60

gtcaccttga aggagtctgg tcctgtgctg ctgaaaccca cagagaccct cacgctgacc    120

tgcaccgtct ctgggttctc actcagcaat gctagaatgg gtgtgagctg gatccgtcag    180

cccccaggga aggccctgga gtggcttgca cacatttttt cgaatgacga aaaatcctac    240

atcacatctc tgaagagcag gctcaccatc tccaaggaca cctccaaaag ccaggtggtc    300

cttaccatga ccaacatgga ccctgtggac acagccacat attactgtgc acggataccc    360

ctacgatccc cgggtgcttt tgatatctgg ggccaaggga caatggtcac cgtctcttca    420

gcctccacca agggcccatc ggtcttcccc ctggcaccct cctccaagag cacctctggg    480

ggcacagcgg ccctgggctg cctggtcaag gactacttcc ccgaaccggt gacggtgtcg    540

tggaactcag gcgccctgac cagcggcgtg cacaccttcc cggctgtcct acagtcctca    600

ggactctact ccctcagcag cgtggtgacc gtgccctcca gcagcttggg cacccagacc    660

tacatctgca acgtgaatca caagcccagc aacaccaagg tggacaagag agttgagccc    720

aaatcttgtg acaaaactca cacatgccca ccgtgcccag cacctgaact cctgggggga    780

ccgtcagtct tcctcttccc cccaaaaccc aaggacaccc tcatgatctc ccggacccct    840

gaggtcacat gcgtggtggt ggacgtgagc cacgaagacc ctgaggtcaa gttcaactgg    900

tacgtggacg gcgtggaggt gcataatgcc aagacaaagc cgcgggagga gcagtacaac    960
```

```
agcacgtacc gtgtggtcag cgtcctcacc gtcctgcacc aggactggct gaatggcaag   1020

gagtacaagt gcaaggtctc caacaaagcc ctcccagccc ccatcgagaa aaccatctcc   1080

aaagccaaag ggcagccccg agaaccacag gtgtacaccc tgcccccatc ccgggaggag   1140

atgaccaaga accaggtcag cctgacctgc ctggtcaaag gcttctatcc cagcgacatc   1200

gccgtggagt gggagagcaa tgggcagccg gagaacaact acaagaccac gcctcccgtg   1260

ctggactccg acggctcctt cttcctctat agcaagctca ccgtggacaa gagcaggtgg   1320

cagcagggga acgtcttctc atgctccgtg atgcatgagg ctctgcacaa ccactacacg   1380

cagaagagcc tctcactgtc tccgggtaaa                                    1410


<210> SEQ ID NO 168
<211> LENGTH: 470
<212> TYPE: PRT
<213> ORGANISM: Homo sapiens

<400> SEQUENCE: 168

Met Asp Thr Leu Cys Tyr Thr Leu Leu Leu Leu Thr Thr Pro Ser Trp
1               5                   10                  15

Val Leu Ser Gln Val Thr Leu Lys Glu Ser Gly Pro Val Leu Leu Lys
            20                  25                  30

Pro Thr Glu Thr Leu Thr Leu Thr Cys Thr Val Ser Gly Phe Ser Leu
        35                  40                  45

Ser Asn Ala Arg Met Gly Val Ser Trp Ile Arg Gln Pro Pro Gly Lys
    50                  55                  60

Ala Leu Glu Trp Leu Ala His Ile Phe Ser Asn Asp Glu Lys Ser Tyr
65                  70                  75                  80

Ile Thr Ser Leu Lys Ser Arg Leu Thr Ile Ser Lys Asp Thr Ser Lys
                85                  90                  95

Ser Gln Val Val Leu Thr Met Thr Asn Met Asp Pro Val Asp Thr Ala
            100                 105                 110

Thr Tyr Tyr Cys Ala Arg Ile Pro Leu Arg Ser Pro Gly Ala Phe Asp
        115                 120                 125

Ile Trp Gly Gln Gly Thr Met Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
```

290 295 300

Val Glu Val His Asn Ala Lys Thr Lys Pro Arg Glu Glu Gln Tyr Asn
305 310 315 320

Ser Thr Tyr Arg Val Val Ser Val Leu Thr Val Leu His Gln Asp Trp
325 330 335

Leu Asn Gly Lys Glu Tyr Lys Cys Lys Val Ser Asn Lys Ala Leu Pro
340 345 350

Ala Pro Ile Glu Lys Thr Ile Ser Lys Ala Lys Gly Gln Pro Arg Glu
355 360 365

Pro Gln Val Tyr Thr Leu Pro Pro Ser Arg Glu Glu Met Thr Lys Asn
370 375 380

Gln Val Ser Leu Thr Cys Leu Val Lys Gly Phe Tyr Pro Ser Asp Ile
385 390 395 400

Ala Val Glu Trp Glu Ser Asn Gly Gln Pro Glu Asn Asn Tyr Lys Thr
405 410 415

Thr Pro Pro Val Leu Asp Ser Asp Gly Ser Phe Phe Leu Tyr Ser Lys
420 425 430

Leu Thr Val Asp Lys Ser Arg Trp Gln Gln Gly Asn Val Phe Ser Cys
435 440 445

Ser Val Met His Glu Ala Leu His Asn His Tyr Thr Gln Lys Ser Leu
450 455 460

Ser Leu Ser Pro Gly Lys
465 470

<210> SEQ ID NO 169
<211> LENGTH: 705
<212> TYPE: DNA
<213> ORGANISM: Homo sapiens

<400> SEQUENCE: 169
atggaaaccc cagcgcagct tctcttcctc ctgctactct ggctcccaga taccaccgga 60
gaaattgtgt tgacgcagtc tccaggcacc ctgtctttgt ctccagggga aagagccacc 120
ctctcctgta gggccagtca gagtgttcgc ggcaggtact tagcctggta ccagcagaaa 180
cctggccagg ctcccaggct cctcatctat ggtgcatcca gcagggccac tggcatccca 240
gacaggttca gtggcagtgg gtctgggaca gacttcactc tcaccatcag cagactggag 300
cctgaagatt ttgcagtgtt ttactgtcag cagtatggta gttcacctcg gacgttcggc 360
caagggacca aggtggaaat caaacgaact gtggctgcac catctgtctt catcttcccg 420
ccatctgatg agcagttgaa atctggaact gcctctgttg tgtgcctgct gaataacttc 480
tatcccagag aggccaaagt acagtggaag gtggataacg ccctccaatc gggtaactcc 540
caggagagtg tcacagagca ggacagcaag gacagcacct acagcctcag cagcaccctg 600
acgctgagca aagcagacta cgagaaacac aaagtctacg cctgcgaagt cacccatcag 660
ggcctgagct cgcccgtcac aaagagcttc aacaggggag agtgt 705

<210> SEQ ID NO 170
<211> LENGTH: 235
<212> TYPE: PRT
<213> ORGANISM: Homo sapiens

<400> SEQUENCE: 170

Met Glu Thr Pro Ala Gln Leu Leu Phe Leu Leu Leu Leu Trp Leu Pro
1 5 10 15

Asp Thr Thr Gly Glu Ile Val Leu Thr Gln Ser Pro Gly Thr Leu Ser

```
            20                  25                  30

Leu Ser Pro Gly Glu Arg Ala Thr Leu Ser Cys Arg Ala Ser Gln Ser
        35                  40                  45

Val Arg Gly Arg Tyr Leu Ala Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Phe Tyr Cys Gln Gln Tyr
            100                 105                 110

Gly Ser Ser Pro Arg Thr Phe Gly Gln Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

<210> SEQ ID NO 171
<211> LENGTH: 1401
<212> TYPE: DNA
<213> ORGANISM: Homo sapiens

<400> SEQUENCE: 171

```
atggagtttg ggctgagctg gctttttctt gtggctattt taaaaggtgt ccagtgtgag     60

gtgcagctgt tggagtctgg gggaggcttg gtacagcctg gggggtccct gagactctcc    120

tgtgcagcct ctggattcac ctttagcagc tatgccatga gctgggtccg ccaggctcca    180

gggaaggggc tggagtgggt ctcaggtatt actgggagtg gtggtagtac atactacgca    240

gactccgtga agggccggtt caccatctcc agagacaatt ccaagaacac gctgtatctg    300

caaatgaaca gcctgagagc cgaggacacg gccgtatatt actgtgcgaa agatccaggg    360

actacggtga ttatgagttg gttcgacccc tggggccagg gaaccctggt caccgtctcc    420

tcagcctcca ccaagggccc atcggtcttc cccctggcgc cctgctccag gagcacctcc    480

gagagcacag cggccctggg ctgcctggtc aaggactact tccccgaacc ggtgacggtg    540

tcgtggaact caggcgctct gaccagcggc gtgcacacct tcccagctgt cctacagtcc    600

tcaggactct actccctcag cagcgtggtg accgtgccct ccagcaactt cggcacccag    660

acctacacct gcaacgtaga tcacaagccc agcaacacca aggtggacaa gacagttgag    720

cgcaaatgtt gtgtcgagtg cccaccgtgc ccagcaccac ctgtggcagg accgtcagtc    780

ttcctcttcc ccccaaaacc caaggacacc ctcatgatct cccggacccc tgaggtcacg    840

tgcgtggtgg tggacgtgag ccacgaagac cccgaggtcc agttcaactg gtacgtggac    900
```

-continued

```
ggcgtggagg tgcataatgc caagacaaag ccacgggagg agcagttcaa cagcacgttc    960

cgtgtggtca gcgtcctcac cgttgtgcac caggactggc tgaacggcaa ggagtacaag   1020

tgcaaggtct ccaacaaagg cctcccagcc cccatcgaga aaaccatctc caaaaccaaa   1080

gggcagcccc gagaaccaca ggtgtacacc ctgcccccat cccgggagga gatgaccaag   1140

aaccaggtca gcctgacctg cctggtcaaa ggcttctacc ccagcgacat cgccgtggag   1200

tgggagagca atgggcagcc ggagaacaac tacaagacca cacctcccat gctggactcc   1260

gacggctcct tcttcctcta cagcaagctc accgtggaca agagcaggtg gcagcagggg   1320

aacgtcttct catgctccgt gatgcatgag gctctgcaca accactacac gcagaagagc   1380

ctctccctgt ctccgggtaa a                                             1401


<210> SEQ ID NO 172
<211> LENGTH: 467
<212> TYPE: PRT
<213> ORGANISM: Homo sapiens

<400> SEQUENCE: 172

Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Met Ser Trp Val Arg Gln Ala Pro Gly Lys Gly Leu
    50                  55                  60

Glu Trp Val Ser Gly Ile Thr Gly Ser Gly Gly Ser Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Asp Pro Gly Thr Thr Val Ile Met Ser Trp Phe
        115                 120                 125

Asp Pro Trp Gly Gln Gly Thr Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Asn Phe Gly Thr Gln Thr Tyr Thr Cys
    210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285
```

```
Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Phe
305                 310                 315                 320

Arg Val Val Ser Val Leu Thr Val Val His Gln Asp Trp Leu Asn Gly
                325                 330                 335

Lys Glu Tyr Lys Cys Lys Val Ser Asn Lys Gly Leu Pro Ala Pro Ile
            340                 345                 350

Glu Lys Thr Ile Ser Lys Thr Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Met Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465


<210> SEQ ID NO 173
<211> LENGTH: 714
<212> TYPE: DNA
<213> ORGANISM: Homo sapiens

<400> SEQUENCE: 173

atggtgttgc agacccaggt cttcatttct ctgttgctct ggatctctgg tgcctacggg      60

gacatcgtga tgacccagtc tccagactcc ctggctgtgt ctctgggcga gagggccacc     120

atcaactgca gagccagtga aagtgttgat atttatggca atagttttat gcactggtac     180

cagcagaaac caggacagcc tcctaagctg ctcatttacc ttgcatccaa cctagaatct     240

ggggtccctg accgattcag tggcagcggg tctgggacag atttcactct caccatcagc     300

agcctgcagg ctgaagatgt ggcagtttat tactgtcagc aaaataatga ggatccgtac     360

acgttcggag gtgggaccaa ggtggaaata aaacgtacgg tggctgcacc atctgtcttc     420

atcttcccgc catctgatga gcagttgaaa tctggaactg cctctgttgt gtgcctgctg     480

aataacttct atcccagaga ggccaaagta cagtggaagg tggataacgc cctccaatcg     540

ggtaactccc aggagagtgt cacagagcag gacagcaagg acagcaccta cagcctcagc     600

agcaccctga cgctgagcaa agcagactac gagaaacaca aagtctacgc ctgcgaagtc     660

acccatcagg gcctgagctc gcccgtcaca aagagcttca acaggggaga gtgt           714


<210> SEQ ID NO 174
<211> LENGTH: 238
<212> TYPE: PRT
<213> ORGANISM: Homo sapiens

<400> SEQUENCE: 174

Met Val Leu Gln Thr Gln Val Phe Ile Ser Leu Leu Leu Trp Ile Ser
1               5                   10                  15
```

```
Gly Ala Tyr Gly Asp Ile Val Met Thr Gln Ser Pro Asp Ser Leu Ala
            20                  25                  30

Val Ser Leu Gly Glu Arg Ala Thr Ile Asn Cys Arg Ala Ser Glu Ser
        35                  40                  45

Val Asp Ile Tyr Gly Asn Ser Phe Met His Trp Tyr Gln Gln Lys Pro
    50                  55                  60

Gly Gln Pro Pro Lys Leu Leu Ile Tyr Leu Ala Ser Asn Leu Glu Ser
65                  70                  75                  80

Gly Val Pro Asp Arg Phe Ser Gly Ser Gly Ser Gly Thr Asp Phe Thr
                85                  90                  95

Leu Thr Ile Ser Ser Leu Gln Ala Glu Asp Val Ala Val Tyr Tyr Cys
            100                 105                 110

Gln Gln Asn Asn Glu Asp Pro Tyr Thr Phe Gly Gly Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 175
<211> LENGTH: 1398
<212> TYPE: DNA
<213> ORGANISM: Homo sapiens

<400> SEQUENCE: 175

```
atggactgga cctggagggt cttctgcttg ctggcagtgg ccccaggtgc ccactcccag     60

gtgcagctgg tgcagtctgg ggctgaggtg aagaagcctg gggcctcagt gaaggtctcc    120

tgcaaggctt ctggatacac cttcaccagt tacaatatgc actgggtgcg ccaggcccct    180

ggacaagggc ttgagtggat gggagttatt tattcaggaa atggtgatac ttcctacaat    240

cagaagttca aaggcagggt caccattacc gctgacaaat ccaccagcac agcctacatg    300

gagctgagca gcctgagatc tgaggacacg gccgtgtatt actgtgcgag agagagggat    360

actcgttttg gtaactgggg ccaagggact ctggtcaccg tctctagtgc ctccaccaag    420

ggcccatcgg tcttccccct ggcaccctcc tccaagagca cctctggggg cacagcggcc    480

ctgggctgcc tggtcaagga ctacttcccc gaaccggtga cggtgtcgtg gaactcaggc    540

gccctgacca gcggcgtgca caccttcccg gctgtcctac agtcctcagg actctactcc    600

ctcagcagcg tggtgaccgt gccctccagc agcttgggca cccagaccta catctgcaac    660

gtgaatcaca agcccagcaa caccaaggtg gacaagaaag ttgagcccaa atcttgtgac    720

aaaactcaca catgcccacc gtgcccagca cctgaactcc tggggggacc gtcagtcttc    780

ctcttccccc caaaacccaa ggacaccctc atgatctccc ggacccctga ggtcacatgc    840
```

```
gtggtggtgg acgtgagcca cgaagaccct gaggtcaagt tcaactggta cgtggacggc    900

gtggaggtgc ataatgccaa gacaaagccg cgggaggagc agtaccagag cacgtaccgt    960

gtggtcagcg tcctcaccgt cctgcaccag gactggctga atggcaagga gtacaagtgc   1020

aaggtctcca acaaagccct cccagccccc atcgagaaaa ccatctccaa agccaaaggg   1080

cagccccgag aaccacaggt gtacaccctg cccccatccc gggatgagct gaccaagaac   1140

caggtcagcc tgacctgcct ggtcaaaggc ttctatccca gcgacatcgc cgtggagtgg   1200

gagagcaatg ggcagccgga gaacaactac aagaccacgc ctcccgtgct ggactccgac   1260

ggctccttct tcctctatag caagctcacc gtggacaaga gcaggtggca gcaggggaac   1320

gtcttctcat gctccgtgat gcatgaggct ctgcacaacc actacacgca gaagagcctc   1380

tccctgtctc cgggtaaa                                                 1398
```

<210> SEQ ID NO 176
<211> LENGTH: 466
<212> TYPE: PRT
<213> ORGANISM: Homo sapiens

<400> SEQUENCE: 176

```
Met Asp Trp Thr Trp Arg Val Phe Cys Leu Leu Ala Val Ala Pro Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Asn Met His Trp Val Arg Gln Ala Pro Gly Gln Gly Leu
    50                  55                  60

Glu Trp Met Gly Val Ile Tyr Ser Gly Asn Gly Asp Thr Ser Tyr Asn
65                  70                  75                  80

Gln Lys Phe Lys Gly Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Glu Arg Asp Thr Arg Phe Gly Asn Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270
```

```
Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Gln Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Asp Glu Leu Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465


<210> SEQ ID NO 177
<211> LENGTH: 705
<212> TYPE: DNA
<213> ORGANISM: Homo sapiens

<400> SEQUENCE: 177

atggcctggg ctctgctgct cctcactctc ctcactcagg acacagggtc ctgggcccag      60

tctgtgctga ctcagtcacc ctcagcgtct gggacccccg ggcagagagt caccatctct     120

tgttctggaa gcagctccaa catcggcagt aattatgtat actggtacca gcagctccca     180

ggagcggccc ccaaactcct catccttagg aataatcagc ggccctcagg ggtccctgac     240

cgattctctg gctccaagtc tggcacctca gcctccctga ccatcagtgg gctccggtcc     300

gaggatgagg ctgactatta ttgtgcagca tgggatgaca gcctgagtgg ttgggtgttc     360

ggcggaggga ccaagctgac cgtcctaggt cagcccaagg ccaaccccac tgtcactctg     420

ttcccgccct cctctgagga gctccaagcc aacaaggcca cactagtgtg tctgatcagt     480

gacttctacc cgggagctgt gacagtggcc tggaaggcag atggcagccc cgtcaaggcg     540

ggagtggaga ccaccaaacc ctccaaacag agcaacaaca agtacgcggc cagcagctac     600

ctgagcctga cgcccgagca gtggaagtcc cacagaagct acagctgcca ggtcacgcat     660

gaagggagca ccgtggagaa gacagtggcc cctacagaat gttca                    705


<210> SEQ ID NO 178
<211> LENGTH: 235
<212> TYPE: PRT
<213> ORGANISM: Homo sapiens

<400> SEQUENCE: 178
```

```
Met Ala Trp Ala Leu Leu Leu Leu Thr Leu Leu Thr Gln Asp Thr Gly
1               5                   10                  15

Ser Trp Ala Gln Ser Val Leu Thr Gln Ser Pro Ser Ala Ser Gly Thr
            20                  25                  30

Pro Gly Gln Arg Val Thr Ile Ser Cys Ser Gly Ser Ser Ser Asn Ile
        35                  40                  45

Gly Ser Asn Tyr Val Tyr Trp Tyr Gln Gln Leu Pro Gly Ala Ala Pro
    50                  55                  60

Lys Leu Leu Ile Leu Arg Asn Asn Gln Arg Pro Ser Gly Val Pro Asp
65                  70                  75                  80

Arg Phe Ser Gly Ser Lys Ser Gly Thr Ser Ala Ser Leu Thr Ile Ser
                85                  90                  95

Gly Leu Arg Ser Glu Asp Glu Ala Asp Tyr Tyr Cys Ala Ala Trp Asp
            100                 105                 110

Asp Ser Leu Ser Gly Trp Val Phe Gly Gly Gly Thr Lys Leu Thr Val
        115                 120                 125

Leu Gly Gln Pro Lys Ala Asn Pro Thr Val Thr Leu Phe Pro Pro Ser
    130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Gly Ser
                165                 170                 175

Pro Val Lys Ala Gly Val Glu Thr Thr Lys Pro Ser Lys Gln Ser Asn
            180                 185                 190

Asn Lys Tyr Ala Ala Ser Ser Tyr Leu Ser Leu Thr Pro Glu Gln Trp
        195                 200                 205

Lys Ser His Arg Ser Tyr Ser Cys Gln Val Thr His Glu Gly Ser Thr
    210                 215                 220

Val Glu Lys Thr Val Ala Pro Thr Glu Cys Ser
225                 230                 235
```

<210> SEQ ID NO 179
<211> LENGTH: 1437
<212> TYPE: DNA
<213> ORGANISM: Homo sapiens

<400> SEQUENCE: 179

```
atggacatga gggtgcccgc tcagctcctg gggctcctgc tgctgtggct gagaggtgcg      60

cgctgtgagg tgcagctggt ggagtctggg ggaggcttgg taaagcctgg ggggtccctt     120

agactctcct gtgcagcctc tggattcact ttcagtaacg cctggatgag ctgggtccgc     180

caggctccag ggaaggggct ggagtgggtt ggccgtatta aaagcaaaac tgatggtggg     240

acaacagact acactgcacc cgtgaaaggc agattcacca tctcaagaga tgattcaaaa     300

aacacgctgt atctgcaaat gaatagcctg aaagccgagg acacagccgt gtattactgt     360

accacagatc ggaccgggta tagcatcagc tggtctagtt actactacta ctacggtatg     420

gacgtctggg gccaagggac cacggtcacc gtctctagtg cctccaccaa gggcccatcg     480

gtcttccccc tggcgccctg ctccaggagc acctccgaga gcacagcggc cctgggctgc     540

ctggtcaagg actacttccc cgaaccggtg acggtgtcgt ggaactcagg cgctctgacc     600

agcggcgtgc acaccttccc agctgtccta cagtcctcag gactctactc cctcagcagc     660

gtggtgaccg tgccctccag caacttcggc acccagacct acacctgcaa cgtagatcac     720

aagcccagca acaccaaggt ggacaagaca gttgagcgca aatgttgtgt cgagtgccca     780
```

```
ccgtgcccag caccacctgt ggcaggaccg tcagtcttcc tcttcccccc aaaacccaag    840

gacaccctca tgatctcccg gacccctgag gtcacgtgcg tggtggtgga cgtgagccac    900

gaagaccccg aggtccagtt caactggtac gtggacggcg tggaggtgca taatgccaag    960

acaaagccac gggaggagca gttcaacagc acgttccgtg tggtcagcgt cctcaccgtt   1020

gtgcaccagg actggctgaa cggcaaggag tacaagtgca aggtctccaa caaaggcctc   1080

ccagccccca tcgagaaaac catctccaaa accaaagggc agccccgaga accacaggtg   1140

tacaccctgc ccccatcccg ggaggagatg accaagaacc aggtcagcct gacctgcctg   1200

gtcaaaggct tctaccccag cgacatcgcc gtggagtggg agagcaatgg gcagccggag   1260

aacaactaca agaccacacc tcccatgctg gactccgacg gctccttctt cctctacagc   1320

aagctcaccg tggacaagag caggtggcag caggggaacg tcttctcatg ctccgtgatg   1380

catgaggctc tgcacaacca ctacacgcag aagagcctct ccctgtctcc gggtaaa      1437
```

<210> SEQ ID NO 180
<211> LENGTH: 479
<212> TYPE: PRT
<213> ORGANISM: Homo sapiens

<400> SEQUENCE: 180

```
Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
            20                  25                  30

Leu Val Lys Pro Gly Gly Ser Leu Arg Leu Ser Cys Ala Ala Ser Gly
        35                  40                  45

Phe Thr Phe Ser Asn Ala Trp Met Ser Trp Val Arg Gln Ala Pro Gly
    50                  55                  60

Lys Gly Leu Glu Trp Val Gly Arg Ile Lys Ser Lys Thr Asp Gly Gly
65                  70                  75                  80

Thr Thr Asp Tyr Thr Ala Pro Val Lys Gly Arg Phe Thr Ile Ser Arg
                85                  90                  95

Asp Asp Ser Lys Asn Thr Leu Tyr Leu Gln Met Asn Ser Leu Lys Ala
            100                 105                 110

Glu Asp Thr Ala Val Tyr Tyr Cys Thr Thr Asp Arg Thr Gly Tyr Ser
        115                 120                 125

Ile Ser Trp Ser Ser Tyr Tyr Tyr Tyr Tyr Gly Met Asp Val Trp Gly
    130                 135                 140

Gln Gly Thr Thr Val Thr Val Ser Ser Ala Ser Thr Lys Gly Pro Ser
145                 150                 155                 160

Val Phe Pro Leu Ala Pro Cys Ser Arg Ser Thr Ser Glu Ser Thr Ala
                165                 170                 175

Ala Leu Gly Cys Leu Val Lys Asp Tyr Phe Pro Glu Pro Val Thr Val
            180                 185                 190

Ser Trp Asn Ser Gly Ala Leu Thr Ser Gly Val His Thr Phe Pro Ala
        195                 200                 205

Val Leu Gln Ser Ser Gly Leu Tyr Ser Leu Ser Ser Val Val Thr Val
    210                 215                 220

Pro Ser Ser Asn Phe Gly Thr Gln Thr Tyr Thr Cys Asn Val Asp His
225                 230                 235                 240

Lys Pro Ser Asn Thr Lys Val Asp Lys Thr Val Glu Arg Lys Cys Cys
                245                 250                 255

Val Glu Cys Pro Pro Cys Pro Ala Pro Pro Val Ala Gly Pro Ser Val
```

```
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Gln Phe Asn Trp Tyr Val Asp Gly Val Glu Val His Asn Ala Lys
305                 310                 315                 320

Thr Lys Pro Arg Glu Glu Gln Phe Asn Ser Thr Phe Arg Val Val Ser
            325                 330                 335

Val Leu Thr Val Val His Gln Asp Trp Leu Asn Gly Lys Glu Tyr Lys
            340                 345                 350

Cys Lys Val Ser Asn Lys Gly Leu Pro Ala Pro Ile Glu Lys Thr Ile
        355                 360                 365

Ser Lys Thr Lys Gly Gln Pro Arg Glu Pro Gln Val Tyr Thr Leu Pro
    370                 375                 380

Pro Ser Arg Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
            405                 410                 415

Gly Gln Pro Glu Asn Asn Tyr Lys Thr Thr Pro Pro Met Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Lys
465                 470                 475


<210> SEQ ID NO 181
<211> LENGTH: 23
<212> TYPE: PRT
<213> ORGANISM: Homo sapiens

<400> SEQUENCE: 181

Glu Ile Val Met Thr Gln Ser Pro Ala Thr Leu Ser Val Ser Pro Gly
1               5                   10                  15

Glu Arg Ala Thr Leu Ser Cys
            20


<210> SEQ ID NO 182
<211> LENGTH: 15
<212> TYPE: PRT
<213> ORGANISM: Homo sapiens

<400> SEQUENCE: 182

Trp Tyr Arg Gln Lys Pro Gly Gln Ala Pro Arg Leu Leu Ile Tyr
1               5                   10                  15


<210> SEQ ID NO 183
<211> LENGTH: 32
<212> TYPE: PRT
<213> ORGANISM: Homo sapiens

<400> SEQUENCE: 183

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30
```

<210> SEQ ID NO 184
<211> LENGTH: 10
<212> TYPE: PRT
<213> ORGANISM: Homo sapiens

<400> SEQUENCE: 184

Phe Gly Gln Gly Thr Arg Leu Glu Ile Lys
1               5                   10

<210> SEQ ID NO 185
<211> LENGTH: 23
<212> TYPE: PRT
<213> ORGANISM: Homo sapiens

<400> SEQUENCE: 185

Glu Ile Val Leu Thr Gln Ser Pro Asp Phe Gln Ser Val Thr Pro Lys
1               5                   10                  15

Glu Lys Val Thr Ile Thr Cys
            20

<210> SEQ ID NO 186
<211> LENGTH: 15
<212> TYPE: PRT
<213> ORGANISM: Homo sapiens

<400> SEQUENCE: 186

Trp Tyr Gln Gln Lys Pro Asp Gln Ser Pro Lys Leu Leu Ile Lys
1               5                   10                  15

<210> SEQ ID NO 187
<211> LENGTH: 32
<212> TYPE: PRT
<213> ORGANISM: Homo sapiens

<400> SEQUENCE: 187

Gly Val Pro Ser Arg Phe Ser Gly Ser Gly Ser Gly Thr Asp Phe Thr
1               5                   10                  15

Leu Thr Ile Asn Ser Leu Glu Ala Glu Asp Ala Ala Ala Tyr Tyr Cys
            20                  25                  30

<210> SEQ ID NO 188
<211> LENGTH: 10
<212> TYPE: PRT
<213> ORGANISM: Homo sapiens

<400> SEQUENCE: 188

Phe Gly Gly Gly Thr Lys Val Glu Ile Lys
1               5                   10

<210> SEQ ID NO 189
<211> LENGTH: 23
<212> TYPE: PRT
<213> ORGANISM: Homo sapiens

<400> SEQUENCE: 189

Asp Ile Val Met Thr Gln Thr Pro Leu Ser Ser Pro Val Thr Leu Gly
1               5                   10                  15

Gln Pro Ala Ser Ile Ser Cys
            20

<210> SEQ ID NO 190
<211> LENGTH: 15

<212> TYPE: PRT
<213> ORGANISM: Homo sapiens

<400> SEQUENCE: 190

Trp Leu Gln Gln Arg Pro Gly Gln Pro Pro Arg Leu Leu Ile Tyr
1 5 10 15

<210> SEQ ID NO 191
<211> LENGTH: 32
<212> TYPE: PRT
<213> ORGANISM: Homo sapiens

<400> SEQUENCE: 191

Gly Val Pro Asp Arg Phe Thr Gly Ser Gly Ala Gly Thr Asp Phe Thr
1 5 10 15

Leu Lys Ile Ser Arg Val Glu Ala Glu Asp Val Gly Val Tyr Thr Cys
20 25 30

<210> SEQ ID NO 192
<211> LENGTH: 10
<212> TYPE: PRT
<213> ORGANISM: Homo sapiens

<400> SEQUENCE: 192

Phe Gly Gln Gly Thr Arg Leu Glu Ile Lys
1 5 10

<210> SEQ ID NO 193
<211> LENGTH: 23
<212> TYPE: PRT
<213> ORGANISM: Homo sapiens

<400> SEQUENCE: 193

Glu Ile Val Leu Thr Gln Ser Pro Gly Thr Leu Ser Leu Ser Pro Gly
1 5 10 15

Glu Arg Ala Thr Leu Ser Cys
20

<210> SEQ ID NO 194
<211> LENGTH: 15
<212> TYPE: PRT
<213> ORGANISM: Homo sapiens

<400> SEQUENCE: 194

Trp Tyr Gln Gln Lys Pro Gly Gln Ala Pro Arg Leu Leu Ile Tyr
1 5 10 15

<210> SEQ ID NO 195
<211> LENGTH: 32
<212> TYPE: PRT
<213> ORGANISM: Homo sapiens

<400> SEQUENCE: 195

Gly Ile Pro Asp Arg Phe Ser Gly Ser Gly Ser Gly Thr Asp Phe Thr
1 5 10 15

Leu Thr Ile Ser Arg Leu Glu Pro Glu Asp Phe Ala Val Phe Tyr Cys
20 25 30

<210> SEQ ID NO 196
<211> LENGTH: 10
<212> TYPE: PRT
<213> ORGANISM: Homo sapiens

<400> SEQUENCE: 196

Phe Gly Gln Gly Thr Lys Val Glu Ile Lys
1               5                   10

<210> SEQ ID NO 197
<211> LENGTH: 23
<212> TYPE: PRT
<213> ORGANISM: Homo sapiens

<400> SEQUENCE: 197

Glu Ile Val Leu Thr Gln Ser Pro Gly Thr Leu Ser Leu Ser Pro Gly
1               5                   10                  15

Asp Arg Ala Thr Leu Ser Cys
            20

<210> SEQ ID NO 198
<211> LENGTH: 32
<212> TYPE: PRT
<213> ORGANISM: Homo sapiens

<400> SEQUENCE: 198

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 199
<211> LENGTH: 15
<212> TYPE: PRT
<213> ORGANISM: Homo sapiens

<400> SEQUENCE: 199

Trp His Gln Gln Lys Pro Gly Gln Ala Pro Arg Leu Leu Ile Tyr
1               5                   10                  15

<210> SEQ ID NO 200
<211> LENGTH: 15
<212> TYPE: PRT
<213> ORGANISM: Homo sapiens

<400> SEQUENCE: 200

Trp His Gln Gln Lys Pro Gly Gln Ala Pro Arg Leu Leu Ile Tyr
1               5                   10                  15

<210> SEQ ID NO 201
<211> LENGTH: 32
<212> TYPE: PRT
<213> ORGANISM: Homo sapiens

<400> SEQUENCE: 201

Gly Ile Pro Asp Arg Phe Ser Gly Ser Gly Ser Gly Thr Asp Phe Thr
1               5                   10                  15

Leu Thr Val Ser Arg Leu Glu Pro Glu Asp Phe Ala Val Tyr Tyr Cys
            20                  25                  30

<210> SEQ ID NO 202
<211> LENGTH: 15
<212> TYPE: PRT
<213> ORGANISM: Homo sapiens

<400> SEQUENCE: 202

Trp Phe Gln Gln Lys Pro Gly Gln Ala Pro Arg Leu Leu Ile Tyr
1               5                   10                  15

<210> SEQ ID NO 203
<211> LENGTH: 32
<212> TYPE: PRT
<213> ORGANISM: Homo sapiens

<400> SEQUENCE: 203

Gly Ile Pro Asp Arg Phe Ser Gly Ser Gly Ser Gly Thr Asp Phe Thr
1               5                   10                  15

Phe Thr Ile Ser Arg Leu Glu Pro Glu Asp Phe Ala Val Tyr Tyr Cys
            20                  25                  30

<210> SEQ ID NO 204
<211> LENGTH: 10
<212> TYPE: PRT
<213> ORGANISM: Homo sapiens

<400> SEQUENCE: 204

Phe Gly Gln Gly Thr Thr Val Glu Ile Lys
1               5                   10

<210> SEQ ID NO 205
<211> LENGTH: 23
<212> TYPE: PRT
<213> ORGANISM: Homo sapiens

<400> SEQUENCE: 205

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 206
<211> LENGTH: 15
<212> TYPE: PRT
<213> ORGANISM: Homo sapiens

<400> SEQUENCE: 206

Trp Tyr Gln Gln Lys Pro Gly Lys Ala Pro Lys Leu Leu Ile Tyr
1               5                   10                  15

<210> SEQ ID NO 207
<211> LENGTH: 32
<212> TYPE: PRT
<213> ORGANISM: Homo sapiens

<400> SEQUENCE: 207

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 208
<211> LENGTH: 23
<212> TYPE: PRT
<213> ORGANISM: Homo sapiens

<400> SEQUENCE: 208

Asp Ile Gln Met Thr Gln Ser Pro Ser Ser Val Ser Ala Ser Val Gly
1               5                   10                  15

Asp Arg Val Thr Ile Thr Cys
            20

<210> SEQ ID NO 209
<211> LENGTH: 32
<212> TYPE: PRT
<213> ORGANISM: Homo sapiens

<400> SEQUENCE: 209

Gly Val Pro Ser Arg Phe Ser Gly Ser Gly Ser Gly Thr Asp Phe Thr
1 5 10 15

Leu Thr Ile Ser Ser Leu Gln Pro Glu Asp Phe Ala Asn Tyr Tyr Cys
20 25 30

<210> SEQ ID NO 210
<211> LENGTH: 23
<212> TYPE: PRT
<213> ORGANISM: Homo sapiens

<400> SEQUENCE: 210

Asp Ile Val Met Thr Gln Ser Pro Asp Ser Leu Ala Val Ser Leu Gly
1 5 10 15

Glu Arg Ala Thr Ile Asn Cys
20

<210> SEQ ID NO 211
<211> LENGTH: 15
<212> TYPE: PRT
<213> ORGANISM: Homo sapiens

<400> SEQUENCE: 211

Trp Tyr Gln Gln Lys Pro Gly Gln Pro Pro Lys Leu Leu Ile Tyr
1 5 10 15

<210> SEQ ID NO 212
<211> LENGTH: 32
<212> TYPE: PRT
<213> ORGANISM: Homo sapiens

<400> SEQUENCE: 212

Gly Val Pro Asp Arg Phe Ser Gly Ser Gly Ser Gly Thr Asp Phe Thr
1 5 10 15

Leu Thr Ile Ser Ser Leu Gln Ala Glu Asp Val Ala Val Tyr Tyr Cys
20 25 30

<210> SEQ ID NO 213
<211> LENGTH: 32
<212> TYPE: PRT
<213> ORGANISM: Homo sapiens

<400> SEQUENCE: 213

Gly Val Pro Asp Arg Phe Ser Gly Ser Gly Ala Gly Thr Asp Phe Thr
1 5 10 15

Leu Lys Ile Ser Arg Val Glu Ala Glu Asp Val Gly Val Tyr Tyr Cys
20 25 30

<210> SEQ ID NO 214
<211> LENGTH: 10
<212> TYPE: PRT
<213> ORGANISM: Homo sapiens

<400> SEQUENCE: 214

Phe Gly Pro Gly Thr Lys Val Asp Ile Lys
1 5 10

<210> SEQ ID NO 215

<211> LENGTH: 23
<212> TYPE: PRT
<213> ORGANISM: Homo sapiens

<400> SEQUENCE: 215

Asp Ile Val Leu Thr Gln Ser Pro Asp Ser Leu Ala Val Ser Leu Gly
1 5 10 15

Glu Arg Ala Thr Ile Asn Cys
20

<210> SEQ ID NO 216
<211> LENGTH: 32
<212> TYPE: PRT
<213> ORGANISM: Homo sapiens

<400> SEQUENCE: 216

Gly Val Pro Asp Arg Phe Ser Gly Ser Gly Ser Gly Thr Asp Phe Thr
1 5 10 15

Leu Thr Ile Ser Ser Leu Gln Pro Glu Asp Val Ala Val Tyr Tyr Cys
20 25 30

<210> SEQ ID NO 217
<211> LENGTH: 10
<212> TYPE: PRT
<213> ORGANISM: Homo sapiens

<400> SEQUENCE: 217

Phe Gly Gln Gly Thr Arg Val Glu Ile Lys
1 5 10

<210> SEQ ID NO 218
<211> LENGTH: 23
<212> TYPE: PRT
<213> ORGANISM: Homo sapiens

<400> SEQUENCE: 218

Asp Ile Gln Leu Thr Gln Ser Pro Ser Ser Leu Ser Ala Ser Val Gly
1 5 10 15

Asp Arg Val Thr Met Ser Cys
20

<210> SEQ ID NO 219
<211> LENGTH: 32
<212> TYPE: PRT
<213> ORGANISM: Homo sapiens

<400> SEQUENCE: 219

Gly Val Pro Ser Arg Phe Ser Gly Ser Gly Ser Gly Thr Asp Phe Thr
1 5 10 15

Phe Thr Ile Ser Ser Leu Gln Pro Glu Asp Ile Ala Thr Tyr Tyr Cys
20 25 30

<210> SEQ ID NO 220
<211> LENGTH: 10
<212> TYPE: PRT
<213> ORGANISM: Homo sapiens

<400> SEQUENCE: 220

Phe Gly Gly Gly Thr Lys Val Gln Ile Lys
1 5 10

<210> SEQ ID NO 221
<211> LENGTH: 32

<212> TYPE: PRT
<213> ORGANISM: Homo sapiens

<400> SEQUENCE: 221

Gly Val Pro Ser Arg Phe Ser Gly Ser Gly Ser Gly Thr Asp Phe Thr
1 5 10 15

Phe Thr Ile Ser Ser Leu Gln Pro Glu Asp Ile Ala Thr Tyr Phe Cys
20 25 30

<210> SEQ ID NO 222
<211> LENGTH: 15
<212> TYPE: PRT
<213> ORGANISM: Homo sapiens

<400> SEQUENCE: 222

Trp Tyr Gln Gln Lys Pro Gly Lys Ala Pro Lys Arg Leu Ile Tyr
1 5 10 15

<210> SEQ ID NO 223
<211> LENGTH: 32
<212> TYPE: PRT
<213> ORGANISM: Homo sapiens

<400> SEQUENCE: 223

Gly Val Pro Ser Arg Phe Ser Gly Ser Gly Ser Gly Thr Glu Phe Thr
1 5 10 15

Leu Thr Ile Ser Ser Val Gln Pro Glu Asp Phe Val Thr Tyr Tyr Cys
20 25 30

<210> SEQ ID NO 224
<211> LENGTH: 23
<212> TYPE: PRT
<213> ORGANISM: Homo sapiens

<400> SEQUENCE: 224

Asp Val Val Met Thr Gln Ser Pro Leu Ser Leu Pro Val Thr Pro Gly
1 5 10 15

Glu Pro Ala Ser Ile Ser Cys
20

<210> SEQ ID NO 225
<211> LENGTH: 15
<212> TYPE: PRT
<213> ORGANISM: Homo sapiens

<400> SEQUENCE: 225

Trp Tyr Leu Gln Lys Pro Gly Gln Ser Pro Gln Leu Leu Ile Tyr
1 5 10 15

<210> SEQ ID NO 226
<211> LENGTH: 32
<212> TYPE: PRT
<213> ORGANISM: Homo sapiens

<400> SEQUENCE: 226

Gly Val Pro Asp Arg Phe Ser Gly Ser Gly Ser Gly Thr Asp Phe Thr
1 5 10 15

Leu Lys Ile Ser Arg Val Glu Ala Glu Asp Val Gly Val Tyr Tyr Cys
20 25 30

<210> SEQ ID NO 227
<211> LENGTH: 23
<212> TYPE: PRT

-continued

<213> ORGANISM: Homo sapiens

<400> SEQUENCE: 227

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 228
<211> LENGTH: 32
<212> TYPE: PRT
<213> ORGANISM: Homo sapiens

<400> SEQUENCE: 228

Gly Val Pro Asp Arg Phe Ser Gly Ser Gly Ser Gly Thr His Leu Thr
1               5                   10                  15

Leu Lys Ile Ser Arg Val Glu Ala Glu Asp Val Gly Val Tyr Tyr Cys
            20                  25                  30

<210> SEQ ID NO 229
<211> LENGTH: 15
<212> TYPE: PRT
<213> ORGANISM: Homo sapiens

<400> SEQUENCE: 229

Trp Tyr Gln Gln Lys Pro Glu Lys Ala Pro Lys Ser Leu Ile Tyr
1               5                   10                  15

<210> SEQ ID NO 230
<211> LENGTH: 10
<212> TYPE: PRT
<213> ORGANISM: Homo sapiens

<400> SEQUENCE: 230

Phe Gly Gln Gly Thr Lys Leu Glu Ile Ser
1               5                   10

<210> SEQ ID NO 231
<211> LENGTH: 10
<212> TYPE: PRT
<213> ORGANISM: Homo sapiens

<400> SEQUENCE: 231

Phe Gly Gln Gly Thr Lys Leu Glu Ile Lys
1               5                   10

<210> SEQ ID NO 232
<211> LENGTH: 15
<212> TYPE: PRT
<213> ORGANISM: Homo sapiens

<400> SEQUENCE: 232

Trp Phe Gln Gln Lys Pro Gly Gln Ala Pro Arg Pro Leu Ile Tyr
1               5                   10                  15

<210> SEQ ID NO 233
<211> LENGTH: 32
<212> TYPE: PRT
<213> ORGANISM: Homo sapiens

<400> SEQUENCE: 233

Gly Val Pro Ala Arg Phe Ser Gly Ser Gly Ser Gly Thr Asp Phe Thr
1               5                   10                  15

-continued

```
Leu Thr Ile Ser Ser Leu Gln Ser Glu Asp Phe Ala Val Tyr Tyr Cys
            20                  25                  30


<210> SEQ ID NO 234
<211> LENGTH: 32
<212> TYPE: PRT
<213> ORGANISM: Homo sapiens

<400> SEQUENCE: 234

Gly Ile Pro Ala Arg Val Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30


<210> SEQ ID NO 235
<211> LENGTH: 23
<212> TYPE: PRT
<213> ORGANISM: Homo sapiens

<400> SEQUENCE: 235

Asp Val Leu Met Thr Gln Ser Pro Leu Ser Leu Pro Val Thr Leu Gly
1               5                   10                  15

Gln Pro Ala Ser Ile Ser Cys
            20


<210> SEQ ID NO 236
<211> LENGTH: 15
<212> TYPE: PRT
<213> ORGANISM: Homo sapiens

<400> SEQUENCE: 236

Trp Tyr Leu Gln Arg Pro Gly Gln Ser Pro Lys Leu Leu Ile Tyr
1               5                   10                  15


<210> SEQ ID NO 237
<211> LENGTH: 10
<212> TYPE: PRT
<213> ORGANISM: Homo sapiens

<400> SEQUENCE: 237

Phe Gly Ala Gly Thr Lys Leu Glu Ile Lys
1               5                   10


<210> SEQ ID NO 238
<211> LENGTH: 23
<212> TYPE: PRT
<213> ORGANISM: Homo sapiens

<400> SEQUENCE: 238

Glu Ile Val Leu Thr Gln Ser Pro Ala Thr Leu Ser Leu Ser Pro Gly
1               5                   10                  15

Glu Arg Ala Thr Leu Ser Cys
            20


<210> SEQ ID NO 239
<211> LENGTH: 32
<212> TYPE: PRT
<213> ORGANISM: Homo sapiens

<400> SEQUENCE: 239

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
```

20 25 30

<210> SEQ ID NO 240
<211> LENGTH: 23
<212> TYPE: PRT
<213> ORGANISM: Homo sapiens

<400> SEQUENCE: 240

Asp Ile Val Met Thr Gln Thr Pro Leu Ser Leu Ser Val Thr Pro Gly
1 5 10 15

Gln Pro Ala Ser Ile Ser Cys
20

<210> SEQ ID NO 241
<211> LENGTH: 15
<212> TYPE: PRT
<213> ORGANISM: Homo sapiens

<400> SEQUENCE: 241

Trp Tyr Leu Gln Lys Pro Gly Gln Pro Pro Gln Phe Leu Ile Tyr
1 5 10 15

<210> SEQ ID NO 242
<211> LENGTH: 32
<212> TYPE: PRT
<213> ORGANISM: Homo sapiens

<400> SEQUENCE: 242

Arg Val Pro Asp Arg Phe Ser Gly Ser Gly Ser Gly Thr Asp Phe Thr
1 5 10 15

Leu Arg Ile Ser Arg Val Glu Ala Glu Asp Val Gly Ile Tyr Tyr Cys
20 25 30

<210> SEQ ID NO 243
<211> LENGTH: 10
<212> TYPE: PRT
<213> ORGANISM: Homo sapiens

<400> SEQUENCE: 243

Phe Gly Gln Gly Thr Gln Val Glu Ile Lys
1 5 10

<210> SEQ ID NO 244
<211> LENGTH: 32
<212> TYPE: PRT
<213> ORGANISM: Homo sapiens

<400> SEQUENCE: 244

Gly Ile Pro Asp Arg Val Ser Gly Ser Gly Ser Gly Thr Glu Phe Thr
1 5 10 15

Leu Thr Ile Ser Arg Leu Glu Pro Glu Asp Phe Ala Val Tyr Tyr Cys
20 25 30

<210> SEQ ID NO 245
<211> LENGTH: 15
<212> TYPE: PRT
<213> ORGANISM: Homo sapiens

<400> SEQUENCE: 245

Trp Tyr Gln Gln Lys Pro Gly Thr Ala Pro Lys Leu Leu Ile Tyr
1 5 10 15

<210> SEQ ID NO 246

<211> LENGTH: 23
<212> TYPE: PRT
<213> ORGANISM: Homo sapiens

<400> SEQUENCE: 246

Asp Ile Val Met Thr Gln Thr Pro Leu Ser Leu Pro Val Thr Pro Gly
1 5 10 15

Glu Pro Ala Ser Ile Ser Cys
20

<210> SEQ ID NO 247
<211> LENGTH: 22
<212> TYPE: PRT
<213> ORGANISM: Homo sapiens

<400> SEQUENCE: 247

Glu Ser Ala Leu Thr Gln Pro Ala Ser Val Ser Gly Ser Pro Gly Gln
1 5 10 15

Ser Ile Thr Ile Ser Cys
20

<210> SEQ ID NO 248
<211> LENGTH: 15
<212> TYPE: PRT
<213> ORGANISM: Homo sapiens

<400> SEQUENCE: 248

Trp Tyr Gln Gln His Pro Gly Lys Ala Pro Lys Leu Met Ile Tyr
1 5 10 15

<210> SEQ ID NO 249
<211> LENGTH: 32
<212> TYPE: PRT
<213> ORGANISM: Homo sapiens

<400> SEQUENCE: 249

Gly Val Ser Asn Arg Phe Ser Gly Ser Lys Ser Gly Asn Thr Ala Ser
1 5 10 15

Leu Thr Ile Ser Gly Leu Gln Ala Glu Asp Glu Ala Asp Tyr Tyr Cys
20 25 30

<210> SEQ ID NO 250
<211> LENGTH: 10
<212> TYPE: PRT
<213> ORGANISM: Homo sapiens

<400> SEQUENCE: 250

Phe Gly Gly Gly Thr Lys Leu Thr Val Leu
1 5 10

<210> SEQ ID NO 251
<211> LENGTH: 22
<212> TYPE: PRT
<213> ORGANISM: Homo sapiens

<400> SEQUENCE: 251

Ser Tyr Val Leu Thr Gln Pro Pro Ser Val Ser Val Ala Pro Gly Gln
1 5 10 15

Thr Ala Arg Ile Thr Cys
20

<210> SEQ ID NO 252
<211> LENGTH: 15

<212> TYPE: PRT
<213> ORGANISM: Homo sapiens

<400> SEQUENCE: 252

Trp Tyr Gln Gln Lys Pro Gly Gln Ala Pro Val Leu Val Val Tyr
1 5 10 15

<210> SEQ ID NO 253
<211> LENGTH: 32
<212> TYPE: PRT
<213> ORGANISM: Homo sapiens

<400> SEQUENCE: 253

Trp Ile Pro Glu Arg Phe Ser Gly Ser Asn Ser Gly Asn Thr Ala Thr
1 5 10 15

Leu Thr Ile Ser Arg Gly Glu Ala Gly Asp Glu Ala Asp Tyr Tyr Cys
20 25 30

<210> SEQ ID NO 254
<211> LENGTH: 22
<212> TYPE: PRT
<213> ORGANISM: Homo sapiens

<400> SEQUENCE: 254

Gln Ser Val Leu Thr Gln Pro Pro Ser Val Ser Ala Ala Pro Gly Gln
1 5 10 15

Lys Val Thr Ile Ser Cys
20

<210> SEQ ID NO 255
<211> LENGTH: 15
<212> TYPE: PRT
<213> ORGANISM: Homo sapiens

<400> SEQUENCE: 255

Trp Tyr Gln Gln Leu Pro Gly Thr Ala Pro Lys Leu Leu Ile Tyr
1 5 10 15

<210> SEQ ID NO 256
<211> LENGTH: 32
<212> TYPE: PRT
<213> ORGANISM: Homo sapiens

<400> SEQUENCE: 256

Gly Ile Pro Asp Arg Phe Ser Gly Ser Lys Ser Gly Thr Ser Thr Thr
1 5 10 15

Leu Gly Ile Thr Gly Leu Gln Thr Gly Asp Glu Ala Asp Tyr Tyr Cys
20 25 30

<210> SEQ ID NO 257
<211> LENGTH: 22
<212> TYPE: PRT
<213> ORGANISM: Homo sapiens

<400> SEQUENCE: 257

Gln Ser Val Leu Thr Gln Ser Pro Ser Ala Ser Gly Thr Pro Gly Gln
1 5 10 15

Arg Val Thr Ile Ser Cys
20

<210> SEQ ID NO 258
<211> LENGTH: 15
<212> TYPE: PRT

-continued

<213> ORGANISM: Homo sapiens

<400> SEQUENCE: 258

Trp Tyr Gln Gln Leu Pro Gly Ala Ala Pro Lys Leu Leu Ile Leu
1 5 10 15

<210> SEQ ID NO 259
<211> LENGTH: 32
<212> TYPE: PRT
<213> ORGANISM: Homo sapiens

<400> SEQUENCE: 259

Gly Val Pro Asp Arg Phe Ser Gly Ser Lys Ser Gly Thr Ser Ala Ser
1 5 10 15

Leu Thr Ile Ser Gly Leu Arg Ser Glu Asp Glu Ala Asp Tyr Tyr Cys
20 25 30

<210> SEQ ID NO 260
<211> LENGTH: 22
<212> TYPE: PRT
<213> ORGANISM: Homo sapiens

<400> SEQUENCE: 260

Ser Tyr Glu Val Thr Gln Ala Pro Ser Val Ser Val Ser Pro Gly Gln
1 5 10 15

Thr Ala Ser Ile Thr Cys
20

<210> SEQ ID NO 261
<211> LENGTH: 15
<212> TYPE: PRT
<213> ORGANISM: Homo sapiens

<400> SEQUENCE: 261

Trp Tyr Gln Gln Lys Pro Gly Gln Ser Pro Val Leu Val Ile Tyr
1 5 10 15

<210> SEQ ID NO 262
<211> LENGTH: 32
<212> TYPE: PRT
<213> ORGANISM: Homo sapiens

<400> SEQUENCE: 262

Gly Ile Pro Glu Arg Phe Ser Gly Ser Asn Ser Gly Asn Thr Ala Thr
1 5 10 15

Leu Thr Ile Ser Gly Thr Gln Ala Met Asp Glu Ala Asp Tyr Tyr Cys
20 25 30

<210> SEQ ID NO 263
<211> LENGTH: 22
<212> TYPE: PRT
<213> ORGANISM: Homo sapiens

<400> SEQUENCE: 263

Cys Tyr Glu Leu Thr Gln Pro Pro Ser Val Ser Val Ser Pro Gly Gln
1 5 10 15

Thr Ala Thr Ile Thr Cys
20

<210> SEQ ID NO 264
<211> LENGTH: 15
<212> TYPE: PRT
<213> ORGANISM: Homo sapiens

<400> SEQUENCE: 264

Trp Tyr Gln Gln Arg Pro Gly Gln Ser Pro Val Leu Val Ile Tyr
1 5 10 15

<210> SEQ ID NO 265
<211> LENGTH: 32
<212> TYPE: PRT
<213> ORGANISM: Homo sapiens

<400> SEQUENCE: 265

Gly Ile Pro Glu Arg Phe Ser Gly Ser Asn Ser Gly Asn Thr Ala Thr
1 5 10 15

Leu Thr Ile Ser Gly Thr Gln Ala Met Asp Glu Ala Asp Tyr Phe Cys
20 25 30

<210> SEQ ID NO 266
<211> LENGTH: 22
<212> TYPE: PRT
<213> ORGANISM: Homo sapiens

<400> SEQUENCE: 266

Ser Ser Glu Leu Thr Gln Asp Pro Thr Val Ser Val Ala Leu Gly Gln
1 5 10 15

Thr Val Lys Ile Thr Cys
20

<210> SEQ ID NO 267
<211> LENGTH: 15
<212> TYPE: PRT
<213> ORGANISM: Homo sapiens

<400> SEQUENCE: 267

Trp Tyr Gln Gln Lys Pro Gly Gln Ala Pro Val Leu Val Phe Tyr
1 5 10 15

<210> SEQ ID NO 268
<211> LENGTH: 32
<212> TYPE: PRT
<213> ORGANISM: Homo sapiens

<400> SEQUENCE: 268

Gly Ile Pro Asp Arg Phe Ser Gly Ser Ser Ser Gly Asn Thr Ala Ser
1 5 10 15

Leu Thr Ile Thr Gly Ala Gln Ala Glu Asp Glu Ala Asp Tyr Tyr Cys
20 25 30

<210> SEQ ID NO 269
<211> LENGTH: 10
<212> TYPE: PRT
<213> ORGANISM: Homo sapiens

<400> SEQUENCE: 269

Leu Gly Gly Gly Thr Lys Leu Thr Val Leu
1 5 10

<210> SEQ ID NO 270
<211> LENGTH: 22
<212> TYPE: PRT
<213> ORGANISM: Homo sapiens

<400> SEQUENCE: 270

Asn Phe Met Leu Thr Gln Pro His Ser Val Ser Glu Ser Pro Gly Lys 1 5 10 15

Thr Val Ala Ile Ser Cys
20

<210> SEQ ID NO 271
<211> LENGTH: 15
<212> TYPE: PRT
<213> ORGANISM: Homo sapiens

<400> SEQUENCE: 271

Trp Tyr Gln Gln Arg Pro Gly Ser Ser Pro Thr Thr Val Ile Phe
1 5 10 15

<210> SEQ ID NO 272
<211> LENGTH: 34
<212> TYPE: PRT
<213> ORGANISM: Homo sapiens

<400> SEQUENCE: 272

Gly Val Pro Asp Arg Phe Ser Gly Ser Ile Asp Ser Ser Ser Asn Ser
1 5 10 15

Ala Ser Leu Thr Ile Ser Gly Leu Lys Thr Glu Asp Glu Ala Asp Tyr
20 25 30

Tyr Cys

<210> SEQ ID NO 273
<211> LENGTH: 30
<212> TYPE: PRT
<213> ORGANISM: Homo sapiens

<400> SEQUENCE: 273

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser
20 25 30

<210> SEQ ID NO 274
<211> LENGTH: 14
<212> TYPE: PRT
<213> ORGANISM: Homo sapiens

<400> SEQUENCE: 274

Trp Ile Arg Gln Pro Pro Gly Lys Gly Leu Glu Trp Ile Gly
1 5 10

<210> SEQ ID NO 275
<211> LENGTH: 32
<212> TYPE: PRT
<213> ORGANISM: Homo sapiens

<400> SEQUENCE: 275

Arg Val Thr Ile Ser Val Asp Thr Ser Lys Asn Gln Phe Ser Leu Lys
1 5 10 15

Leu Asn Ser Val Thr Ala Ala Asp Thr Ala Val Tyr Tyr Cys Ala Arg
20 25 30

<210> SEQ ID NO 276
<211> LENGTH: 11
<212> TYPE: PRT
<213> ORGANISM: Homo sapiens

<400> SEQUENCE: 276

Trp Gly Gln Gly Thr Leu Val Thr Val Ser Ser
1 5 10

<210> SEQ ID NO 277
<211> LENGTH: 30
<212> TYPE: PRT
<213> ORGANISM: Homo sapiens

<400> SEQUENCE: 277

Glu Val Gln Leu Met Gln Ser Gly Ala Glu Val Lys Lys Pro Gly Glu
1 5 10 15

Ser Leu Lys Ile Ser Cys Lys Gly Ser Gly Tyr Ser Phe Ser
20 25 30

<210> SEQ ID NO 278
<211> LENGTH: 14
<212> TYPE: PRT
<213> ORGANISM: Homo sapiens

<400> SEQUENCE: 278

Trp Val Arg Gln Met Pro Gly Lys Gly Leu Glu Trp Met Gly
1 5 10

<210> SEQ ID NO 279
<211> LENGTH: 32
<212> TYPE: PRT
<213> ORGANISM: Homo sapiens

<400> SEQUENCE: 279

Gln Val Thr Ile Ser Ala Asp Asn Ser Asn Ser Ala Thr Tyr Leu Gln
1 5 10 15

Trp Ser Ser Leu Lys Ala Ser Asp Thr Ala Met Tyr Phe Cys Ala Arg
20 25 30

<210> SEQ ID NO 280
<211> LENGTH: 30
<212> TYPE: PRT
<213> ORGANISM: Homo sapiens

<400> SEQUENCE: 280

Gln Val Thr Leu Lys Glu Ser Gly Pro Val Leu Leu Lys Pro Thr Glu
1 5 10 15

Thr Leu Thr Leu Thr Cys Thr Val Ser Gly Phe Ser Leu Ser
20 25 30

<210> SEQ ID NO 281
<211> LENGTH: 14
<212> TYPE: PRT
<213> ORGANISM: Homo sapiens

<400> SEQUENCE: 281

Trp Ile Arg Gln Pro Pro Gly Lys Ala Leu Glu Trp Leu Ala
1 5 10

<210> SEQ ID NO 282
<211> LENGTH: 32
<212> TYPE: PRT
<213> ORGANISM: Homo sapiens

<400> SEQUENCE: 282

Arg Leu Thr Ile Ser Lys Asp Thr Ser Lys Ser Gln Val Val Leu Thr
1 5 10 15

Met Thr Asn Met Asp Pro Val Asp Thr Ala Thr Tyr Tyr Cys Ala Arg 20 25 30

<210> SEQ ID NO 283
<211> LENGTH: 11
<212> TYPE: PRT
<213> ORGANISM: Homo sapiens

<400> SEQUENCE: 283

Trp Gly Gln Gly Thr Met Val Thr Val Ser Ser
1 5 10

<210> SEQ ID NO 284
<211> LENGTH: 30
<212> TYPE: PRT
<213> ORGANISM: Homo sapiens

<400> SEQUENCE: 284

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Leu Thr
20 25 30

<210> SEQ ID NO 285
<211> LENGTH: 14
<212> TYPE: PRT
<213> ORGANISM: Homo sapiens

<400> SEQUENCE: 285

Trp Val Arg Gln Ala Pro Gly Gln Gly Leu Glu Trp Met Gly
1 5 10

<210> SEQ ID NO 286
<211> LENGTH: 32
<212> TYPE: PRT
<213> ORGANISM: Homo sapiens

<400> SEQUENCE: 286

Arg Gly Thr Met Thr Thr Asp Pro Ser Thr Ser Thr Ala Tyr Met Glu
1 5 10 15

Leu Arg Ser Leu Arg Ser Asp Asp Thr Ala Val Tyr Tyr Cys Ala Arg
20 25 30

<210> SEQ ID NO 287
<211> LENGTH: 11
<212> TYPE: PRT
<213> ORGANISM: Homo sapiens

<400> SEQUENCE: 287

Trp Gly Gln Gly Thr Thr Val Thr Val Ser Ser
1 5 10

<210> SEQ ID NO 288
<211> LENGTH: 30
<212> TYPE: PRT
<213> ORGANISM: Homo sapiens

<400> SEQUENCE: 288

Gln Met Gln Leu Val Glu Ser Gly Gly Gly Val Val Gln Pro Gly Arg
1 5 10 15

Ser Leu Arg Leu Ser Cys Ala Ala Ser Gly Phe Thr Phe Arg
20 25 30

<210> SEQ ID NO 289

<211> LENGTH: 14
<212> TYPE: PRT
<213> ORGANISM: Homo sapiens

<400> SEQUENCE: 289

Trp Val Arg Gln Ala Pro Gly Lys Gly Leu Glu Trp Val Ala
1 5 10

<210> SEQ ID NO 290
<211> LENGTH: 32
<212> TYPE: PRT
<213> ORGANISM: Homo sapiens

<400> SEQUENCE: 290

Arg Phe Thr Ile Thr Arg Asp Asn Ser Lys Asn Thr Leu Asn Leu Gln
1 5 10 15

Met Asn Ser Leu Arg Ala Glu Asp Thr Ala Val Tyr Tyr Cys Ala Arg
20 25 30

<210> SEQ ID NO 291
<211> LENGTH: 30
<212> TYPE: PRT
<213> ORGANISM: Homo sapiens

<400> SEQUENCE: 291

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser
20 25 30

<210> SEQ ID NO 292
<211> LENGTH: 14
<212> TYPE: PRT
<213> ORGANISM: Homo sapiens

<400> SEQUENCE: 292

Trp Val Arg Gln Ala Pro Gly Lys Gly Leu Glu Trp Val Ser
1 5 10

<210> SEQ ID NO 293
<211> LENGTH: 32
<212> TYPE: PRT
<213> ORGANISM: Homo sapiens

<400> SEQUENCE: 293

Arg Phe Thr Ile Ser Arg Asp Asn Ser Lys Asn Thr Leu Tyr Leu Gln
1 5 10 15

Met Asn Ser Leu Arg Ala Glu Asp Thr Ala Val Tyr Tyr Cys Ala Lys
20 25 30

<210> SEQ ID NO 294
<211> LENGTH: 30
<212> TYPE: PRT
<213> ORGANISM: Homo sapiens

<400> SEQUENCE: 294

Glu Val Gln Leu Val Gln Ser Gly Ala Glu Val Lys Lys Pro Gly Ser
1 5 10 15

Ser Val Lys Val Ser Cys Lys Ala Ser Gly Phe Thr Phe Thr
20 25 30

<210> SEQ ID NO 295
<211> LENGTH: 32

```
<212> TYPE: PRT
<213> ORGANISM: Homo sapiens

<400> SEQUENCE: 295

Arg Val Thr Ile Thr Ala Asp Lys Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30


<210> SEQ ID NO 296
<211> LENGTH: 30
<212> TYPE: PRT
<213> ORGANISM: Homo sapiens

<400> SEQUENCE: 296

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Ser
            20                  25                  30


<210> SEQ ID NO 297
<211> LENGTH: 14
<212> TYPE: PRT
<213> ORGANISM: Homo sapiens

<400> SEQUENCE: 297

Trp Val Arg Gln Ala Pro Gly Lys Gly Leu Glu Trp Met Gly
1               5                   10


<210> SEQ ID NO 298
<211> LENGTH: 32
<212> TYPE: PRT
<213> ORGANISM: Homo sapiens

<400> SEQUENCE: 298

Arg Val Thr Met Thr Glu Asp Thr Ser Thr Asp Thr Ala Tyr Met Glu
1               5                   10                  15

Leu Ser Ser Leu Lys Ser Glu Asp Thr Ala Val Tyr Tyr Cys Ala Thr
            20                  25                  30


<210> SEQ ID NO 299
<211> LENGTH: 30
<212> TYPE: PRT
<213> ORGANISM: Homo sapiens

<400> SEQUENCE: 299

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30


<210> SEQ ID NO 300
<211> LENGTH: 30
<212> TYPE: PRT
<213> ORGANISM: Homo sapiens

<400> SEQUENCE: 300

Gln Val Gln Leu Val Gln Ser Gly Ala Glu Val Lys Lys Pro Gly Ala
1               5                   10                  15

Ser Val Lys Val Ser Cys Lys Ser Ser Gly Tyr Thr Phe Thr
            20                  25                  30
```

<210> SEQ ID NO 301
<211> LENGTH: 32
<212> TYPE: PRT
<213> ORGANISM: Homo sapiens

<400> SEQUENCE: 301

```
Arg Val Thr Met Thr Arg Asp Thr Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30
```

<210> SEQ ID NO 302
<211> LENGTH: 30
<212> TYPE: PRT
<213> ORGANISM: Homo sapiens

<400> SEQUENCE: 302

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser
            20                  25                  30
```

<210> SEQ ID NO 303
<211> LENGTH: 33
<212> TYPE: PRT
<213> ORGANISM: Homo sapiens

<400> SEQUENCE: 303

```
Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

Gly
```

<210> SEQ ID NO 304
<211> LENGTH: 30
<212> TYPE: PRT
<213> ORGANISM: Homo sapiens

<400> SEQUENCE: 304

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30
```

<210> SEQ ID NO 305
<211> LENGTH: 32
<212> TYPE: PRT
<213> ORGANISM: Homo sapiens

<400> SEQUENCE: 305

```
Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30
```

<210> SEQ ID NO 306
<211> LENGTH: 32
<212> TYPE: PRT
<213> ORGANISM: Homo sapiens

<400> SEQUENCE: 306

Arg Phe Thr Ile Ser Arg Asp Asn Ser Lys Asn Thr Leu Phe Leu Gln
1 5 10 15

Met Asn Ser Leu Arg Ala Glu Asp Thr Ala Val Tyr Tyr Cys Ala Arg
20 25 30

<210> SEQ ID NO 307
<211> LENGTH: 30
<212> TYPE: PRT
<213> ORGANISM: Homo sapiens

<400> SEQUENCE: 307

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr
20 25 30

<210> SEQ ID NO 308
<211> LENGTH: 14
<212> TYPE: PRT
<213> ORGANISM: Homo sapiens

<400> SEQUENCE: 308

Trp Val Arg Gln Ala Pro Gly Gln Gly Leu Glu Trp Ile Gly
1 5 10

<210> SEQ ID NO 309
<211> LENGTH: 32
<212> TYPE: PRT
<213> ORGANISM: Homo sapiens

<400> SEQUENCE: 309

Lys Ala Thr Ile Thr Ala Asp Glu Ser Thr Asn Thr Ala Tyr Met Glu
1 5 10 15

Leu Ser Ser Leu Arg Ser Glu Asp Thr Ala Phe Tyr Phe Cys Ala Arg
20 25 30

<210> SEQ ID NO 310
<211> LENGTH: 32
<212> TYPE: PRT
<213> ORGANISM: Homo sapiens

<400> SEQUENCE: 310

Arg Phe Thr Ile Ser Arg Asp Asn Ser Lys Asn Thr Leu Tyr Leu Gln
1 5 10 15

Met Asn Arg Leu Arg Ala Glu Asp Thr Ala Val Tyr Tyr Cys Ala Arg
20 25 30

<210> SEQ ID NO 311
<211> LENGTH: 30
<212> TYPE: PRT
<213> ORGANISM: Homo sapiens

<400> SEQUENCE: 311

Gln Val Gln Leu Gln Glu Ser Gly Pro Gly Leu Val Lys Pro Ser Gly
1 5 10 15

Thr Leu Ser Leu Thr Cys Ala Val Ser Gly Gly Ser Ile Ser
20 25 30

<210> SEQ ID NO 312
<211> LENGTH: 14
<212> TYPE: PRT
<213> ORGANISM: Homo sapiens

<400> SEQUENCE: 312

Trp Val Arg Gln Pro Pro Gly Lys Gly Leu Glu Trp Ile Gly
1 5 10

<210> SEQ ID NO 313
<211> LENGTH: 32
<212> TYPE: PRT
<213> ORGANISM: Homo sapiens

<400> SEQUENCE: 313

Arg Val Thr Ile Ser Val Asp Lys Ser Lys Asn Gln Phe Ser Leu Lys
1 5 10 15

Leu Ser Ser Val Thr Ala Ala Asp Thr Ala Val Tyr Tyr Cys Ala Arg
20 25 30

<210> SEQ ID NO 314
<211> LENGTH: 32
<212> TYPE: PRT
<213> ORGANISM: Homo sapiens

<400> SEQUENCE: 314

Arg Phe Ala Ile Ser Arg Asp Asn Ala Lys Asn Ser Leu Phe Leu Gln
1 5 10 15

Met Asn Ser Leu Arg Ala Glu Asp Thr Ala Val Tyr Tyr Cys Ala Arg
20 25 30

<210> SEQ ID NO 315
<211> LENGTH: 32
<212> TYPE: PRT
<213> ORGANISM: Homo sapiens

<400> SEQUENCE: 315

Arg Phe Thr Ile Ser Arg Asp Asn Ala Arg Asn Ser Leu Tyr Leu Gln
1 5 10 15

Met Asn Ser Leu Arg Ala Glu Asp Thr Ala Val Tyr Tyr Cys Ala Arg
20 25 30

<210> SEQ ID NO 316
<211> LENGTH: 30
<212> TYPE: PRT
<213> ORGANISM: Homo sapiens

<400> SEQUENCE: 316

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser
20 25 30

<210> SEQ ID NO 317
<211> LENGTH: 14
<212> TYPE: PRT
<213> ORGANISM: Homo sapiens

<400> SEQUENCE: 317

Trp Val Arg Gln Ala Pro Gly Lys Gly Leu Glu Trp Val Gly
1 5 10

<210> SEQ ID NO 318
<211> LENGTH: 32
<212> TYPE: PRT
<213> ORGANISM: Homo sapiens

<400> SEQUENCE: 318

Arg Phe Thr Ile Ser Arg Asp Asp Ser Lys Asn Thr Leu Tyr Leu Gln
1 5 10 15

Met Asn Ser Leu Lys Ala Glu Asp Thr Ala Val Tyr Tyr Cys Thr Thr
20 25 30

<210> SEQ ID NO 319
<211> LENGTH: 30
<212> TYPE: PRT
<213> ORGANISM: Homo sapiens

<400> SEQUENCE: 319

Gln Val Gln Leu Gln Glu Ser Gly Pro Gly Leu Val Lys Pro Ser Gln
1 5 10 15

Thr Leu Ser Leu Thr Cys Thr Val Ser Gly Gly Ser Ile Ser
20 25 30

<210> SEQ ID NO 320
<211> LENGTH: 14
<212> TYPE: PRT
<213> ORGANISM: Homo sapiens

<400> SEQUENCE: 320

Trp Ile Arg Gln Leu Pro Gly Lys Gly Leu Glu Trp Ile Gly
1 5 10

<210> SEQ ID NO 321
<211> LENGTH: 32
<212> TYPE: PRT
<213> ORGANISM: Homo sapiens

<400> SEQUENCE: 321

Arg Val Thr Ile Ser Val Asp Thr Ser Lys Lys Gln Phe Ser Leu Arg
1 5 10 15

Leu Ser Ser Val Thr Ala Ala Asp Thr Ala Val Tyr Tyr Cys Ala Arg
20 25 30

<210> SEQ ID NO 322
<211> LENGTH: 30
<212> TYPE: PRT
<213> ORGANISM: Homo sapiens

<400> SEQUENCE: 322

Glu Val Gln Leu Val Gln Ser Gly Ala Glu Val Lys Lys Pro Gly Glu
1 5 10 15

Ser Leu Lys Ile Ser Cys Lys Val Ser Gly Tyr Phe Phe Thr
20 25 30

<210> SEQ ID NO 323
<211> LENGTH: 14
<212> TYPE: PRT
<213> ORGANISM: Homo sapiens

<400> SEQUENCE: 323

Trp Val Arg Gln Met Pro Gly Lys Gly Leu Glu Tyr Met Gly
1 5 10

<210> SEQ ID NO 324
<211> LENGTH: 32
<212> TYPE: PRT
<213> ORGANISM: Homo sapiens

<400> SEQUENCE: 324

```
Gln Val Thr Ile Ser Ala Asp Lys Ser Ile Ser Thr Ala Tyr Leu Gln
1               5                   10                  15

Trp Ser Ser Leu Lys Ala Ser Asp Thr Ala Met Tyr Tyr Cys Ala Arg
            20                  25                  30


<210> SEQ ID NO 325
<211> LENGTH: 32
<212> TYPE: PRT
<213> ORGANISM: Homo sapiens

<400> SEQUENCE: 325

Arg Val Thr Met Thr Thr Asp Thr Ser Thr Ser Thr Ala Tyr Met Glu
1               5                   10                  15

Leu Arg Ser Leu Arg Ser Asp Asp Thr Ala Val Tyr Phe Cys Ala Arg
            20                  25                  30


<210> SEQ ID NO 326
<211> LENGTH: 30
<212> TYPE: PRT
<213> ORGANISM: Homo sapiens

<400> SEQUENCE: 326

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser
            20                  25                  30


<210> SEQ ID NO 327
<211> LENGTH: 30
<212> TYPE: PRT
<213> ORGANISM: Homo sapiens

<400> SEQUENCE: 327

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30


<210> SEQ ID NO 328
<211> LENGTH: 32
<212> TYPE: PRT
<213> ORGANISM: Homo sapiens

<400> SEQUENCE: 328

Arg Val Thr Met Thr Thr Asp Thr Ser Thr Ser Thr Ala Tyr Met Glu
1               5                   10                  15

Leu Arg Ser Leu Arg Ser Asp Asp Thr Ala Val Tyr Tyr Cys Ala Arg
            20                  25                  30


<210> SEQ ID NO 329
<211> LENGTH: 30
<212> TYPE: PRT
<213> ORGANISM: Homo sapiens

<400> SEQUENCE: 329

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Asn Phe Thr
            20                  25                  30


<210> SEQ ID NO 330
<211> LENGTH: 14
```

<212> TYPE: PRT
<213> ORGANISM: Homo sapiens

<400> SEQUENCE: 330

Trp Val Arg Gln Met Pro Gly Lys Gly Leu Glu Leu Met Gly
1               5                   10

<210> SEQ ID NO 331
<211> LENGTH: 32
<212> TYPE: PRT
<213> ORGANISM: Homo sapiens

<400> SEQUENCE: 331

Gln Val Thr Ile Ser Ala Asp Lys Ser Ile Ser Thr Ala Tyr Leu Gln
1               5                   10                  15

Trp Ser Ser Leu Lys Ala Ser Asp Thr Ala Met Tyr Tyr Cys Gly Ser
            20                  25                  30

<210> SEQ ID NO 332
<211> LENGTH: 11
<212> TYPE: PRT
<213> ORGANISM: Homo sapiens

<400> SEQUENCE: 332

Trp Gly Arg Gly Thr Leu Val Thr Val Ser Ser
1               5                   10

<210> SEQ ID NO 333
<211> LENGTH: 30
<212> TYPE: PRT
<213> ORGANISM: Homo sapiens

<400> SEQUENCE: 333

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Arg
            20                  25                  30

<210> SEQ ID NO 334
<211> LENGTH: 32
<212> TYPE: PRT
<213> ORGANISM: Homo sapiens

<400> SEQUENCE: 334

Gln Leu Thr Ile Ser Lys Asp Thr Ser Lys Asn Gln Val Val Leu Thr
1               5                   10                  15

Met Thr Asn Met Asp Pro Val Asp Thr Ala Thr Tyr Tyr Cys Ala Arg
            20                  25                  30

<210> SEQ ID NO 335
<211> LENGTH: 30
<212> TYPE: PRT
<213> ORGANISM: Homo sapiens

<400> SEQUENCE: 335

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser
            20                  25                  30

<210> SEQ ID NO 336
<211> LENGTH: 14
<212> TYPE: PRT

<213> ORGANISM: Homo sapiens

<400> SEQUENCE: 336

Trp Ile Arg Gln Ser Pro Gly Lys Gly Leu Glu Trp Ile Gly
1 5 10

<210> SEQ ID NO 337
<211> LENGTH: 32
<212> TYPE: PRT
<213> ORGANISM: Homo sapiens

<400> SEQUENCE: 337

Arg Leu Thr Ile Ser Ile Asp Thr Ser Lys Thr Gln Phe Ser Leu Lys
1 5 10 15

Leu Ser Ser Val Thr Ala Ala Asp Thr Ala Ile Tyr Tyr Cys Val Arg
20 25 30

<210> SEQ ID NO 338
<211> LENGTH: 32
<212> TYPE: PRT
<213> ORGANISM: Homo sapiens

<400> SEQUENCE: 338

Arg Phe Ile Ile Ser Arg Asp Lys Ser Lys Asn Thr Leu Tyr Leu Gln
1 5 10 15

Met Asn Ser Leu Arg Ala Glu Asp Thr Ala Val Tyr Tyr Cys Ala Arg
20 25 30

<210> SEQ ID NO 339
<211> LENGTH: 32
<212> TYPE: PRT
<213> ORGANISM: Homo sapiens

<400> SEQUENCE: 339

Arg Val Thr Met Thr Arg Asp Thr Ser Ile Ser Thr Ala Tyr Met Glu
1 5 10 15

Leu Ser Arg Leu Arg Ser Asp Asp Thr Ala Val Tyr Phe Cys Ala Arg
20 25 30

<210> SEQ ID NO 340
<211> LENGTH: 30
<212> TYPE: PRT
<213> ORGANISM: Homo sapiens

<400> SEQUENCE: 340

Glu Val Gln Leu Val Gln Ser Gly Gly Gly Leu Val Gln Pro Gly Gly
1 5 10 15

Ser Leu Arg Leu Ser Cys Thr Ala Ser Gly Phe Thr Phe Ser
20 25 30

<210> SEQ ID NO 341
<211> LENGTH: 32
<212> TYPE: PRT
<213> ORGANISM: Homo sapiens

<400> SEQUENCE: 341

Arg Phe Thr Ile Ser Arg Asp Asn Ala Lys Asn Thr Leu Tyr Leu Gln
1 5 10 15

Met Asn Ser Leu Arg Ala Glu Asp Thr Ala Val Tyr Tyr Cys Ala Arg
20 25 30

<210> SEQ ID NO 342

<211> LENGTH: 14
<212> TYPE: PRT
<213> ORGANISM: Homo sapiens

<400> SEQUENCE: 342

Trp Val Arg Gln Ala Pro Gly Glu Gly Leu Glu Trp Val Ala
1               5                   10

<210> SEQ ID NO 343
<211> LENGTH: 30
<212> TYPE: PRT
<213> ORGANISM: Homo sapiens

<400> SEQUENCE: 343

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser
            20                  25                  30

<210> SEQ ID NO 344
<211> LENGTH: 30
<212> TYPE: PRT
<213> ORGANISM: Homo sapiens

<400> SEQUENCE: 344

Gln Val Gln Leu Val Gln Ser Gly Ala Ala Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 345
<211> LENGTH: 32
<212> TYPE: PRT
<213> ORGANISM: Homo sapiens

<400> SEQUENCE: 345

Arg Val Thr Met Thr Arg Asp Thr Ser Ile Ser Thr Ala Ser Met Glu
1               5                   10                  15

Leu Ser Arg Leu Arg Ser Asp Asp Thr Ala Val Tyr Phe Cys Ala Arg
            20                  25                  30

<210> SEQ ID NO 346
<211> LENGTH: 32
<212> TYPE: PRT
<213> ORGANISM: Homo sapiens

<400> SEQUENCE: 346

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Thr Glu
            20                  25                  30

<210> SEQ ID NO 347
<211> LENGTH: 30
<212> TYPE: PRT
<213> ORGANISM: Homo sapiens

<400> SEQUENCE: 347

Gln Val Gln Leu Val Gln Ser Gly Thr Glu Val Lys Lys Pro Gly Ala
1               5                   10                  15

Ser Met Lys Val Ser Cys Lys Ala Ser Gly Tyr Thr Phe Thr
            20                  25                  30

<210> SEQ ID NO 348
<211> LENGTH: 32
<212> TYPE: PRT
<213> ORGANISM: Homo sapiens

<400> SEQUENCE: 348

```
Arg Val Thr Met Thr Arg Asp Thr Ser Thr Asn Thr Val Tyr Met Glu
1               5                   10                  15

Leu Ser Ser Leu Arg Ser Glu Asp Thr Ala Met Tyr Tyr Cys Ala Arg
            20                  25                  30
```

<210> SEQ ID NO 349
<211> LENGTH: 32
<212> TYPE: PRT
<213> ORGANISM: Homo sapiens

<400> SEQUENCE: 349

```
Arg Phe Thr Ile Ser Arg Asp Asn Ala Lys Asn Ser Leu Tyr Leu Gln
1               5                   10                  15

Met Asn Ser Leu Arg Asp Glu Asp Thr Ala Val Tyr Tyr Cys Ala Arg
            20                  25                  30
```

<210> SEQ ID NO 350
<211> LENGTH: 441
<212> TYPE: PRT
<213> ORGANISM: Homo sapiens

<400> SEQUENCE: 350

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
            20                  25                  30

Gly Ile Ser Trp Val Arg Gln Ala Pro Gly Gln Gly Leu Glu Trp Met
        35                  40                  45

Gly Trp Val Ser Phe Tyr Asn Gly Asn Thr Asn Tyr Ala Gln Lys Leu
    50                  55                  60

Gln Gly Arg Gly Thr Met Thr Thr Asp Pro Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Gly Met Asp Val Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205

Val Asp Lys Thr Val Glu Arg Lys Cys Cys Val Glu Cys Pro Pro Cys
    210                 215                 220

Pro Ala Pro Pro Val Ala Gly Pro Ser Val Phe Leu Phe Pro Pro Lys
```

```
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285

Gln Phe Asn Ser Thr Phe Arg Val Val Ser Val Leu Thr Val Val His
    290                 295                 300

Gln Asp Trp Leu Asn Gly Lys Glu Tyr Lys Cys Lys Val Ser Asn Lys
305                 310                 315                 320

Gly Leu Pro Ala Pro Ile Glu Lys Thr Ile Ser Lys Thr Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Met Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440


<210> SEQ ID NO 351
<211> LENGTH: 215
<212> TYPE: PRT
<213> ORGANISM: Homo sapiens

<400> SEQUENCE: 351

Glu Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Asn Ser Tyr Thr Ser Thr
                85                  90                  95

Ser Met Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160
```

-continued

```
Gly Val Glu Thr Thr Thr Pro Ser Lys Gln Ser Asn Asn Lys Tyr Ala
            165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215


<210> SEQ ID NO 352
<211> LENGTH: 441
<212> TYPE: PRT
<213> ORGANISM: Homo sapiens

<400> SEQUENCE: 352

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
            20                  25                  30

Gly Ile Ser Trp Val Arg Gln Ala Pro Gly Gln Gly Leu Glu Trp Met
        35                  40                  45

Gly Trp Val Ser Phe Tyr Asn Gly Asn Thr Asn Tyr Ala Gln Lys Leu
    50                  55                  60

Gln Gly Arg Gly Thr Met Thr Arg Asp Pro Ser Thr Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Tyr Gly Met Asp Val Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205

Val Asp Lys Thr Val Glu Arg Lys Cys Cys Val Glu Cys Pro Pro Cys
    210                 215                 220

Pro Ala Pro Pro Val Ala Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285

Gln Phe Asn Ser Thr Phe Arg Val Val Ser Val Leu Thr Val Val His
    290                 295                 300

Gln Asp Trp Leu Asn Gly Lys Glu Tyr Lys Cys Lys Val Ser Asn Lys
305                 310                 315                 320
```

```
Gly Leu Pro Ala Pro Ile Glu Lys Thr Ile Ser Lys Thr Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Met Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440


<210> SEQ ID NO 353
<211> LENGTH: 441
<212> TYPE: PRT
<213> ORGANISM: Homo sapiens

<400> SEQUENCE: 353

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
            20                  25                  30

Gly Ile Ser Trp Val Arg Gln Ala Pro Gly Gln Gly Leu Glu Trp Met
        35                  40                  45

Gly Trp Val Ser Phe Tyr Asn Gly Asn Thr Asn Tyr Ala Gln Lys Leu
    50                  55                  60

Gln Gly Arg Gly Thr Met Thr Thr Asp Pro Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Gly Met Asp Val Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205

Val Asp Lys Thr Val Glu Arg Lys Cys Cys Val Glu Cys Pro Pro Cys
    210                 215                 220

Pro Ala Pro Pro Val Ala Gly Pro Ser Val Phe Leu Phe Pro Pro Lys
225                 230                 235                 240

Pro Lys Asp Thr Leu Met Ile Ser Arg Thr Pro Glu Val Thr Cys Val
```

```
                245                 250                 255

Val Val Asp Val Ser His Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285

Gln Phe Asn Ser Thr Phe Arg Val Val Ser Val Leu Thr Val Val His
    290                 295                 300

Gln Asp Trp Leu Asn Gly Lys Glu Tyr Lys Cys Lys Val Ser Asn Lys
305                 310                 315                 320

Gly Leu Pro Ala Pro Ile Glu Lys Thr Ile Ser Lys Thr Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Met Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Lys Leu Ser Leu Ser Pro Gly Lys
        435                 440


<210> SEQ ID NO 354
<211> LENGTH: 441
<212> TYPE: PRT
<213> ORGANISM: Homo sapiens

<400> SEQUENCE: 354

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
            20                  25                  30

Gly Ile Ser Trp Val Arg Gln Ala Pro Gly Gln Gly Leu Glu Trp Met
        35                  40                  45

Gly Trp Val Ser Phe Tyr Asn Gly Asn Thr Asn Tyr Ala Gln Lys Leu
    50                  55                  60

Gln Gly Arg Gly Thr Met Thr Arg Asp Pro Ser Thr Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Tyr Gly Met Asp Val Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175
```

```
Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205

Val Asp Lys Thr Val Glu Arg Lys Cys Cys Val Glu Cys Pro Pro Cys
    210                 215                 220

Pro Ala Pro Pro Val Ala Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285

Gln Phe Asn Ser Thr Phe Arg Val Val Ser Val Leu Thr Val Val His
    290                 295                 300

Gln Asp Trp Leu Asn Gly Lys Glu Tyr Lys Cys Lys Val Ser Asn Lys
305                 310                 315                 320

Gly Leu Pro Ala Pro Ile Glu Lys Thr Ile Ser Lys Thr Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Met Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Lys Leu Ser Leu Ser Pro Gly Lys
        435                 440


<210> SEQ ID NO 355
<211> LENGTH: 220
<212> TYPE: PRT
<213> ORGANISM: Homo sapiens

<400> SEQUENCE: 355

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Asp Ser
            20                  25                  30

Ser Asp Asn Lys Asn Tyr Leu Ala Trp Tyr Gln Gln Lys Pro Gly Gln
        35                  40                  45

Pro Pro Lys Leu Leu Ile Tyr Trp Ala Ser Asn Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Asp Pro Phe Thr Phe Gly Pro Gly Thr Lys Val Asp Ile
            100                 105                 110
```

```
Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 356
<211> LENGTH: 446
<212> TYPE: PRT
<213> ORGANISM: Homo sapiens

<400> SEQUENCE: 356

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ser Trp Phe Gly Glu Val Phe Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
```

```
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 357
<211> LENGTH: 446
<212> TYPE: PRT
<213> ORGANISM: Homo sapiens

<400> SEQUENCE: 357

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Arg Asp Thr Ser Thr Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Ser Trp Phe Gly Glu Val Phe Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 358
<211> LENGTH: 446
<212> TYPE: PRT
<213> ORGANISM: Homo sapiens

<400> SEQUENCE: 358

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Lys Ala Tyr Asn Gly Asn Thr Asn Tyr Ala Gln Lys Leu
    50                  55                  60

Gln Gly Arg Val Thr Met Thr Arg Asp Thr Ser Thr Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Ser Trp Phe Gly Glu Val Phe Phe Asp Tyr Trp Gly Gln
            100                 105                 110

Gly Thr Leu Val Thr Val Ser Ser Ala Ser Thr Lys Gly Pro Ser Val
        115                 120                 125
```

```
Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 359
<211> LENGTH: 450
<212> TYPE: PRT
<213> ORGANISM: Homo sapiens

<400> SEQUENCE: 359

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Glu Gly Leu Glu Trp Val
        35                  40                  45

Ala Ala Ile Trp Phe Asp Ala Ser Asp Lys Tyr Tyr Ala Asp Ala Val
```

```
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Ala Ile Phe Gly Val Val Pro Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Cys Glu Glu Gln Tyr Gly Ser Thr Tyr Arg
    290                 295                 300

Cys Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 360

<211> LENGTH: 214
<212> TYPE: PRT
<213> ORGANISM: Homo sapiens

<400> SEQUENCE: 360

Glu Ile Val Met Thr Gln Ser Pro Ala Thr Leu Ser Val Ser Pro Gly
1 5 10 15

Glu Arg Ala Thr Leu Ser Cys Arg Ala Ser Gln Ser Val Ser Ser Asn
20 25 30

Leu Ala Trp Tyr Gln Gln Lys Pro Gly Gln Ala Pro Arg Leu Leu Ile
35 40 45

Tyr Gly Ala Ala Thr Arg Ala Thr Gly Ile Pro Ala Arg Val Ser Gly
50 55 60

Ser Gly Ser Gly Thr Glu Phe Thr Leu Thr Ile Ser Ser Leu Gln Ser
65 70 75 80

Glu Asp Phe Ala Val Tyr Tyr Cys Gln Gln Tyr Asn Asn Trp Pro Leu
85 90 95

Thr Phe Gly Gly Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 361
<211> LENGTH: 450
<212> TYPE: PRT
<213> ORGANISM: Homo sapiens

<400> SEQUENCE: 361

Glu Val Gln Leu Val Glu Ser Gly Gly Gly Val Val Gln Pro Gly Gly
1 5 10 15

Ser Leu Arg Leu Ser Cys Ala Ala Ser Gly Phe Thr Phe Ser Asn Tyr
20 25 30

Gly Met His Trp Val Arg Gln Ala Pro Gly Glu Gly Leu Glu Trp Val
35 40 45

Ala Ala Ile Trp Phe Asp Ala Ser Asp Lys Tyr Tyr Ala Asp Ala Val
50 55 60

Lys Gly Arg Phe Thr Ile Ser Arg Asp Asn Ala Lys Asn Thr Leu Tyr
65 70 75 80

Leu Gln Met Asn Ser Leu Arg Ala Glu Asp Thr Ala Val Tyr Tyr Cys
85 90 95

Ala Arg Asp Gln Ala Ile Phe Gly Val Val Pro Asp Tyr Trp Gly Gln
100 105 110

Gly Thr Leu Val Thr Val Ser Ser Ala Ser Thr Lys Gly Pro Ser Val
115 120 125

```
Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Cys Glu Glu Gln Tyr Gly Ser Thr Tyr Arg
    290                 295                 300

Cys Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 362
<211> LENGTH: 450
<212> TYPE: PRT
<213> ORGANISM: Homo sapiens

<400> SEQUENCE: 362

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Glu Gly Leu Glu Trp Val
```

```
        35                  40                  45

Ala Ala Ile Trp Phe Asp Ala Ser Asp Lys Tyr Tyr Ala Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Ala Ile Phe Gly Val Val Pro Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Cys Glu Glu Gln Tyr Gly Ser Thr Tyr Arg
    290                 295                 300

Cys Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 363
<211> LENGTH: 214
<212> TYPE: PRT
<213> ORGANISM: Homo sapiens

<400> SEQUENCE: 363

Glu Ile Val Met Thr Gln Ser Pro Ala Thr Leu Ser Val Ser Pro Gly
1 5 10 15

Glu Arg Ala Thr Leu Ser Cys Arg Ala Ser Gln Ser Val Ser Ser Asn
20 25 30

Leu Ala Trp Tyr Gln Gln Lys Pro Gly Gln Ala Pro Arg Leu Leu Ile
35 40 45

Tyr Gly Ala Ala Thr Arg Ala Thr Gly Ile Pro Asp Arg Val Ser Gly
50 55 60

Ser Gly Ser Gly Thr Glu Phe Thr Leu Thr Ile Ser Arg Leu Glu Pro
65 70 75 80

Glu Asp Phe Ala Val Tyr Tyr Cys Gln Gln Tyr Asn Asn Trp Pro Leu
85 90 95

Thr Phe Gly Gly Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 364
<211> LENGTH: 450
<212> TYPE: PRT
<213> ORGANISM: Homo sapiens

<400> SEQUENCE: 364

Glu Val Gln Leu Val Glu Ser Gly Gly Gly Val Val Gln Pro Gly Gly
1 5 10 15

Ser Leu Arg Leu Ser Cys Ala Ala Ser Gly Phe Thr Phe Ser Asn Tyr
20 25 30

Gly Met His Trp Val Arg Gln Ala Pro Gly Glu Gly Leu Glu Trp Val
35 40 45

Ala Ala Ile Trp Phe Asp Ala Ser Asp Lys Tyr Tyr Ala Asp Ala Val
50 55 60

Lys Gly Arg Phe Thr Ile Ser Arg Asp Asn Ala Lys Asn Thr Leu Tyr
65 70 75 80

Leu Gln Met Asn Ser Leu Arg Ala Glu Asp Thr Ala Val Tyr Tyr Cys
85 90 95

Ala Arg Asp Gln Ala Ile Phe Gly Val Val Pro Asp Tyr Trp Gly Gln
100 105 110

-continued

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Cys Glu Glu Gln Tyr Gly Ser Thr Tyr Arg
290 295 300

Cys Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Ser Arg Glu Glu Met Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly Lys
450

<210> SEQ ID NO 365
<211> LENGTH: 214
<212> TYPE: PRT
<213> ORGANISM: Homo sapiens

<400> SEQUENCE: 365

Glu Ile Val Met Thr Gln Ser Pro Ala Thr Leu Ser Val Ser Pro Gly
1 5 10 15

Glu Arg Ala Thr Leu Ser Cys Arg Ala Ser Gln Ser Val Ser Ser Asn

```
            20                  25                  30

Leu Ala Trp Tyr Gln Gln Lys Pro Gly Gln Ala Pro Arg Leu Leu Ile
        35                  40                  45

Tyr Gly Ala Ala Thr Arg Ala Thr Gly Ile Pro Asp Arg Val Ser Gly
    50                  55                  60

Ser Gly Ser Gly Thr Glu Phe Thr Leu Thr Ile Ser Arg Leu Glu Pro
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 366
<211> LENGTH: 441
<212> TYPE: PRT
<213> ORGANISM: Homo sapiens

<400> SEQUENCE: 366

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
            20                  25                  30

Gly Ile Ser Trp Val Arg Gln Ala Pro Gly Gln Gly Leu Glu Trp Met
        35                  40                  45

Gly Trp Val Ser Phe Tyr Asn Gly Asn Thr Asn Tyr Ala Gln Lys Leu
    50                  55                  60

Gln Gly Arg Gly Thr Met Thr Thr Asp Pro Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Gly Met Asp Val Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175
```

```
Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205

Val Asp Lys Thr Val Glu Arg Lys Cys Cys Val Glu Cys Pro Pro Cys
    210                 215                 220

Pro Ala Pro Pro Val Ala Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285

Gln Phe Asn Ser Thr Phe Arg Val Val Ser Val Leu Thr Val Val His
    290                 295                 300

Gln Asp Trp Leu Asn Gly Lys Glu Tyr Lys Cys Lys Val Ser Asn Lys
305                 310                 315                 320

Gly Leu Pro Ala Pro Ile Glu Lys Thr Ile Ser Lys Thr Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Met Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Lys Leu Ser Leu Ser Pro Gly Lys
        435                 440


<210> SEQ ID NO 367
<211> LENGTH: 214
<212> TYPE: PRT
<213> ORGANISM: Homo sapiens

<400> SEQUENCE: 367

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ala Thr Arg Ala Thr Gly Ile Pro Ala Arg Val Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys Arg Thr Val Ala Ala
            100                 105                 110
```

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 368
<211> LENGTH: 450
<212> TYPE: PRT
<213> ORGANISM: Homo sapiens

<400> SEQUENCE: 368

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Glu Gly Leu Glu Trp Val
        35                  40                  45

Ala Ala Ile Trp Phe Asp Ala Ser Asp Lys Tyr Tyr Ala Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Ala Ile Phe Gly Val Val Pro Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
```

-continued

```
            260                 265                 270

Asp Pro Glu Val Lys Phe Asn Trp Tyr Val Asp Gly Val Glu Val His
        275                 280                 285

Asn Ala Lys Thr Lys Pro Cys Glu Glu Gln Tyr Gly Ser Thr Tyr Arg
    290                 295                 300

Cys Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Lys Leu Ser Leu Ser Pro
        435                 440                 445

Gly Lys
    450


<210> SEQ ID NO 369
<211> LENGTH: 692
<212> TYPE: PRT
<213> ORGANISM: Homo sapiens

<400> SEQUENCE: 369

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175
```

```
Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
    370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
    450                 455                 460

Ser Gly Pro Thr Arg Met Ala Thr Ala Ile Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
    530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
```

```
        595                 600                 605

Lys Val Lys Glu His Gly Ile Pro Ala Pro Gln Gly Gln Val Thr Val
    610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Glu Ala Val
            660                 665                 670

Thr Ala Val Ala Ile Cys Cys Arg Ser Arg His Leu Ala Gln Ala Ser
        675                 680                 685

Gln Glu Leu Gln
    690


<210> SEQ ID NO 370
<211> LENGTH: 14
<212> TYPE: PRT
<213> ORGANISM: Homo sapiens

<400> SEQUENCE: 370

Thr Gly Thr Ser Ser Asp Val Gly Gly Tyr Asn Ser Val Ser
1               5                   10


<210> SEQ ID NO 371
<211> LENGTH: 7
<212> TYPE: PRT
<213> ORGANISM: Homo sapiens

<400> SEQUENCE: 371

Glu Val Ser Asn Arg Pro Ser
1               5


<210> SEQ ID NO 372
<211> LENGTH: 9
<212> TYPE: PRT
<213> ORGANISM: Homo sapiens

<400> SEQUENCE: 372

Asn Ser Tyr Thr Ser Thr Ser Met Val
1               5


<210> SEQ ID NO 373
<211> LENGTH: 10
<212> TYPE: PRT
<213> ORGANISM: Homo sapiens

<400> SEQUENCE: 373

Gly Tyr Thr Leu Thr Ser Tyr Gly Ile Ser
1               5                   10


<210> SEQ ID NO 374
<211> LENGTH: 16
<212> TYPE: PRT
<213> ORGANISM: Homo sapiens

<400> SEQUENCE: 374

Trp Val Ser Phe Tyr Asn Gly Asn Thr Asn Tyr Ala Gln Lys Leu Gln
1               5                   10                  15


<210> SEQ ID NO 375
<211> LENGTH: 6
<212> TYPE: PRT
```

<213> ORGANISM: Homo sapiens

<400> SEQUENCE: 375

Gly Tyr Gly Met Asp Val
1 5

<210> SEQ ID NO 376
<211> LENGTH: 115
<212> TYPE: PRT
<213> ORGANISM: Homo sapiens

<400> SEQUENCE: 376

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Leu Thr Ser Tyr
20 25 30

Gly Ile Ser Trp Val Arg Gln Ala Pro Gly Gln Gly Leu Glu Trp Met
35 40 45

Gly Trp Val Ser Phe Tyr Asn Gly Asn Thr Asn Tyr Ala Gln Lys Leu
50 55 60

Gln Gly Arg Gly Thr Met Thr Thr Asp Pro Ser Thr Ser Thr Ala Tyr
65 70 75 80

Met Glu Leu Arg Ser Leu Arg Ser Asp Asp Thr Ala Val Tyr Tyr Cys
85 90 95

Ala Arg Gly Tyr Gly Met Asp Val Trp Gly Gln Gly Thr Thr Val Thr
100 105 110

Val Ser Ser
115

<210> SEQ ID NO 377
<211> LENGTH: 109
<212> TYPE: PRT
<213> ORGANISM: Homo sapiens

<400> SEQUENCE: 377

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Gly Tyr
20 25 30

Asn Ser Val Ser Trp Tyr Gln Gln His Pro Gly Lys Ala Pro Lys Leu
35 40 45

Met Ile Tyr Glu Val Ser Asn Arg Pro Ser Gly Val Ser Asn Arg Phe
50 55 60

Ser Gly Ser Lys Ser Gly Asn Thr Ala Ser Leu Thr Ile Ser Gly Leu
65 70 75 80

Gln Ala Glu Asp Glu Ala Asp Tyr Tyr Cys Asn Ser Tyr Thr Ser Thr
85 90 95

Ser Met Val Phe Gly Gly Gly Thr Lys Leu Thr Val Leu
100 105

<210> SEQ ID NO 378
<211> LENGTH: 115
<212> TYPE: PRT
<213> ORGANISM: Homo sapiens

<400> SEQUENCE: 378

Gln Val Gln Leu Val Gln Ser Gly Ala Glu Val Lys Lys Pro Gly Ala
1 5 10 15

```
Ser Val Lys Val Ser Cys Lys Ala Ser Gly Tyr Thr Leu Thr Ser Tyr
            20                  25                  30

Gly Ile Ser Trp Val Arg Gln Ala Pro Gly Gln Gly Leu Glu Trp Met
        35                  40                  45

Gly Trp Val Ser Phe Tyr Asn Gly Asn Thr Asn Tyr Ala Gln Lys Leu
    50                  55                  60

Gln Gly Arg Gly Thr Met Thr Thr Asp Pro Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Gly Met Asp Val Trp Gly Gln Gly Thr Thr Val Thr
            100                 105                 110

Val Ser Ser
        115


<210> SEQ ID NO 379
<211> LENGTH: 109
<212> TYPE: PRT
<213> ORGANISM: Homo sapiens

<400> SEQUENCE: 379

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Asn Ser Tyr Thr Ser Thr
                85                  90                  95

Ser Met Val Phe Gly Gly Gly Thr Lys Leu Thr Val Leu
            100                 105


<210> SEQ ID NO 380
<211> LENGTH: 4
<212> TYPE: PRT
<213> ORGANISM: Homo sapiens

<400> SEQUENCE: 380

Lys Lys Lys Pro
1


<210> SEQ ID NO 381
<211> LENGTH: 4
<212> TYPE: PRT
<213> ORGANISM: Homo sapiens

<400> SEQUENCE: 381

Pro Gly Lys Pro
1


<210> SEQ ID NO 382
<211> LENGTH: 5
<212> TYPE: PRT
<213> ORGANISM: Homo sapiens

<400> SEQUENCE: 382
```

-continued

```
Pro Gly Lys Lys Pro
1               5


<210> SEQ ID NO 383
<211> LENGTH: 6
<212> TYPE: PRT
<213> ORGANISM: Homo sapiens

<400> SEQUENCE: 383

Pro Gly Lys Lys Lys Pro
1               5
```